(12) United States Patent
Tzahor et al.

(10) Patent No.: US 10,589,132 B2
(45) Date of Patent: Mar. 17, 2020

(54) METHOD OF INDUCING CARDIOMYOCYTES PROLIFERATION AND TREATING HEART DISEASES

(71) Applicant: Yeda Research and Development Co., Ltd., Rehovot (IL)

(72) Inventors: Eldad Tzahor, Rehovot (IL); Elad Bassat, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 144 days.

(21) Appl. No.: 15/772,065

(22) PCT Filed: Oct. 27, 2016

(86) PCT No.: PCT/IL2016/051165
§ 371 (c)(1),
(2) Date: Apr. 29, 2018

(87) PCT Pub. No.: WO2017/072772
PCT Pub. Date: May 4, 2017

(65) Prior Publication Data
US 2018/0318612 A1    Nov. 8, 2018

(30) Foreign Application Priority Data

Oct. 29, 2015 (IL) .......................................... 242380

(51) Int. Cl.
| | |
|---|---|
| A61K 38/17 | (2006.01) |
| A61P 9/10 | (2006.01) |
| C12N 5/077 | (2010.01) |
| C07K 14/47 | (2006.01) |
| A61L 27/54 | (2006.01) |

(52) U.S. Cl.
CPC ............ *A61P 9/10* (2018.01); *A61K 38/1709* (2013.01); *A61L 27/54* (2013.01); *C07K 14/4725* (2013.01); *C12N 5/0657* (2013.01); *A61L 2300/252* (2013.01); *C12N 2501/998* (2013.01)

(58) Field of Classification Search
None
See application file for complete search history.

(56) References Cited

U.S. PATENT DOCUMENTS

| | | | |
|---|---|---|---|
| 5,814,478 A | 9/1998 | Valenzuela et al. | |
| 6,413,740 B1 | 7/2002 | Valenzuela et al. | |
| 6,852,838 B2 | 2/2005 | Valenzuela et al. | |
| 8,685,915 B2* | 4/2014 | Hettwer ................. | A61P 25/02 514/1.1 |
| 2006/0216279 A1 | 9/2006 | Glass et al. | |
| 2007/0014773 A1 | 1/2007 | Matheny et al. | |
| 2007/0014869 A1 | 1/2007 | Matheny | |
| 2007/0014871 A1 | 1/2007 | Matheny | |
| 2010/0095387 A1 | 4/2010 | Smith et al. | |

FOREIGN PATENT DOCUMENTS

| | | |
|---|---|---|
| EP | 2295068 | 3/2011 |
| WO | WO 2008/021896 | 2/2008 |
| WO | WO 2017/072772 | 5/2017 |
| WO | WO 2019/106680 | 6/2019 |

OTHER PUBLICATIONS

Hilgenberg et al., J Biol Chem. Jun. 19, 2009;284(25):16956-16965 (Year: 2009).*
International Search Report and the Written Opinion dated Mar. 21, 2019 From the International Searching Authority Re. Application No. PCT/IL2018/051323. (16 pages).
Bassat et al. "The Extracellular Matrix Protein Agrin Promotes Heart Regeneration in Mice", Nature, XP055565028, 547(7662): 179-184, Jul. 13, 2017.
Eroglu et al. "Heart Regeneration 4.9: Matrix Medicine", Developmental Cell, XP085124219, 42(1): 7-8, Jul. 10, 2017.
International Preliminary Report on Patentability dated May 11, 2018 From the International Bureau of WIPO Re. Application No. PCT/IL2016/051165. (9 Pages).
International Search Report and the Written Opinion dated Feb. 1, 2017 From the International Searching Authority Re. Application No. PCT/IL2016/051165. (15 Pages).
Search Report—ILPO dated May 26, 2016 From the Israel Patent Office Re. Application No. 242380.
Campanelli et al. "Alternative RNA Splicing That Determines Agrin Activity Regulates Binding to Heparin and Alpha-Dystroglycan", Development, XP055336413, 122: 1663-1672, May 1, 1996. Abstract, p. 1663, 1-h col., Para 1-p. 1671, r-h col., Para 4.
Gesemann et al. "Alternative Splicing of angrin alters Its Binding to Heparin, Dystroglycan, and the Putative Agrin Receptor", Neuron, 16(4): 755-767, Apr. 1996. Fig.1.
Hinkel et al. "Inhibition of MicroRNA-92a Protects Against Ischemia/Reperfusion Injury in a Large-Animal Model", Circulation, 128(10): 1066-1075, Published Online Jul. 29, 2013.
Hohenester et al. "The Crystal Structure of a Laminin G-Like Module Reveals the Molecular Basis of Alpha-Dystroglycan Binding to Laminins, Perlecan, and Agrin", Molecular Cell, 4(5): 783-792, Nov. 1999. Summary, p. 786, r-h col., 2nd Para-p. 787, 1-h col., 1st Para.
Hoover et al. "The COOH-Terminal Domain of Agrin Signals via a Synaptic Receptor in Central Nervous System Neurons", The Journal of Cell Biology, XP055336430, 161(5): 923-932, Jun. 9, 2003. Abstract, p. 923, 1-h col., Para 1-p. 931, r-h col., Para 4.
Hopf et al. "Agrin Binding to Alpha-Dystroglycan. Domains of Agrin Necessary to Induce Acetylcholine Receptor Clustering Are Overlapping But Not Identical to the Alpha-Dystroglycan-Binding Region", The Journal of Biological Chemistry, 271(9): 5231-5236, Mar. 1, 1996. Figs.1, 6.
Sasse et al. "Perlecan is Critical for Heart Stability", Cardiovascular Research, 80(3): 435-444, Published Online Aug. 10, 2008. Abstract, p. 440-441, Section 3.4.

(Continued)

*Primary Examiner* — Daniel C Gamett

(57) ABSTRACT

An Agrin peptide which induces proliferation of cardiomyocytes for treating a heart disease is provided.

Figure 1A:
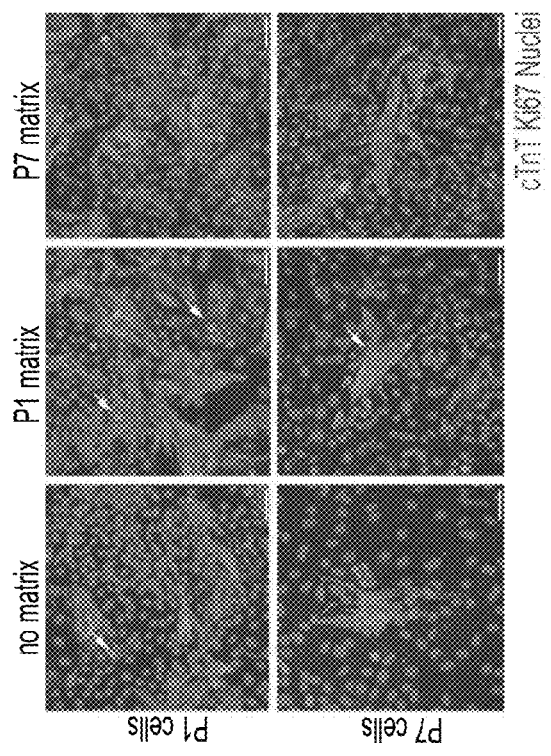

12 Claims, 21 Drawing Sheets
(19 of 21 Drawing Sheet(s) Filed in Color)
Specification includes a Sequence Listing.

(56) References Cited

OTHER PUBLICATIONS

Singhai et al. "Role of Extracellular Matrix Proteins and Their Receptors in the Development of the Vertebrate Neuromuscular Junction", Developmental Neurobiology 71(11):982-1005, Nov. 2011.
Yurchenco et al. "Recombinant Laminin G Domain Mediates Myoblast Adhesion and Heparin Binding", The Journal of Biological Chemistry, 268(11): 8356-8365, Apr. 15, 1993. Abstract.

* cited by examiner

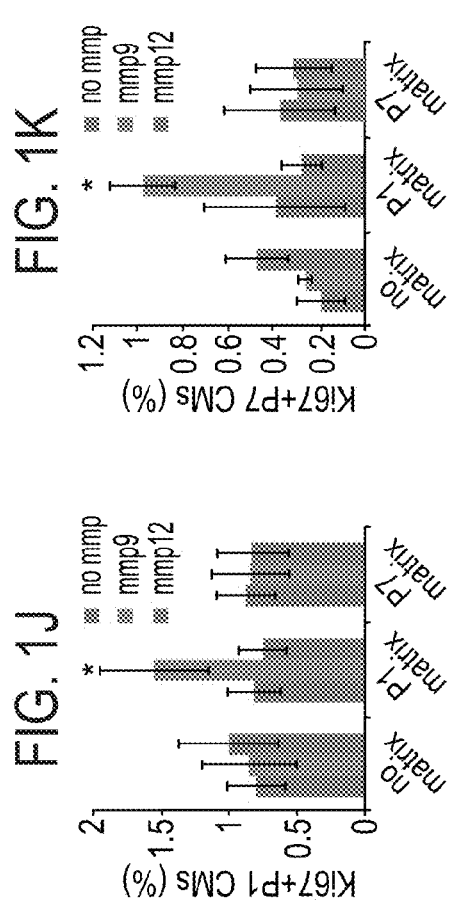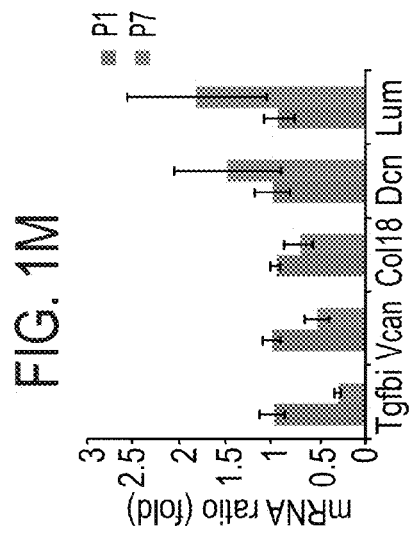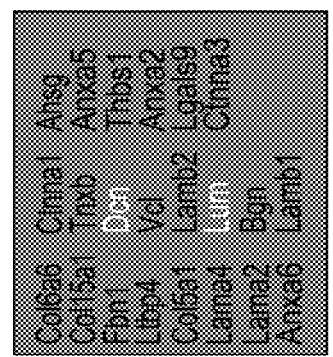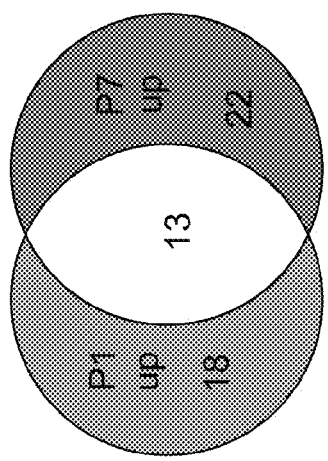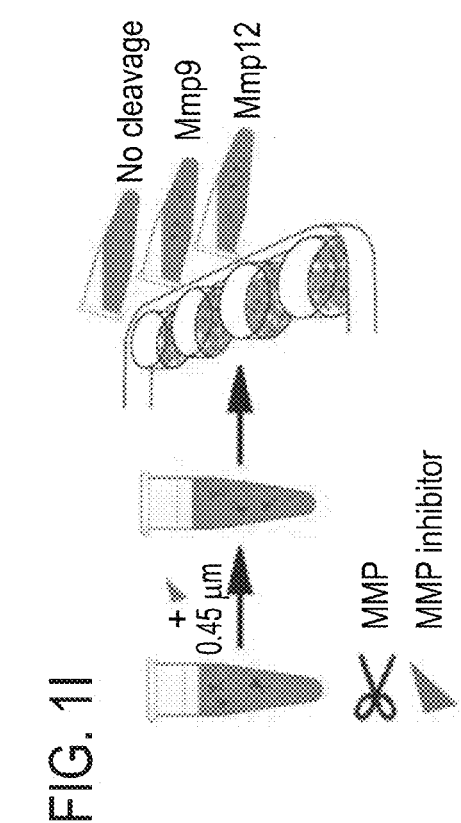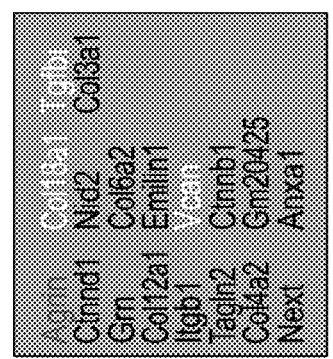

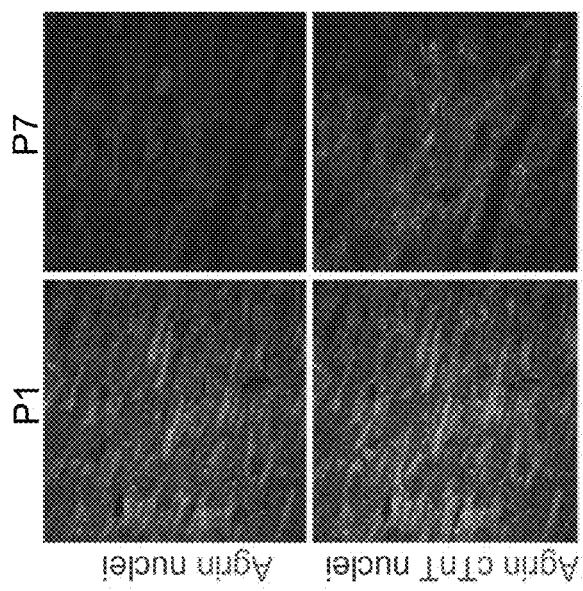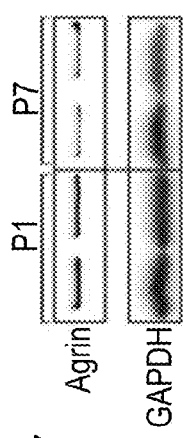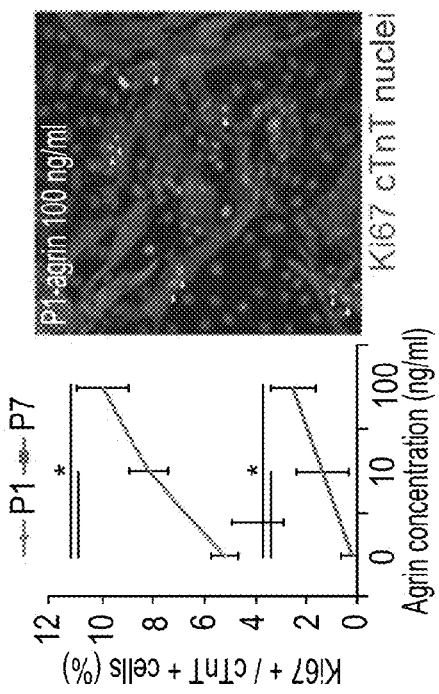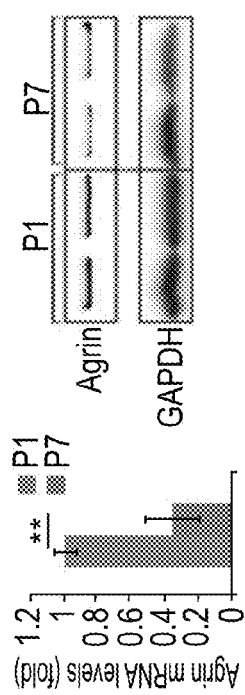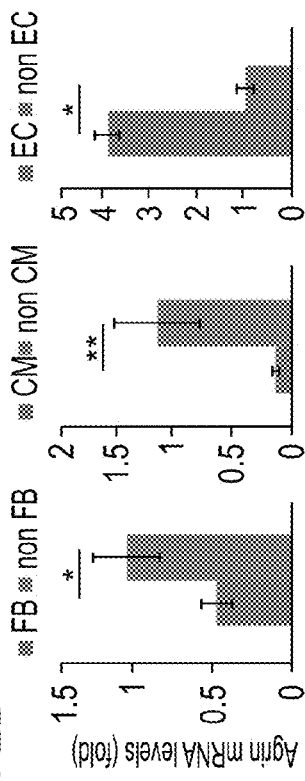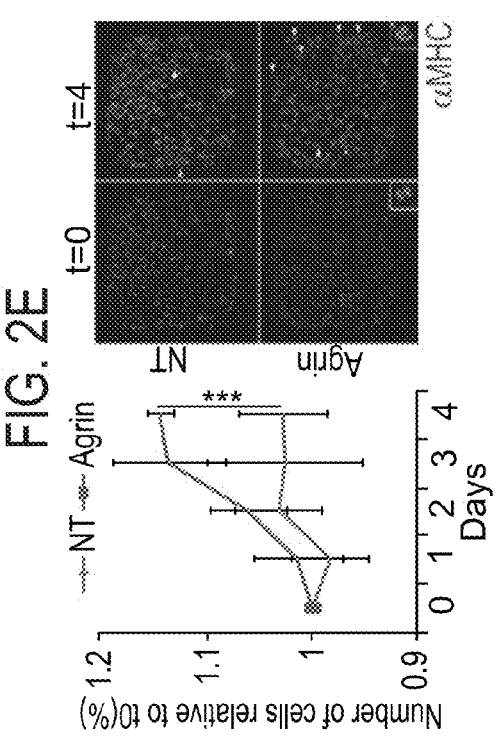

FIG. 3A
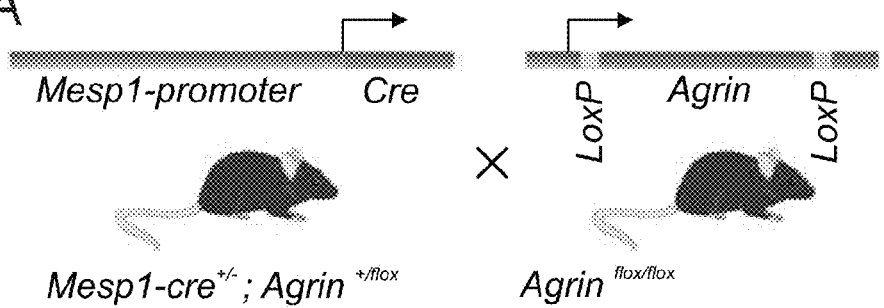
FIG. 3B
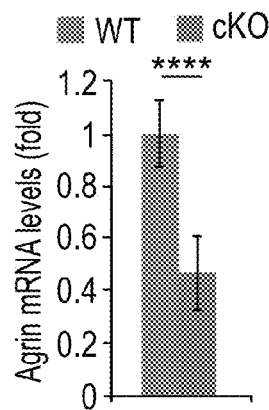
FIG. 3C
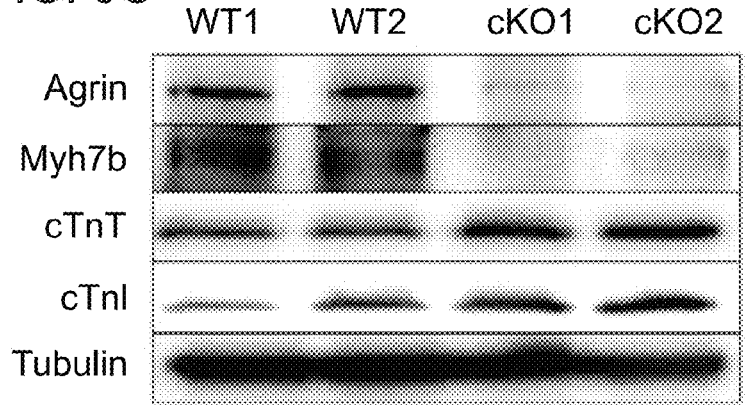
FIG. 3D
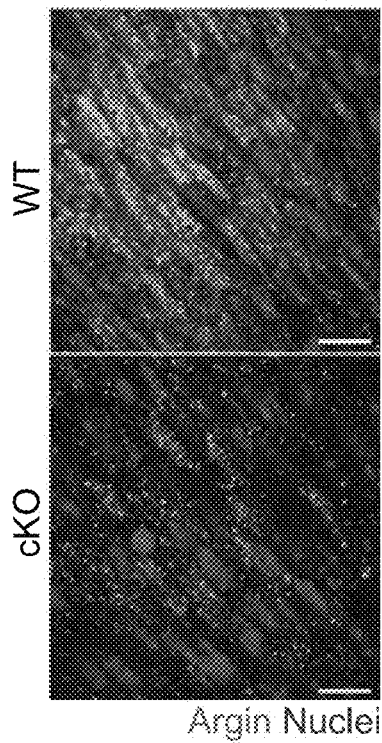
FIG. 3E
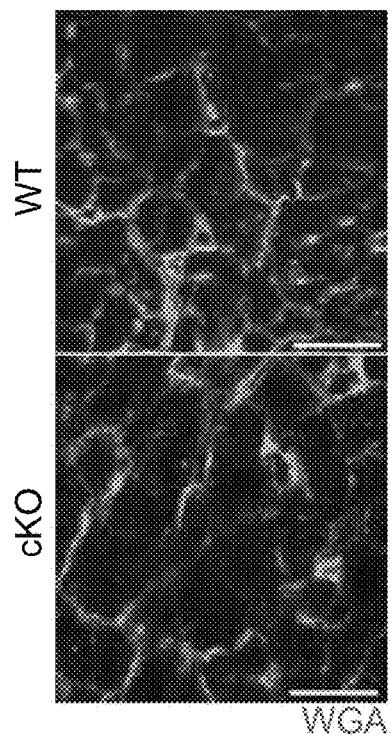
FIG. 3F
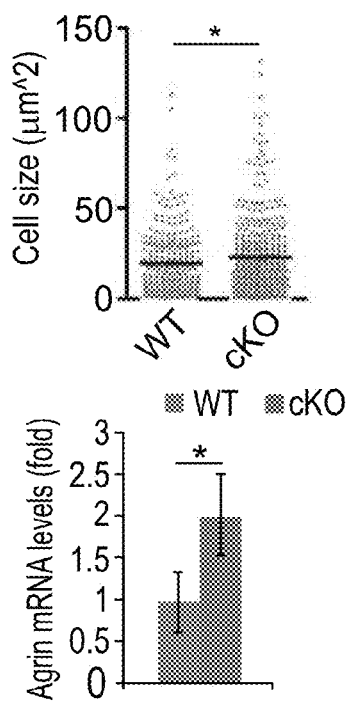
FIG. 3G FIG. 3J
Resection — Proliferation analysis — Fibrosis analysis
P1 — P7 — p28
Apical resection
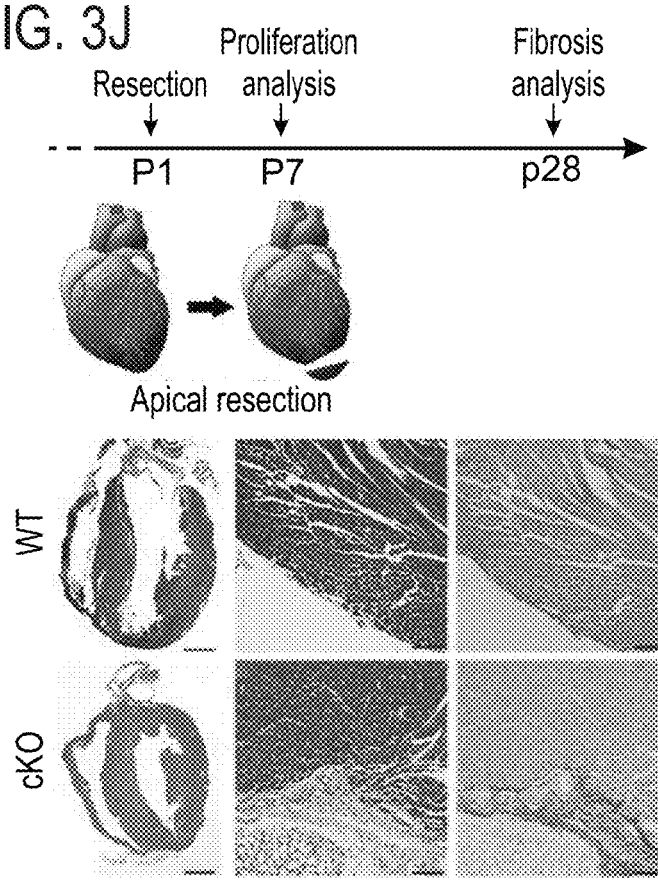
FIG. 3K
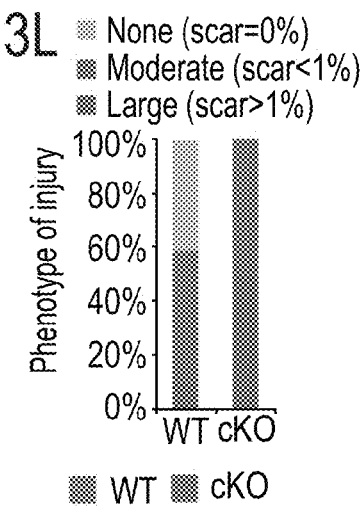
FIG. 3L
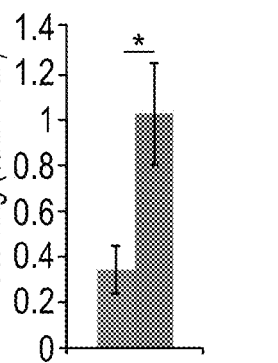
FIG. 3M
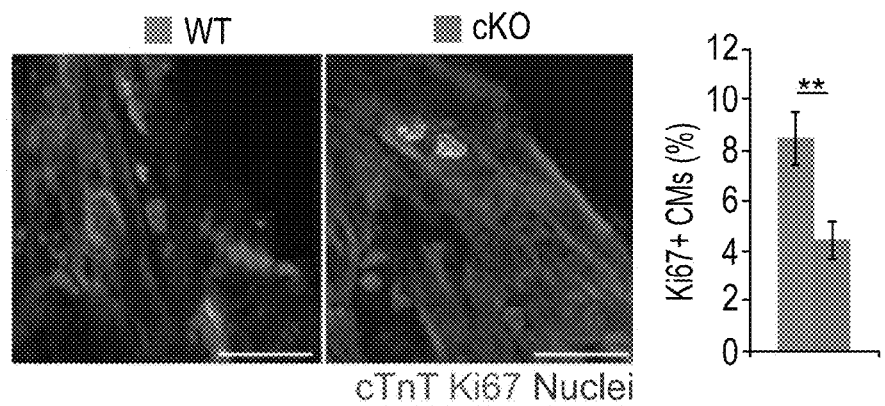
FIG. 3N
cTnT Ki67 Nuclei
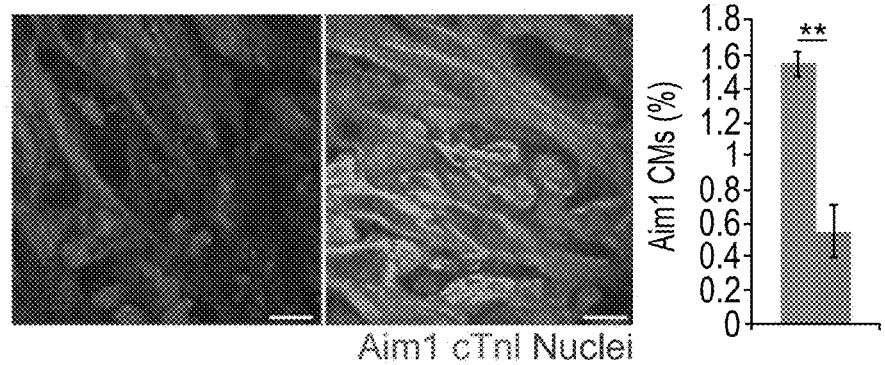
FIG. 3O
Aim1 cTnI Nuclei FIG. 4B Juveline MI

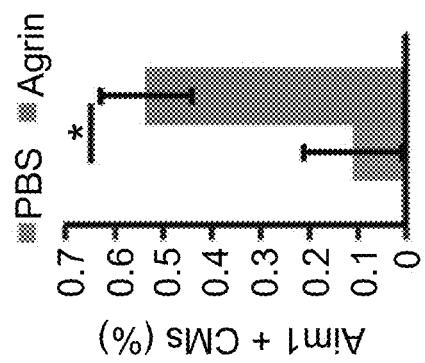
FIG. 4D
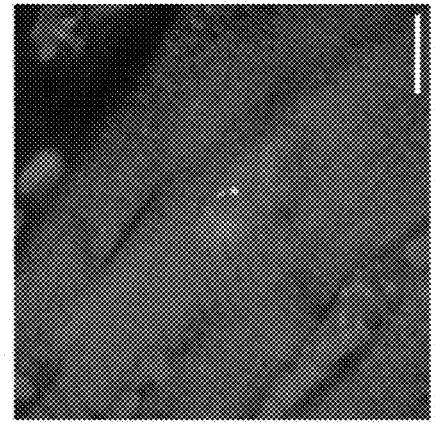
FIG. 4E
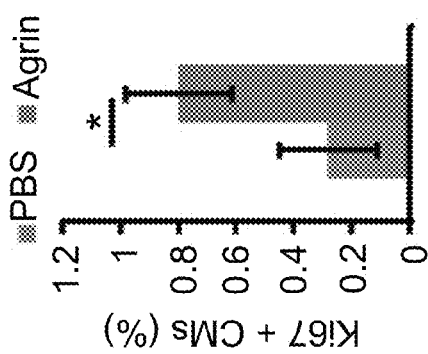
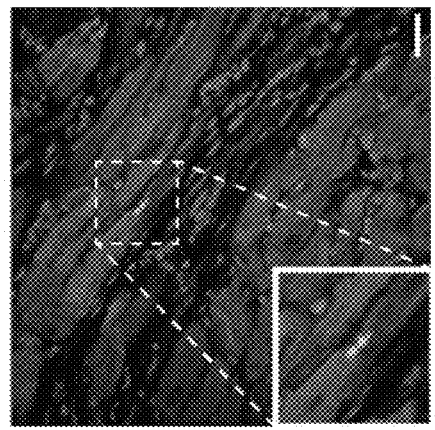
FIG. 4F
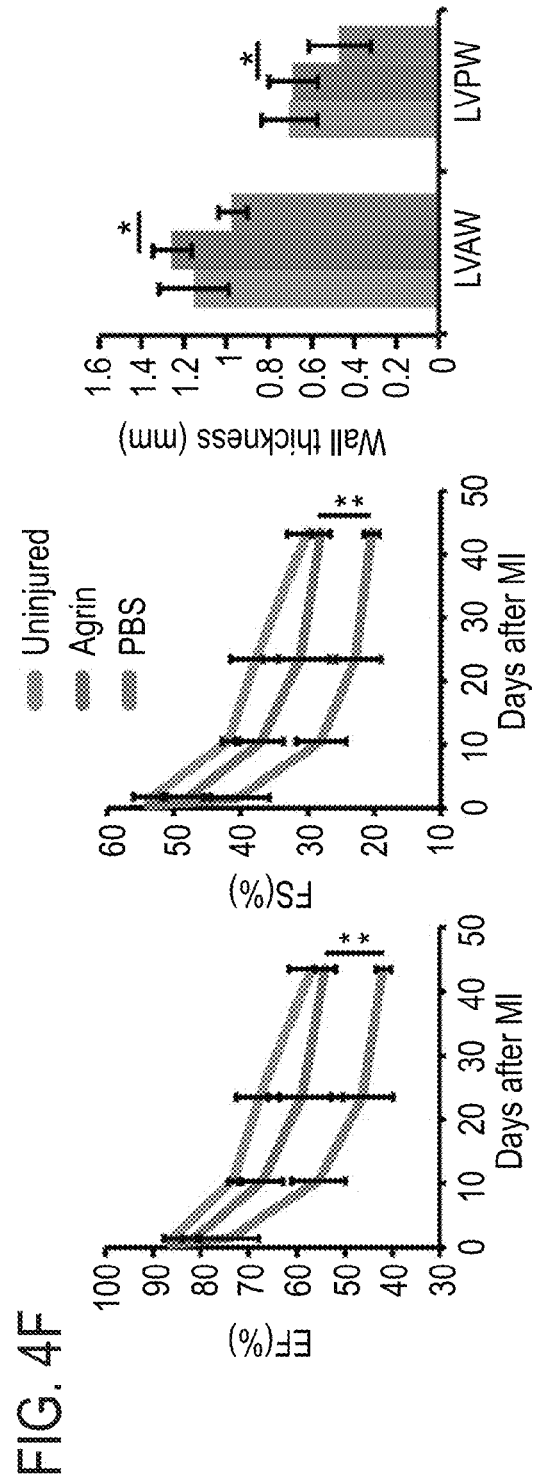

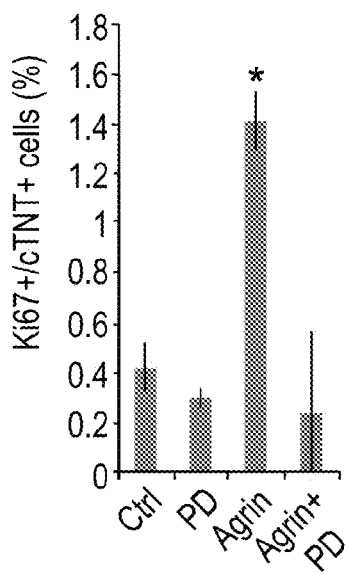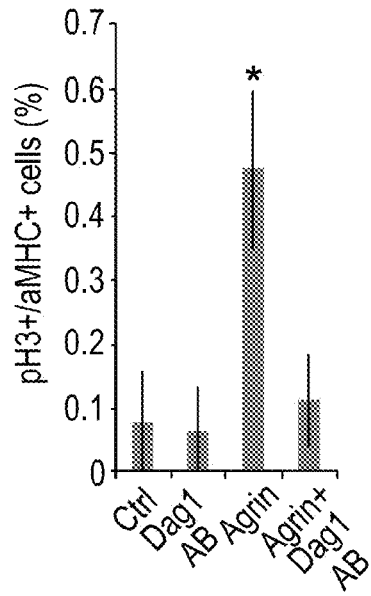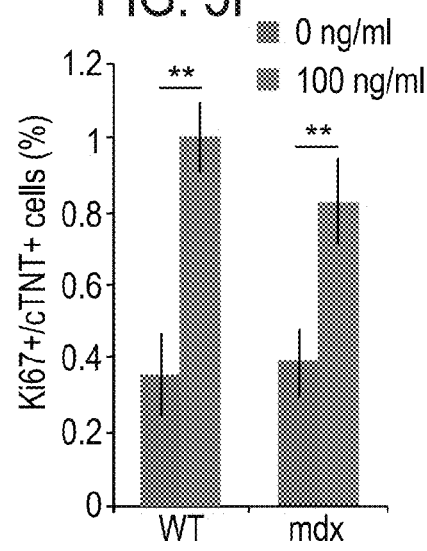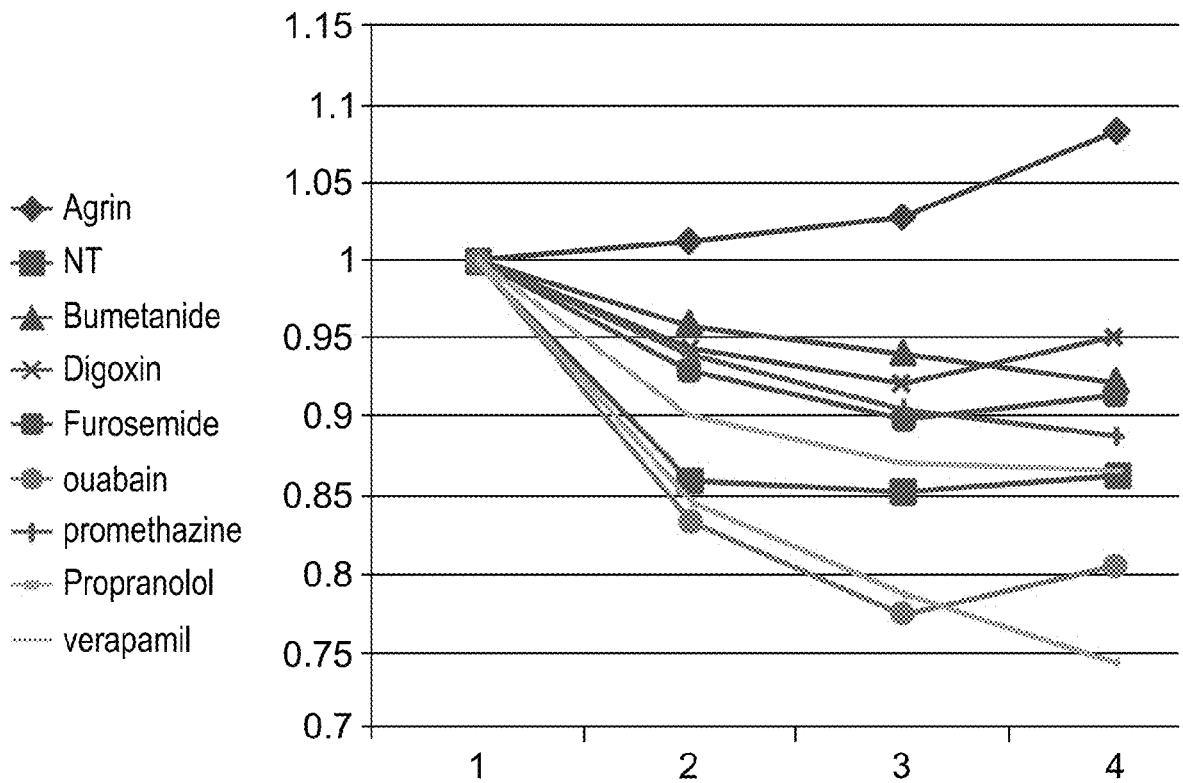

| | | |
|---|---|---|
| Human_Agrin | MAGRSHPGPLRPLLPLLVVAACVLPGAGGTCPERALERREEEANVVLTGTVEEILNVDPV | 60 |
| Rat_Agrin | ------------------------------------------------------------ | 0 |
| Recombinat_Agrin | ------------------------------------------------------------ | 0 |
| Human_Agrin | QHTYSCKVRVWRYLKGKDLVARESLLDGGNKVVISGFGDPLICDNQ--VSTGDT--RIFF | 115 |
| Rat_Agrin | --------------------------------MPPLPLEHRPRQEPGASMLVRYF | 23 |
| Recombinat_Agrin | ------------------------------------------------------------ | 0 |
| Human_Agrin | VNPAPPYLWPAHKNELMLNSSLMRITLRNLEEVEFCVEDKPGTHFTPVPPTPPDACRGML | 176 |
| Rat_Agrin | -------MIPCNICLI-----LLATSTLGFAVLLFLSNYKPGIHFTPAPPTPPDVCRGML | 71 |
| Recombinat_Agrin | ------------------------------------------------------------ | 0 |
| Human_Agrin | CGFGAVCEPNAEGPGRASCVCKKSPCPSVVAPVCGSDASTYSNECELQRAQCSQQRRIRL | 236 |
| Rat_Agrin | CGFGAVCEPSVEDPGRASCVCKKNACPATVAPVCGSDASTYSNECELQRAQCNQQRRIRL | 131 |
| Recombinat_Agrin | ------------------------------------------------------------ | 0 |
| Human_Agrin | LSRGPCGSRDPCSNVTCSFGSTCARSADGLTASCLCPATCRGAPEGTVCGSDGADYPGEC | 296 |
| Rat_Agrin | LRQGPCGSRDPCANVTCSFGSTCVPSADGQTASCLCPTTCFGAPDGTVCGSDGVDYPSEC | 191 |
| Recombinat_Agrin | ------------------------------------------------------------ | 0 |
| Human_Agrin | QLLRRACARQENVFKKFDGPCDPCQGALPDPSRSCRVNPRTRRPEMLLRPESCPARQAPV | 356 |
| Rat_Agrin | QLLSHACASQEIHFKKFNGPCDPCQGSMSDLNHICRVNPRTRHPEMLLRPENCPAQHTPI | 251 |
| Recombinat_Agrin | ------------------------------------------------------------ | 0 |
| Human_Agrin | CGDDGVTYENDCVMGRSGAARGLLLQKVREGQCQGRDQCPEPCRFNAVCLSRRGRPRCSC | 416 |
| Rat_Agrin | CGDDGVTYENDCVMSRIGATRGLLLQKVRSGQCQTRDQCPETCQFNSVCLSRRGRPHCSC | 311 |
| Recombinat_Agrin | ------------------------------------------------------------ | 0 |
| Human_Agrin | DRVTCDGAYRPVCAQDGRTYDSDCWRQQAECRQQRAIPSKHQGPCDQAPSPCLGVQCAFG | 476 |
| Rat_Agrin | DRVTCDGSYRPVCAQDGHTYNNDCWRQQAECRQQRAIPSKHQGPCDQTPSPCHGVQCAFG | 371 |
| Recombinat_Agrin | ------------------------------------------------------------ | 0 |
| Human_Agrin | ATCAVKNGDAACECLQACSSLYDPVCGSDGVTYGSACELEATACTLGREIQVARKGPCDR | 536 |
| Rat_Agrin | AVCTVKNGKAECECQRVCSGIYDPVCGSDGVTYGSVCELESMACTLGREIQVARRGPCDP | 431 |
| Recombinat_Agrin | ------------------------------------------------------------ | 0 |
| Human_Agrin | CGQCRFGALCEAETGRCVCPSECVALAQPVCGSDGHTYPSECMLHVHACTHQISLHVASA | 596 |
| Rat_Agrin | CGQCRFGSLCEVETGRCVCPSECVESAQPVCGSDGHTYASECELHVHACTHQISLYVASA | 491 |
| Recombinat_Agrin | ------------------------------------------------------------ | 0 |
| Human_Agrin | GPCETCGDAVCAFGAVCSAGQCVCPRCEHPPPGPVCGSDGVTYGSACELREAACLQQTQI | 656 |
| Rat_Agrin | GHCQTCGEAVCAFGAVCSAGQCVCPRCEHPPPGPVCGSDGVTYLSACELREAACQQQVQI | 551 |
| Recombinat_Agrin | ------------------------------------------------------------ | 0 |
| Human_Agrin | EEARAGPCEQAECGSGGSGSGEDGDCEQELCRQRGGIWDEDSEDGPCVCDFSCQSVPGSP | 716 |
| Rat_Agrin | EEAHAGPCEPAECGSGGSGSGEDDECEQELCRQRGGIWDEDSEDGPCVCDFSCQSVPGSP | 611 |
| Recombinat_Agrin | ------------------------------------------------------------ | 0 |

FIG. 7B

| | | |
|---|---|---|
| Human_Agrin | VCGSDGVTYSTECELKKARCESQRGLYVAAQGACRGPTFAPLPPVAPLHCAQTPYGCCQD | 776 |
| Rat_Agrin | VCGSDGVTYSTECELKKARCESQRGLYVAAQGACRGPTFAPLPPVAPLHCAQTPYGCCQD | 671 |
| Recombinat_Agrin | ------------------------------------------------------------ | 0 |
| | | |
| Human_Agrin | NITAARGVGLAGCPSACQCNPHGSYGGTCDPATGQGSCRPGVGGLRCDRCEPGFWNFRGI | 836 |
| Rat_Agrin | NITAARGVGLAGCPSACQCNPHGSYGGTCDPATGQGSCRPGVGGLRCDRCEPGFWNFRGI | 731 |
| Recombinat_Agrin | ------------------------------------------------------------ | 0 |
| | | |
| Human_Agrin | VTDGRSGCTPCSCDPQGAVRDDCEQMTGLCSCKPGVAGPKCGQCPDGRALGPAGCEADAS | 896 |
| Rat_Agrin | VTDGHSGCTPCSCDPQGAVRDDCEQMTGLCSCRPGVAGPKCGQCPDGQVLGHLGCEADPM | 791 |
| Recombinat_Agrin | ------------------------------------------------------------ | 0 |
| | | |
| Human_Agrin | APATCAEMRCEFGARCVEESGSAHCVCPMLTCPEANATKVCGSDGVTYGNECQLKTIACR | 956 |
| Rat_Agrin | TPVTCVEIHCEFGASCVEKAGFAQCICPTLTCPEANSTKVCGSDGVTYGNECQLKAIACR | 851 |
| Recombinat_Agrin | ------------------------------------------------------------ | 0 |
| | | |
| Human_Agrin | QGLQISIQSLGPCQEAVAPSTHPTSASVTVTTPGLLLSQALPAPPGALPLAPSSTAHSQT | 1016 |
| Rat_Agrin | QRLDISTQSLGPCQESVTPGASPTSASM--TTPRHILSKTLPFPHNSLPLSPGSTTHDWP | 909 |
| Recombinat_Agrin | ------------------------------------------------------------ | 0 |
| | | |
| Human_Agrin | TPPPSSRPRTTASVPRTTVWPVLTVPPTAPS-PAPSLVASAFGESGSTDGSSDEELSGDQ | 1075 |
| Rat_Agrin | TPLPI-SPHTTVSIPRSTVWPVLTVPPTAAASDVTSLATSIFSESGSANGSGDEELSGDE | 968 |
| Recombinat_Agrin | ------------------------------------------------------------ | 0 |
| | | |
| Human_Agrin | EASGGGSGGLEPLEGSSVATPGPPVERASCYNSALGCCSDGKTPSLDAEGSNCPATKVFQ | 1135 |
| Rat_Agrin | EASGGGSGGLEPPVGSIVVTHGPPIERASCYNSPLGCCSDGKTPSLDSEGSNCPATKAFQ | 1028 |
| Recombinat_Agrin | ------------------------------------------------------------ | 0 |
| | | |
| Human_Agrin | GVLELEGVEGQELFYTPEHADPKSELFGETARSIESTLDDLFRNSDVKKDFRSVRLRDLG | 1195 |
| Rat_Agrin | GVLELEGVEGQELFYTPEMADPKSELFGETARSIESTLDDLFRNSDVKKDFWSVRLRELG | 1088 |
| Recombinat_Agrin | ------------------------------------------------------------ | 0 |
| | | |
| Human_Agrin | PGKSVRAIVDVHFDPTTAFRAPDVARALLRQIQVSRRRSLGVRRPLQEHVRFMDFCWFPA | 1255 |
| Rat_Agrin | PGKLVRAIVDVHFDPTTAFQASDVGQALLRQIQVSRPWALAVRRPLQEHVRFLDFDWFPT | 1148 |
| Recombinat_Agrin | ------------------------------------------------------------ | 0 |
| | | |
| Human_Agrin | FITGATSGAIAAGATARATTASRLPSSAVTPRAPHPSHTSQPVAKTTAAPTTRRPPTTAP | 1315 |
| Rat_Agrin | FFTGAATGTTAAMATARATTVSRLPASSVTPRV-YPSHTSRPVGRTTAAPTTRRPPTTAT | 1207 |
| Recombinat_Agrin | ----AATGTTAAMATARATTVSRLPASAVTPRV-YPSHTSRPVGRTTAPPTTRRPPTTAT | 55 |
| | *..*:. **.**.*.**..*. .* ******* | |

FIG. 7B Continuous

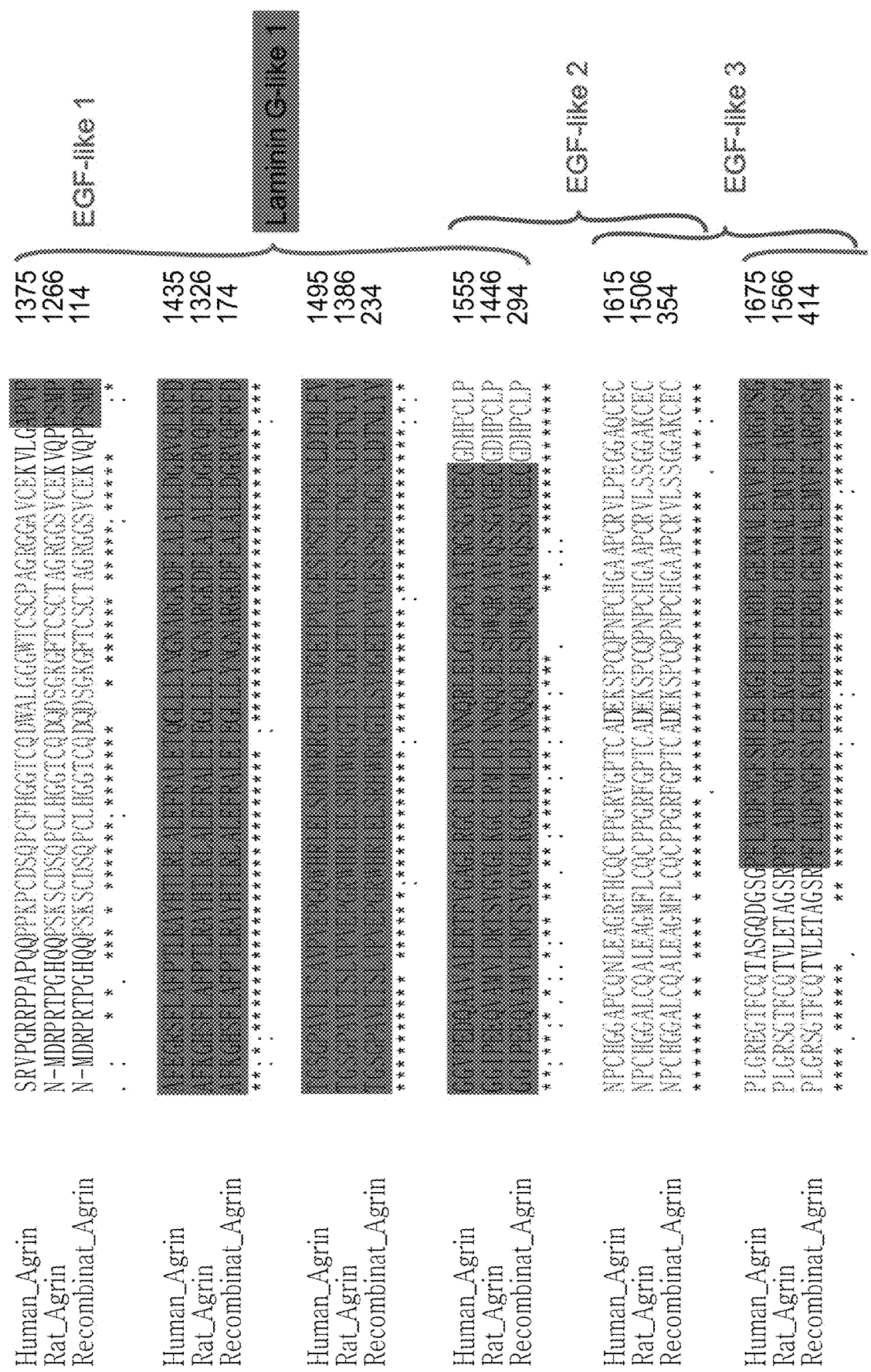
FIG. 7B Continuous

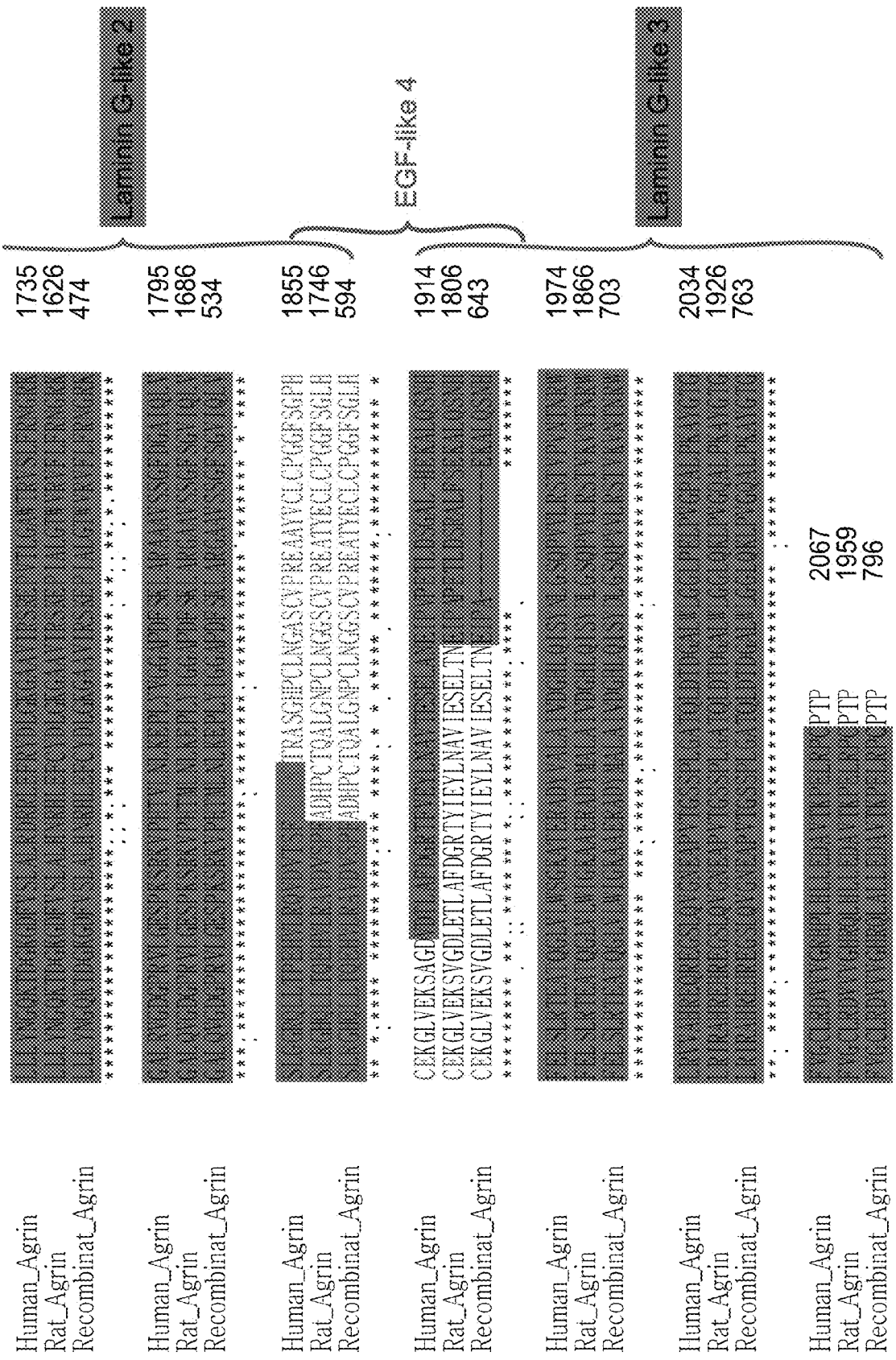
FIG. 7B Continuous

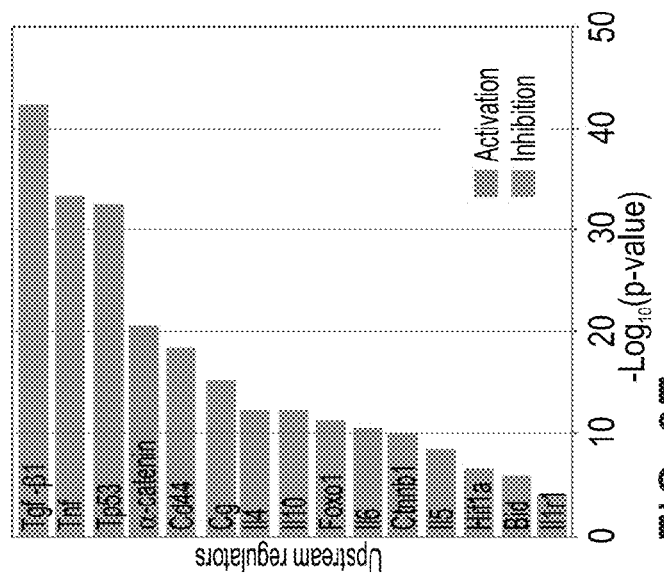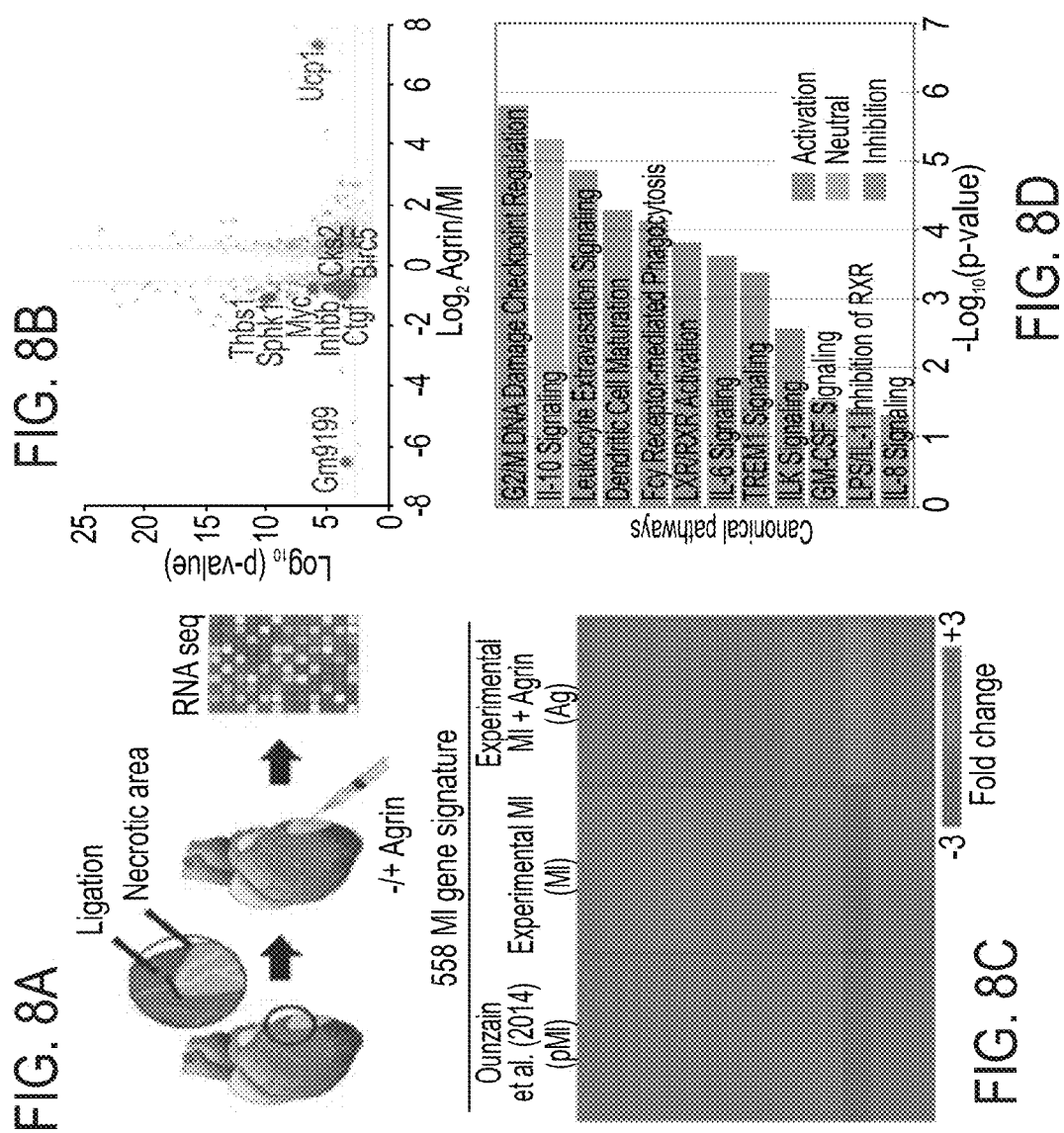
FIG. 8A FIG. 8B FIG. 8C FIG. 8D FIG. 8E

SEQUENCE LISTING

<160> NUMBER OF SEQ ID NOS: 38

<210> SEQ ID NO 1
<211> LENGTH: 4392
<212> TYPE: PRT

<213> ORGANISM: Homo sapiens

<400> SEQUENCE: 1

Met Gly Trp Arg Ala Gly Ala Leu Leu Ala Leu Leu Leu His
1               5                   10                  15

Gly Arg Leu Leu Ala Val Thr His Gly Leu Arg Ala Tyr Asp Gly Leu
            20                  25                  30

Ser Leu Pro Glu Asp Ile Glu Thr Val Thr Ala Ser Gln Met Arg Trp
            35                  40                  45

Thr His Ser Tyr Leu Ser Asp Asp Glu Asp Met Leu Ala Asp Ser Ile
        50                  55                  60

Ser Gly Asp Asp Leu Gly Ser Gly Asp Leu Gly Ser Gly Asp Phe Gln
65                  70                  75                  80

Met Val Tyr Phe Arg Ala Leu Val Asn Phe Thr Arg Ser Ile Glu Tyr
                85                  90                  95

Ser Pro Gln Leu Glu Asp Ala Gly Ser Arg Glu Phe Arg Glu Val Ser
            100                 105                 110

Glu Ala Val Val Asp Thr Leu Glu Ser Glu Tyr Leu Lys Ile Pro Gly
            115                 120                 125

Asp Gln Val Val Ser Val Val Phe Ile Lys Glu Leu Asp Gly Trp Val
130                 135                 140

Phe Val Glu Leu Asp Val Gly Ser Glu Gly Asn Ala Asp Gly Ala Gln
145                 150                 155                 160

Ile Gln Glu Met Leu Leu Arg Val Ile Ser Ser Gly Ser Val Ala Ser
                165                 170                 175

Tyr Val Thr Ser Pro Gln Gly Phe Gln Phe Arg Arg Leu Gly Thr Val
            180                 185                 190

Pro Gln Phe Pro Arg Ala Cys Thr Glu Ala Glu Phe Ala Cys His Ser
        195                 200                 205

Tyr Asn Glu Cys Val Ala Leu Glu Tyr Arg Cys Asp Arg Arg Pro Asp
    210                 215                 220

Cys Arg Asp Met Ser Asp Glu Leu Asn Cys Glu Glu Pro Val Leu Gly
225                 230                 235                 240

Ile Ser Pro Thr Phe Ser Leu Leu Val Glu Thr Thr Ser Leu Pro Pro
                245                 250                 255

Arg Pro Glu Thr Thr Ile Met Arg Gln Pro Pro Val Thr His Ala Pro
            260                 265                 270

Gln Pro Leu Leu Pro Gly Ser Val Arg Pro Leu Pro Cys Gly Pro Gln
        275                 280                 285

Glu Ala Ala Cys Arg Asn Gly His Cys Ile Pro Arg Asp Tyr Leu Cys
    290                 295                 300

Asp Gly Gln Glu Asp Cys Glu Asp Gly Ser Asp Glu Leu Asp Cys Gly
305                 310                 315                 320

Pro Pro Pro Pro Cys Glu Pro Asn Glu Phe Pro Cys Gly Asn Gly His
                325                 330                 335

Cys Ala Leu Lys Leu Trp Arg Cys Asp Gly Asp Phe Asp Cys Glu Asp
            340                 345                 350

Arg Thr Asp Glu Ala Asn Cys Pro Thr Lys Arg Pro Glu Glu Val Cys
        355                 360                 365

Gly Pro Thr Gln Phe Arg Cys Val Ser Thr Asn Met Cys Ile Pro Ala
    370                 375                 380

Ser Phe His Cys Asp Glu Glu Ser Asp Cys Pro Asp Arg Ser Asp Glu
385                 390                 395                 400

-continued

```
Phe Gly Cys Met Pro Pro Gln Val Val Thr Pro Arg Glu Ser Ile
                405                 410                 415
Gln Ala Ser Arg Gly Gln Thr Val Thr Phe Thr Cys Val Ala Ile Gly
            420                 425                 430
Val Pro Thr Pro Ile Ile Asn Trp Arg Leu Asn Trp Gly His Ile Pro
            435                 440                 445
Ser His Pro Arg Val Thr Val Thr Ser Glu Gly Gly Arg Gly Thr Leu
        450                 455                 460
Ile Ile Arg Asp Val Lys Glu Ser Asp Gln Ala Tyr Thr Cys Glu
465                 470                 475                 480
Ala Met Asn Ala Arg Gly Met Val Phe Gly Ile Pro Asp Gly Val Leu
                485                 490                 495
Glu Leu Val Pro Gln Arg Ala Gly Pro Cys Pro Asp Gly His Phe Tyr
            500                 505                 510
Leu Glu His Ser Ala Ala Cys Leu Pro Cys Phe Cys Phe Gly Ile Thr
        515                 520                 525
Ser Val Cys Gln Ser Thr Arg Arg Phe Arg Asp Gln Ile Arg Leu Arg
    530                 535                 540
Phe Asp Gln Pro Asp Asp Phe Lys Gly Val Asn Val Thr Met Pro Ala
545                 550                 555                 560
Gln Pro Gly Thr Pro Pro Leu Ser Ser Thr Gln Leu Gln Ile Asp Pro
                565                 570                 575
Ser Leu His Glu Phe Gln Leu Val Asp Leu Ser Arg Arg Phe Leu Val
            580                 585                 590
His Asp Ser Phe Trp Ala Leu Pro Glu Gln Phe Leu Gly Asn Lys Val
        595                 600                 605
Asp Ser Tyr Gly Gly Ser Leu Arg Tyr Asn Val Arg Tyr Glu Leu Ala
    610                 615                 620
Arg Gly Met Leu Glu Pro Val Gln Arg Pro Asp Val Val Leu Met Gly
625                 630                 635                 640
Ala Gly Tyr Arg Leu Leu Ser Arg Gly His Thr Pro Thr Gln Pro Gly
                645                 650                 655
Ala Leu Asn Gln Arg Gln Val Gln Phe Ser Glu Glu His Trp Val His
            660                 665                 670
Glu Ser Gly Arg Pro Val Gln Arg Ala Glu Leu Leu Gln Val Leu Gln
        675                 680                 685
Ser Leu Glu Ala Val Leu Ile Gln Thr Val Tyr Asn Thr Lys Met Ala
    690                 695                 700
Ser Val Gly Leu Ser Asp Ile Ala Met Asp Thr Thr Val Thr His Ala
705                 710                 715                 720
Thr Ser His Gly Arg Ala His Ser Val Glu Glu Cys Arg Cys Pro Ile
                725                 730                 735
Gly Tyr Ser Gly Leu Ser Cys Glu Ser Cys Asp Ala His Phe Thr Arg
            740                 745                 750
Val Pro Gly Gly Pro Tyr Leu Gly Thr Cys Ser Gly Cys Asn Cys Asn
        755                 760                 765
Gly His Ala Ser Ser Cys Asp Pro Val Tyr Gly His Cys Leu Asn Cys
    770                 775                 780
Gln His Asn Thr Glu Gly Pro Gln Cys Asn Lys Cys Lys Ala Gly Phe
785                 790                 795                 800
Phe Gly Asp Ala Met Lys Ala Thr Ala Thr Ser Cys Arg Pro Cys Pro
                805                 810                 815
Cys Pro Tyr Ile Asp Ala Ser Arg Arg Phe Ser Asp Thr Cys Phe Leu
```

```
                    820                 825                 830
Asp Thr Asp Gly Gln Ala Thr Cys Asp Ala Cys Ala Pro Gly Tyr Thr
                835                 840                 845
Gly Arg Arg Cys Glu Ser Cys Ala Pro Gly Tyr Glu Gly Asn Pro Ile
                850                 855                 860
Gln Pro Gly Gly Lys Cys Arg Pro Val Asn Gln Glu Ile Val Arg Cys
865                 870                 875                 880
Asp Glu Arg Gly Ser Met Gly Thr Ser Gly Glu Ala Cys Arg Cys Lys
                885                 890                 895
Asn Asn Val Val Gly Arg Leu Cys Asn Glu Cys Ala Asp Gly Ser Phe
                900                 905                 910
His Leu Ser Thr Arg Asn Pro Asp Gly Cys Leu Lys Cys Phe Cys Met
915                 920                 925
Gly Val Ser Arg His Cys Thr Ser Ser Ser Trp Ser Arg Ala Gln Leu
            930                 935                 940
His Gly Ala Ser Glu Glu Pro Gly His Phe Ser Leu Thr Asn Ala Ala
945                 950                 955                 960
Ser Thr His Thr Thr Asn Glu Gly Ile Phe Ser Pro Thr Pro Gly Glu
                965                 970                 975
Leu Gly Phe Ser Ser Phe His Arg Leu Leu Ser Gly Pro Tyr Phe Trp
                980                 985                 990
Ser Leu Pro Ser Arg Phe Leu Gly Asp Lys Val Thr Ser Tyr Gly Gly
                995                1000                1005
Glu Leu Arg Phe Thr Val Thr Gln Arg Ser Gln Pro Gly Ser Thr
            1010                1015                1020
Pro Leu His Gly Gln Pro Leu Val Val Leu Gln Gly Asn Asn Ile
            1025                1030                1035
Ile Leu Glu His His Val Ala Gln Glu Pro Ser Pro Gly Gln Pro
            1040                1045                1050
Ser Thr Phe Ile Val Pro Phe Arg Glu Gln Ala Trp Gln Arg Pro
            1055                1060                1065
Asp Gly Gln Pro Ala Thr Arg Glu His Leu Leu Met Ala Leu Ala
            1070                1075                1080
Gly Ile Asp Thr Leu Leu Ile Arg Ala Ser Tyr Ala Gln Gln Pro
            1085                1090                1095
Ala Glu Ser Arg Val Ser Gly Ile Ser Met Asp Val Ala Val Pro
            1100                1105                1110
Glu Glu Thr Gly Gln Asp Pro Ala Leu Glu Val Glu Gln Cys Ser
            1115                1120                1125
Cys Pro Pro Gly Tyr Arg Gly Pro Ser Cys Gln Asp Cys Asp Thr
            1130                1135                1140
Gly Tyr Thr Arg Thr Pro Ser Gly Leu Tyr Leu Gly Thr Cys Glu
            1145                1150                1155
Arg Cys Ser Cys His Gly His Ser Glu Ala Cys Glu Pro Glu Thr
            1160                1165                1170
Gly Ala Cys Gln Gly Cys Gln His His Thr Glu Gly Pro Arg Cys
            1175                1180                1185
Glu Gln Cys Gln Pro Gly Tyr Tyr Gly Asp Ala Gln Arg Gly Thr
            1190                1195                1200
Pro Gln Asp Cys Gln Leu Cys Pro Cys Tyr Gly Asp Pro Ala Ala
            1205                1210                1215
Gly Gln Ala Ala His Thr Cys Phe Leu Asp Thr Asp Gly His Pro
            1220                1225                1230
```

```
Thr Cys Asp Ala Cys Ser Pro Gly His Ser Gly Arg His Cys Glu
1235                 1240                1245

Arg Cys Ala Pro Gly Tyr Tyr Gly Asn Pro Ser Gln Gly Gln Pro
    1250             1255                1260

Cys Gln Arg Asp Ser Gln Val Pro Gly Pro Ile Gly Cys Asn Cys
1265                 1270                1275

Asp Pro Gln Gly Ser Val Ser Ser Gln Cys Asp Ala Ala Gly Gln
1280                 1285                1290

Cys Gln Cys Lys Ala Gln Val Glu Gly Leu Thr Cys Ser His Cys
1295                 1300                1305

Arg Pro His His Phe His Leu Ser Ala Ser Asn Pro Asp Gly Cys
    1310             1315                1320

Leu Pro Cys Phe Cys Met Gly Ile Thr Gln Gln Cys Ala Ser Ser
    1325             1330                1335

Ala Tyr Thr Arg His Leu Ile Ser Thr His Phe Ala Pro Gly Asp
    1340             1345                1350

Phe Gln Gly Phe Ala Leu Val Asn Pro Gln Arg Asn Ser Arg Leu
    1355             1360                1365

Thr Gly Glu Phe Thr Val Glu Pro Val Pro Glu Gly Ala Gln Leu
    1370             1375                1380

Ser Phe Gly Asn Phe Ala Gln Leu Gly His Glu Ser Phe Tyr Trp
    1385             1390                1395

Gln Leu Pro Glu Thr Tyr Gln Gly Asp Lys Val Ala Ala Tyr Gly
    1400             1405                1410

Gly Lys Leu Arg Tyr Thr Leu Ser Tyr Thr Ala Gly Pro Gln Gly
    1415             1420                1425

Ser Pro Leu Ser Asp Pro Asp Val Gln Ile Thr Gly Asn Asn Ile
    1430             1435                1440

Met Leu Val Ala Ser Gln Pro Ala Leu Gln Gly Pro Glu Arg Arg
    1445             1450                1455

Ser Tyr Glu Ile Met Phe Arg Glu Glu Phe Trp Arg Arg Pro Asp
    1460             1465                1470

Gly Gln Pro Ala Thr Arg Glu His Leu Leu Met Ala Leu Ala Asp
    1475             1480                1485

Leu Asp Glu Leu Leu Ile Arg Ala Thr Phe Ser Ser Val Pro Leu
    1490             1495                1500

Ala Ala Ser Ile Ser Ala Val Ser Leu Glu Val Ala Gln Pro Gly
    1505             1510                1515

Pro Ser Asn Arg Pro Arg Ala Leu Glu Val Glu Glu Cys Arg Cys
    1520             1525                1530

Pro Pro Gly Tyr Ile Gly Leu Ser Cys Gln Asp Cys Ala Pro Gly
    1535             1540                1545

Tyr Thr Arg Thr Gly Ser Gly Leu Tyr Leu Gly His Cys Glu Leu
    1550             1555                1560

Cys Glu Cys Asn Gly His Ser Asp Leu Cys His Pro Glu Thr Gly
    1565             1570                1575

Ala Cys Ser Gln Cys Gln His Asn Ala Ala Gly Glu Phe Cys Glu
    1580             1585                1590

Leu Cys Ala Pro Gly Tyr Tyr Gly Asp Ala Thr Ala Gly Thr Pro
    1595             1600                1605

Glu Asp Cys Gln Pro Cys Ala Cys Pro Leu Thr Asn Pro Glu Asn
    1610             1615                1620
```

```
Met Phe Ser Arg Thr Cys Glu Ser Leu Gly Ala Gly Gly Tyr Arg
1625                1630                1635

Cys Thr Ala Cys Glu Pro Gly Tyr Thr Gly Gln Tyr Cys Glu Gln
1640                1645                1650

Cys Gly Pro Gly Tyr Val Gly Asn Pro Ser Val Gln Gly Gly Gln
1655                1660                1665

Cys Leu Pro Glu Thr Asn Gln Ala Pro Leu Val Val Glu Val His
1670                1675                1680

Pro Ala Arg Ser Ile Val Pro Gln Gly Gly Ser His Ser Leu Arg
1685                1690                1695

Cys Gln Val Ser Gly Ser Pro Pro His Tyr Phe Tyr Trp Ser Arg
1700                1705                1710

Glu Asp Gly Arg Pro Val Pro Ser Gly Thr Gln Gln Arg His Gln
1715                1720                1725

Gly Ser Glu Leu His Phe Pro Ser Val Gln Pro Ser Asp Ala Gly
1730                1735                1740

Val Tyr Ile Cys Thr Cys Arg Asn Leu His Gln Ser Asn Thr Ser
1745                1750                1755

Arg Ala Glu Leu Leu Val Thr Glu Ala Pro Ser Lys Pro Ile Thr
1760                1765                1770

Val Thr Val Glu Glu Gln Arg Ser Gln Ser Val Arg Pro Gly Ala
1775                1780                1785

Asp Val Thr Phe Ile Cys Thr Ala Lys Ser Lys Ser Pro Ala Tyr
1790                1795                1800

Thr Leu Val Trp Thr Arg Leu His Asn Gly Lys Leu Pro Thr Arg
1805                1810                1815

Ala Met Asp Phe Asn Gly Ile Leu Thr Ile Arg Asn Val Gln Leu
1820                1825                1830

Ser Asp Ala Gly Thr Tyr Val Cys Thr Gly Ser Asn Met Phe Ala
1835                1840                1845

Met Asp Gln Gly Thr Ala Thr Leu His Val Gln Ala Ser Gly Thr
1850                1855                1860

Leu Ser Ala Pro Val Val Ser Ile His Pro Pro Gln Leu Thr Val
1865                1870                1875

Gln Pro Gly Gln Leu Ala Glu Phe Arg Cys Ser Ala Thr Gly Ser
1880                1885                1890

Pro Thr Pro Thr Leu Glu Trp Thr Gly Gly Pro Gly Gly Gln Leu
1895                1900                1905

Pro Ala Lys Ala Gln Ile His Gly Gly Ile Leu Arg Leu Pro Ala
1910                1915                1920

Val Glu Pro Thr Asp Gln Ala Gln Tyr Leu Cys Arg Ala His Ser
1925                1930                1935

Ser Ala Gly Gln Gln Val Ala Arg Ala Val Leu His Val His Gly
1940                1945                1950

Gly Gly Gly Pro Arg Val Gln Val Ser Pro Glu Arg Thr Gln Val
1955                1960                1965

His Ala Gly Arg Thr Val Arg Leu Tyr Cys Arg Ala Ala Gly Val
1970                1975                1980

Pro Ser Ala Thr Ile Thr Trp Arg Lys Glu Gly Gly Ser Leu Pro
1985                1990                1995

Pro Gln Ala Arg Ser Glu Arg Thr Asp Ile Ala Thr Leu Leu Ile
2000                2005                2010

Pro Ala Ile Thr Thr Ala Asp Ala Gly Phe Tyr Leu Cys Val Ala
```

-continued

```
                2015                2020                2025
Thr Ser Pro Ala Gly Thr Ala Gln Ala Arg Ile Gln Val Val Val
    2030                2035                2040
Leu Ser Ala Ser Asp Ala Ser Pro Pro Val Lys Ile Glu Ser
    2045                2050                2055
Ser Ser Pro Ser Val Thr Glu Gly Gln Thr Leu Asp Leu Asn Cys
    2060                2065                2070
Val Val Ala Gly Ser Ala His Ala Gln Val Thr Trp Tyr Arg Arg
    2075                2080                2085
Gly Gly Ser Leu Pro Pro His Thr Gln Val His Gly Ser Arg Leu
    2090                2095                2100
Arg Leu Pro Gln Val Ser Pro Ala Asp Ser Gly Glu Tyr Val Cys
    2105                2110                2115
Arg Val Glu Asn Gly Ser Gly Pro Lys Glu Ala Ser Ile Thr Val
    2120                2125                2130
Ser Val Leu His Gly Thr His Ser Gly Pro Ser Tyr Thr Pro Val
    2135                2140                2145
Pro Gly Ser Thr Arg Pro Ile Arg Ile Glu Pro Ser Ser Ser His
    2150                2155                2160
Val Ala Glu Gly Gln Thr Leu Asp Leu Asn Cys Val Val Pro Gly
    2165                2170                2175
Gln Ala His Ala Gln Val Thr Trp His Lys Arg Gly Gly Ser Leu
    2180                2185                2190
Pro Ala Arg His Gln Thr His Gly Ser Leu Leu Arg Leu His Gln
    2195                2200                2205
Val Thr Pro Ala Asp Ser Gly Glu Tyr Val Cys His Val Val Gly
    2210                2215                2220
Thr Ser Gly Pro Leu Glu Ala Ser Val Leu Val Thr Ile Glu Ala
    2225                2230                2235
Ser Val Ile Pro Gly Pro Ile Pro Pro Val Arg Ile Glu Ser Ser
    2240                2245                2250
Ser Ser Thr Val Ala Glu Gly Gln Thr Leu Asp Leu Ser Cys Val
    2255                2260                2265
Val Ala Gly Gln Ala His Ala Gln Val Thr Trp Tyr Lys Arg Gly
    2270                2275                2280
Gly Ser Leu Pro Ala Arg His Gln Val Arg Gly Ser Arg Leu Tyr
    2285                2290                2295
Ile Phe Gln Ala Ser Pro Ala Asp Ala Gly Gln Tyr Val Cys Arg
    2300                2305                2310
Ala Ser Asn Gly Met Glu Ala Ser Ile Thr Val Thr Val Thr Gly
    2315                2320                2325
Thr Gln Gly Ala Asn Leu Ala Tyr Pro Ala Gly Ser Thr Gln Pro
    2330                2335                2340
Ile Arg Ile Glu Pro Ser Ser Ser Gln Val Ala Glu Gly Gln Thr
    2345                2350                2355
Leu Asp Leu Asn Cys Val Val Pro Gly Gln Ser His Ala Gln Val
    2360                2365                2370
Thr Trp His Lys Arg Gly Gly Ser Leu Pro Val Arg His Gln Thr
    2375                2380                2385
His Gly Ser Leu Leu Arg Leu Tyr Gln Ala Ser Pro Ala Asp Ser
    2390                2395                2400
Gly Glu Tyr Val Cys Arg Val Leu Gly Ser Ser Val Pro Leu Glu
    2405                2410                2415
```

-continued

```
Ala Ser Val Leu Val Thr Ile Glu Pro Ala Gly Ser Val Pro Ala
    2420                2425                2430

Leu Gly Val Thr Pro Thr Val Arg Ile Glu Ser Ser Ser Ser Gln
    2435                2440                2445

Val Ala Glu Gly Gln Thr Leu Asp Leu Asn Cys Leu Val Ala Gly
    2450                2455                2460

Gln Ala His Ala Gln Val Thr Trp His Lys Arg Gly Gly Ser Leu
    2465                2470                2475

Pro Ala Arg His Gln Val His Gly Ser Arg Leu Arg Leu Leu Gln
    2480                2485                2490

Val Thr Pro Ala Asp Ser Gly Glu Tyr Val Cys Arg Val Val Gly
    2495                2500                2505

Ser Ser Gly Thr Gln Glu Ala Ser Val Leu Val Thr Ile Gln Gln
    2510                2515                2520

Arg Leu Ser Gly Ser His Ser Gln Gly Val Ala Tyr Pro Val Arg
    2525                2530                2535

Ile Glu Ser Ser Ser Ala Ser Leu Ala Asn Gly His Thr Leu Asp
    2540                2545                2550

Leu Asn Cys Leu Val Ala Ser Gln Ala Pro His Thr Ile Thr Trp
    2555                2560                2565

Tyr Lys Arg Gly Gly Ser Leu Pro Ser Arg His Gln Ile Val Gly
    2570                2575                2580

Ser Arg Leu Arg Ile Pro Gln Val Thr Pro Ala Asp Ser Gly Glu
    2585                2590                2595

Tyr Val Cys His Val Ser Asn Gly Ala Gly Ser Arg Glu Thr Ser
    2600                2605                2610

Leu Ile Val Thr Ile Gln Gly Ser Gly Ser Ser His Val Pro Ser
    2615                2620                2625

Val Ser Pro Pro Ile Arg Ile Glu Ser Ser Ser Pro Thr Val Val
    2630                2635                2640

Glu Gly Gln Thr Leu Asp Leu Asn Cys Val Val Ala Arg Gln Pro
    2645                2650                2655

Gln Ala Ile Ile Thr Trp Tyr Lys Arg Gly Gly Ser Leu Pro Ser
    2660                2665                2670

Arg His Gln Thr His Gly Ser His Leu Arg Leu His Gln Met Ser
    2675                2680                2685

Val Ala Asp Ser Gly Glu Tyr Val Cys Arg Ala Asn Asn Asn Ile
    2690                2695                2700

Asp Ala Leu Glu Ala Ser Ile Val Ile Ser Val Ser Pro Ser Ala
    2705                2710                2715

Gly Ser Pro Ser Ala Pro Gly Ser Ser Met Pro Ile Arg Ile Glu
    2720                2725                2730

Ser Ser Ser Ser His Val Ala Glu Gly Glu Thr Leu Asp Leu Asn
    2735                2740                2745

Cys Val Val Pro Gly Gln Ala His Ala Gln Val Thr Trp His Lys
    2750                2755                2760

Arg Gly Gly Ser Leu Pro Ser His His Gln Thr Arg Gly Ser Arg
    2765                2770                2775

Leu Arg Leu His His Val Ser Pro Ala Asp Ser Gly Glu Tyr Val
    2780                2785                2790

Cys Arg Val Met Gly Ser Ser Gly Pro Leu Glu Ala Ser Val Leu
    2795                2800                2805
```

```
Val Thr Ile Glu Ala Ser Gly Ser Ser Ala Val His Val Pro Ala
2810                2815                2820

Pro Gly Gly Ala Pro Pro Ile Arg Ile Glu Pro Ser Ser Ser Arg
2825                2830                2835

Val Ala Glu Gly Gln Thr Leu Asp Leu Lys Cys Val Val Pro Gly
2840                2845                2850

Gln Ala His Ala Gln Val Thr Trp His Lys Arg Gly Gly Asn Leu
2855                2860                2865

Pro Ala Arg His Gln Val His Gly Pro Leu Leu Arg Leu Asn Gln
2870                2875                2880

Val Ser Pro Ala Asp Ser Gly Glu Tyr Ser Cys Gln Val Thr Gly
2885                2890                2895

Ser Ser Gly Thr Leu Glu Ala Ser Val Leu Val Thr Ile Glu Pro
2900                2905                2910

Ser Ser Pro Gly Pro Ile Pro Ala Pro Gly Leu Ala Gln Pro Ile
2915                2920                2925

Tyr Ile Glu Ala Ser Ser Ser His Val Thr Glu Gly Gln Thr Leu
2930                2935                2940

Asp Leu Asn Cys Val Val Pro Gly Gln Ala His Ala Gln Val Thr
2945                2950                2955

Trp Tyr Lys Arg Gly Gly Ser Leu Pro Ala Arg His Gln Thr His
2960                2965                2970

Gly Ser Gln Leu Arg Leu His Leu Val Ser Pro Ala Asp Ser Gly
2975                2980                2985

Glu Tyr Val Cys Arg Ala Ala Ser Gly Pro Gly Pro Glu Gln Glu
2990                2995                3000

Ala Ser Phe Thr Val Thr Val Pro Pro Ser Glu Gly Ser Ser Tyr
3005                3010                3015

Arg Leu Arg Ser Pro Val Ile Ser Ile Asp Pro Pro Ser Ser Thr
3020                3025                3030

Val Gln Gln Gly Gln Asp Ala Ser Phe Lys Cys Leu Ile His Asp
3035                3040                3045

Gly Ala Ala Pro Ile Ser Leu Glu Trp Lys Thr Arg Asn Gln Glu
3050                3055                3060

Leu Glu Asp Asn Val His Ile Ser Pro Asn Gly Ser Ile Ile Thr
3065                3070                3075

Ile Val Gly Thr Arg Pro Ser Asn His Gly Thr Tyr Arg Cys Val
3080                3085                3090

Ala Ser Asn Ala Tyr Gly Val Ala Gln Ser Val Val Asn Leu Ser
3095                3100                3105

Val His Gly Pro Pro Thr Val Ser Val Leu Pro Glu Gly Pro Val
3110                3115                3120

Trp Val Lys Val Gly Lys Ala Val Thr Leu Glu Cys Val Ser Ala
3125                3130                3135

Gly Glu Pro Arg Ser Ser Ala Arg Trp Thr Arg Ile Ser Ser Thr
3140                3145                3150

Pro Ala Lys Leu Glu Gln Arg Thr Tyr Gly Leu Met Asp Ser His
3155                3160                3165

Ala Val Leu Gln Ile Ser Ser Ala Lys Pro Ser Asp Ala Gly Thr
3170                3175                3180

Tyr Val Cys Leu Ala Gln Asn Ala Leu Gly Thr Ala Gln Lys Gln
3185                3190                3195

Val Glu Val Ile Val Asp Thr Gly Ala Met Ala Pro Gly Ala Pro
```

-continued

```
                3200                3205                3210
Gln Val Gln Ala Glu Glu Ala Glu Leu Thr Val Glu Ala Gly His
    3215                3220                3225
Thr Ala Thr Leu Arg Cys Ser Ala Thr Gly Ser Pro Ala Pro Thr
    3230                3235                3240
Ile His Trp Ser Lys Leu Arg Ser Pro Leu Pro Trp Gln His Arg
    3245                3250                3255
Leu Glu Gly Asp Thr Leu Ile Ile Pro Arg Val Ala Gln Gln Asp
    3260                3265                3270
Ser Gly Gln Tyr Ile Cys Asn Ala Thr Ser Pro Ala Gly His Ala
    3275                3280                3285
Glu Ala Thr Ile Ile Leu His Val Glu Ser Pro Tyr Ala Thr
    3290                3295                3300
Thr Val Pro Glu His Ala Ser Val Gln Ala Gly Glu Thr Val Gln
    3305                3310                3315
Leu Gln Cys Leu Ala His Gly Thr Pro Pro Leu Thr Phe Gln Trp
    3320                3325                3330
Ser Arg Val Gly Ser Ser Leu Pro Gly Arg Ala Thr Ala Arg Asn
    3335                3340                3345
Glu Leu Leu His Phe Glu Arg Ala Ala Pro Glu Asp Ser Gly Arg
    3350                3355                3360
Tyr Arg Cys Arg Val Thr Asn Lys Val Gly Ser Ala Glu Ala Phe
    3365                3370                3375
Ala Gln Leu Leu Val Gln Gly Pro Pro Gly Ser Leu Pro Ala Thr
    3380                3385                3390
Ser Ile Pro Ala Gly Ser Thr Pro Thr Val Gln Val Thr Pro Gln
    3395                3400                3405
Leu Glu Thr Lys Ser Ile Gly Ala Ser Val Glu Phe His Cys Ala
    3410                3415                3420
Val Pro Ser Asp Arg Gly Thr Gln Leu Arg Trp Phe Lys Glu Gly
    3425                3430                3435
Gly Gln Leu Pro Pro Gly His Ser Val Gln Asp Gly Val Leu Arg
    3440                3445                3450
Ile Gln Asn Leu Asp Gln Ser Cys Gln Gly Thr Tyr Ile Cys Gln
    3455                3460                3465
Ala His Gly Pro Trp Gly Lys Ala Gln Ala Ser Ala Gln Leu Val
    3470                3475                3480
Ile Gln Ala Leu Pro Ser Val Leu Ile Asn Ile Arg Thr Ser Val
    3485                3490                3495
Gln Thr Val Val Val Gly His Ala Val Glu Phe Glu Cys Leu Ala
    3500                3505                3510
Leu Gly Asp Pro Lys Pro Gln Val Thr Trp Ser Lys Val Gly Gly
    3515                3520                3525
His Leu Arg Pro Gly Ile Val Gln Ser Gly Gly Val Val Arg Ile
    3530                3535                3540
Ala His Val Glu Leu Ala Asp Ala Gly Gln Tyr Arg Cys Thr Ala
    3545                3550                3555
Thr Asn Ala Ala Gly Thr Thr Gln Ser His Val Leu Leu Leu Val
    3560                3565                3570
Gln Ala Leu Pro Gln Ile Ser Met Pro Gln Glu Val Arg Val Pro
    3575                3580                3585
Ala Gly Ser Ala Ala Val Phe Pro Cys Ile Ala Ser Gly Tyr Pro
    3590                3595                3600
```

```
Thr Pro Asp Ile Ser Trp Ser Lys Leu Asp Gly Ser Leu Pro Pro
3605                3610                3615

Asp Ser Arg Leu Glu Asn Asn Met Leu Met Leu Pro Ser Val Arg
3620                3625                3630

Pro Gln Asp Ala Gly Thr Tyr Val Cys Thr Ala Thr Asn Arg Gln
3635                3640                3645

Gly Lys Val Lys Ala Phe Ala His Leu Gln Val Pro Glu Arg Val
3650                3655                3660

Val Pro Tyr Phe Thr Gln Thr Pro Tyr Ser Phe Leu Pro Leu Pro
3665                3670                3675

Thr Ile Lys Asp Ala Tyr Arg Lys Phe Glu Ile Lys Ile Thr Phe
3680                3685                3690

Arg Pro Asp Ser Ala Asp Gly Met Leu Leu Tyr Asn Gly Gln Lys
3695                3700                3705

Arg Val Pro Gly Ser Pro Thr Asn Leu Ala Asn Arg Gln Pro Asp
3710                3715                3720

Phe Ile Ser Phe Gly Leu Val Gly Gly Arg Pro Glu Phe Arg Phe
3725                3730                3735

Asp Ala Gly Ser Gly Met Ala Thr Ile Arg His Pro Thr Pro Leu
3740                3745                3750

Ala Leu Gly His Phe His Thr Val Thr Leu Leu Arg Ser Leu Thr
3755                3760                3765

Gln Gly Ser Leu Ile Val Gly Asp Leu Ala Pro Val Asn Gly Thr
3770                3775                3780

Ser Gln Gly Lys Phe Gln Gly Leu Asp Leu Asn Glu Glu Leu Tyr
3785                3790                3795

Leu Gly Gly Tyr Pro Asp Tyr Gly Ala Ile Pro Lys Ala Gly Leu
3800                3805                3810

Ser Ser Gly Phe Ile Gly Cys Val Arg Glu Leu Arg Ile Gln Gly
3815                3820                3825

Glu Glu Ile Val Phe His Asp Leu Asn Leu Thr Ala His Gly Ile
3830                3835                3840

Ser His Cys Pro Thr Cys Arg Asp Arg Pro Cys Gln Asn Gly Gly
3845                3850                3855

Gln Cys His Asp Ser Glu Ser Ser Ser Tyr Val Cys Val Cys Pro
3860                3865                3870

Ala Gly Phe Thr Gly Ser Arg Cys Glu His Ser Gln Ala Leu His
3875                3880                3885

Cys His Pro Glu Ala Cys Gly Pro Asp Ala Thr Cys Val Asn Arg
3890                3895                3900

Pro Asp Gly Arg Gly Tyr Thr Cys Arg Cys His Leu Gly Arg Ser
3905                3910                3915

Gly Leu Arg Cys Glu Glu Gly Val Thr Val Thr Thr Pro Ser Leu
3920                3925                3930

Ser Gly Ala Gly Ser Tyr Leu Ala Leu Pro Ala Leu Thr Asn Thr
3935                3940                3945

His His Glu Leu Arg Leu Asp Val Glu Phe Lys Pro Leu Ala Pro
3950                3955                3960

Asp Gly Val Leu Leu Phe Ser Gly Gly Lys Ser Gly Pro Val Glu
3965                3970                3975

Asp Phe Val Ser Leu Ala Met Val Gly Gly His Leu Glu Phe Arg
3980                3985                3990
```

```
Tyr Glu Leu Gly Ser Gly Leu Ala Val Leu Arg Ser Ala Glu Pro
    3995                4000                4005
Leu Ala Leu Gly Arg Trp His Arg Val Ser Ala Glu Arg Leu Asn
    4010                4015                4020
Lys Asp Gly Ser Leu Arg Val Asn Gly Gly Arg Pro Val Leu Arg
    4025                4030                4035
Ser Ser Pro Gly Lys Ser Gln Gly Leu Asn Leu His Thr Leu Leu
    4040                4045                4050
Tyr Leu Gly Gly Val Glu Pro Ser Val Pro Leu Ser Pro Ala Thr
    4055                4060                4065
Asn Met Ser Ala His Phe Arg Gly Cys Val Gly Glu Val Ser Val
    4070                4075                4080
Asn Gly Lys Arg Leu Asp Leu Thr Tyr Ser Phe Leu Gly Ser Gln
    4085                4090                4095
Gly Ile Gly Gln Cys Tyr Asp Ser Ser Pro Cys Glu Arg Gln Pro
    4100                4105                4110
Cys Gln His Gly Ala Thr Cys Met Pro Ala Gly Glu Tyr Glu Phe
    4115                4120                4125
Gln Cys Leu Cys Arg Asp Gly Phe Lys Gly Asp Leu Cys Glu His
    4130                4135                4140
Glu Glu Asn Pro Cys Gln Leu Arg Glu Pro Cys Leu His Gly Gly
    4145                4150                4155
Thr Cys Gln Gly Thr Arg Cys Leu Cys Leu Pro Gly Phe Ser Gly
    4160                4165                4170
Pro Arg Cys Gln Gln Gly Ser Gly His Gly Ile Ala Glu Ser Asp
    4175                4180                4185
Trp His Leu Glu Gly Ser Gly Gly Asn Asp Ala Pro Gly Gln Tyr
    4190                4195                4200
Gly Ala Tyr Phe His Asp Asp Gly Phe Leu Ala Phe Pro Gly His
    4205                4210                4215
Val Phe Ser Arg Ser Leu Pro Glu Val Pro Glu Thr Ile Glu Leu
    4220                4225                4230
Glu Val Arg Thr Ser Thr Ala Ser Gly Leu Leu Leu Trp Gln Gly
    4235                4240                4245
Val Glu Val Gly Glu Ala Gly Gln Gly Lys Asp Phe Ile Ser Leu
    4250                4255                4260
Gly Leu Gln Asp Gly His Leu Val Phe Arg Tyr Gln Leu Gly Ser
    4265                4270                4275
Gly Glu Ala Arg Leu Val Ser Glu Asp Pro Ile Asn Asp Gly Glu
    4280                4285                4290
Trp His Arg Val Thr Ala Leu Arg Glu Gly Arg Arg Gly Ser Ile
    4295                4300                4305
Gln Val Asp Gly Glu Glu Leu Val Ser Gly Arg Ser Pro Gly Pro
    4310                4315                4320
Asn Val Ala Val Asn Ala Lys Gly Ser Val Tyr Ile Gly Gly Ala
    4325                4330                4335
Pro Asp Val Ala Thr Leu Thr Gly Gly Arg Phe Ser Ser Gly Ile
    4340                4345                4350
Thr Gly Cys Val Lys Asn Leu Val Leu His Ser Ala Arg Pro Gly
    4355                4360                4365
Ala Pro Pro Pro Gln Pro Leu Asp Leu Gln His Arg Ala Gln Ala
    4370                4375                4380
Gly Ala Asn Thr Arg Pro Cys Pro Ser
```

```
                              4385                    4390

<210> SEQ ID NO 2
<211> LENGTH: 4391
<212> TYPE: PRT
<213> ORGANISM: Homo sapiens

<400> SEQUENCE: 2

Met Gly Trp Arg Ala Gly Ala Leu Leu Ala Leu Leu Leu His
1               5                   10                  15

Gly Arg Leu Leu Ala Val Thr His Gly Leu Arg Ala Tyr Asp Gly Leu
            20                  25                  30

Ser Leu Pro Glu Asp Ile Glu Thr Val Thr Ala Ser Gln Met Arg Trp
        35                  40                  45

Thr His Ser Tyr Leu Ser Asp Asp Glu Asp Met Leu Ala Asp Ser Ile
    50                  55                  60

Ser Gly Asp Asp Leu Gly Ser Gly Asp Leu Gly Ser Gly Asp Phe Gln
65                  70                  75                  80

Met Val Tyr Phe Arg Ala Leu Val Asn Phe Thr Arg Ser Ile Glu Tyr
                85                  90                  95

Ser Pro Gln Leu Glu Asp Ala Gly Ser Arg Glu Phe Arg Glu Val Ser
            100                 105                 110

Glu Ala Val Val Asp Thr Leu Glu Ser Glu Tyr Leu Lys Ile Pro Gly
        115                 120                 125

Asp Gln Val Val Ser Val Val Phe Ile Lys Glu Leu Asp Gly Trp Val
130                 135                 140

Phe Val Glu Leu Asp Val Gly Ser Glu Gly Asn Ala Asp Gly Ala Gln
145                 150                 155                 160

Ile Gln Glu Met Leu Leu Arg Val Ile Ser Ser Gly Ser Val Ala Ser
                165                 170                 175

Tyr Val Thr Ser Pro Gln Gly Phe Gln Phe Arg Arg Leu Gly Thr Val
            180                 185                 190

Pro Gln Phe Pro Arg Ala Cys Thr Glu Ala Glu Phe Ala Cys His Ser
        195                 200                 205

Tyr Asn Glu Cys Val Ala Leu Glu Tyr Arg Cys Asp Arg Arg Pro Asp
    210                 215                 220

Cys Arg Asp Met Ser Asp Glu Leu Asn Cys Glu Glu Pro Val Leu Gly
225                 230                 235                 240

Ile Ser Pro Thr Phe Ser Leu Leu Val Glu Thr Thr Ser Leu Pro Pro
                245                 250                 255

Arg Pro Glu Thr Thr Ile Met Arg Gln Pro Pro Val Thr His Ala Pro
            260                 265                 270

Gln Pro Leu Leu Pro Gly Ser Val Arg Pro Leu Pro Cys Gly Pro Gln
        275                 280                 285

Glu Ala Ala Cys Arg Asn Gly His Cys Ile Pro Arg Asp Tyr Leu Cys
    290                 295                 300

Asp Gly Gln Glu Asp Cys Glu Asp Gly Ser Asp Glu Leu Asp Cys Gly
305                 310                 315                 320

Pro Pro Pro Pro Cys Glu Pro Asn Glu Phe Pro Cys Gly Asn Gly His
                325                 330                 335

Cys Ala Leu Lys Leu Trp Arg Cys Asp Gly Asp Phe Asp Cys Glu Asp
            340                 345                 350

Arg Thr Asp Glu Ala Asn Cys Pro Thr Lys Arg Pro Glu Glu Val Cys
        355                 360                 365
```

-continued

Gly Pro Thr Gln Phe Arg Cys Val Ser Thr Asn Met Cys Ile Pro Ala
370             375                 380

Ser Phe His Cys Asp Glu Glu Ser Asp Cys Pro Asp Arg Ser Asp Glu
385             390                 395                 400

Phe Gly Cys Met Pro Pro Gln Val Val Thr Pro Pro Arg Glu Ser Ile
            405                 410                 415

Gln Ala Ser Arg Gly Gln Thr Val Thr Phe Thr Cys Val Ala Ile Gly
            420                 425                 430

Val Pro Thr Pro Ile Ile Asn Trp Arg Leu Asn Trp Gly His Ile Pro
            435                 440                 445

Ser His Pro Arg Val Thr Val Thr Ser Glu Gly Gly Arg Gly Thr Leu
450                 455                 460

Ile Ile Arg Asp Val Lys Glu Ser Asp Gln Gly Ala Tyr Thr Cys Glu
465                 470                 475                 480

Ala Met Asn Ala Arg Gly Met Val Phe Gly Ile Pro Asp Gly Val Leu
                485                 490                 495

Glu Leu Val Pro Gln Arg Gly Pro Cys Pro Asp Gly His Phe Tyr Leu
            500                 505                 510

Glu His Ser Ala Ala Cys Leu Pro Cys Phe Cys Phe Gly Ile Thr Ser
            515                 520                 525

Val Cys Gln Ser Thr Arg Arg Phe Arg Asp Gln Ile Arg Leu Arg Phe
530                 535                 540

Asp Gln Pro Asp Asp Phe Lys Gly Val Asn Val Thr Met Pro Ala Gln
545                 550                 555                 560

Pro Gly Thr Pro Pro Leu Ser Ser Thr Gln Leu Gln Ile Asp Pro Ser
                565                 570                 575

Leu His Glu Phe Gln Leu Val Asp Leu Ser Arg Arg Phe Leu Val His
            580                 585                 590

Asp Ser Phe Trp Ala Leu Pro Glu Gln Phe Leu Gly Asn Lys Val Asp
            595                 600                 605

Ser Tyr Gly Gly Ser Leu Arg Tyr Asn Val Arg Tyr Glu Leu Ala Arg
610                 615                 620

Gly Met Leu Glu Pro Val Gln Arg Pro Asp Val Val Leu Met Gly Ala
625                 630                 635                 640

Gly Tyr Arg Leu Leu Ser Arg Gly His Thr Pro Thr Gln Pro Gly Ala
                645                 650                 655

Leu Asn Gln Arg Gln Val Gln Phe Ser Glu Glu His Trp Val His Glu
            660                 665                 670

Ser Gly Arg Pro Val Gln Arg Ala Glu Leu Leu Gln Val Leu Gln Ser
            675                 680                 685

Leu Glu Ala Val Leu Ile Gln Thr Val Tyr Asn Thr Lys Met Ala Ser
690                 695                 700

Val Gly Leu Ser Asp Ile Ala Met Asp Thr Thr Val Thr His Ala Thr
705                 710                 715                 720

Ser His Gly Arg Ala His Ser Val Glu Glu Cys Arg Cys Pro Ile Gly
                725                 730                 735

Tyr Ser Gly Leu Ser Cys Glu Ser Cys Asp Ala His Phe Thr Arg Val
            740                 745                 750

Pro Gly Gly Pro Tyr Leu Gly Thr Cys Ser Gly Cys Asn Cys Asn Gly
            755                 760                 765

His Ala Ser Ser Cys Asp Pro Val Tyr Gly His Cys Leu Asn Cys Gln
770                 775                 780

His Asn Thr Glu Gly Pro Gln Cys Asn Lys Cys Lys Ala Gly Phe Phe

-continued

```
            785                 790                 795                 800
Gly Asp Ala Met Lys Ala Thr Ala Thr Ser Cys Arg Pro Cys Pro Cys
                    805                 810                 815

Pro Tyr Ile Asp Ala Ser Arg Arg Phe Ser Asp Thr Cys Phe Leu Asp
                820                 825                 830

Thr Asp Gly Gln Ala Thr Cys Asp Ala Cys Ala Pro Gly Tyr Thr Gly
                835                 840                 845

Arg Arg Cys Glu Ser Cys Ala Pro Gly Tyr Glu Gly Asn Pro Ile Gln
            850                 855                 860

Pro Gly Gly Lys Cys Arg Pro Val Asn Gln Glu Ile Val Arg Cys Asp
865                 870                 875                 880

Glu Arg Gly Ser Met Gly Thr Ser Gly Glu Ala Cys Arg Cys Lys Asn
                    885                 890                 895

Asn Val Val Gly Arg Leu Cys Asn Glu Cys Ala Asp Gly Ser Phe His
                900                 905                 910

Leu Ser Thr Arg Asn Pro Asp Gly Cys Leu Lys Cys Phe Cys Met Gly
                915                 920                 925

Val Ser Arg His Cys Thr Ser Ser Trp Ser Arg Ala Gln Leu His
                930                 935                 940

Gly Ala Ser Glu Glu Pro Gly His Phe Ser Leu Thr Asn Ala Ala Ser
945                 950                 955                 960

Thr His Thr Thr Asn Glu Gly Ile Phe Ser Pro Thr Pro Gly Glu Leu
                965                 970                 975

Gly Phe Ser Ser Phe His Arg Leu Leu Ser Gly Pro Tyr Phe Trp Ser
                980                 985                 990

Leu Pro Ser Arg Phe Leu Gly Asp  Lys Val Thr Ser Tyr  Gly Gly Glu
            995                 1000                 1005

Leu Arg  Phe Thr Val Thr Gln  Arg Ser Gln Pro Gly  Ser Thr Pro
    1010                 1015                 1020

Leu His  Gly Gln Pro Leu Val  Val Leu Gln Gly Asn  Asn Ile Ile
    1025                 1030                 1035

Leu Glu  His His Val Ala Gln  Glu Pro Ser Pro Gly  Gln Pro Ser
    1040                 1045                 1050

Thr Phe  Ile Val Pro Phe Arg  Glu Gln Ala Trp Gln  Arg Pro Asp
    1055                 1060                 1065

Gly Gln  Pro Ala Thr Arg Glu  His Leu Leu Met Ala  Leu Ala Gly
    1070                 1075                 1080

Ile Asp  Thr Leu Leu Ile Arg  Ala Ser Tyr Ala Gln  Gln Pro Ala
    1085                 1090                 1095

Glu Ser  Arg Val Ser Gly Ile  Ser Met Asp Val Ala  Val Pro Glu
    1100                 1105                 1110

Glu Thr  Gly Gln Asp Pro Ala  Leu Glu Val Glu Gln  Cys Ser Cys
    1115                 1120                 1125

Pro Pro  Gly Tyr Arg Gly Pro  Ser Cys Gln Asp Cys  Asp Thr Gly
    1130                 1135                 1140

Tyr Thr  Arg Thr Pro Ser Gly  Leu Tyr Leu Gly Thr  Cys Glu Arg
    1145                 1150                 1155

Cys Ser  Cys His Gly His Ser  Glu Ala Cys Glu Pro  Glu Thr Gly
    1160                 1165                 1170

Ala Cys  Gln Gly Cys Gln His  His Thr Glu Gly Pro  Arg Cys Glu
    1175                 1180                 1185

Gln Cys  Gln Pro Gly Tyr Tyr  Gly Asp Ala Gln Arg  Gly Thr Pro
    1190                 1195                 1200
```

```
Gln Asp Cys Gln Leu Cys Pro Cys Tyr Gly Asp Pro Ala Ala Gly
1205                1210                1215

Gln Ala Ala His Thr Cys Phe Leu Asp Thr Asp Gly His Pro Thr
1220                1225                1230

Cys Asp Ala Cys Ser Pro Gly His Ser Gly Arg His Cys Glu Arg
1235                1240                1245

Cys Ala Pro Gly Tyr Tyr Gly Asn Pro Ser Gln Gly Gln Pro Cys
1250                1255                1260

Gln Arg Asp Ser Gln Val Pro Gly Pro Ile Gly Cys Asn Cys Asp
1265                1270                1275

Pro Gln Gly Ser Val Ser Gln Cys Asp Ala Ala Gly Gln Cys
1280                1285                1290

Gln Cys Lys Ala Gln Val Glu Gly Leu Thr Cys Ser His Cys Arg
1295                1300                1305

Pro His His Phe His Leu Ser Ala Ser Asn Pro Asp Gly Cys Leu
1310                1315                1320

Pro Cys Phe Cys Met Gly Ile Thr Gln Gln Cys Ala Ser Ser Ala
1325                1330                1335

Tyr Thr Arg His Leu Ile Ser Thr His Phe Ala Pro Gly Asp Phe
1340                1345                1350

Gln Gly Phe Ala Leu Val Asn Pro Gln Arg Asn Ser Arg Leu Thr
1355                1360                1365

Gly Glu Phe Thr Val Glu Pro Val Pro Glu Gly Ala Gln Leu Ser
1370                1375                1380

Phe Gly Asn Phe Ala Gln Leu Gly His Glu Ser Phe Tyr Trp Gln
1385                1390                1395

Leu Pro Glu Thr Tyr Gln Gly Asp Lys Val Ala Ala Tyr Gly Gly
1400                1405                1410

Lys Leu Arg Tyr Thr Leu Ser Tyr Thr Ala Gly Pro Gln Gly Ser
1415                1420                1425

Pro Leu Ser Asp Pro Asp Val Gln Ile Thr Gly Asn Asn Ile Met
1430                1435                1440

Leu Val Ala Ser Gln Pro Ala Leu Gln Gly Pro Glu Arg Arg Ser
1445                1450                1455

Tyr Glu Ile Met Phe Arg Glu Glu Phe Trp Arg Arg Pro Asp Gly
1460                1465                1470

Gln Pro Ala Thr Arg Glu His Leu Leu Met Ala Leu Ala Asp Leu
1475                1480                1485

Asp Glu Leu Leu Ile Arg Ala Thr Phe Ser Ser Val Pro Leu Ala
1490                1495                1500

Ala Ser Ile Ser Ala Val Ser Leu Glu Val Ala Gln Pro Gly Pro
1505                1510                1515

Ser Asn Arg Pro Arg Ala Leu Glu Val Glu Cys Arg Cys Pro
1520                1525                1530

Pro Gly Tyr Ile Gly Leu Ser Cys Gln Asp Cys Ala Pro Gly Tyr
1535                1540                1545

Thr Arg Thr Gly Ser Gly Leu Tyr Leu Gly His Cys Glu Leu Cys
1550                1555                1560

Glu Cys Asn Gly His Ser Asp Leu Cys His Pro Glu Thr Gly Ala
1565                1570                1575

Cys Ser Gln Cys Gln His Asn Ala Ala Gly Glu Phe Cys Glu Leu
1580                1585                1590
```

```
Cys Ala Pro Gly Tyr Tyr Gly Asp Ala Thr Ala Gly Thr Pro Glu
1595                 1600                1605

Asp Cys Gln Pro Cys Ala Cys Pro Leu Thr Asn Pro Glu Asn Met
1610                 1615                1620

Phe Ser Arg Thr Cys Glu Ser Leu Gly Ala Gly Gly Tyr Arg Cys
1625                 1630                1635

Thr Ala Cys Glu Pro Gly Tyr Thr Gly Gln Tyr Cys Glu Gln Cys
1640                 1645                1650

Gly Pro Gly Tyr Val Gly Asn Pro Ser Val Gln Gly Gly Gln Cys
1655                 1660                1665

Leu Pro Glu Thr Asn Gln Ala Pro Leu Val Val Glu Val His Pro
1670                 1675                1680

Ala Arg Ser Ile Val Pro Gln Gly Gly Ser His Ser Leu Arg Cys
1685                 1690                1695

Gln Val Ser Gly Ser Pro Pro His Tyr Phe Tyr Trp Ser Arg Glu
1700                 1705                1710

Asp Gly Arg Pro Val Pro Ser Gly Thr Gln Gln Arg His Gln Gly
1715                 1720                1725

Ser Glu Leu His Phe Pro Ser Val Gln Pro Ser Asp Ala Gly Val
1730                 1735                1740

Tyr Ile Cys Thr Cys Arg Asn Leu His Gln Ser Asn Thr Ser Arg
1745                 1750                1755

Ala Glu Leu Leu Val Thr Glu Ala Pro Ser Lys Pro Ile Thr Val
1760                 1765                1770

Thr Val Glu Glu Gln Arg Ser Gln Ser Val Arg Pro Gly Ala Asp
1775                 1780                1785

Val Thr Phe Ile Cys Thr Ala Lys Ser Lys Ser Pro Ala Tyr Thr
1790                 1795                1800

Leu Val Trp Thr Arg Leu His Asn Gly Lys Leu Pro Thr Arg Ala
1805                 1810                1815

Met Asp Phe Asn Gly Ile Leu Thr Ile Arg Asn Val Gln Leu Ser
1820                 1825                1830

Asp Ala Gly Thr Tyr Val Cys Thr Gly Ser Asn Met Phe Ala Met
1835                 1840                1845

Asp Gln Gly Thr Ala Thr Leu His Val Gln Ala Ser Gly Thr Leu
1850                 1855                1860

Ser Ala Pro Val Val Ser Ile His Pro Pro Gln Leu Thr Val Gln
1865                 1870                1875

Pro Gly Gln Leu Ala Glu Phe Arg Cys Ser Ala Thr Gly Ser Pro
1880                 1885                1890

Thr Pro Thr Leu Glu Trp Thr Gly Gly Pro Gly Gly Gln Leu Pro
1895                 1900                1905

Ala Lys Ala Gln Ile His Gly Gly Ile Leu Arg Leu Pro Ala Val
1910                 1915                1920

Glu Pro Thr Asp Gln Ala Gln Tyr Leu Cys Arg Ala His Ser Ser
1925                 1930                1935

Ala Gly Gln Gln Val Ala Arg Ala Val Leu His Val His Gly Gly
1940                 1945                1950

Gly Gly Pro Arg Val Gln Val Ser Pro Glu Arg Thr Gln Val His
1955                 1960                1965

Ala Gly Arg Thr Val Arg Leu Tyr Cys Arg Ala Ala Gly Val Pro
1970                 1975                1980

Ser Ala Thr Ile Thr Trp Arg Lys Glu Gly Gly Ser Leu Pro Pro
```

-continued

```
            1985                1990                1995
Gln Ala Arg Ser Glu Arg Thr Asp Ile Ala Thr Leu Leu Ile Pro
        2000                2005                2010
Ala Ile Thr Thr Ala Asp Ala Gly Phe Tyr Leu Cys Val Ala Thr
        2015                2020                2025
Ser Pro Ala Gly Thr Ala Gln Ala Arg Ile Gln Val Val Val Leu
        2030                2035                2040
Ser Ala Ser Asp Ala Ser Pro Pro Val Lys Ile Glu Ser Ser
        2045                2050                2055
Ser Pro Ser Val Thr Glu Gly Gln Thr Leu Asp Leu Asn Cys Val
        2060                2065                2070
Val Ala Gly Ser Ala His Ala Gln Val Thr Trp Tyr Arg Arg Gly
        2075                2080                2085
Gly Ser Leu Pro Pro His Thr Gln Val His Gly Ser Arg Leu Arg
        2090                2095                2100
Leu Pro Gln Val Ser Pro Ala Asp Ser Gly Glu Tyr Val Cys Arg
        2105                2110                2115
Val Glu Asn Gly Ser Gly Pro Lys Glu Ala Ser Ile Thr Val Ser
        2120                2125                2130
Val Leu His Gly Thr His Ser Gly Pro Ser Tyr Thr Pro Val Pro
        2135                2140                2145
Gly Ser Thr Arg Pro Ile Arg Ile Glu Pro Ser Ser Ser His Val
        2150                2155                2160
Ala Glu Gly Gln Thr Leu Asp Leu Asn Cys Val Val Pro Gly Gln
        2165                2170                2175
Ala His Ala Gln Val Thr Trp His Lys Arg Gly Gly Ser Leu Pro
        2180                2185                2190
Ala Arg His Gln Thr His Gly Ser Leu Leu Arg Leu His Gln Val
        2195                2200                2205
Thr Pro Ala Asp Ser Gly Glu Tyr Val Cys His Val Val Gly Thr
        2210                2215                2220
Ser Gly Pro Leu Glu Ala Ser Val Leu Val Thr Ile Glu Ala Ser
        2225                2230                2235
Val Ile Pro Gly Pro Ile Pro Pro Val Arg Ile Glu Ser Ser Ser
        2240                2245                2250
Ser Thr Val Ala Glu Gly Gln Thr Leu Asp Leu Ser Cys Val Val
        2255                2260                2265
Ala Gly Gln Ala His Ala Gln Val Thr Trp Tyr Lys Arg Gly Gly
        2270                2275                2280
Ser Leu Pro Ala Arg His Gln Val Arg Gly Ser Arg Leu Tyr Ile
        2285                2290                2295
Phe Gln Ala Ser Pro Ala Asp Ala Gly Gln Tyr Val Cys Arg Ala
        2300                2305                2310
Ser Asn Gly Met Glu Ala Ser Ile Thr Val Thr Val Thr Gly Thr
        2315                2320                2325
Gln Gly Ala Asn Leu Ala Tyr Pro Ala Gly Ser Thr Gln Pro Ile
        2330                2335                2340
Arg Ile Glu Pro Ser Ser Ser Gln Val Ala Glu Gly Gln Thr Leu
        2345                2350                2355
Asp Leu Asn Cys Val Val Pro Gly Gln Ser His Ala Gln Val Thr
        2360                2365                2370
Trp His Lys Arg Gly Gly Ser Leu Pro Val Arg His Gln Thr His
        2375                2380                2385
```

```
Gly Ser Leu Leu Arg Leu Tyr Gln Ala Ser Pro Ala Asp Ser Gly
            2390                2395            2400

Glu Tyr Val Cys Arg Val Leu Gly Ser Ser Val Pro Leu Glu Ala
    2405                2410            2415

Ser Val Leu Val Thr Ile Glu Pro Ala Gly Ser Val Pro Ala Leu
    2420                2425            2430

Gly Val Thr Pro Thr Val Arg Ile Glu Ser Ser Ser Gln Val
    2435                2440            2445

Ala Glu Gly Gln Thr Leu Asp Leu Asn Cys Leu Val Ala Gly Gln
    2450                2455            2460

Ala His Ala Gln Val Thr Trp His Lys Arg Gly Gly Ser Leu Pro
    2465                2470            2475

Ala Arg His Gln Val His Gly Ser Arg Leu Arg Leu Leu Gln Val
    2480                2485            2490

Thr Pro Ala Asp Ser Gly Glu Tyr Val Cys Arg Val Val Gly Ser
    2495                2500            2505

Ser Gly Thr Gln Glu Ala Ser Val Leu Val Thr Ile Gln Gln Arg
    2510                2515            2520

Leu Ser Gly Ser His Ser Gln Gly Val Ala Tyr Pro Val Arg Ile
    2525                2530            2535

Glu Ser Ser Ser Ala Ser Leu Ala Asn Gly His Thr Leu Asp Leu
    2540                2545            2550

Asn Cys Leu Val Ala Ser Gln Ala Pro His Thr Ile Thr Trp Tyr
    2555                2560            2565

Lys Arg Gly Gly Ser Leu Pro Ser Arg His Gln Ile Val Gly Ser
    2570                2575            2580

Arg Leu Arg Ile Pro Gln Val Thr Pro Ala Asp Ser Gly Glu Tyr
    2585                2590            2595

Val Cys His Val Ser Asn Gly Ala Gly Ser Arg Glu Thr Ser Leu
    2600                2605            2610

Ile Val Thr Ile Gln Gly Ser Gly Ser Ser His Val Pro Ser Val
    2615                2620            2625

Ser Pro Pro Ile Arg Ile Glu Ser Ser Ser Pro Thr Val Val Glu
    2630                2635            2640

Gly Gln Thr Leu Asp Leu Asn Cys Val Val Ala Arg Gln Pro Gln
    2645                2650            2655

Ala Ile Ile Thr Trp Tyr Lys Arg Gly Gly Ser Leu Pro Ser Arg
    2660                2665            2670

His Gln Thr His Gly Ser His Leu Arg Leu His Gln Met Ser Val
    2675                2680            2685

Ala Asp Ser Gly Glu Tyr Val Cys Arg Ala Asn Asn Asn Ile Asp
    2690                2695            2700

Ala Leu Glu Ala Ser Ile Val Ile Ser Val Ser Pro Ser Ala Gly
    2705                2710            2715

Ser Pro Ser Ala Pro Gly Ser Ser Met Pro Ile Arg Ile Glu Ser
    2720                2725            2730

Ser Ser Ser His Val Ala Glu Gly Glu Thr Leu Asp Leu Asn Cys
    2735                2740            2745

Val Val Pro Gly Gln Ala His Ala Gln Val Thr Trp His Lys Arg
    2750                2755            2760

Gly Gly Ser Leu Pro Ser His His Gln Thr Arg Gly Ser Arg Leu
    2765                2770            2775
```

```
Arg Leu His His Val Ser Pro Ala Asp Ser Gly Glu Tyr Val Cys
2780                2785                2790

Arg Val Met Gly Ser Ser Gly Pro Leu Glu Ala Ser Val Leu Val
2795                2800                2805

Thr Ile Glu Ala Ser Gly Ser Ser Ala Val His Val Pro Ala Pro
2810                2815                2820

Gly Gly Ala Pro Pro Ile Arg Ile Glu Pro Ser Ser Ser Arg Val
2825                2830                2835

Ala Glu Gly Gln Thr Leu Asp Leu Lys Cys Val Val Pro Gly Gln
2840                2845                2850

Ala His Ala Gln Val Thr Trp His Lys Arg Gly Gly Asn Leu Pro
2855                2860                2865

Ala Arg His Gln Val His Gly Pro Leu Leu Arg Leu Asn Gln Val
2870                2875                2880

Ser Pro Ala Asp Ser Gly Glu Tyr Ser Cys Gln Val Thr Gly Ser
2885                2890                2895

Ser Gly Thr Leu Glu Ala Ser Val Leu Val Thr Ile Glu Pro Ser
2900                2905                2910

Ser Pro Gly Pro Ile Pro Ala Pro Gly Leu Ala Gln Pro Ile Tyr
2915                2920                2925

Ile Glu Ala Ser Ser Ser His Val Thr Glu Gly Gln Thr Leu Asp
2930                2935                2940

Leu Asn Cys Val Val Pro Gly Gln Ala His Ala Gln Val Thr Trp
2945                2950                2955

Tyr Lys Arg Gly Gly Ser Leu Pro Ala Arg His Gln Thr His Gly
2960                2965                2970

Ser Gln Leu Arg Leu His Leu Val Ser Pro Ala Asp Ser Gly Glu
2975                2980                2985

Tyr Val Cys Arg Ala Ala Ser Gly Pro Gly Pro Glu Gln Glu Ala
2990                2995                3000

Ser Phe Thr Val Thr Val Pro Pro Ser Glu Gly Ser Ser Tyr Arg
3005                3010                3015

Leu Arg Ser Pro Val Ile Ser Ile Asp Pro Pro Ser Ser Thr Val
3020                3025                3030

Gln Gln Gly Gln Asp Ala Ser Phe Lys Cys Leu Ile His Asp Gly
3035                3040                3045

Ala Ala Pro Ile Ser Leu Glu Trp Lys Thr Arg Asn Gln Glu Leu
3050                3055                3060

Glu Asp Asn Val His Ile Ser Pro Asn Gly Ser Ile Ile Thr Ile
3065                3070                3075

Val Gly Thr Arg Pro Ser Asn His Gly Thr Tyr Arg Cys Val Ala
3080                3085                3090

Ser Asn Ala Tyr Gly Val Ala Gln Ser Val Val Asn Leu Ser Val
3095                3100                3105

His Gly Pro Pro Thr Val Ser Val Leu Pro Glu Gly Pro Val Trp
3110                3115                3120

Val Lys Val Gly Lys Ala Val Thr Leu Glu Cys Val Ser Ala Gly
3125                3130                3135

Glu Pro Arg Ser Ser Ala Arg Trp Thr Arg Ile Ser Ser Thr Pro
3140                3145                3150

Ala Lys Leu Glu Gln Arg Thr Tyr Gly Leu Met Asp Ser His Ala
3155                3160                3165

Val Leu Gln Ile Ser Ser Ala Lys Pro Ser Asp Ala Gly Thr Tyr
```

-continued

|  |  |  |  |  |  |  |  |  |  |
|---|---|---|---|---|---|---|---|---|---|
|  | 3170 |  |  | 3175 |  |  | 3180 |  |  |
| Val | Cys | Leu | Ala | Gln | Asn | Ala | Leu | Gly | Thr | Ala | Gln | Lys | Gln | Val |
|  | 3185 |  |  | 3190 |  |  | 3195 |  |  |
| Glu | Val | Ile | Val | Asp | Thr | Gly | Ala | Met | Ala | Pro | Gly | Ala | Pro | Gln |
|  | 3200 |  |  | 3205 |  |  | 3210 |  |  |
| Val | Gln | Ala | Glu | Glu | Ala | Glu | Leu | Thr | Val | Glu | Ala | Gly | His | Thr |
|  | 3215 |  |  | 3220 |  |  | 3225 |  |  |
| Ala | Thr | Leu | Arg | Cys | Ser | Ala | Thr | Gly | Ser | Pro | Ala | Pro | Thr | Ile |
|  | 3230 |  |  | 3235 |  |  | 3240 |  |  |
| His | Trp | Ser | Lys | Leu | Arg | Ser | Pro | Leu | Pro | Trp | Gln | His | Arg | Leu |
|  | 3245 |  |  | 3250 |  |  | 3255 |  |  |
| Glu | Gly | Asp | Thr | Leu | Ile | Ile | Pro | Arg | Val | Ala | Gln | Gln | Asp | Ser |
|  | 3260 |  |  | 3265 |  |  | 3270 |  |  |
| Gly | Gln | Tyr | Ile | Cys | Asn | Ala | Thr | Ser | Pro | Ala | Gly | His | Ala | Glu |
|  | 3275 |  |  | 3280 |  |  | 3285 |  |  |
| Ala | Thr | Ile | Ile | Leu | His | Val | Glu | Ser | Pro | Pro | Tyr | Ala | Thr | Thr |
|  | 3290 |  |  | 3295 |  |  | 3300 |  |  |
| Val | Pro | Glu | His | Ala | Ser | Val | Gln | Ala | Gly | Glu | Thr | Val | Gln | Leu |
|  | 3305 |  |  | 3310 |  |  | 3315 |  |  |
| Gln | Cys | Leu | Ala | His | Gly | Thr | Pro | Pro | Leu | Thr | Phe | Gln | Trp | Ser |
|  | 3320 |  |  | 3325 |  |  | 3330 |  |  |
| Arg | Val | Gly | Ser | Ser | Leu | Pro | Gly | Arg | Ala | Thr | Ala | Arg | Asn | Glu |
|  | 3335 |  |  | 3340 |  |  | 3345 |  |  |
| Leu | Leu | His | Phe | Glu | Arg | Ala | Ala | Pro | Glu | Asp | Ser | Gly | Arg | Tyr |
|  | 3350 |  |  | 3355 |  |  | 3360 |  |  |
| Arg | Cys | Arg | Val | Thr | Asn | Lys | Val | Gly | Ser | Ala | Glu | Ala | Phe | Ala |
|  | 3365 |  |  | 3370 |  |  | 3375 |  |  |
| Gln | Leu | Leu | Val | Gln | Gly | Pro | Pro | Gly | Ser | Leu | Pro | Ala | Thr | Ser |
|  | 3380 |  |  | 3385 |  |  | 3390 |  |  |
| Ile | Pro | Ala | Gly | Ser | Thr | Pro | Thr | Val | Gln | Val | Thr | Pro | Gln | Leu |
|  | 3395 |  |  | 3400 |  |  | 3405 |  |  |
| Glu | Thr | Lys | Ser | Ile | Gly | Ala | Ser | Val | Glu | Phe | His | Cys | Ala | Val |
|  | 3410 |  |  | 3415 |  |  | 3420 |  |  |
| Pro | Ser | Asp | Arg | Gly | Thr | Gln | Leu | Arg | Trp | Phe | Lys | Glu | Gly | Gly |
|  | 3425 |  |  | 3430 |  |  | 3435 |  |  |
| Gln | Leu | Pro | Pro | Gly | His | Ser | Val | Gln | Asp | Gly | Val | Leu | Arg | Ile |
|  | 3440 |  |  | 3445 |  |  | 3450 |  |  |
| Gln | Asn | Leu | Asp | Gln | Ser | Cys | Gln | Gly | Thr | Tyr | Ile | Cys | Gln | Ala |
|  | 3455 |  |  | 3460 |  |  | 3465 |  |  |
| His | Gly | Pro | Trp | Gly | Lys | Ala | Gln | Ala | Ser | Ala | Gln | Leu | Val | Ile |
|  | 3470 |  |  | 3475 |  |  | 3480 |  |  |
| Gln | Ala | Leu | Pro | Ser | Val | Leu | Ile | Asn | Ile | Arg | Thr | Ser | Val | Gln |
|  | 3485 |  |  | 3490 |  |  | 3495 |  |  |
| Thr | Val | Val | Gly | His | Ala | Val | Glu | Phe | Glu | Cys | Leu | Ala | Leu |
|  | 3500 |  |  | 3505 |  |  | 3510 |  |  |
| Gly | Asp | Pro | Lys | Pro | Gln | Val | Thr | Trp | Ser | Lys | Val | Gly | Gly | His |
|  | 3515 |  |  | 3520 |  |  | 3525 |  |  |
| Leu | Arg | Pro | Gly | Ile | Val | Gln | Ser | Gly | Gly | Val | Val | Arg | Ile | Ala |
|  | 3530 |  |  | 3535 |  |  | 3540 |  |  |
| His | Val | Glu | Leu | Ala | Asp | Ala | Gly | Gln | Tyr | Arg | Cys | Thr | Ala | Thr |
|  | 3545 |  |  | 3550 |  |  | 3555 |  |  |
| Asn | Ala | Ala | Gly | Thr | Thr | Gln | Ser | His | Val | Leu | Leu | Leu | Val | Gln |
|  | 3560 |  |  | 3565 |  |  | 3570 |  |  |

-continued

Ala Leu Pro Gln Ile Ser Met Pro Gln Glu Val Arg Val Pro Ala
3575                3580                3585

Gly Ser Ala Ala Val Phe Pro Cys Ile Ala Ser Gly Tyr Pro Thr
    3590                3595                3600

Pro Asp Ile Ser Trp Ser Lys Leu Asp Gly Ser Leu Pro Pro Asp
3605                3610                3615

Ser Arg Leu Glu Asn Asn Met Leu Met Leu Pro Ser Val Arg Pro
3620                3625                3630

Gln Asp Ala Gly Thr Tyr Val Cys Thr Ala Thr Asn Arg Gln Gly
3635                3640                3645

Lys Val Lys Ala Phe Ala His Leu Gln Val Pro Glu Arg Val Val
3650                3655                3660

Pro Tyr Phe Thr Gln Thr Pro Tyr Ser Phe Leu Pro Leu Pro Thr
3665                3670                3675

Ile Lys Asp Ala Tyr Arg Lys Phe Glu Ile Lys Ile Thr Phe Arg
3680                3685                3690

Pro Asp Ser Ala Asp Gly Met Leu Leu Tyr Asn Gly Gln Lys Arg
3695                3700                3705

Val Pro Gly Ser Pro Thr Asn Leu Ala Asn Arg Gln Pro Asp Phe
3710                3715                3720

Ile Ser Phe Gly Leu Val Gly Gly Arg Pro Glu Phe Arg Phe Asp
3725                3730                3735

Ala Gly Ser Gly Met Ala Thr Ile Arg His Pro Thr Pro Leu Ala
3740                3745                3750

Leu Gly His Phe His Thr Val Thr Leu Leu Arg Ser Leu Thr Gln
3755                3760                3765

Gly Ser Leu Ile Val Gly Asp Leu Ala Pro Val Asn Gly Thr Ser
3770                3775                3780

Gln Gly Lys Phe Gln Gly Leu Asp Leu Asn Glu Glu Leu Tyr Leu
3785                3790                3795

Gly Gly Tyr Pro Asp Tyr Gly Ala Ile Pro Lys Ala Gly Leu Ser
3800                3805                3810

Ser Gly Phe Ile Gly Cys Val Arg Glu Leu Arg Ile Gln Gly Glu
3815                3820                3825

Glu Ile Val Phe His Asp Leu Asn Leu Thr Ala His Gly Ile Ser
3830                3835                3840

His Cys Pro Thr Cys Arg Asp Arg Pro Cys Gln Asn Gly Gly Gln
3845                3850                3855

Cys His Asp Ser Glu Ser Ser Tyr Val Cys Val Cys Pro Ala
3860                3865                3870

Gly Phe Thr Gly Ser Arg Cys Glu His Ser Gln Ala Leu His Cys
3875                3880                3885

His Pro Glu Ala Cys Gly Pro Asp Ala Thr Cys Val Asn Arg Pro
3890                3895                3900

Asp Gly Arg Gly Tyr Thr Cys Arg Cys His Leu Gly Arg Ser Gly
3905                3910                3915

Leu Arg Cys Glu Glu Gly Val Thr Val Thr Thr Pro Ser Leu Ser
3920                3925                3930

Gly Ala Gly Ser Tyr Leu Ala Leu Pro Ala Leu Thr Asn Thr His
3935                3940                3945

His Glu Leu Arg Leu Asp Val Glu Phe Lys Pro Leu Ala Pro Asp
3950                3955                3960

-continued

```
Gly Val Leu Leu Phe Ser Gly Gly Lys Ser Gly Pro Val Glu Asp
3965                3970                3975

Phe Val Ser Leu Ala Met Val Gly Gly His Leu Glu Phe Arg Tyr
3980                3985                3990

Glu Leu Gly Ser Gly Leu Ala Val Leu Arg Ser Ala Glu Pro Leu
3995                4000                4005

Ala Leu Gly Arg Trp His Arg Val Ser Ala Glu Arg Leu Asn Lys
4010                4015                4020

Asp Gly Ser Leu Arg Val Asn Gly Gly Arg Pro Val Leu Arg Ser
4025                4030                4035

Ser Pro Gly Lys Ser Gln Gly Leu Asn Leu His Thr Leu Leu Tyr
4040                4045                4050

Leu Gly Gly Val Glu Pro Ser Val Pro Leu Ser Pro Ala Thr Asn
4055                4060                4065

Met Ser Ala His Phe Arg Gly Cys Val Gly Glu Val Ser Val Asn
4070                4075                4080

Gly Lys Arg Leu Asp Leu Thr Tyr Ser Phe Leu Gly Ser Gln Gly
4085                4090                4095

Ile Gly Gln Cys Tyr Asp Ser Ser Pro Cys Glu Arg Gln Pro Cys
4100                4105                4110

Gln His Gly Ala Thr Cys Met Pro Ala Gly Glu Tyr Glu Phe Gln
4115                4120                4125

Cys Leu Cys Arg Asp Gly Phe Lys Gly Asp Leu Cys Glu His Glu
4130                4135                4140

Glu Asn Pro Cys Gln Leu Arg Glu Pro Cys Leu His Gly Gly Thr
4145                4150                4155

Cys Gln Gly Thr Arg Cys Leu Cys Leu Pro Gly Phe Ser Gly Pro
4160                4165                4170

Arg Cys Gln Gln Gly Ser Gly His Gly Ile Ala Glu Ser Asp Trp
4175                4180                4185

His Leu Glu Gly Ser Gly Gly Asn Asp Ala Pro Gly Gln Tyr Gly
4190                4195                4200

Ala Tyr Phe His Asp Asp Gly Phe Leu Ala Phe Pro Gly His Val
4205                4210                4215

Phe Ser Arg Ser Leu Pro Glu Val Pro Glu Thr Ile Glu Leu Glu
4220                4225                4230

Val Arg Thr Ser Thr Ala Ser Gly Leu Leu Leu Trp Gln Gly Val
4235                4240                4245

Glu Val Gly Glu Ala Gly Gln Gly Lys Asp Phe Ile Ser Leu Gly
4250                4255                4260

Leu Gln Asp Gly His Leu Val Phe Arg Tyr Gln Leu Gly Ser Gly
4265                4270                4275

Glu Ala Arg Leu Val Ser Glu Asp Pro Ile Asn Asp Gly Glu Trp
4280                4285                4290

His Arg Val Thr Ala Leu Arg Glu Gly Arg Arg Gly Ser Ile Gln
4295                4300                4305

Val Asp Gly Glu Glu Leu Val Ser Gly Arg Ser Pro Gly Pro Asn
4310                4315                4320

Val Ala Val Asn Ala Lys Gly Ser Val Tyr Ile Gly Gly Ala Pro
4325                4330                4335

Asp Val Ala Thr Leu Thr Gly Gly Arg Phe Ser Ser Gly Ile Thr
4340                4345                4350

Gly Cys Val Lys Asn Leu Val Leu His Ser Ala Arg Pro Gly Ala
```

-continued

```
                4355                4360                4365
Pro Pro Pro Gln Pro Leu Asp Leu Gln His Arg Ala Gln Ala Gly
        4370                4375                4380
Ala Asn Thr Arg Pro Cys Pro Ser
        4385                4390

<210> SEQ ID NO 3
<211> LENGTH: 4383
<212> TYPE: PRT
<213> ORGANISM: Mus musculus

<400> SEQUENCE: 3

Met Gly Gln Arg Ala Val Gly Ser Leu Leu Gly Leu Leu Leu His
1               5                   10                  15

Ala Arg Leu Leu Ala Val Thr His Gly Leu Arg Ala Tyr Asp Gly Leu
            20                  25                  30

Ser Leu Pro Glu Asp Thr Glu Thr Val Thr Ala Ser Arg Tyr Gly Trp
        35                  40                  45

Thr Tyr Ser Tyr Leu Ser Asp Asp Glu Leu Leu Ala Asp Ala
    50                  55                  60

Ser Gly Asp Gly Leu Gly Ser Gly Asp Val Gly Ser Gly Asp Phe Gln
65                  70                  75                  80

Met Val Tyr Phe Arg Ala Leu Val Asn Phe Thr Arg Ser Ile Glu Tyr
                85                  90                  95

Ser Pro Gln Leu Glu Asp Ala Ser Ala Lys Glu Phe Arg Glu Val Ser
            100                 105                 110

Glu Ala Val Val Glu Lys Leu Glu Pro Glu Tyr Arg Lys Ile Pro Gly
        115                 120                 125

Asp Gln Ile Val Ser Val Val Phe Ile Lys Glu Leu Asp Gly Trp Val
    130                 135                 140

Phe Val Glu Leu Asp Val Gly Ser Glu Gly Asn Ala Asp Gly Ser Gln
145                 150                 155                 160

Ile Gln Glu Val Leu His Thr Val Val Ser Ser Gly Ser Ile Gly Pro
                165                 170                 175

Tyr Val Thr Ser Pro Trp Gly Phe Lys Phe Arg Arg Leu Gly Thr Val
            180                 185                 190

Pro Gln Phe Pro Arg Val Cys Thr Glu Thr Glu Phe Ala Cys His Ser
        195                 200                 205

Tyr Asn Glu Cys Val Ala Leu Glu Tyr Arg Cys Asp Arg Arg Pro Asp
    210                 215                 220

Cys Arg Asp Met Ser Asp Glu Leu Asn Cys Glu Pro Val Pro Glu
225                 230                 235                 240

Leu Ser Ser Ser Thr Pro Ala Val Gly Lys Val Ser Pro Leu Pro Leu
                245                 250                 255

Trp Pro Glu Ala Ala Thr Thr Pro Pro Pro Val Thr His Gly Pro
            260                 265                 270

Gln Phe Leu Leu Pro Ser Val Pro Gly Pro Ser Ala Cys Gly Pro Gln
        275                 280                 285

Glu Ala Ser Cys His Ser Gly His Cys Ile Pro Arg Asp Tyr Leu Cys
    290                 295                 300

Asp Gly Gln Glu Asp Cys Arg Asp Gly Ser Asp Glu Leu Gly Cys Ala
305                 310                 315                 320

Ser Pro Pro Pro Cys Glu Pro Asn Glu Phe Ala Cys Glu Asn Gly His
                325                 330                 335
```

```
Cys Ala Leu Lys Leu Trp Arg Cys Asp Gly Asp Phe Asp Cys Glu Asp
            340                 345                 350

Arg Thr Asp Glu Ala Asn Cys Ser Val Lys Gln Pro Gly Glu Val Cys
        355                 360                 365

Gly Pro Thr His Phe Gln Cys Val Ser Thr Asn Arg Cys Ile Pro Ala
    370                 375                 380

Ser Phe His Cys Asp Glu Glu Ser Asp Cys Pro Asp Arg Ser Asp Glu
385                 390                 395                 400

Phe Gly Cys Met Pro Pro Gln Val Val Thr Pro Pro Gln Gln Ser Ile
                405                 410                 415

Gln Ala Ser Arg Gly Gln Thr Val Thr Phe Thr Cys Val Ala Thr Gly
            420                 425                 430

Val Pro Thr Pro Ile Ile Asn Trp Arg Leu Asn Trp Gly His Ile Pro
        435                 440                 445

Ala His Pro Arg Val Thr Met Thr Ser Glu Gly Gly Arg Gly Thr Leu
    450                 455                 460

Ile Ile Arg Asp Val Lys Glu Ala Asp Gln Gly Ala Tyr Thr Cys Glu
465                 470                 475                 480

Ala Met Asn Ser Arg Gly Met Val Phe Gly Ile Pro Asp Gly Val Leu
                485                 490                 495

Glu Leu Val Pro Gln Arg Gly Pro Cys Pro Asp Gly His Phe Tyr Leu
            500                 505                 510

Glu Asp Ser Ala Ser Cys Leu Pro Cys Phe Cys Phe Gly Val Thr Asn
        515                 520                 525

Val Cys Gln Ser Ser Leu Arg Phe Arg Asp Gln Ile Arg Leu Ser Phe
    530                 535                 540

Asp Gln Pro Asn Asp Phe Lys Gly Val Asn Val Thr Met Pro Ser Gln
545                 550                 555                 560

Pro Gly Val Pro Pro Leu Ser Ser Thr Gln Leu Gln Ile Asp Pro Ala
                565                 570                 575

Leu Gln Glu Phe Gln Leu Val Asp Leu Ser Arg Arg Phe Leu Val His
            580                 585                 590

Asp Ala Phe Trp Ala Leu Pro Lys Gln Phe Leu Gly Asn Lys Val Asp
        595                 600                 605

Ser Tyr Gly Gly Phe Leu Arg Tyr Lys Val Arg Tyr Glu Leu Ala Arg
    610                 615                 620

Gly Met Leu Glu Pro Val Gln Lys Pro Asp Val Ile Leu Val Gly Ala
625                 630                 635                 640

Gly Tyr Arg Leu His Ser Arg Gly His Thr Pro Thr His Pro Gly Thr
                645                 650                 655

Leu Asn Gln Arg Gln Val Gln Leu Ser Glu Glu His Trp Val His Glu
            660                 665                 670

Ser Gly Arg Pro Val Gln Arg Ala Glu Met Leu Gln Ala Leu Ala Ser
        675                 680                 685

Leu Glu Ala Val Leu Leu Gln Thr Val Tyr Asn Thr Lys Met Ala Ser
    690                 695                 700

Val Gly Leu Ser Asp Ile Val Met Asp Thr Thr Val Thr His Thr Thr
705                 710                 715                 720

Ile His Gly Arg Ala His Ser Val Glu Glu Cys Arg Cys Pro Ile Gly
                725                 730                 735

Tyr Ser Gly Leu Ser Cys Glu Ser Cys Asp Ala His Phe Thr Arg Val
            740                 745                 750

Pro Gly Gly Pro Tyr Leu Gly Thr Cys Ser Gly Cys Asn Cys Asn Gly
```

-continued

```
            755                 760                 765
His Ala Ser Ser Cys Asp Pro Val Tyr Gly His Cys Leu Asn Cys Gln
770                 775                 780
His Asn Thr Glu Gly Pro Gln Cys Asp Lys Cys Lys Pro Gly Phe Phe
785                 790                 795                 800
Gly Asp Ala Thr Lys Ala Thr Ala Thr Ala Cys Arg Pro Cys Pro Cys
                    805                 810                 815
Pro Tyr Ile Asp Ala Ser Arg Arg Phe Ser Asp Thr Cys Phe Leu Asp
            820                 825                 830
Thr Asp Gly Gln Ala Thr Cys Asp Ala Cys Ala Pro Gly Tyr Thr Gly
            835                 840                 845
Arg Arg Cys Glu Ser Cys Ala Pro Gly Tyr Glu Gly Asn Pro Ile Gln
850                 855                 860
Pro Gly Gly Lys Cys Arg Pro Thr Thr Gln Glu Ile Val Arg Cys Asp
865                 870                 875                 880
Glu Arg Gly Ser Leu Gly Thr Ser Gly Glu Thr Cys Arg Cys Lys Asn
                    885                 890                 895
Asn Val Val Gly Arg Leu Cys Asn Glu Cys Ser Asp Gly Ser Phe His
            900                 905                 910
Leu Ser Lys Gln Asn Pro Asp Gly Cys Leu Lys Cys Phe Cys Met Gly
            915                 920                 925
Val Ser Arg Gln Cys Ser Ser Ser Trp Ser Arg Ala Gln Val Leu
930                 935                 940
Gly Ala Ser Glu Gln Pro Ser Gln Phe Ser Leu Ser Asn Ala Ala Gly
945                 950                 955                 960
Thr His Thr Thr Ser Glu Gly Val Ser Pro Ala Pro Gly Glu Leu
                    965                 970                 975
Ser Phe Ser Ser Phe His Asn Leu Leu Ser Glu Pro Tyr Phe Trp Ser
            980                 985                 990
Leu Pro Ala Ser Phe Arg Gly Asp Lys Val Thr Ser Tyr Gly Gly Glu
            995                 1000                1005
Leu Arg Phe Thr Val Thr Gln Arg Pro Arg Pro Ser  Ser Ala Pro
1010                1015                1020
Leu His Arg Gln Pro Leu Val  Val Leu Gln Gly Asn  Asn Ile Val
1025                1030                1035
Leu Glu His His Ala Ser Arg Asp Pro Ser Pro Gly  Gln Pro Ser
1040                1045                1050
Asn Phe Ile Val Pro Phe Gln Glu Gln Ala Trp Gln  Arg Pro Asp
1055                1060                1065
Gly Gln Pro Ala Thr Arg Glu His Leu Leu Met Ala  Leu Ala Gly
1070                1075                1080
Ile Asp Ala Leu Leu Ile Gln Ala Ser Tyr Thr Gln  Gln Pro Ala
1085                1090                1095
Glu Ser Arg Val Ser Gly Ile Ser Met Asp Val Ala  Val Pro Glu
1100                1105                1110
Asn Thr Gly Gln Asp Ser Ala Arg Glu Val Glu Gln  Cys Thr Cys
1115                1120                1125
Pro Pro Gly Tyr Arg Gly Pro Ser Cys Gln Asp Cys  Asp Thr Gly
1130                1135                1140
Tyr Thr Arg Val Pro Ser Gly Leu Tyr Leu Gly Thr  Cys Glu Arg
1145                1150                1155
Cys Asn Cys His Gly His Ser Glu Thr Cys Glu Pro  Glu Thr Gly
1160                1165                1170
```

```
Ala Cys Gln Ser Cys Gln His His Thr Glu Gly Ala Ser Cys Glu
    1175            1180                1185

Gln Cys Gln Pro Gly Tyr Tyr Gly Asp Ala Gln Arg Gly Thr Pro
    1190            1195                1200

Gln Asp Cys Gln Pro Cys Pro Cys Tyr Gly Ala Pro Ala Ala Gly
    1205            1210                1215

Gln Ala Ala His Thr Cys Phe Leu Asp Thr Asp Gly His Pro Thr
    1220            1225                1230

Cys Asp Ser Cys Ser Pro Gly His Ser Gly Arg His Cys Glu Arg
    1235            1240                1245

Cys Ala Pro Gly Tyr Tyr Gly Asn Pro Ser Gln Gly Gln Pro Cys
    1250            1255                1260

His Arg Asp Gly Gln Val Pro Glu Val Leu Gly Cys Gly Cys Asp
    1265            1270                1275

Pro His Gly Ser Ile Ser Ser Gln Cys Asp Ala Ala Gly Gln Cys
    1280            1285                1290

Gln Cys Lys Ala Gln Val Glu Gly Arg Thr Cys Ser His Cys Arg
    1295            1300                1305

Pro His His Phe His Leu Ser Ala Ser Asn Pro Glu Gly Cys Leu
    1310            1315                1320

Pro Cys Phe Cys Met Gly Val Thr Gln Gln Cys Ala Ser Ser Ser
    1325            1330                1335

Tyr Ser Arg Gln Leu Ile Ser Thr His Phe Ala Pro Gly Asp Phe
    1340            1345                1350

Gln Gly Phe Ala Leu Val Asn Pro Gln Arg Asn Ser Gln Leu Thr
    1355            1360                1365

Gly Gly Phe Thr Val Glu Pro Val His Asp Gly Ala Arg Leu Ser
    1370            1375                1380

Phe Ser Asn Phe Ala His Leu Gly Gln Glu Ser Phe Tyr Trp Gln
    1385            1390                1395

Leu Pro Glu Ile Tyr Gln Gly Asp Lys Val Ala Ala Tyr Gly Gly
    1400            1405                1410

Lys Leu Arg Tyr Thr Leu Ser Tyr Thr Ala Gly Pro Gln Gly Ser
    1415            1420                1425

Pro Leu Leu Asp Pro Asp Ile Gln Ile Thr Gly Asn Asn Ile Met
    1430            1435                1440

Leu Val Ala Ser Gln Pro Ala Leu Gln Gly Pro Glu Arg Arg Ser
    1445            1450                1455

Tyr Glu Ile Ile Phe Arg Glu Glu Phe Trp Arg Arg Pro Asp Gly
    1460            1465                1470

Gln Pro Ala Thr Arg Glu His Leu Leu Met Ala Leu Ala Asp Leu
    1475            1480                1485

Asp Glu Leu Leu Val Arg Ala Thr Phe Ser Ser Val Pro Arg Ala
    1490            1495                1500

Ala Ser Ile Ser Ala Val Ser Leu Glu Val Ala Gln Pro Gly Pro
    1505            1510                1515

Ser Ser Gly Pro Arg Ala Leu Glu Val Glu Glu Cys Arg Cys Pro
    1520            1525                1530

Pro Gly Tyr Val Gly Leu Ser Cys Gln Asp Cys Ala Pro Gly Tyr
    1535            1540                1545

Thr Arg Thr Gly Ser Gly Leu Tyr Leu Gly Gln Cys Glu Leu Cys
    1550            1555                1560
```

-continued

| | | | | | | | | | |
|---|---|---|---|---|---|---|---|---|---|
|Glu|Cys|Asn|Gly|His|Ser|Asp|Leu|Cys|His|Pro|Glu|Thr|Gly|Ala|
| |1565| | | |1570| | | |1575| | | | | |

Cys Ser Arg Cys Gln His Asn Thr Ala Gly Glu Phe Cys Glu Leu
    1580              1585              1590

Cys Ala Thr Gly Tyr Tyr Gly Asp Ala Thr Ala Gly Thr Pro Glu
    1595              1600              1605

Asp Cys Gln Pro Cys Ala Cys Pro Leu Thr Asn Pro Glu Asn Met
    1610              1615              1620

Phe Ser Arg Thr Cys Glu Ser Leu Gly Ala Gly Gly Tyr Arg Cys
    1625              1630              1635

Thr Ala Cys Glu Pro Gly Tyr Thr Gly Gln Tyr Cys Glu Gln Cys
    1640              1645              1650

Ala Pro Gly Tyr Glu Gly Asp Pro Asn Val Gln Gly Gly Arg Cys
    1655              1660              1665

Gln Pro Leu Thr Lys Glu Ser Leu Glu Val Gln Ile His Pro Ser
    1670              1675              1680

Arg Ser Val Val Pro Gln Gly Gly Pro His Ser Leu Arg Cys Gln
    1685              1690              1695

Val Ser Gly Ser Pro Pro His Tyr Phe Tyr Trp Ser Arg Glu Asp
    1700              1705              1710

Gly Arg Pro Leu Pro Ser Ser Ala Gln Gln Arg His Gln Gly Ser
    1715              1720              1725

Glu Leu His Phe Pro Ser Val Gln Pro Ser Asp Ala Gly Val Tyr
    1730              1735              1740

Ile Cys Thr Cys Arg Asn Leu Ile His Thr Ser Asn Ser Arg Ala
    1745              1750              1755

Glu Leu Leu Val Ala Glu Ala Pro Ser Lys Pro Ile Thr Val Thr
    1760              1765              1770

Val Glu Glu Gln Arg Ser Gln Ser Val Arg Pro Gly Ala Asp Val
    1775              1780              1785

Thr Phe Ile Cys Thr Ala Lys Ser Lys Ser Pro Ala Tyr Thr Leu
    1790              1795              1800

Val Trp Thr Arg Leu His Asn Gly Lys Leu Pro Ser Arg Ala Met
    1805              1810              1815

Asp Phe Asn Gly Ile Leu Thr Ile Arg Asn Val Gln Pro Ser Asp
    1820              1825              1830

Ala Gly Thr Tyr Val Cys Thr Gly Ser Asn Met Phe Ala Met Asp
    1835              1840              1845

Gln Gly Thr Ala Thr Leu His Val Gln Val Ser Gly Thr Ser Thr
    1850              1855              1860

Ala Pro Val Ala Ser Ile His Pro Pro Gln Leu Thr Val Gln Pro
    1865              1870              1875

Gly Gln Gln Ala Glu Phe Arg Cys Ser Ala Thr Gly Asn Pro Thr
    1880              1885              1890

Pro Met Leu Glu Trp Ile Gly Gly Pro Ser Gly Gln Leu Pro Ala
    1895              1900              1905

Lys Ala Gln Ile His Asn Gly Ile Leu Arg Leu Pro Ala Ile Glu
    1910              1915              1920

Pro Ser Asp Gln Gly Gln Tyr Leu Cys Arg Ala Leu Ser Ser Ala
    1925              1930              1935

Gly Gln His Val Ala Arg Ala Met Leu Gln Val His Gly Gly Ser
    1940              1945              1950

Gly Pro Arg Val Gln Val Ser Pro Glu Arg Thr Gln Val His Glu

-continued

```
              1955                1960                1965
Gly Arg Thr Val Arg Leu Tyr Cys Arg Ala Ala Gly Val Pro Ser
    1970                1975                1980
Ala Ser Ile Thr Trp Arg Lys Glu Gly Gly Ser Leu Pro Pro Gln
    1985                1990                1995
Ala Arg Ser Glu Asn Thr Asp Ile Pro Thr Leu Leu Ile Pro Ala
    2000                2005                2010
Ile Thr Ala Ala Asp Ala Gly Phe Tyr Leu Cys Val Ala Thr Ser
    2015                2020                2025
Pro Thr Gly Thr Ala Gln Ala Arg Ile Gln Val Val Val Leu Ser
    2030                2035                2040
Ala Ser Gly Ala Asn Ser Val Pro Val Arg Ile Glu Ser Ser Ser
    2045                2050                2055
Pro Ser Val Thr Glu Gly Gln Thr Leu Asp Leu Asn Cys Ala Val
    2060                2065                2070
Met Gly Leu Thr Tyr Thr Gln Val Thr Trp Tyr Lys Arg Gly Gly
    2075                2080                2085
Ser Leu Pro Pro His Ala Gln Val His Gly Ser Arg Leu Arg Leu
    2090                2095                2100
Pro Gln Val Ser Pro Ala Asp Ser Gly Asp Tyr Val Cys Arg Val
    2105                2110                2115
Glu Ser Asp Val Gly Pro Lys Glu Ala Ser Ile Val Val Ser Val
    2120                2125                2130
Leu His Ser Pro His Ser Gly Pro Ser Tyr Thr Pro Ala Thr Ser
    2135                2140                2145
Ile Thr Pro Pro Ile Arg Ile Glu Ser Ser Ser His Val Ala
    2150                2155                2160
Glu Gly Gln Thr Leu Asp Leu Asn Cys Val Val Pro Gly Gln Ala
    2165                2170                2175
Gln Val Thr Trp Arg Lys Arg Gly Gly Ser Leu Pro Ala Arg His
    2180                2185                2190
Gln Thr His Gly Ser Leu Leu Arg Leu His Gln Val Ser Pro Ala
    2195                2200                2205
Asp Ser Gly Glu Tyr Val Cys His Val Val Leu Gly Ser Glu His
    2210                2215                2220
Thr Glu Thr Ser Val Leu Val Thr Ile Glu Pro Ala Glu Ser Ile
    2225                2230                2235
Pro Ala Pro Gly Pro Ala Pro Pro Val Arg Ile Glu Ala Ser Ser
    2240                2245                2250
Ser Thr Val Thr Glu Gly His Met Leu Asp Leu Asn Cys Val Val
    2255                2260                2265
Ala Gly Gln Ala His Ala Gln Val Thr Trp Tyr Lys Arg Gly Gly
    2270                2275                2280
Ser Leu Pro Ala Arg His Gln Val Arg Gly Ser Arg Leu Tyr Ile
    2285                2290                2295
Leu Gln Ala Ser Pro Ala Asp Ala Gly Glu Tyr Val Cys Arg Ala
    2300                2305                2310
Gly Asn Gly Gln Glu Ala Thr Ile Thr Val Thr Val Thr Arg Asn
    2315                2320                2325
His Gly Ala Asn Leu Ala Tyr Pro Pro Gly Ser Thr Ser Pro Ile
    2330                2335                2340
Arg Ile Glu Ser Ser Ser Ser His Val Ala Glu Gly Gln Thr Leu
    2345                2350                2355
```

```
Asp Leu Asn Cys Val Val Gln Gly Gln Ala His Ala Gln Val Thr
    2360            2365            2370

Trp His Lys Arg Gly Gly Ser Leu Pro Ala Arg His Gln Thr His
    2375            2380            2385

Gly Ser Leu Leu Arg Leu His Gln Val Ser Pro Val Asp Ser Gly
    2390            2395            2400

Glu Tyr Val Cys Arg Val Glu Gly Gly Ala Val Pro Leu Glu Ser
    2405            2410            2415

Ser Val Leu Val Thr Ile Glu Pro Ala Gly Thr Ala Pro Gly Val
    2420            2425            2430

Ile Pro Pro Val Arg Ile Glu Ser Ser Ser His Val Ser Glu
    2435            2440            2445

Gly Gln Ser Leu Asp Leu Asn Cys Leu Val Ser Gly Gln Thr His
    2450            2455            2460

Pro Gln Ile Ser Trp His Lys Arg Gly Gly Ser Leu Pro Ala Arg
    2465            2470            2475

His Gln Val His Gly Ser Arg Leu Arg Leu Leu Gln Val Thr Pro
    2480            2485            2490

Thr Asp Ser Gly Glu Tyr Val Cys Arg Val Val Ser Gly Ser Gly
    2495            2500            2505

Thr Gln Glu Ala Ser Ile Leu Val Thr Ile Gln Gln Thr Leu Ser
    2510            2515            2520

Pro Ser His Ser Gln Ser Val Val His Pro Val Arg Ile Glu Ser
    2525            2530            2535

Ser Ser Pro Ser Leu Ala Asn Gly His Thr Leu Asp Leu Asn Cys
    2540            2545            2550

Leu Val Ala Ser Leu Thr Pro His Thr Ile Thr Trp Tyr Lys Arg
    2555            2560            2565

Gly Gly Ser Leu Pro Ser Arg His Gln Ile Val Gly Ser Arg Leu
    2570            2575            2580

Arg Ile Pro Gln Val Thr Pro Ala Asp Ser Gly Glu Tyr Val Cys
    2585            2590            2595

His Val Ser Asn Gly Ala Gly Ser Gln Glu Thr Ser Leu Ile Val
    2600            2605            2610

Thr Ile Glu Ser Arg Gly Pro Ser His Val Pro Ser Val Ser Pro
    2615            2620            2625

Pro Met Arg Ile Glu Thr Ser Ser Pro Thr Val Thr Glu Gly Gln
    2630            2635            2640

Thr Leu Asp Leu Asn Cys Val Val Val Gly Arg Pro Gln Ala Thr
    2645            2650            2655

Ile Thr Trp Tyr Lys Arg Gly Gly Ser Leu Pro Phe Arg His Gln
    2660            2665            2670

Ala His Gly Ser Arg Leu Arg Leu His His Met Ser Val Ala Asp
    2675            2680            2685

Ser Gly Glu Tyr Val Cys Arg Ala Asn Asn Asn Ile Asp Ala Gln
    2690            2695            2700

Glu Thr Ser Ile Met Ile Ser Val Ser Pro Ser Thr Asn Ser Pro
    2705            2710            2715

Pro Ala Pro Ala Ser Pro Ala Pro Ile Arg Ile Glu Ser Ser Ser
    2720            2725            2730

Ser Arg Val Ala Glu Gly Gln Thr Leu Asp Leu Asn Cys Val Val
    2735            2740            2745
```

```
Pro Gly His Ala His Ala Gln Val Thr Trp His Lys Arg Gly Gly
    2750                2755                2760

Ser Leu Pro Thr His His Gln Thr His Gly Ser Arg Leu Arg Leu
    2765                2770                2775

Tyr Gln Val Ser Ser Ala Asp Ser Gly Glu Tyr Val Cys Ser Val
    2780                2785                2790

Leu Ser Ser Ser Gly Pro Leu Glu Ala Ser Val Leu Val Ser Ile
    2795                2800                2805

Thr Pro Ala Ala Ala Asn Val His Ile Pro Gly Glu Val Pro Phe
    2810                2815                2820

Pro Pro Ile Arg Ile Glu Thr Ser Ser Ser Arg Val Ala Glu Gly
    2825                2830                2835

Gln Thr Leu Asp Leu Ser Cys Val Val Pro Gly Gln Ala His Ala
    2840                2845                2850

Gln Val Thr Trp His Lys Arg Gly Gly Ser Leu Pro Ala Gly His
    2855                2860                2865

Gln Val His Gly His Met Leu Arg Leu Asn Arg Val Ser Pro Ala
    2870                2875                2880

Asp Ser Gly Glu Tyr Ser Cys Gln Val Thr Gly Ser Ser Gly Thr
    2885                2890                2895

Leu Glu Ala Ser Val Leu Val Thr Ile Glu Ala Ser Glu Pro Ser
    2900                2905                2910

Pro Ile Pro Ala Pro Gly Leu Ala Gln Pro Val Tyr Ile Glu Ser
    2915                2920                2925

Ser Ser Ser His Leu Thr Glu Gly Gln Thr Val Asp Leu Lys Cys
    2930                2935                2940

Val Val Pro Gly Gln Ala His Ala Gln Val Thr Trp His Lys Arg
    2945                2950                2955

Gly Ser Ser Leu Pro Ala Arg His Gln Thr His Gly Ser Leu Leu
    2960                2965                2970

Arg Leu Tyr Gln Leu Ser Pro Ala Asp Ser Gly Glu Tyr Val Cys
    2975                2980                2985

Gln Val Ala Gly Ser Ser His Pro Glu His Glu Ala Ser Phe Lys
    2990                2995                3000

Leu Thr Val Pro Ser Ser Gln Asn Ser Ser Phe Arg Leu Arg Ser
    3005                3010                3015

Pro Val Ile Ser Ile Glu Pro Pro Ser Ser Thr Val Gln Gln Gly
    3020                3025                3030

Gln Asp Ala Ser Phe Lys Cys Leu Ile His Glu Gly Ala Thr Pro
    3035                3040                3045

Ile Lys Val Glu Trp Lys Ile Arg Asp Gln Glu Leu Glu Asp Asn
    3050                3055                3060

Val His Ile Ser Pro Asn Gly Ser Ile Ile Thr Ile Val Gly Thr
    3065                3070                3075

Arg Pro Ser Asn His Gly Ala Tyr Arg Cys Val Ala Ser Asn Val
    3080                3085                3090

Tyr Gly Met Ala Gln Ser Val Val Asn Leu Ser Val His Gly Pro
    3095                3100                3105

Pro Thr Val Ser Val Leu Pro Glu Gly Pro Val His Val Lys Met
    3110                3115                3120

Gly Lys Asp Ile Thr Leu Glu Cys Ile Ser Ser Gly Glu Pro Arg
    3125                3130                3135

Ser Ser Pro Arg Trp Thr Arg Leu Gly Ile Pro Val Lys Leu Glu
```

-continued

Pro Arg Met Phe Gly Leu Met Asn Ser His Ala Met Leu Lys Ile
3140            3145            3150
                3155            3160            3165

Ala Ser Val Lys Pro Ser Asp Ala Gly Thr Tyr Val Cys Gln Ala
3170            3175            3180

Gln Asn Ala Leu Gly Thr Ala Gln Lys Gln Val Glu Leu Ile Val
3185            3190            3195

Asp Thr Gly Thr Val Ala Pro Gly Ala Pro Gln Val Gln Val Glu
3200            3205            3210

Glu Ser Glu Leu Thr Leu Glu Ala Gly His Thr Ala Thr Leu His
3215            3220            3225

Cys Ser Ala Thr Gly Asn Pro Pro Pro Thr Ile His Trp Ser Lys
3230            3235            3240

Leu Arg Ala Pro Leu Pro Trp Gln His Arg Ile Glu Gly Asn Thr
3245            3250            3255

Leu Val Ile Pro Arg Val Ala Gln Gln Asp Ser Gly Gln Tyr Ile
3260            3265            3270

Cys Asn Ala Thr Asn Ser Ala Gly His Thr Glu Ala Thr Val Val
3275            3280            3285

Leu His Val Glu Ser Pro Pro Tyr Ala Thr Ile Pro Glu His
3290            3295            3300

Thr Ser Ala Gln Pro Gly Asn Leu Val Gln Leu Gln Cys Leu Ala
3305            3310            3315

His Gly Thr Pro Pro Leu Thr Tyr Gln Trp Ser Leu Val Gly Gly
3320            3325            3330

Val Leu Pro Glu Lys Ala Val Ala Arg Asn Gln Val Leu Arg Leu
3335            3340            3345

Glu Pro Thr Val Pro Glu Asp Ser Gly Arg Tyr Arg Cys Gln Val
3350            3355            3360

Ser Asn Arg Val Gly Ser Ala Glu Ala Phe Ala Gln Val Leu Val
3365            3370            3375

Gln Gly Ser Ser Ser Asn Leu Pro Asp Thr Ser Ile Pro Gly Gly
3380            3385            3390

Ser Thr Pro Thr Val Gln Val Thr Pro Gln Leu Glu Thr Arg Asn
3395            3400            3405

Ile Gly Ala Ser Val Glu Phe His Cys Ala Val Pro Asn Glu Arg
3410            3415            3420

Gly Thr His Leu Arg Trp Leu Lys Glu Gly Gly Gln Leu Pro Pro
3425            3430            3435

Gly His Ser Val Gln Asp Gly Val Leu Arg Ile Gln Asn Leu Asp
3440            3445            3450

Gln Ser Cys Gln Gly Thr Tyr Val Cys Gln Ala His Gly Pro Trp
3455            3460            3465

Gly Gln Ala Gln Ala Thr Ala Gln Leu Ile Val Gln Ala Leu Pro
3470            3475            3480

Ser Val Leu Ile Asn Val Arg Thr Ser Val His Ser Val Val Val
3485            3490            3495

Gly His Ser Val Glu Phe Glu Cys Leu Ala Leu Gly Asp Pro Lys
3500            3505            3510

Pro Gln Val Thr Trp Ser Lys Val Gly Gly His Leu Arg Pro Gly
3515            3520            3525

Ile Val Gln Ser Gly Ser Ile Ile Arg Ile Ala His Val Glu Leu
3530            3535            3540

```
Ala Asp Ala Gly Gln Tyr Arg Cys Ala Ala Thr Asn Ala Ala Gly
3545                3550                3555

Thr Thr Gln Ser His Val Leu Leu Val Gln Ala Leu Pro Gln
3560                3565                3570

Ile Ser Thr Pro Pro Glu Ile Arg Val Pro Ala Gly Ser Ala Ala
3575                3580                3585

Val Phe Pro Cys Met Ala Ser Gly Tyr Pro Thr Pro Ala Ile Thr
3590                3595                3600

Trp Ser Lys Val Asp Gly Asp Leu Pro Pro Asp Ser Arg Leu Glu
3605                3610                3615

Asn Asn Met Leu Met Leu Pro Ser Val Arg Pro Glu Asp Ala Gly
3620                3625                3630

Thr Tyr Val Cys Thr Ala Thr Asn Arg Gln Gly Lys Val Lys Ala
3635                3640                3645

Phe Ala Tyr Leu Gln Val Pro Glu Arg Val Ile Pro Tyr Phe Thr
3650                3655                3660

Gln Thr Pro Tyr Ser Phe Leu Pro Leu Pro Thr Ile Lys Asp Ala
3665                3670                3675

Tyr Arg Lys Phe Glu Ile Lys Ile Thr Phe Arg Pro Asp Ser Ala
3680                3685                3690

Asp Gly Met Leu Leu Tyr Asn Gly Gln Lys Arg Ser Pro Thr Asn
3695                3700                3705

Leu Ala Asn Arg Gln Pro Asp Phe Ile Ser Phe Gly Leu Val Gly
3710                3715                3720

Gly Arg Pro Glu Phe Arg Phe Asp Ala Gly Ser Gly Met Ala Thr
3725                3730                3735

Ile Arg His Pro Thr Pro Leu Ala Leu Gly Gln Phe His Thr Val
3740                3745                3750

Thr Leu Leu Arg Ser Leu Thr Gln Gly Ser Leu Ile Val Gly Asn
3755                3760                3765

Leu Ala Pro Val Asn Gly Thr Ser Gln Gly Lys Phe Gln Gly Leu
3770                3775                3780

Asp Leu Asn Glu Glu Leu Tyr Leu Gly Gly Tyr Pro Asp Tyr Gly
3785                3790                3795

Ala Ile Pro Lys Ala Gly Leu Ser Ser Gly Phe Val Gly Cys Val
3800                3805                3810

Arg Glu Leu Arg Ile Gln Gly Glu Glu Val Val Phe His Asp Val
3815                3820                3825

Asn Leu Thr Thr His Gly Ile Ser His Cys Pro Thr Cys Gln Asp
3830                3835                3840

Arg Pro Cys Gln Asn Gly Gly Gln Cys Gln Asp Ser Glu Ser Ser
3845                3850                3855

Ser Tyr Thr Cys Val Cys Pro Ala Gly Phe Thr Gly Ser Arg Cys
3860                3865                3870

Glu His Ser Gln Ala Leu His Cys His Pro Glu Ala Cys Gly Pro
3875                3880                3885

Asp Ala Thr Cys Val Asn Arg Pro Asp Gly Arg Gly Tyr Thr Cys
3890                3895                3900

Arg Cys His Leu Gly Arg Ser Gly Val Arg Cys Glu Glu Gly Val
3905                3910                3915

Thr Val Thr Thr Pro Ser Met Ser Gly Ala Gly Ser Tyr Leu Ala
3920                3925                3930
```

-continued

| | | | | | | | | | | |
|---|---|---|---|---|---|---|---|---|---|---|
|Leu|Pro|Ala|Leu|Thr|Asn|Met|His|His|Glu|Leu|Arg|Leu|Asp|Val|
| |3935| | | |3940| | | | |3945| | | | |

Glu Phe Lys Pro Leu Glu Pro Asn Gly Ile Leu Leu Phe Ser Gly
    3950            3955            3960

Gly Lys Ser Gly Pro Val Glu Asp Phe Val Ser Leu Ala Met Val
    3965            3970            3975

Gly Gly His Leu Glu Phe Arg Tyr Glu Leu Gly Ser Gly Leu Ala
    3980            3985            3990

Val Leu Arg Ser His Glu Pro Leu Thr Leu Gly Arg Trp His Arg
    3995            4000            4005

Val Ser Ala Glu Arg Leu Asn Lys Asp Gly Ser Leu Arg Val Asp
    4010            4015            4020

Gly Gly Arg Pro Val Leu Arg Ser Ser Pro Gly Lys Ser Gln Gly
    4025            4030            4035

Leu Asn Leu His Thr Leu Leu Tyr Leu Gly Gly Val Glu Pro Ser
    4040            4045            4050

Val Gln Leu Ser Pro Ala Thr Asn Met Ser Ala His Phe His Gly
    4055            4060            4065

Cys Val Gly Glu Val Ser Val Asn Gly Lys Arg Leu Asp Leu Thr
    4070            4075            4080

Tyr Ser Phe Leu Gly Ser Gln Gly Val Gly Gln Cys Tyr Asp Ser
    4085            4090            4095

Ser Pro Cys Glu Arg Gln Pro Cys Gln Asn Gly Ala Thr Cys Met
    4100            4105            4110

Pro Ala Gly Glu Tyr Glu Phe Gln Cys Leu Cys Gln Asp Gly Phe
    4115            4120            4125

Lys Gly Asp Leu Cys Glu His Glu Glu Asn Pro Cys Gln Leu His
    4130            4135            4140

Glu Pro Cys Leu Asn Gly Gly Thr Cys Arg Gly Ala Arg Cys Leu
    4145            4150            4155

Cys Leu Pro Gly Phe Ser Gly Pro Arg Cys Gln Gln Gly Ala Gly
    4160            4165            4170

Tyr Gly Val Val Glu Ser Asp Trp His Pro Glu Gly Ser Gly Gly
    4175            4180            4185

Asn Asp Ala Pro Gly Gln Tyr Gly Ala Tyr Phe Tyr Asp Asn Gly
    4190            4195            4200

Phe Leu Gly Leu Pro Gly Asn Ser Phe Ser Arg Ser Leu Pro Glu
    4205            4210            4215

Val Pro Glu Thr Ile Glu Phe Glu Val Arg Thr Ser Thr Ala Asp
    4220            4225            4230

Gly Leu Leu Leu Trp Gln Gly Val Val Arg Glu Ala Ser Arg Ser
    4235            4240            4245

Lys Asp Phe Ile Ser Leu Gly Leu Gln Asp Gly His Leu Val Phe
    4250            4255            4260

Ser Tyr Gln Leu Gly Ser Gly Glu Ala Arg Leu Val Ser Glu Asp
    4265            4270            4275

Pro Ile Asn Asp Gly Glu Trp His Arg Ile Thr Ala Leu Arg Glu
    4280            4285            4290

Gly Gln Arg Gly Ser Ile Gln Val Asp Gly Glu Asp Leu Val Thr
    4295            4300            4305

Gly Arg Ser Pro Gly Pro Asn Val Ala Val Asn Thr Lys Asp Ile
    4310            4315            4320

Ile Tyr Ile Gly Gly Ala Pro Asp Val Ala Thr Leu Thr Arg Gly

```
                4325                4330                4335
Lys Phe Ser Ser Gly Ile Thr Gly Cys Ile Lys Asn Leu Val Leu
        4340                4345                4350
His Thr Ala Arg Pro Gly Ala Pro Pro Pro Gln Pro Leu Asp Leu
        4355                4360                4365
Gln His Arg Ala Gln Ala Gly Ala Asn Thr Arg Pro Cys Pro Ser
        4370                4375                4380

<210> SEQ ID NO 4
<211> LENGTH: 2068
<212> TYPE: PRT
<213> ORGANISM: Homo sapiens

<400> SEQUENCE: 4

Met Ala Gly Arg Ser His Pro Gly Pro Leu Arg Pro Leu Pro Leu
1               5                   10                  15
Leu Val Val Ala Ala Cys Val Leu Pro Gly Ala Gly Gly Thr Cys Pro
                20                  25                  30
Glu Arg Ala Leu Glu Arg Arg Glu Glu Ala Asn Val Val Leu Thr
                35                  40                  45
Gly Thr Val Glu Glu Ile Leu Asn Val Asp Pro Val Gln His Thr Tyr
50                  55                  60
Ser Cys Lys Val Arg Val Trp Arg Tyr Leu Lys Gly Lys Asp Leu Val
65                  70                  75                  80
Ala Arg Glu Ser Leu Leu Asp Gly Gly Asn Lys Val Val Ile Ser Gly
                85                  90                  95
Phe Gly Asp Pro Leu Ile Cys Asp Asn Gln Val Ser Thr Gly Asp Thr
                100                 105                 110
Arg Ile Phe Phe Val Asn Pro Ala Pro Pro Tyr Leu Trp Pro Ala His
                115                 120                 125
Lys Asn Glu Leu Met Leu Asn Ser Ser Leu Met Arg Ile Thr Leu Arg
130                 135                 140
Asn Leu Glu Glu Val Glu Phe Cys Val Glu Asp Lys Pro Gly Thr His
145                 150                 155                 160
Phe Thr Pro Val Pro Pro Thr Pro Pro Asp Ala Cys Arg Gly Met Leu
                165                 170                 175
Cys Gly Phe Gly Ala Val Cys Glu Pro Asn Ala Glu Gly Pro Gly Arg
                180                 185                 190
Ala Ser Cys Val Cys Lys Lys Ser Pro Cys Pro Ser Val Val Ala Pro
                195                 200                 205
Val Cys Gly Ser Asp Ala Ser Thr Tyr Ser Asn Glu Cys Glu Leu Gln
                210                 215                 220
Arg Ala Gln Cys Ser Gln Gln Arg Arg Ile Arg Leu Leu Ser Arg Gly
225                 230                 235                 240
Pro Cys Gly Ser Arg Asp Pro Cys Ser Asn Val Thr Cys Ser Phe Gly
                245                 250                 255
Ser Thr Cys Ala Arg Ser Ala Asp Gly Leu Thr Ala Ser Cys Leu Cys
                260                 265                 270
Pro Ala Thr Cys Arg Gly Ala Pro Glu Gly Thr Val Cys Gly Ser Asp
                275                 280                 285
Gly Ala Asp Tyr Pro Gly Glu Cys Gln Leu Leu Arg Arg Ala Cys Ala
                290                 295                 300
Arg Gln Glu Asn Val Phe Lys Lys Phe Asp Gly Pro Cys Asp Pro Cys
305                 310                 315                 320
```

-continued

```
Gln Gly Ala Leu Pro Asp Pro Ser Arg Ser Cys Arg Val Asn Pro Arg
            325                 330                 335
Thr Arg Arg Pro Glu Met Leu Leu Arg Pro Glu Ser Cys Pro Ala Arg
            340                 345                 350
Gln Ala Pro Val Cys Gly Asp Asp Gly Val Thr Tyr Glu Asn Asp Cys
            355                 360                 365
Val Met Gly Arg Ser Gly Ala Ala Arg Gly Leu Leu Leu Gln Lys Val
            370                 375             380
Arg Ser Gly Gln Cys Gln Gly Arg Asp Gln Pro Glu Pro Cys Arg
385                 390                 395                 400
Phe Asn Ala Val Cys Leu Ser Arg Arg Gly Arg Pro Arg Cys Ser Cys
                405                 410                 415
Asp Arg Val Thr Cys Asp Gly Ala Tyr Arg Pro Val Cys Ala Gln Asp
                420                 425                 430
Gly Arg Thr Tyr Asp Ser Asp Cys Trp Arg Gln Gln Ala Glu Cys Arg
            435                 440                 445
Gln Gln Arg Ala Ile Pro Ser Lys His Gln Gly Pro Cys Asp Gln Ala
            450                 455                 460
Pro Ser Pro Cys Leu Gly Val Gln Cys Ala Phe Gly Ala Thr Cys Ala
465                 470                 475                 480
Val Lys Asn Gly Gln Ala Ala Cys Glu Cys Leu Gln Ala Cys Ser Ser
                485                 490                 495
Leu Tyr Asp Pro Val Cys Gly Ser Asp Gly Val Thr Tyr Gly Ser Ala
                500                 505                 510
Cys Glu Leu Glu Ala Thr Ala Cys Thr Leu Gly Arg Glu Ile Gln Val
            515                 520                 525
Ala Arg Lys Gly Pro Cys Asp Arg Cys Gly Gln Cys Arg Phe Gly Ala
            530                 535                 540
Leu Cys Glu Ala Glu Thr Gly Arg Cys Val Cys Pro Ser Glu Cys Val
545                 550                 555                 560
Ala Leu Ala Gln Pro Val Cys Gly Ser Asp Gly His Thr Tyr Pro Ser
                565                 570                 575
Glu Cys Met Leu His Val His Ala Cys Thr His Gln Ile Ser Leu His
            580                 585                 590
Val Ala Ser Ala Gly Pro Cys Glu Thr Cys Gly Asp Ala Val Cys Ala
            595                 600                 605
Phe Gly Ala Val Cys Ser Ala Gly Gln Cys Val Cys Pro Arg Cys Glu
            610                 615                 620
His Pro Pro Pro Gly Pro Val Cys Gly Ser Asp Gly Val Thr Tyr Gly
625                 630                 635                 640
Ser Ala Cys Glu Leu Arg Glu Ala Ala Cys Leu Gln Gln Thr Gln Ile
                645                 650                 655
Glu Glu Ala Arg Ala Gly Pro Cys Glu Gln Ala Glu Cys Gly Ser Gly
            660                 665                 670
Gly Ser Gly Ser Gly Glu Asp Gly Asp Cys Glu Gln Glu Leu Cys Arg
            675                 680                 685
Gln Arg Gly Gly Ile Trp Asp Glu Asp Ser Glu Asp Gly Pro Cys Val
            690                 695                 700
Cys Asp Phe Ser Cys Gln Ser Val Pro Gly Ser Pro Val Cys Gly Ser
705                 710                 715                 720
Asp Gly Val Thr Tyr Ser Thr Glu Cys Glu Leu Lys Lys Ala Arg Cys
                725                 730                 735
Glu Ser Gln Arg Gly Leu Tyr Val Ala Ala Gln Gly Ala Cys Arg Gly
```

-continued

```
            740                 745                 750
Pro Thr Phe Ala Pro Leu Pro Pro Val Ala Pro Leu His Cys Ala Gln
            755                 760                 765
Thr Pro Tyr Gly Cys Cys Gln Asp Asn Ile Thr Ala Ala Arg Gly Val
    770                 775                 780
Gly Leu Ala Gly Cys Pro Ser Ala Cys Gln Cys Asn Pro His Gly Ser
785                 790                 795                 800
Tyr Gly Gly Thr Cys Asp Pro Ala Thr Gly Gln Cys Ser Cys Arg Pro
                805                 810                 815
Gly Val Gly Gly Leu Arg Cys Asp Arg Cys Glu Pro Gly Phe Trp Asn
            820                 825                 830
Phe Arg Gly Ile Val Thr Asp Gly Arg Ser Gly Cys Thr Pro Cys Ser
            835                 840                 845
Cys Asp Pro Gln Gly Ala Val Arg Asp Asp Cys Glu Gln Met Thr Gly
        850                 855                 860
Leu Cys Ser Cys Lys Pro Gly Val Ala Gly Pro Lys Cys Gly Gln Cys
865                 870                 875                 880
Pro Asp Gly Arg Ala Leu Gly Pro Ala Gly Cys Glu Ala Asp Ala Ser
                885                 890                 895
Ala Pro Ala Thr Cys Ala Glu Met Arg Cys Glu Phe Gly Ala Arg Cys
                900                 905                 910
Val Glu Glu Ser Gly Ser Ala His Cys Val Cys Pro Met Leu Thr Cys
            915                 920                 925
Pro Glu Ala Asn Ala Thr Lys Val Cys Gly Ser Asp Gly Val Thr Tyr
        930                 935                 940
Gly Asn Glu Cys Gln Leu Lys Thr Ile Ala Cys Arg Gln Gly Leu Gln
945                 950                 955                 960
Ile Ser Ile Gln Ser Leu Gly Pro Cys Gln Glu Ala Val Ala Pro Ser
                965                 970                 975
Thr His Pro Thr Ser Ala Ser Val Thr Val Thr Thr Pro Gly Leu Leu
            980                 985                 990
Leu Ser Gln Ala Leu Pro Ala Pro  Pro Gly Ala Leu Pro  Leu Ala Pro
            995                 1000                1005
Ser Ser  Thr Ala His Ser Gln  Thr Thr Pro Pro  Ser Ser Arg
        1010                1015                1020
Pro Arg  Thr Thr Ala Ser Val  Pro Arg Thr Thr Val  Trp Pro Val
        1025                1030                1035
Leu Thr  Val Pro Pro Thr Ala  Pro Ser Pro Ala Pro  Ser Leu Val
        1040                1045                1050
Ala Ser  Ala Phe Gly Glu Ser  Gly Ser Thr Asp Gly  Ser Ser Asp
        1055                1060                1065
Glu Glu  Leu Ser Gly Asp Gln  Glu Ala Ser Gly Gly  Gly Ser Gly
        1070                1075                1080
Gly Leu  Glu Pro Leu Glu Gly  Ser Ser Val Ala Thr  Pro Gly Pro
        1085                1090                1095
Pro Val  Glu Arg Ala Ser Cys  Tyr Asn Ser Ala Leu  Gly Cys Cys
        1100                1105                1110
Ser Asp  Gly Lys Thr Pro Ser  Leu Asp Ala Glu Gly  Ser Asn Cys
        1115                1120                1125
Pro Ala  Thr Lys Val Phe Gln  Gly Val Leu Glu Leu  Glu Gly Val
        1130                1135                1140
Glu Gly  Gln Glu Leu Phe Tyr  Thr Pro Glu Met Ala  Asp Pro Lys
        1145                1150                1155
```

```
Ser Glu Leu Phe Gly Glu Thr Ala Arg Ser Ile Glu Ser Thr Leu
    1160            1165            1170

Asp Asp Leu Phe Arg Asn Ser Asp Val Lys Lys Asp Phe Arg Ser
    1175            1180            1185

Val Arg Leu Arg Asp Leu Gly Pro Gly Lys Ser Val Arg Ala Ile
    1190            1195            1200

Val Asp Val His Phe Asp Pro Thr Thr Ala Phe Arg Ala Pro Asp
    1205            1210            1215

Val Ala Arg Ala Leu Leu Arg Gln Ile Gln Val Ser Arg Arg Arg
    1220            1225            1230

Ser Leu Gly Val Arg Arg Pro Leu Gln Glu His Val Arg Phe Met
    1235            1240            1245

Asp Phe Asp Trp Phe Pro Ala Phe Ile Thr Gly Ala Thr Ser Gly
    1250            1255            1260

Ala Ile Ala Ala Gly Ala Thr Ala Arg Ala Thr Thr Ala Ser Arg
    1265            1270            1275

Leu Pro Ser Ser Ala Val Thr Pro Arg Ala Pro His Pro Ser His
    1280            1285            1290

Thr Ser Gln Pro Val Ala Lys Thr Thr Ala Ala Pro Thr Thr Arg
    1295            1300            1305

Arg Pro Pro Thr Thr Ala Pro Ser Arg Val Pro Gly Arg Arg Pro
    1310            1315            1320

Pro Ala Pro Gln Gln Pro Pro Lys Pro Cys Asp Ser Gln Pro Cys
    1325            1330            1335

Phe His Gly Gly Thr Cys Gln Asp Trp Ala Leu Gly Gly Gly Phe
    1340            1345            1350

Thr Cys Ser Cys Pro Ala Gly Arg Gly Gly Ala Val Cys Glu Lys
    1355            1360            1365

Val Leu Gly Ala Pro Val Pro Ala Phe Glu Gly Arg Ser Phe Leu
    1370            1375            1380

Ala Phe Pro Thr Leu Arg Ala Tyr His Thr Leu Arg Leu Ala Leu
    1385            1390            1395

Glu Phe Arg Ala Leu Glu Pro Gln Gly Leu Leu Leu Tyr Asn Gly
    1400            1405            1410

Asn Ala Arg Gly Lys Asp Phe Leu Ala Leu Ala Leu Leu Asp Gly
    1415            1420            1425

Arg Val Gln Leu Arg Phe Asp Thr Gly Ser Gly Pro Ala Val Leu
    1430            1435            1440

Thr Ser Ala Val Pro Val Glu Pro Gly Gln Trp His Arg Leu Glu
    1445            1450            1455

Leu Ser Arg His Trp Arg Arg Gly Thr Leu Ser Val Asp Gly Glu
    1460            1465            1470

Thr Pro Val Leu Gly Glu Ser Pro Ser Gly Thr Asp Gly Leu Asn
    1475            1480            1485

Leu Asp Thr Asp Leu Phe Val Gly Gly Val Pro Glu Asp Gln Ala
    1490            1495            1500

Ala Val Ala Leu Glu Arg Thr Phe Val Gly Ala Gly Leu Arg Gly
    1505            1510            1515

Cys Ile Arg Leu Leu Asp Val Asn Asn Gln Arg Leu Glu Leu Gly
    1520            1525            1530

Ile Gly Pro Gly Ala Ala Thr Arg Gly Ser Gly Val Gly Glu Cys
    1535            1540            1545
```

```
Gly Asp His Pro Cys Leu Pro Asn Pro Cys His Gly Ala Pro
1550                1555                1560

Cys Gln Asn Leu Glu Ala Gly Arg Phe His Cys Gln Cys Pro Pro
    1565                1570                1575

Gly Arg Val Gly Pro Thr Cys Ala Asp Glu Lys Ser Pro Cys Gln
1580                1585                1590

Pro Asn Pro Cys His Gly Ala Ala Pro Cys Arg Val Leu Pro Glu
    1595                1600                1605

Gly Gly Ala Gln Cys Glu Cys Pro Leu Gly Arg Glu Gly Thr Phe
1610                1615                1620

Cys Gln Thr Ala Ser Gly Gln Asp Gly Ser Gly Pro Phe Leu Ala
    1625                1630                1635

Asp Phe Asn Gly Phe Ser His Leu Glu Leu Arg Gly Leu His Thr
1640                1645                1650

Phe Ala Arg Asp Leu Gly Glu Lys Met Ala Leu Glu Val Val Phe
    1655                1660                1665

Leu Ala Arg Gly Pro Ser Gly Leu Leu Leu Tyr Asn Gly Gln Lys
1670                1675                1680

Thr Asp Gly Lys Gly Asp Phe Val Ser Leu Ala Leu Arg Asp Arg
    1685                1690                1695

Arg Leu Glu Phe Arg Tyr Asp Leu Gly Lys Gly Ala Ala Val Ile
1700                1705                1710

Arg Ser Arg Glu Pro Val Thr Leu Gly Ala Trp Thr Arg Val Ser
    1715                1720                1725

Leu Glu Arg Asn Gly Arg Lys Gly Ala Leu Arg Val Gly Asp Gly
1730                1735                1740

Pro Arg Val Leu Gly Glu Ser Pro Lys Ser Arg Lys Val Pro His
    1745                1750                1755

Thr Val Leu Asn Leu Lys Glu Pro Leu Tyr Val Gly Gly Ala Pro
1760                1765                1770

Asp Phe Ser Lys Leu Ala Arg Ala Ala Ala Val Ser Ser Gly Phe
    1775                1780                1785

Asp Gly Ala Ile Gln Leu Val Ser Leu Gly Gly Arg Gln Leu Leu
1790                1795                1800

Thr Pro Glu His Val Leu Arg Gln Val Asp Val Thr Ser Phe Ala
    1805                1810                1815

Gly His Pro Cys Thr Arg Ala Ser Gly His Pro Cys Leu Asn Gly
1820                1825                1830

Ala Ser Cys Val Pro Arg Glu Ala Ala Tyr Val Cys Leu Cys Pro
    1835                1840                1845

Gly Gly Phe Ser Gly Pro His Cys Glu Lys Gly Leu Val Glu Lys
1850                1855                1860

Ser Ala Gly Asp Val Asp Thr Leu Ala Phe Asp Gly Arg Thr Phe
    1865                1870                1875

Val Glu Tyr Leu Asn Ala Val Thr Glu Ser Glu Leu Ala Asn Glu
1880                1885                1890

Ile Pro Val Pro Glu Thr Leu Asp Ser Gly Ala Leu His Ser Glu
    1895                1900                1905

Lys Ala Leu Gln Ser Asn His Phe Glu Leu Ser Leu Arg Thr Glu
1910                1915                1920

Ala Thr Gln Gly Leu Val Leu Trp Ser Gly Lys Ala Thr Glu Arg
    1925                1930                1935

Ala Asp Tyr Val Ala Leu Ala Ile Val Asp Gly His Leu Gln Leu
```

```
                    1940               1945               1950

Ser Tyr Asn Leu Gly Ser Gln Pro Val Val Leu Arg Ser Thr Val
    1955               1960               1965

Pro Val Asn Thr Asn Arg Trp Leu Arg Val Val Ala His Arg Glu
    1970               1975               1980

Gln Arg Glu Gly Ser Leu Gln Val Gly Asn Glu Ala Pro Val Thr
    1985               1990               1995

Gly Ser Ser Pro Leu Gly Ala Thr Gln Leu Asp Thr Asp Gly Ala
    2000               2005               2010

Leu Trp Leu Gly Gly Leu Pro Glu Leu Pro Val Gly Pro Ala Leu
    2015               2020               2025

Pro Lys Ala Tyr Gly Thr Gly Phe Val Gly Cys Leu Arg Asp Val
    2030               2035               2040

Val Val Gly Arg His Pro Leu His Leu Leu Glu Asp Ala Val Thr
    2045               2050               2055

Lys Pro Glu Leu Arg Pro Cys Pro Thr Pro
    2060               2065

<210> SEQ ID NO 5
<211> LENGTH: 2045
<212> TYPE: PRT
<213> ORGANISM: Homo sapiens

<400> SEQUENCE: 5

Met Ala Gly Arg Ser His Pro Gly Pro Leu Arg Pro Leu Leu Pro Leu
1               5                   10                  15

Leu Val Val Ala Ala Cys Val Leu Pro Gly Ala Gly Gly Thr Cys Pro
                20                  25                  30

Glu Arg Ala Leu Glu Arg Arg Glu Glu Ala Asn Val Val Leu Thr
            35                  40                  45

Gly Thr Val Glu Glu Ile Leu Asn Val Asp Pro Val Gln His Thr Tyr
        50                  55                  60

Ser Cys Lys Val Arg Val Trp Arg Tyr Leu Lys Gly Lys Asp Leu Val
65                  70                  75                  80

Ala Arg Glu Ser Leu Leu Asp Gly Gly Asn Lys Val Val Ile Ser Gly
                85                  90                  95

Phe Gly Asp Pro Leu Ile Cys Asp Asn Gln Val Ser Thr Gly Asp Thr
            100                 105                 110

Arg Ile Phe Phe Val Asn Pro Ala Pro Pro Tyr Leu Trp Pro Ala His
        115                 120                 125

Lys Asn Glu Leu Met Leu Asn Ser Ser Leu Met Arg Ile Thr Leu Arg
    130                 135                 140

Asn Leu Glu Glu Val Glu Phe Cys Val Glu Asp Lys Pro Gly Thr His
145                 150                 155                 160

Phe Thr Pro Val Pro Pro Thr Pro Pro Asp Ala Cys Arg Gly Met Leu
                165                 170                 175

Cys Gly Phe Gly Ala Val Cys Glu Pro Asn Ala Glu Gly Pro Gly Arg
            180                 185                 190

Ala Ser Cys Val Cys Lys Lys Ser Pro Cys Pro Ser Val Val Ala Pro
        195                 200                 205

Val Cys Gly Ser Asp Ala Ser Thr Tyr Ser Asn Glu Cys Glu Leu Gln
    210                 215                 220

Arg Ala Gln Cys Ser Gln Gln Arg Arg Ile Arg Leu Leu Ser Arg Gly
225                 230                 235                 240
```

-continued

```
Pro Cys Gly Ser Arg Asp Pro Cys Ser Asn Val Thr Cys Ser Phe Gly
            245                 250                 255
Ser Thr Cys Ala Arg Ser Ala Asp Gly Leu Thr Ala Ser Cys Leu Cys
        260                 265                 270
Pro Ala Thr Cys Arg Gly Ala Pro Glu Gly Thr Val Cys Gly Ser Asp
            275                 280                 285
Gly Ala Asp Tyr Pro Gly Glu Cys Gln Leu Leu Arg Arg Ala Cys Ala
        290                 295                 300
Arg Gln Glu Asn Val Phe Lys Lys Phe Asp Gly Pro Cys Asp Pro Cys
305                 310                 315                 320
Gln Gly Ala Leu Pro Asp Pro Ser Arg Ser Cys Arg Val Asn Pro Arg
            325                 330                 335
Thr Arg Arg Pro Glu Met Leu Leu Arg Pro Glu Ser Cys Pro Ala Arg
        340                 345                 350
Gln Ala Pro Val Cys Gly Asp Asp Gly Val Thr Tyr Glu Asn Asp Cys
            355                 360                 365
Val Met Gly Arg Ser Gly Ala Ala Arg Gly Leu Leu Leu Gln Lys Val
        370                 375                 380
Arg Ser Gly Gln Cys Gln Gly Arg Asp Gln Cys Pro Glu Pro Cys Arg
385                 390                 395                 400
Phe Asn Ala Val Cys Leu Ser Arg Arg Gly Arg Pro Arg Cys Ser Cys
            405                 410                 415
Asp Arg Val Thr Cys Asp Gly Ala Tyr Arg Pro Val Cys Ala Gln Asp
            420                 425                 430
Gly Arg Thr Tyr Asp Ser Asp Cys Trp Arg Gln Gln Ala Glu Cys Arg
        435                 440                 445
Gln Gln Arg Ala Ile Pro Ser Lys His Gln Gly Pro Cys Asp Gln Ala
        450                 455                 460
Pro Ser Pro Cys Leu Gly Val Gln Cys Ala Phe Gly Ala Thr Cys Ala
465                 470                 475                 480
Val Lys Asn Gly Gln Ala Ala Cys Glu Cys Leu Gln Ala Cys Ser Ser
            485                 490                 495
Leu Tyr Asp Pro Val Cys Gly Ser Asp Gly Val Thr Tyr Gly Ser Ala
            500                 505                 510
Cys Glu Leu Glu Ala Thr Ala Cys Thr Leu Gly Arg Glu Ile Gln Val
        515                 520                 525
Ala Arg Lys Gly Pro Cys Asp Arg Cys Gly Gln Cys Arg Phe Gly Ala
        530                 535                 540
Leu Cys Glu Ala Glu Thr Gly Arg Cys Val Cys Pro Ser Glu Cys Val
545                 550                 555                 560
Ala Leu Ala Gln Pro Val Cys Gly Ser Asp Gly His Thr Tyr Pro Ser
            565                 570                 575
Glu Cys Met Leu His Val His Ala Cys Thr His Gln Ile Ser Leu His
        580                 585                 590
Val Ala Ser Ala Gly Pro Cys Glu Thr Cys Gly Asp Ala Val Cys Ala
        595                 600                 605
Phe Gly Ala Val Cys Ser Ala Gly Gln Cys Val Cys Pro Arg Cys Glu
        610                 615                 620
His Pro Pro Pro Gly Pro Val Cys Gly Ser Asp Gly Val Thr Tyr Gly
625                 630                 635                 640
Ser Ala Cys Glu Leu Arg Glu Ala Ala Cys Leu Gln Gln Thr Gln Ile
            645                 650                 655
Glu Glu Ala Arg Ala Gly Pro Cys Glu Gln Ala Glu Cys Gly Ser Gly
```

```
            660                 665                 670
Gly Ser Gly Ser Gly Glu Asp Gly Asp Cys Glu Gln Glu Leu Cys Arg
            675                 680                 685
Gln Arg Gly Gly Ile Trp Asp Glu Asp Ser Asp Gly Pro Cys Val
            690                 695                 700
Cys Asp Phe Ser Cys Gln Ser Val Pro Gly Ser Pro Val Cys Gly Ser
705                 710                 715                 720
Asp Gly Val Thr Tyr Ser Thr Glu Cys Glu Leu Lys Lys Ala Arg Cys
                    725                 730                 735
Glu Ser Gln Arg Gly Leu Tyr Val Ala Ala Gln Gly Ala Cys Arg Gly
                    740                 745                 750
Pro Thr Phe Ala Pro Leu Pro Pro Val Ala Pro Leu His Cys Ala Gln
            755                 760                 765
Thr Pro Tyr Gly Cys Cys Gln Asp Asn Ile Thr Ala Ala Arg Gly Val
            770                 775                 780
Gly Leu Ala Gly Cys Pro Ser Ala Cys Gln Cys Asn Pro His Gly Ser
785                 790                 795                 800
Tyr Gly Gly Thr Cys Asp Pro Ala Thr Gly Gln Cys Ser Cys Arg Pro
                    805                 810                 815
Gly Val Gly Gly Leu Arg Cys Asp Arg Cys Glu Pro Gly Phe Trp Asn
                    820                 825                 830
Phe Arg Gly Ile Val Thr Asp Gly Arg Ser Gly Cys Thr Pro Cys Ser
            835                 840                 845
Cys Asp Pro Gln Gly Ala Val Arg Asp Asp Cys Glu Gln Met Thr Gly
850                 855                 860
Leu Cys Ser Cys Lys Pro Gly Val Ala Gly Pro Lys Cys Gly Gln Cys
865                 870                 875                 880
Pro Asp Gly Arg Ala Leu Gly Pro Ala Gly Cys Glu Ala Asp Ala Ser
                    885                 890                 895
Ala Pro Ala Thr Cys Ala Glu Met Arg Cys Glu Phe Gly Ala Arg Cys
                    900                 905                 910
Val Glu Glu Ser Gly Ser Ala His Cys Val Cys Pro Met Leu Thr Cys
            915                 920                 925
Pro Glu Ala Asn Ala Thr Lys Val Cys Gly Ser Asp Gly Val Thr Tyr
            930                 935                 940
Gly Asn Glu Cys Gln Leu Lys Thr Ile Ala Cys Arg Gln Gly Leu Gln
945                 950                 955                 960
Ile Ser Ile Gln Ser Leu Gly Pro Cys Gln Glu Ala Val Ala Pro Ser
                    965                 970                 975
Thr His Pro Thr Ser Ala Ser Val Thr Val Thr Thr Pro Gly Leu Leu
                    980                 985                 990
Leu Ser Gln Ala Leu Pro Ala Pro Pro Gly Ala Leu Pro Leu Ala Pro
            995                 1000                1005
Ser Ser Thr Ala His Ser Gln Thr Thr Pro Pro Ser Ser Arg
            1010                1015                1020
Pro Arg Thr Thr Ala Ser Val Pro Arg Thr Thr Val Trp Pro Val
            1025                1030                1035
Leu Thr Val Pro Pro Thr Ala Pro Ser Pro Ala Pro Ser Leu Val
            1040                1045                1050
Ala Ser Ala Phe Gly Glu Ser Gly Ser Thr Asp Gly Ser Ser Asp
            1055                1060                1065
Glu Glu Leu Ser Gly Asp Gln Glu Ala Ser Gly Gly Gly Ser Gly
            1070                1075                1080
```

-continued

```
Gly Leu Glu Pro Leu Glu Gly Ser Ser Val Ala Thr Pro Gly Pro
    1085                1090                1095

Pro Val Glu Arg Ala Ser Cys Tyr Asn Ser Ala Leu Gly Cys Cys
    1100                1105                1110

Ser Asp Gly Lys Thr Pro Ser Leu Asp Ala Glu Gly Ser Asn Cys
    1115                1120                1125

Pro Ala Thr Lys Val Phe Gln Gly Val Leu Glu Leu Glu Gly Val
    1130                1135                1140

Glu Gly Gln Glu Leu Phe Tyr Thr Pro Glu Met Ala Asp Pro Lys
    1145                1150                1155

Ser Glu Leu Phe Gly Glu Thr Ala Arg Ser Ile Glu Ser Thr Leu
    1160                1165                1170

Asp Asp Leu Phe Arg Asn Ser Asp Val Lys Lys Asp Phe Arg Ser
    1175                1180                1185

Val Arg Leu Arg Asp Leu Gly Pro Gly Lys Ser Val Arg Ala Ile
    1190                1195                1200

Val Asp Val His Phe Asp Pro Thr Thr Ala Phe Arg Ala Pro Asp
    1205                1210                1215

Val Ala Arg Ala Leu Leu Arg Gln Ile Gln Val Ser Arg Arg Arg
    1220                1225                1230

Ser Leu Gly Val Arg Arg Pro Leu Gln Glu His Val Arg Phe Met
    1235                1240                1245

Asp Phe Asp Trp Phe Pro Ala Phe Ile Thr Gly Ala Thr Ser Gly
    1250                1255                1260

Ala Ile Ala Ala Gly Ala Thr Ala Arg Ala Thr Thr Ala Ser Arg
    1265                1270                1275

Leu Pro Ser Ser Ala Val Thr Pro Arg Ala Pro His Pro Ser His
    1280                1285                1290

Thr Ser Gln Pro Val Ala Lys Thr Thr Ala Ala Pro Thr Thr Arg
    1295                1300                1305

Arg Pro Pro Thr Thr Ala Pro Ser Arg Val Pro Gly Arg Arg Pro
    1310                1315                1320

Pro Ala Pro Gln Gln Pro Pro Lys Pro Cys Asp Ser Gln Pro Cys
    1325                1330                1335

Phe His Gly Gly Thr Cys Gln Asp Trp Ala Leu Gly Gly Gly Phe
    1340                1345                1350

Thr Cys Ser Cys Pro Ala Gly Arg Gly Gly Ala Val Cys Glu Lys
    1355                1360                1365

Val Leu Gly Ala Pro Val Pro Ala Phe Glu Gly Arg Ser Phe Leu
    1370                1375                1380

Ala Phe Pro Thr Leu Arg Ala Tyr His Thr Leu Arg Leu Ala Leu
    1385                1390                1395

Glu Phe Arg Ala Leu Glu Pro Gln Gly Leu Leu Leu Tyr Asn Gly
    1400                1405                1410

Asn Ala Arg Gly Lys Asp Phe Leu Ala Leu Ala Leu Leu Asp Gly
    1415                1420                1425

Arg Val Gln Leu Arg Phe Asp Thr Gly Ser Gly Pro Ala Val Leu
    1430                1435                1440

Thr Ser Ala Val Pro Val Glu Pro Gly Gln Trp His Arg Leu Glu
    1445                1450                1455

Leu Ser Arg His Trp Arg Arg Gly Thr Leu Ser Val Asp Gly Glu
    1460                1465                1470
```

```
Thr Pro Val Leu Gly Glu Ser Pro Ser Gly Thr Asp Gly Leu Asn
    1475                1480                1485

Leu Asp Thr Asp Leu Phe Val Gly Gly Val Pro Glu Asp Gln Ala
    1490                1495                1500

Ala Val Ala Leu Glu Arg Thr Phe Val Gly Ala Gly Leu Arg Gly
    1505                1510                1515

Cys Ile Arg Leu Leu Asp Val Asn Asn Gln Arg Leu Glu Leu Gly
    1520                1525                1530

Ile Gly Pro Gly Ala Ala Thr Arg Gly Ser Gly Val Gly Glu Cys
    1535                1540                1545

Gly Asp His Pro Cys Leu Pro Asn Pro Cys His Gly Gly Ala Pro
    1550                1555                1560

Cys Gln Asn Leu Glu Ala Gly Arg Phe His Cys Gln Cys Pro Pro
    1565                1570                1575

Gly Arg Val Gly Pro Thr Cys Ala Asp Glu Lys Ser Pro Cys Gln
    1580                1585                1590

Pro Asn Pro Cys His Gly Ala Ala Pro Cys Arg Val Leu Pro Glu
    1595                1600                1605

Gly Gly Ala Gln Cys Glu Cys Pro Leu Gly Arg Glu Gly Thr Phe
    1610                1615                1620

Cys Gln Thr Ala Ser Gly Gln Asp Gly Ser Gly Pro Phe Leu Ala
    1625                1630                1635

Asp Phe Asn Gly Phe Ser His Leu Glu Leu Arg Gly Leu His Thr
    1640                1645                1650

Phe Ala Arg Asp Leu Gly Glu Lys Met Ala Leu Glu Val Val Phe
    1655                1660                1665

Leu Ala Arg Gly Pro Ser Gly Leu Leu Leu Tyr Asn Gly Gln Lys
    1670                1675                1680

Thr Asp Gly Lys Gly Asp Phe Val Ser Leu Ala Leu Arg Asp Arg
    1685                1690                1695

Arg Leu Glu Phe Arg Tyr Asp Leu Gly Lys Gly Ala Ala Val Ile
    1700                1705                1710

Arg Ser Arg Glu Pro Val Thr Leu Gly Ala Trp Thr Arg Val Ser
    1715                1720                1725

Leu Glu Arg Asn Gly Arg Lys Gly Ala Leu Arg Val Gly Asp Gly
    1730                1735                1740

Pro Arg Val Leu Gly Glu Ser Pro Val Pro His Thr Val Leu Asn
    1745                1750                1755

Leu Lys Glu Pro Leu Tyr Val Gly Gly Ala Pro Asp Phe Ser Lys
    1760                1765                1770

Leu Ala Arg Ala Ala Ala Val Ser Ser Gly Phe Asp Gly Ala Ile
    1775                1780                1785

Gln Leu Val Ser Leu Gly Gly Arg Gln Leu Leu Thr Pro Glu His
    1790                1795                1800

Val Leu Arg Gln Val Asp Val Thr Ser Phe Ala Gly His Pro Cys
    1805                1810                1815

Thr Arg Ala Ser Gly His Pro Cys Leu Asn Gly Ala Ser Cys Val
    1820                1825                1830

Pro Arg Glu Ala Ala Tyr Val Cys Leu Cys Pro Gly Gly Phe Ser
    1835                1840                1845

Gly Pro His Cys Glu Lys Gly Leu Val Glu Lys Ser Ala Gly Asp
    1850                1855                1860

Val Asp Thr Leu Ala Phe Asp Gly Arg Thr Phe Val Glu Tyr Leu
```

```
                1865                1870                1875
Asn Ala Val Thr Glu Ser Glu Lys Ala Leu Gln Ser Asn His Phe
                1880                1885                1890

Glu Leu Ser Leu Arg Thr Glu Ala Thr Gln Gly Leu Val Leu Trp
                1895                1900                1905

Ser Gly Lys Ala Thr Glu Arg Ala Asp Tyr Val Ala Leu Ala Ile
                1910                1915                1920

Val Asp Gly His Leu Gln Leu Ser Tyr Asn Leu Gly Ser Gln Pro
                1925                1930                1935

Val Val Leu Arg Ser Thr Val Pro Val Asn Thr Asn Arg Trp Leu
                1940                1945                1950

Arg Val Val Ala His Arg Glu Gln Arg Glu Gly Ser Leu Gln Val
                1955                1960                1965

Gly Asn Glu Ala Pro Val Thr Gly Ser Ser Pro Leu Gly Ala Thr
                1970                1975                1980

Gln Leu Asp Thr Asp Gly Ala Leu Trp Leu Gly Gly Leu Pro Glu
                1985                1990                1995

Leu Pro Val Gly Pro Ala Leu Pro Lys Ala Tyr Gly Thr Gly Phe
                2000                2005                2010

Val Gly Cys Leu Arg Asp Val Val Gly Arg His Pro Leu His
                2015                2020                2025

Leu Leu Glu Asp Ala Val Thr Lys Pro Glu Leu Arg Pro Cys Pro
                2030                2035                2040

Thr Pro
    2045

<210> SEQ ID NO 6
<211> LENGTH: 1940
<212> TYPE: PRT
<213> ORGANISM: Rattus norvegicus

<400> SEQUENCE: 6

Met Pro Pro Leu Pro Leu Glu His Arg Pro Arg Gln Pro Gly Ala
1               5                   10                  15

Ser Met Leu Val Arg Tyr Phe Met Ile Pro Cys Asn Ile Cys Leu Ile
                20                  25                  30

Leu Leu Ala Thr Ser Thr Leu Gly Phe Ala Val Leu Leu Phe Leu Ser
                35                  40                  45

Asn Tyr Lys Pro Gly Ile His Phe Thr Pro Ala Pro Pro Thr Pro Pro
50                  55                  60

Asp Val Cys Arg Gly Met Leu Cys Gly Phe Gly Ala Val Cys Glu Pro
65                  70                  75                  80

Ser Val Glu Asp Pro Gly Arg Ala Ser Cys Val Cys Lys Lys Asn Ala
                85                  90                  95

Cys Pro Ala Thr Val Ala Pro Val Cys Gly Ser Asp Ala Ser Thr Tyr
                100                 105                 110

Ser Asn Glu Cys Glu Leu Gln Arg Ala Gln Cys Asn Gln Gln Arg Arg
                115                 120                 125

Ile Arg Leu Leu Arg Gln Gly Pro Cys Gly Ser Arg Asp Pro Cys Ala
                130                 135                 140

Asn Val Thr Cys Ser Phe Gly Ser Thr Cys Val Pro Ser Ala Asp Gly
145                 150                 155                 160

Gln Thr Ala Ser Cys Leu Cys Pro Thr Thr Cys Phe Gly Ala Pro Asp
                165                 170                 175
```

-continued

Gly Thr Val Cys Gly Ser Asp Gly Val Asp Tyr Pro Ser Glu Cys Gln
            180                 185                 190

Leu Leu Ser His Ala Cys Ala Ser Gln Glu His Ile Phe Lys Lys Phe
        195                 200                 205

Asn Gly Pro Cys Asp Pro Cys Gln Gly Ser Met Ser Asp Leu Asn His
        210                 215                 220

Ile Cys Arg Val Asn Pro Arg Thr His Pro Glu Met Leu Leu Arg
225                 230                 235                 240

Pro Glu Asn Cys Pro Ala Gln His Thr Pro Ile Cys Gly Asp Asp Gly
                245                 250                 255

Val Thr Tyr Glu Asn Asp Cys Val Met Ser Arg Ile Gly Ala Thr Arg
                260                 265                 270

Gly Leu Leu Leu Gln Lys Val Arg Ser Gly Gln Cys Gln Thr Arg Asp
            275                 280                 285

Gln Cys Pro Glu Thr Cys Gln Phe Asn Ser Val Cys Leu Ser Arg Arg
        290                 295                 300

Gly Arg Pro His Cys Ser Cys Asp Arg Val Thr Cys Asp Gly Ser Tyr
305                 310                 315                 320

Arg Pro Val Cys Ala Gln Asp Gly His Thr Tyr Asn Asn Asp Cys Trp
                325                 330                 335

Arg Gln Gln Ala Glu Cys Arg Gln Gln Arg Ala Ile Pro Pro Lys His
                340                 345                 350

Gln Gly Pro Cys Asp Gln Thr Pro Ser Pro Cys His Gly Val Gln Cys
            355                 360                 365

Ala Phe Gly Ala Val Cys Thr Val Lys Asn Gly Lys Ala Glu Cys Glu
        370                 375                 380

Cys Gln Arg Val Cys Ser Gly Ile Tyr Asp Pro Val Cys Gly Ser Asp
385                 390                 395                 400

Gly Val Thr Tyr Gly Ser Val Cys Glu Leu Glu Ser Met Ala Cys Thr
                405                 410                 415

Leu Gly Arg Glu Ile Gln Val Ala Arg Arg Gly Pro Cys Asp Pro Cys
            420                 425                 430

Gly Gln Cys Arg Phe Gly Ser Leu Cys Glu Val Glu Thr Gly Arg Cys
        435                 440                 445

Val Cys Pro Ser Glu Cys Val Glu Ser Ala Gln Pro Val Cys Gly Ser
    450                 455                 460

Asp Gly His Thr Tyr Ala Ser Glu Cys Glu Leu His Val His Ala Cys
465                 470                 475                 480

Thr His Gln Ile Ser Leu Tyr Val Ala Ser Ala Gly His Cys Gln Thr
                485                 490                 495

Cys Gly Glu Lys Val Cys Thr Phe Gly Ala Val Cys Ser Ala Gly Gln
            500                 505                 510

Cys Val Cys Pro Arg Cys Glu His Pro Pro Gly Pro Val Cys Gly
        515                 520                 525

Ser Asp Gly Val Thr Tyr Leu Ser Ala Cys Glu Leu Arg Glu Ala Ala
        530                 535                 540

Cys Gln Gln Gln Val Gln Ile Glu Glu Ala His Ala Gly Pro Cys Glu
545                 550                 555                 560

Pro Ala Glu Cys Gly Ser Gly Gly Ser Gly Glu Asp Asp Glu
                565                 570                 575

Cys Glu Gln Glu Leu Cys Arg Gln Arg Gly Gly Ile Trp Asp Glu Asp
            580                 585                 590

Ser Glu Asp Gly Pro Cys Val Cys Asp Phe Ser Cys Gln Ser Val Pro

-continued

```
            595                 600                 605
Arg Ser Pro Val Cys Gly Ser Asp Gly Val Thr Tyr Gly Thr Glu Cys
610                 615                 620

Asp Leu Lys Lys Ala Arg Cys Glu Ser Gln Gln Glu Leu Tyr Val Ala
625                 630                 635                 640

Ala Gln Gly Ala Cys Arg Gly Pro Thr Leu Ala Pro Leu Leu Pro Val
                    645                 650                 655

Ala Phe Pro His Cys Ala Gln Thr Pro Tyr Gly Cys Cys Gln Asp Asn
                    660                 665                 670

Phe Thr Ala Ala Gln Gly Val Gly Leu Ala Gly Cys Pro Ser Thr Cys
                    675                 680                 685

His Cys Asn Pro His Gly Ser Tyr Ser Gly Thr Cys Asp Pro Ala Thr
690                 695                 700

Gly Gln Cys Ser Cys Arg Pro Gly Val Gly Gly Leu Arg Cys Asp Arg
705                 710                 715                 720

Cys Glu Pro Gly Phe Trp Asn Phe Arg Gly Ile Val Thr Asp Gly His
                    725                 730                 735

Ser Gly Cys Thr Pro Cys Ser Cys Asp Pro Arg Gly Ala Val Arg Asp
                    740                 745                 750

Asp Cys Glu Gln Met Thr Gly Leu Cys Ser Cys Arg Pro Gly Val Ala
                    755                 760                 765

Gly Pro Lys Cys Gly Gln Cys Pro Asp Gly Gln Val Leu Gly His Leu
770                 775                 780

Gly Cys Glu Ala Asp Pro Met Thr Pro Val Thr Cys Val Glu Ile His
785                 790                 795                 800

Cys Glu Phe Gly Ala Ser Cys Val Glu Lys Ala Gly Phe Ala Gln Cys
                    805                 810                 815

Ile Cys Pro Thr Leu Thr Cys Pro Glu Ala Asn Ser Thr Lys Val Cys
                    820                 825                 830

Gly Ser Asp Gly Val Thr Tyr Gly Asn Glu Cys Gln Leu Lys Ala Ile
                    835                 840                 845

Ala Cys Arg Gln Arg Leu Asp Ile Ser Thr Gln Ser Leu Gly Pro Cys
                    850                 855                 860

Gln Glu Ser Val Thr Pro Gly Ala Ser Pro Thr Ser Ala Ser Met Thr
865                 870                 875                 880

Thr Pro Arg His Ile Leu Ser Lys Thr Leu Pro Phe Pro His Asn Ser
                    885                 890                 895

Leu Pro Leu Ser Pro Gly Ser Thr Thr His Asp Trp Pro Thr Pro Leu
                    900                 905                 910

Pro Ile Ser Pro His Thr Thr Val Ser Ile Pro Arg Ser Thr Ala Trp
                    915                 920                 925

Pro Val Leu Thr Val Pro Pro Thr Ala Ala Ala Ser Asp Val Thr Ser
                    930                 935                 940

Leu Ala Thr Ser Ile Phe Ser Glu Ser Gly Ser Ala Asn Gly Ser Gly
945                 950                 955                 960

Asp Glu Glu Leu Ser Gly Asp Glu Ala Ser Gly Gly Ser Gly
                    965                 970                 975

Gly Leu Glu Pro Pro Val Gly Ser Ile Val Val Thr His Gly Pro Pro
                    980                 985                 990

Ile Glu Arg Ala Ser Cys Tyr Asn  Ser Pro Leu Gly Cys  Cys Ser Asp
                    995                 1000                1005

Gly Lys  Thr Pro Ser Leu Asp  Ser Glu Gly Ser Asn  Cys Pro Ala
       1010                  1015                1020
```

```
Thr Lys Ala Phe Gln Gly Val Leu Glu Leu Glu Gly Val Glu Gly
    1025            1030                1035

Gln Glu Leu Phe Tyr Thr Pro Glu Met Ala Asp Pro Lys Ser Glu
    1040            1045                1050

Leu Phe Gly Glu Thr Ala Arg Ser Ile Glu Ser Thr Leu Asp Asp
    1055            1060                1065

Leu Phe Arg Asn Ser Asp Val Lys Lys Asp Phe Trp Ser Val Arg
    1070            1075                1080

Leu Arg Glu Leu Gly Pro Gly Lys Leu Val Arg Ala Ile Val Asp
    1085            1090                1095

Val His Phe Asp Pro Thr Thr Ala Phe Gln Ala Ser Asp Val Gly
    1100            1105                1110

Gln Ala Leu Leu Arg Gln Ile Gln Val Ser Arg Pro Trp Ala Leu
    1115            1120                1125

Ala Val Arg Arg Pro Leu Gln Glu His Val Arg Phe Leu Asp Phe
    1130            1135                1140

Asp Trp Phe Pro Thr Phe Phe Thr Gly Ala Ala Thr Gly Thr Thr
    1145            1150                1155

Ala Ala Met Ala Thr Ala Arg Ala Thr Thr Val Ser Arg Leu Pro
    1160            1165                1170

Ala Ser Ser Val Thr Pro Arg Val Tyr Pro Ser His Thr Ser Arg
    1175            1180                1185

Pro Val Gly Arg Thr Thr Ala Pro Pro Thr Thr Arg Arg Pro Pro
    1190            1195                1200

Thr Thr Ala Thr Asn Met Asp Arg Pro Arg Thr Pro Gly His Gln
    1205            1210                1215

Gln Pro Ser Lys Ser Cys Asp Ser Gln Pro Cys Leu His Gly Gly
    1220            1225                1230

Thr Cys Gln Asp Gln Asp Ser Gly Lys Gly Phe Thr Cys Ser Cys
    1235            1240                1245

Thr Ala Gly Arg Gly Gly Ser Val Cys Glu Lys Val Gln Pro Pro
    1250            1255                1260

Ser Met Pro Ala Phe Lys Gly His Ser Phe Leu Ala Phe Pro Thr
    1265            1270                1275

Leu Arg Ala Tyr His Thr Leu Arg Leu Ala Leu Glu Phe Arg Ala
    1280            1285                1290

Leu Glu Thr Glu Gly Leu Leu Leu Tyr Asn Gly Asn Ala Arg Gly
    1295            1300                1305

Lys Asp Phe Leu Ala Leu Ala Leu Leu Asp Gly Arg Val Gln Phe
    1310            1315                1320

Arg Phe Asp Thr Gly Ser Gly Pro Ala Val Leu Thr Ser Leu Val
    1325            1330                1335

Pro Val Glu Pro Gly Arg Trp His Arg Leu Glu Leu Ser Arg His
    1340            1345                1350

Trp Arg Gln Gly Thr Leu Ser Val Asp Gly Glu Thr Pro Val Val
    1355            1360                1365

Gly Glu Ser Pro Ser Gly Thr Asp Gly Leu Asn Leu Asp Thr Asn
    1370            1375                1380

Leu Tyr Val Gly Gly Ile Pro Glu Glu Gln Val Ala Met Val Leu
    1385            1390                1395

Asp Arg Thr Ser Val Gly Val Gly Leu Lys Gly Cys Ile Arg Met
    1400            1405                1410
```

```
Leu Asp Ile Asn Asn Gln Gln Leu Glu Leu Ser Asp Trp Gln Arg
1415                1420                1425

Ala Ala Val Gln Ser Ser Gly Val Gly Glu Cys Gly Asp His Pro
1430                1435                1440

Cys Leu Pro Asn Pro Cys His Gly Gly Ala Leu Cys Gln Ala Leu
1445                1450                1455

Glu Ala Gly Met Phe Leu Cys Gln Cys Pro Pro Gly Arg Phe Gly
1460                1465                1470

Pro Thr Cys Ala Asp Glu Lys Ser Pro Cys Gln Pro Asn Pro Cys
1475                1480                1485

His Gly Ala Ala Pro Cys Arg Val Leu Ser Ser Gly Gly Ala Lys
1490                1495                1500

Cys Glu Cys Pro Leu Gly Arg Ser Gly Thr Phe Cys Gln Thr Val
1505                1510                1515

Leu Glu Thr Ala Gly Ser Arg Pro Phe Leu Ala Asp Phe Asn Gly
1520                1525                1530

Phe Ser Tyr Leu Glu Leu Lys Gly Leu His Thr Phe Glu Arg Asp
1535                1540                1545

Leu Gly Glu Lys Met Ala Leu Glu Met Val Phe Leu Ala Arg Gly
1550                1555                1560

Pro Ser Gly Leu Leu Leu Tyr Asn Gly Gln Lys Thr Asp Gly Lys
1565                1570                1575

Gly Asp Phe Val Ser Leu Ala Leu His Asn Arg His Leu Glu Phe
1580                1585                1590

Cys Tyr Asp Leu Gly Lys Gly Ala Ala Val Ile Arg Ser Lys Glu
1595                1600                1605

Pro Ile Ala Leu Gly Thr Trp Val Arg Val Phe Leu Glu Arg Asn
1610                1615                1620

Gly Arg Lys Gly Ala Leu Gln Val Gly Asp Gly Pro Arg Val Leu
1625                1630                1635

Gly Glu Ser Pro Lys Ser Arg Lys Val Pro His Thr Met Leu Asn
1640                1645                1650

Leu Lys Glu Pro Leu Tyr Ile Gly Gly Ala Pro Asp Phe Ser Lys
1655                1660                1665

Leu Ala Arg Gly Ala Ala Val Ser Ser Gly Phe Ser Gly Val Ile
1670                1675                1680

Gln Leu Val Ser Leu Arg Gly His Gln Leu Leu Thr Gln Glu His
1685                1690                1695

Val Leu Arg Ala Val Asp Val Ser Pro Phe Ala Asp His Pro Cys
1700                1705                1710

Thr Gln Ala Leu Gly Asn Pro Cys Leu Asn Gly Gly Ser Cys Val
1715                1720                1725

Pro Arg Glu Ala Thr Tyr Glu Cys Leu Cys Pro Gly Gly Phe Ser
1730                1735                1740

Gly Leu His Cys Glu Lys Gly Leu Val Glu Lys Ser Val Gly Asp
1745                1750                1755

Leu Glu Thr Leu Ala Phe Asp Gly Arg Thr Tyr Ile Glu Tyr Leu
1760                1765                1770

Asn Ala Val Ile Glu Ser Glu Lys Ala Leu Gln Ser Asn His Phe
1775                1780                1785

Glu Leu Ser Leu Arg Thr Glu Ala Thr Gln Gly Leu Val Leu Trp
1790                1795                1800

Ile Gly Lys Ala Ala Glu Arg Ala Asp Tyr Met Ala Leu Ala Ile
```

```
                    1805                1810                1815

Val Asp Gly His Leu Gln Leu Ser Tyr Asp Leu Gly Ser Gln Pro
        1820                1825                1830

Val Val Leu Arg Ser Thr Val Lys Val Asn Thr Asn Arg Trp Leu
        1835                1840                1845

Arg Ile Arg Ala His Arg Glu His Arg Glu Gly Ser Leu Gln Val
        1850                1855                1860

Gly Asn Glu Ala Pro Val Thr Gly Ser Ser Pro Leu Gly Ala Thr
        1865                1870                1875

Gln Leu Asp Thr Asp Gly Ala Leu Trp Leu Gly Leu Gln Lys
        1880                1885                1890

Leu Pro Val Gly Gln Ala Leu Pro Lys Ala Tyr Gly Thr Gly Phe
        1895                1900                1905

Val Gly Cys Leu Arg Asp Val Val Val Gly His Arg Gln Leu His
        1910                1915                1920

Leu Leu Glu Asp Ala Val Thr Lys Pro Glu Leu Arg Pro Cys Pro
        1925                1930                1935

Thr Pro
    1940

<210> SEQ ID NO 7
<211> LENGTH: 452
<212> TYPE: PRT
<213> ORGANISM: Artificial Sequence
<220> FEATURE:
<223> OTHER INFORMATION: Amino acid sequence encoding Minimal human
      Agrin human sequence - G1 + G2

<400> SEQUENCE: 7

Gly Ala Pro Val Pro Ala Phe Glu Gly Arg Ser Phe Leu Ala Phe Pro
1               5                   10                  15

Thr Leu Arg Ala Tyr His Thr Leu Arg Leu Ala Leu Glu Phe Arg Ala
            20                  25                  30

Leu Glu Pro Gln Gly Leu Leu Leu Tyr Asn Gly Asn Ala Arg Gly Lys
        35                  40                  45

Asp Phe Leu Ala Leu Ala Leu Leu Asp Gly Arg Val Gln Leu Arg Phe
    50                  55                  60

Asp Thr Gly Ser Gly Pro Ala Val Leu Thr Ser Ala Val Pro Val Glu
65                  70                  75                  80

Pro Gly Gln Trp His Arg Leu Glu Leu Ser Arg His Trp Arg Arg Gly
                85                  90                  95

Thr Leu Ser Val Asp Gly Glu Thr Pro Val Leu Gly Glu Ser Pro Ser
            100                 105                 110

Gly Thr Asp Gly Leu Asn Leu Asp Thr Asp Leu Phe Val Gly Gly Val
        115                 120                 125

Pro Glu Asp Gln Ala Ala Val Ala Leu Glu Arg Thr Phe Val Gly Ala
    130                 135                 140

Gly Leu Arg Gly Cys Ile Arg Leu Leu Asp Val Asn Asn Gln Arg Leu
145                 150                 155                 160

Glu Leu Gly Ile Gly Pro Gly Ala Ala Thr Arg Gly Ser Gly Val Gly
                165                 170                 175

Glu Cys Gly Asp His Pro Cys Leu Pro Asn Pro Cys His Gly Gly Ala
            180                 185                 190

Pro Cys Gln Asn Leu Glu Ala Gly Arg Phe His Cys Gln Cys Pro Pro
        195                 200                 205
```

```
Gly Arg Val Gly Pro Thr Cys Ala Asp Glu Lys Ser Pro Cys Gln Pro
            210                 215                 220

Asn Pro Cys His Gly Ala Ala Pro Cys Arg Val Leu Pro Glu Gly Gly
225                 230                 235                 240

Ala Gln Cys Glu Cys Pro Leu Gly Arg Glu Gly Thr Phe Cys Gln Thr
            245                 250                 255

Ala Ser Gly Gln Asp Gly Ser Gly Pro Phe Leu Ala Asp Phe Asn Gly
            260                 265                 270

Phe Ser His Leu Glu Leu Arg Gly Leu His Thr Phe Ala Arg Asp Leu
            275                 280                 285

Gly Glu Lys Met Ala Leu Glu Val Val Phe Leu Ala Arg Gly Pro Ser
290                 295                 300

Gly Leu Leu Leu Tyr Asn Gly Gln Lys Thr Asp Gly Lys Gly Asp Phe
305                 310                 315                 320

Val Ser Leu Ala Leu Arg Asp Arg Arg Leu Glu Phe Arg Tyr Asp Leu
            325                 330                 335

Gly Lys Gly Ala Ala Val Ile Arg Ser Arg Glu Pro Val Thr Leu Gly
            340                 345                 350

Ala Trp Thr Arg Val Ser Leu Glu Arg Asn Gly Arg Lys Gly Ala Leu
            355                 360                 365

Arg Val Gly Asp Gly Pro Arg Val Leu Gly Glu Ser Pro Lys Ser Arg
370                 375                 380

Lys Val Pro His Thr Val Leu Asn Leu Lys Glu Pro Leu Tyr Val Gly
385                 390                 395                 400

Gly Ala Pro Asp Phe Ser Lys Leu Ala Arg Ala Ala Val Ser Ser
            405                 410                 415

Gly Phe Asp Gly Ala Ile Gln Leu Val Ser Leu Gly Gly Arg Gln Leu
            420                 425                 430

Leu Thr Pro Glu His Val Leu Arg Gln Val Asp Val Thr Ser Phe Ala
            435                 440                 445

Gly His Pro Cys
    450

<210> SEQ ID NO 8
<211> LENGTH: 188
<212> TYPE: PRT
<213> ORGANISM: Artificial Sequence
<220> FEATURE:
<223> OTHER INFORMATION: Amino acid sequence encoding Minimal human
      Agrin human sequence - G2 only

<400> SEQUENCE: 8

Pro Phe Leu Ala Asp Phe Asn Gly Phe Ser His Leu Glu Leu Arg Gly
1               5                   10                  15

Leu His Thr Phe Ala Arg Asp Leu Gly Glu Lys Met Ala Leu Glu Val
            20                  25                  30

Val Phe Leu Ala Arg Gly Pro Ser Gly Leu Leu Leu Tyr Asn Gly Gln
        35                  40                  45

Lys Thr Asp Gly Lys Gly Asp Phe Val Ser Leu Ala Leu Arg Asp Arg
50                  55                  60

Arg Leu Glu Phe Arg Tyr Asp Leu Gly Lys Gly Ala Ala Val Ile Arg
65                  70                  75                  80

Ser Arg Glu Pro Val Thr Leu Gly Ala Trp Thr Arg Val Ser Leu Glu
                85                  90                  95

Arg Asn Gly Arg Lys Gly Ala Leu Arg Val Gly Asp Gly Pro Arg Val
            100                 105                 110
```

```
Leu Gly Glu Ser Pro Lys Ser Arg Lys Val Pro His Thr Val Leu Asn
            115                 120                 125
Leu Lys Glu Pro Leu Tyr Val Gly Ala Pro Asp Phe Ser Lys Leu
    130                 135                 140
Ala Arg Ala Ala Val Ser Ser Gly Phe Asp Gly Ala Ile Gln Leu
145                 150                 155                 160
Val Ser Leu Gly Gly Arg Gln Leu Leu Thr Pro Glu His Val Leu Arg
                165                 170                 175
Gln Val Asp Val Thr Ser Phe Ala Gly His Pro Cys
            180                 185

<210> SEQ ID NO 9
<211> LENGTH: 2034
<212> TYPE: PRT
<213> ORGANISM: Mus musculus

<400> SEQUENCE: 9

Met Val Arg Pro Arg Leu Ser Phe Pro Ala Pro Leu Leu Pro Leu Leu
1               5                   10                  15
Leu Leu Leu Ala Ala Ala Ala Pro Ala Val Pro Gly Ala Ser Gly Thr
            20                  25                  30
Cys Pro Glu Arg Ala Leu Glu Arg Arg Glu Glu Ala Asn Val Val
        35                  40                  45
Leu Thr Gly Thr Val Glu Glu Ile Leu Asn Val Asp Pro Val Gln His
    50                  55                  60
Thr Tyr Ser Cys Lys Val Arg Val Trp Arg Tyr Leu Lys Gly Lys Asp
65                  70                  75                  80
Val Val Ala Gln Glu Ser Leu Leu Asp Gly Gly Asn Lys Val Val Ile
                85                  90                  95
Gly Gly Phe Gly Asp Pro Leu Ile Cys Asp Asn Gln Val Ser Thr Gly
            100                 105                 110
Asp Thr Arg Ile Phe Phe Val Asn Pro Ala Pro Tyr Leu Trp Pro
        115                 120                 125
Ala His Lys Asn Glu Leu Met Leu Asn Ser Ser Leu Met Arg Ile Thr
    130                 135                 140
Leu Arg Asn Leu Glu Glu Val Glu Phe Cys Val Glu Asp Lys Pro Gly
145                 150                 155                 160
Ile His Phe Thr Ala Ala Pro Ser Met Pro Pro Asp Val Cys Arg Gly
                165                 170                 175
Met Leu Cys Gly Phe Gly Ala Val Cys Glu Pro Ser Val Glu Asp Pro
            180                 185                 190
Gly Arg Ala Ser Cys Val Cys Lys Lys Asn Val Cys Pro Ala Met Val
        195                 200                 205
Ala Pro Val Cys Gly Ser Asp Ala Ser Thr Tyr Ser Asn Glu Cys Glu
    210                 215                 220
Leu Gln Arg Ala Gln Cys Asn Gln Gln Arg Arg Ile Arg Leu Leu Arg
225                 230                 235                 240
Gln Gly Pro Cys Gly Ser Arg Asp Pro Cys Ala Asn Val Thr Cys Ser
                245                 250                 255
Phe Gly Ser Thr Cys Val Pro Ser Ala Asp Gly Gln Thr Ala Ser Cys
            260                 265                 270
Leu Cys Pro Thr Thr Cys Phe Gly Ala Pro Asp Gly Thr Val Cys Gly
        275                 280                 285
Ser Asp Gly Val Asp Tyr Pro Ser Glu Cys Gln Leu Leu Arg His Ala
```

```
                290                 295                 300
Cys Ala Asn Gln Glu His Ile Phe Lys Lys Phe Asp Gly Pro Cys Asp
305                 310                 315                 320

Pro Cys Gln Gly Ser Met Ser Asp Leu Asn His Ile Cys Arg Val Asn
                325                 330                 335

Pro Arg Thr Arg His Pro Glu Met Leu Leu Arg Pro Glu Asn Cys Pro
            340                 345                 350

Ala Gln His Thr Pro Ile Cys Gly Asp Gly Val Thr Tyr Glu Asn
                355                 360                 365

Asp Cys Val Met Ser Arg Ile Gly Ala Ala Arg Gly Leu Leu Leu Gln
        370                 375                 380

Lys Val Arg Ser Gly Gln Cys Gln Thr Arg Asp Gln Cys Pro Glu Thr
385                 390                 395                 400

Cys Gln Phe Asn Ser Val Cys Leu Ser Arg Arg Gly Arg Pro His Cys
                405                 410                 415

Ser Cys Asp Arg Val Thr Cys Asp Gly Ala Tyr Arg Pro Val Cys Ala
            420                 425                 430

Gln Asp Gly His Thr Tyr Asp Asn Asp Cys Trp Arg Gln Gln Ala Glu
        435                 440                 445

Cys Arg Gln Gln Thr Ile Pro Pro Lys His Gln Gly Pro Cys Asp
450                 455                 460

Gln Thr Pro Ser Pro Cys Arg Gly Ala Gln Cys Ala Phe Gly Ala Thr
465                 470                 475                 480

Cys Thr Val Lys Asn Gly Lys Ala Val Cys Glu Cys Gln Arg Val Cys
                485                 490                 495

Ser Gly Gly Tyr Asp Pro Val Cys Gly Ser Asp Gly Val Thr Tyr Gly
            500                 505                 510

Ser Val Cys Glu Leu Glu Ser Met Ala Cys Thr Leu Gly Arg Glu Ile
        515                 520                 525

Arg Val Ala Arg Arg Gly Pro Cys Asp Arg Cys Gly Gln Cys Arg Phe
530                 535                 540

Gly Ser Leu Cys Glu Val Glu Thr Gly Arg Cys Val Cys Pro Ser Glu
545                 550                 555                 560

Cys Val Glu Ser Ala Gln Pro Val Cys Gly Ser Asp Gly His Thr Tyr
                565                 570                 575

Ala Ser Glu Cys Glu Leu His Val His Ala Cys Thr His Gln Ile Ser
            580                 585                 590

Leu Tyr Val Ala Ser Ala Gly His Cys Gln Thr Cys Gly Glu Thr Val
        595                 600                 605

Cys Thr Phe Gly Ala Val Cys Ser Ala Gly Gln Cys Val Cys Pro Arg
610                 615                 620

Cys Glu His Pro Pro Gly Pro Val Cys Ser Asp Gly Val Thr
625                 630                 635                 640

Tyr Leu Ser Ala Cys Glu Leu Arg Glu Ala Ala Cys Gln Gln Val
                645                 650                 655

Gln Ile Glu Glu Ala Arg Ala Gly Pro Cys Glu Pro Ala Glu Cys Gly
            660                 665                 670

Ser Gly Gly Ser Gly Ser Gly Glu Asp Asn Ala Cys Glu Gln Glu Leu
        675                 680                 685

Cys Arg Gln His Gly Gly Val Trp Asp Glu Asp Ser Glu Asp Gly Pro
690                 695                 700

Cys Val Cys Asp Phe Ser Cys Gln Ser Val Leu Lys Ser Pro Val Cys
705                 710                 715                 720
```

-continued

Gly Ser Asp Gly Val Thr Tyr Ser Thr Glu Cys His Leu Lys Lys Ala
            725                 730                 735

Arg Cys Glu Ala Arg Gln Glu Leu Tyr Val Ala Ala Gln Gly Ala Cys
            740                 745                 750

Arg Gly Pro Thr Leu Ala Pro Leu Leu Pro Met Ala Ser Pro His Cys
            755                 760                 765

Ala Gln Thr Pro Tyr Gly Cys Cys Gln Asp Asn Val Thr Ala Ala Gln
            770                 775                 780

Gly Val Gly Leu Ala Gly Cys Pro Ser Thr Cys His Cys Asn Pro His
785                 790                 795                 800

Gly Ser Tyr Ser Gly Thr Cys Asp Pro Val Thr Gly Gln Cys Ser Cys
            805                 810                 815

Arg Pro Gly Val Gly Gly Leu Arg Cys Asp Arg Cys Glu Pro Gly Phe
            820                 825                 830

Trp Asn Phe Arg Gly Ile Val Thr Asp Gly His Ser Gly Cys Thr Pro
            835                 840                 845

Cys Ser Cys Asp Pro Arg Gly Ala Val Arg Asp Asp Cys Glu Gln Met
850                 855                 860

Thr Gly Leu Cys Ser Cys Arg Pro Gly Val Ala Gly Pro Lys Cys Gly
865                 870                 875                 880

Gln Cys Pro Asp Gly Gln Ala Leu Gly His Leu Gly Cys Glu Ala Asp
            885                 890                 895

Pro Thr Thr Pro Val Thr Cys Val Glu Met His Cys Glu Phe Gly Ala
            900                 905                 910

Ser Cys Val Glu Ala Gly Phe Ala Gln Cys Val Cys Pro Thr Leu
            915                 920                 925

Thr Cys Pro Glu Ala Asn Ser Thr Lys Val Cys Gly Ser Asp Gly Val
            930                 935                 940

Thr Tyr Gly Asn Glu Cys Gln Leu Lys Thr Ile Ala Cys Arg Gln Arg
945                 950                 955                 960

Leu Asp Ile Ser Ile Gln Ser Leu Gly Pro Cys Arg Glu Ser Val Ala
            965                 970                 975

Pro Gly Val Ser Pro Thr Ser Ala Ser Met Thr Thr Pro Arg His Ile
            980                 985                 990

Leu Ser Arg Thr Leu Ala Ser Pro His Ser Ser Leu Pro Leu Ser Pro
            995                 1000                1005

Ser Thr Thr Ala His Asp Trp Pro Thr Pro Leu Pro Thr Ser Pro
    1010                1015                1020

Gln Thr Val Val Gly Thr Pro Arg Ser Thr Ala Ala Thr Pro Ser
    1025                1030                1035

Asp Val Ala Ser Leu Ala Thr Ala Ile Phe Arg Glu Ser Gly Ser
    1040                1045                1050

Thr Asn Gly Ser Gly Asp Glu Glu Leu Ser Gly Asp Glu Glu Ala
    1055                1060                1065

Ser Gly Gly Gly Ser Gly Gly Leu Glu Pro Pro Val Gly Ser Val
    1070                1075                1080

Val Val Thr His Gly Pro Pro Ile Glu Arg Ala Ser Cys Tyr Asn
    1085                1090                1095

Ser Pro Leu Gly Cys Cys Ser Asp Gly Lys Thr Pro Ser Leu Asp
    1100                1105                1110

Ser Glu Gly Ser Asn Cys Pro Ala Thr Lys Ala Phe Gln Gly Val
    1115                1120                1125

```
Leu Glu  Leu Glu Gly Val Glu  Gly Gln Glu Leu Phe  Tyr Thr Pro
    1130             1135              1140

Glu Met  Ala Asp Pro Lys Ser  Glu Leu Phe Gly Glu  Thr Ala Arg
    1145             1150              1155

Ser Ile  Glu Ser Thr Leu Asp  Asp Leu Phe Arg Asn  Ser Asp Val
    1160             1165              1170

Lys Lys  Asp Phe Trp Ser Ile  Arg Leu Arg Glu Leu  Gly Pro Gly
    1175             1180              1185

Lys Leu  Val Arg Ala Ile Val  Asp Val His Phe Asp  Pro Thr Thr
    1190             1195              1200

Ala Phe  Gln Ala Pro Asp Val  Gly Gln Ala Leu Leu  Gln Gln Ile
    1205             1210              1215

Gln Val  Ser Arg Pro Trp Ala  Leu Ala Val Arg Arg  Pro Leu Arg
    1220             1225              1230

Glu His  Val Arg Phe Leu Asp  Phe Asp Trp Phe Pro  Thr Phe Phe
    1235             1240              1245

Thr Gly  Ala Ala Thr Gly Thr  Thr Ala Ala Val Ala  Thr Ala Arg
    1250             1255              1260

Ala Thr  Thr Val Ser Arg Leu  Ser Ala Ser Ser Val  Thr Pro Arg
    1265             1270              1275

Val Tyr  Pro Ser Tyr Thr Ser  Arg Pro Val Gly Arg  Thr Thr Ala
    1280             1285              1290

Pro Leu  Thr Thr Arg Arg Pro  Pro Thr Thr Thr Ala  Ser Ile Asp
    1295             1300              1305

Arg Pro  Arg Thr Pro Gly Pro  Gln Arg Pro Pro Lys  Ser Cys Asp
    1310             1315              1320

Ser Gln  Pro Cys Leu His Gly  Gly Thr Cys Gln Asp  Leu Asp Ser
    1325             1330              1335

Gly Lys  Gly Phe Ser Cys Ser  Cys Thr Ala Gly Arg  Ala Gly Thr
    1340             1345              1350

Val Cys  Glu Lys Val Gln Leu  Pro Ser Val Pro Ala  Phe Lys Gly
    1355             1360              1365

His Ser  Phe Leu Ala Phe Pro  Thr Leu Arg Ala Tyr  His Thr Leu
    1370             1375              1380

Arg Leu  Ala Leu Glu Phe Arg  Ala Leu Glu Thr Glu  Gly Leu Leu
    1385             1390              1395

Leu Tyr  Asn Gly Asn Ala Arg  Gly Lys Asp Phe Leu  Ala Leu Ala
    1400             1405              1410

Leu Leu  Asp Gly His Val Gln  Phe Arg Phe Asp Thr  Gly Ser Gly
    1415             1420              1425

Pro Ala  Val Leu Thr Ser Leu  Val Pro Val Glu Pro  Gly Arg Trp
    1430             1435              1440

His Arg  Leu Glu Leu Ser Arg  His Trp Arg Gln Gly  Thr Leu Ser
    1445             1450              1455

Val Asp  Gly Glu Ala Pro Val  Val Gly Glu Ser Pro  Ser Gly Thr
    1460             1465              1470

Asp Gly  Leu Asn Leu Asp Thr  Lys Leu Tyr Val Gly  Gly Leu Pro
    1475             1480              1485

Glu Glu  Gln Val Ala Thr Val  Leu Asp Arg Thr Ser  Val Gly Ile
    1490             1495              1500

Gly Leu  Lys Gly Cys Ile Arg  Met Leu Asp Ile Asn  Asn Gln Gln
    1505             1510              1515

Leu Glu  Leu Ser Asp Trp Gln  Arg Ala Val Val Gln  Ser Ser Gly
```

-continued

```
                1520                1525                1530
Val Gly Glu Cys Gly Asp His Pro Cys Ser Pro Asn Pro Cys His
    1535                1540                1545
Gly Gly Ala Leu Cys Gln Ala Leu Glu Ala Gly Val Phe Leu Cys
    1550                1555                1560
Gln Cys Pro Pro Gly Arg Phe Gly Pro Thr Cys Ala Asp Glu Lys
    1565                1570                1575
Asn Pro Cys Gln Pro Asn Pro Cys His Gly Ser Ala Pro Cys His
    1580                1585                1590
Val Leu Ser Arg Gly Gly Ala Lys Cys Ala Cys Pro Leu Gly Arg
    1595                1600                1605
Ser Gly Ser Phe Cys Glu Thr Val Leu Glu Asn Ala Gly Ser Arg
    1610                1615                1620
Pro Phe Leu Ala Asp Phe Asn Gly Phe Ser Tyr Leu Glu Leu Lys
    1625                1630                1635
Gly Leu His Thr Phe Glu Arg Asp Leu Gly Glu Lys Met Ala Leu
    1640                1645                1650
Glu Met Val Phe Leu Ala Arg Gly Pro Ser Gly Leu Leu Leu Tyr
    1655                1660                1665
Asn Gly Gln Lys Thr Asp Gly Lys Gly Asp Phe Val Ser Leu Ala
    1670                1675                1680
Leu His Asn Arg His Leu Glu Phe Arg Tyr Asp Leu Gly Lys Gly
    1685                1690                1695
Ala Ala Ile Ile Arg Ser Lys Glu Pro Ile Ala Leu Gly Thr Trp
    1700                1705                1710
Val Arg Val Phe Leu Glu Arg Asn Gly Arg Lys Gly Ala Leu Gln
    1715                1720                1725
Val Gly Asp Gly Pro Arg Val Leu Gly Glu Ser Pro Val Pro His
    1730                1735                1740
Thr Met Leu Asn Leu Lys Glu Pro Leu Tyr Val Gly Gly Ala Pro
    1745                1750                1755
Asp Phe Ser Lys Leu Ala Arg Gly Ala Ala Val Ala Ser Gly Phe
    1760                1765                1770
Asp Gly Ala Ile Gln Leu Val Ser Leu Arg Gly His Gln Leu Leu
    1775                1780                1785
Thr Gln Glu His Val Leu Arg Ala Val Asp Val Ala Pro Phe Ala
    1790                1795                1800
Gly His Pro Cys Thr Gln Ala Val Asp Asn Pro Cys Leu Asn Gly
    1805                1810                1815
Gly Ser Cys Ile Pro Arg Glu Ala Thr Tyr Glu Cys Leu Cys Pro
    1820                1825                1830
Gly Gly Phe Ser Gly Leu His Cys Glu Lys Gly Ile Val Glu Lys
    1835                1840                1845
Ser Val Gly Asp Leu Glu Thr Leu Ala Phe Asp Gly Arg Thr Tyr
    1850                1855                1860
Ile Glu Tyr Leu Asn Ala Val Thr Glu Ser Glu Lys Ala Leu Gln
    1865                1870                1875
Ser Asn His Phe Glu Leu Ser Leu Arg Thr Glu Ala Thr Gln Gly
    1880                1885                1890
Leu Val Leu Trp Ile Gly Lys Val Gly Glu Arg Ala Asp Tyr Met
    1895                1900                1905
Ala Leu Ala Ile Val Asp Gly His Leu Gln Leu Ser Tyr Asp Leu
    1910                1915                1920
```

-continued

Gly Ser Gln Pro Val Val Leu Arg Ser Thr Val Lys Val Asn Thr
    1925                1930                1935

Asn Arg Trp Leu Arg Val Arg Ala His Arg Glu His Arg Glu Gly
    1940                1945                1950

Ser Leu Gln Val Gly Asn Glu Ala Pro Val Thr Gly Ser Ser Pro
    1955                1960                1965

Leu Gly Ala Thr Gln Leu Asp Thr Asp Gly Ala Leu Trp Leu Gly
    1970                1975                1980

Gly Leu Gln Lys Leu Pro Val Gly Gln Ala Leu Pro Lys Ala Tyr
    1985                1990                1995

Gly Thr Gly Phe Val Gly Cys Leu Arg Asp Val Val Gly His
    2000                2005                2010

Arg Gln Leu His Leu Leu Glu Asp Ala Val Thr Lys Pro Glu Leu
    2015                2020                2025

Arg Pro Cys Pro Thr Leu
    2030

<210> SEQ ID NO 10
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 10
gtcggctcgc ggcaaaaagc                                                    20

<210> SEQ ID NO 11
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 11
gacatcaaag agaagctgtg                                                    20

<210> SEQ ID NO 12
<211> LENGTH: 21
<212> TYPE: DNA
<213> ORGANISM: Artificial Sequence
<220> FEATURE:
<223> OTHER INFORMATION: Single strand DNA oligonucleotide

<400> SEQUENCE: 12
actccatacc gataaaggaa g                                                  21

<210> SEQ ID NO 13
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 13
gagagaaaga aaccagagtg                                                    20

<210> SEQ ID NO 14
<211> LENGTH: 21
<212> TYPE: DNA
<213> ORGANISM: Artificial Sequence
<220> FEATURE:

<223> OTHER INFORMATION: Single strand DNA oligonucleotide

<400> SEQUENCE: 14
gtctagcagg ttcttgaaat c                                              21

<210> SEQ ID NO 15
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 15
aattcaagat gcagaagctg                                                20

<210> SEQ ID NO 16
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 16
gaattttgag gtctctgctg                                                20

<210> SEQ ID NO 17
<211> LENGTH: 21
<212> TYPE: DNA
<213> ORGANISM: Artificial Sequence
<220> FEATURE:
<223> OTHER INFORMATION: Single strand DNA oligonucleotide

<400> SEQUENCE: 17
ccagaaacat catcataacc g                                              21

<210> SEQ ID NO 18
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 18
catcgccacc ttaatagttg                                                20

<210> SEQ ID NO 19
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 19
gtcaggctgg tcaccttctg                                                20

<210> SEQ ID NO 20
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 20
aactcttggc accatgaacc                                                20

```
<210> SEQ ID NO 21
<211> LENGTH: 22
<212> TYPE: DNA
<213> ORGANISM: Artificial Sequence
<220> FEATURE:
<223> OTHER INFORMATION: Single strand DNA oligonucleotide

<400> SEQUENCE: 21
gctgggctcc ctggacattg ac                                            22

<210> SEQ ID NO 22
<211> LENGTH: 22
<212> TYPE: DNA
<213> ORGANISM: Artificial Sequence
<220> FEATURE:
<223> OTHER INFORMATION: Single strand DNA oligonucleotide

<400> SEQUENCE: 22
cctgggcctg gattctggtg at                                            22

<210> SEQ ID NO 23
<211> LENGTH: 25
<212> TYPE: DNA
<213> ORGANISM: Artificial Sequence
<220> FEATURE:
<223> OTHER INFORMATION: Single strand DNA oligonucleotide

<400> SEQUENCE: 23
ccagtgtgaa cttgattttg atgaa                                         25

<210> SEQ ID NO 24
<211> LENGTH: 27
<212> TYPE: DNA
<213> ORGANISM: Artificial Sequence
<220> FEATURE:
<223> OTHER INFORMATION: Single strand DNA oligonucleotide

<400> SEQUENCE: 24
aacataactt gggagacaga gacatct                                       27

<210> SEQ ID NO 25
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 25
catcgacgcc cagatgaaga                                               20

<210> SEQ ID NO 26
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 26
tggtgaacag ggtcccaaac                                               20

<210> SEQ ID NO 27
<211> LENGTH: 18
<212> TYPE: DNA
<213> ORGANISM: Artificial Sequence
<220> FEATURE:
<223> OTHER INFORMATION: Single strand DNA oligonucleotide
```

```
<400> SEQUENCE: 27
cggaggagcg aacacctg                                               18

<210> SEQ ID NO 28
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 28
gttggatcct caccctctgc                                             20

<210> SEQ ID NO 29
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 29
ttcgatggtc cttgtgaccc                                             20

<210> SEQ ID NO 30
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 30
agataggtgt gtgttgggcg                                             20

<210> SEQ ID NO 31
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 31
gtgcccatcg tcaacctgaa                                             20

<210> SEQ ID NO 32
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 32
agttgaccct gggagccaga                                             20

<210> SEQ ID NO 33
<211> LENGTH: 22
<212> TYPE: DNA
<213> ORGANISM: Artificial Sequence
<220> FEATURE:
<223> OTHER INFORMATION: Single strand DNA oligonucleotide

<400> SEQUENCE: 33
ccttctggca caagtctctt gg                                          22

<210> SEQ ID NO 34
<211> LENGTH: 22
```

-continued

```
<212> TYPE: DNA
<213> ORGANISM: Artificial Sequence
<220> FEATURE:
<223> OTHER INFORMATION: Single strand DNA oligonucleotide

<400> SEQUENCE: 34
tcgaagatga cactggcatc gg                                              22

<210> SEQ ID NO 35
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 35
tcgagcttga tctctcctat                                                 20

<210> SEQ ID NO 36
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 36
tggtcccagg tcttacagaa                                                 20

<210> SEQ ID NO 37
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 37
tggccggcag cgtttctgag                                                 20

<210> SEQ ID NO 38
<211> LENGTH: 4380
<212> TYPE: PRT
<213> ORGANISM: Homo sapiens

<400> SEQUENCE: 38

Met Gly Trp Arg Ala Ala Gly Ala Leu Leu Ala Leu Leu Leu His
  1               5                  10                  15

Gly Arg Leu Leu Ala Val Thr His Gly Leu Arg Ala Tyr Asp Gly Leu
                 20                  25                  30

Ser Leu Pro Glu Asp Ile Glu Thr Val Thr Ala Ser Gln Met Arg Trp
             35                  40                  45

Thr His Ser Tyr Leu Ser Asp Asp Glu Asp Met Leu Ala Asp Ser Ile
         50                  55                  60

Ser Gly Asp Asp Leu Gly Ser Gly Asp Leu Gly Ser Gly Asp Phe Gln
 65                  70                  75                  80

Met Val Tyr Phe Arg Ala Leu Val Asn Phe Thr Arg Ser Ile Glu Tyr
                     85                  90                  95

Ser Pro Gln Leu Glu Asp Ala Gly Ser Arg Glu Phe Arg Glu Val Ser
                100                 105                 110

Glu Ala Val Val Asp Thr Leu Glu Ser Glu Tyr Leu Lys Ile Pro Gly
            115                 120                 125

Asp Gln Val Val Ser Val Val Phe Ile Lys Glu Leu Asp Gly Trp Val
        130                 135                 140
```

```
Phe Val Glu Leu Asp Val Gly Ser Glu Gly Asn Ala Asp Gly Ala Gln
145                 150                 155                 160

Ile Gln Glu Met Leu Leu Arg Val Ile Ser Gly Ser Val Ala Ser
                165                 170                 175

Tyr Val Thr Ser Pro Gln Gly Phe Gln Phe Arg Arg Leu Gly Thr Val
                180                 185                 190

Pro Gln Phe Pro Arg Ala Cys Thr Glu Ala Glu Phe Ala Cys His Ser
            195                 200                 205

Tyr Asn Glu Cys Val Ala Leu Glu Tyr Arg Cys Asp Arg Arg Pro Asp
        210                 215                 220

Cys Arg Asp Met Ser Asp Glu Leu Asn Cys Glu Pro Val Leu Gly
225                 230                 235                 240

Ile Ser Pro Thr Phe Ser Leu Leu Val Glu Thr Thr Ser Leu Pro Pro
                245                 250                 255

Arg Pro Glu Thr Thr Ile Met Arg Gln Pro Pro Val Thr His Ala Pro
            260                 265                 270

Gln Pro Leu Leu Pro Gly Ser Val Arg Pro Leu Pro Cys Gly Pro Gln
        275                 280                 285

Glu Ala Ala Cys Arg Asn Gly His Cys Ile Pro Arg Asp Tyr Leu Cys
290                 295                 300

Asp Gly Gln Glu Asp Cys Glu Asp Gly Ser Asp Glu Leu Asp Cys Gly
305                 310                 315                 320

Pro Pro Pro Pro Cys Glu Pro Asn Glu Phe Pro Cys Gly Asn Gly His
                325                 330                 335

Cys Ala Leu Lys Leu Trp Arg Cys Asp Gly Asp Phe Asp Cys Glu Asp
                340                 345                 350

Arg Thr Asp Glu Ala Asn Cys Pro Thr Lys Arg Pro Glu Glu Val Cys
            355                 360                 365

Gly Pro Thr Gln Phe Arg Cys Val Ser Thr Asn Met Cys Ile Pro Ala
        370                 375                 380

Ser Phe His Cys Asp Glu Glu Ser Asp Cys Pro Asp Arg Ser Asp Glu
385                 390                 395                 400

Phe Gly Cys Met Pro Pro Gln Val Val Thr Pro Arg Glu Ser Ile
                405                 410                 415

Gln Ala Ser Arg Gly Gln Thr Thr Phe Thr Cys Val Ala Ile Gly
            420                 425                 430

Val Pro Thr Pro Ile Ile Asn Trp Arg Leu Asn Trp Gly His Ile Pro
            435                 440                 445

Ser His Pro Arg Val Thr Val Thr Ser Glu Gly Gly Arg Gly Thr Leu
        450                 455                 460

Ile Ile Arg Asp Val Lys Glu Ser Asp Gln Gly Ala Tyr Thr Cys Glu
465                 470                 475                 480

Ala Met Asn Ala Arg Gly Met Val Phe Gly Ile Pro Asp Gly Val Leu
                485                 490                 495

Glu Leu Val Pro Gln Arg Gly Pro Cys Pro Asp Gly His Phe Tyr Leu
            500                 505                 510

Glu His Ser Ala Ala Cys Leu Pro Cys Phe Cys Phe Gly Ile Thr Ser
        515                 520                 525

Val Cys Gln Ser Thr Arg Arg Phe Arg Asp Gln Ile Arg Leu Arg Phe
        530                 535                 540

Asp Gln Pro Asp Asp Phe Lys Gly Val Asn Val Thr Met Pro Ala Gln
545                 550                 555                 560
```

```
Pro Gly Thr Pro Pro Leu Ser Ser Thr Gln Leu Gln Ile Asp Pro Ser
            565                 570                 575

Leu His Glu Phe Gln Leu Val Asp Leu Ser Arg Arg Phe Leu Val His
        580                 585                 590

Asp Ser Phe Trp Ala Leu Pro Glu Gln Phe Leu Gly Asn Lys Val Asp
        595                 600                 605

Ser Tyr Gly Gly Ser Leu Arg Tyr Asn Val Arg Tyr Glu Leu Ala Arg
        610                 615                 620

Gly Met Leu Glu Pro Val Gln Arg Pro Asp Val Leu Met Gly Ala
625                 630                 635                 640

Gly Tyr Arg Leu Leu Ser Arg Gly His Thr Pro Thr Gln Pro Gly Ala
            645                 650                 655

Leu Asn Gln Arg Gln Val Gln Phe Ser Glu Glu His Trp Val His Glu
            660                 665                 670

Ser Gly Arg Pro Val Gln Arg Ala Glu Leu Leu Gln Val Leu Gln Ser
            675                 680                 685

Leu Glu Ala Val Leu Ile Gln Thr Val Tyr Asn Thr Lys Met Ala Ser
        690                 695                 700

Val Gly Leu Ser Asp Ile Ala Met Asp Thr Thr Val Thr His Ala Thr
705                 710                 715                 720

Ser His Gly Arg Ala His Ser Val Glu Glu Cys Arg Cys Pro Ile Gly
            725                 730                 735

Tyr Ser Gly Leu Ser Cys Glu Ser Cys Asp Ala His Phe Thr Arg Val
            740                 745                 750

Pro Gly Gly Pro Tyr Leu Gly Thr Cys Ser Gly Cys Asn Cys Asn Gly
            755                 760                 765

His Ala Ser Ser Cys Asp Pro Val Tyr Gly His Cys Leu Asn Cys Gln
            770                 775                 780

His Asn Thr Glu Gly Pro Gln Cys Asn Lys Cys Lys Ala Gly Phe Phe
785                 790                 795                 800

Gly Asp Ala Met Lys Ala Thr Ala Thr Ser Cys Arg Pro Cys Pro Cys
            805                 810                 815

Pro Tyr Ile Asp Ala Ser Arg Arg Phe Ser Asp Thr Cys Phe Leu Asp
            820                 825                 830

Thr Asp Gly Gln Ala Thr Cys Asp Ala Cys Ala Pro Gly Tyr Thr Gly
            835                 840                 845

Arg Arg Cys Glu Ser Cys Ala Pro Gly Tyr Glu Gly Asn Pro Ile Gln
            850                 855                 860

Pro Gly Gly Lys Cys Arg Pro Val Asn Gln Glu Ile Val Arg Cys Asp
865                 870                 875                 880

Glu Arg Gly Ser Met Gly Thr Ser Gly Glu Ala Cys Arg Cys Lys Asn
                885                 890                 895

Asn Val Val Gly Arg Leu Cys Asn Glu Cys Ala Asp Gly Ser Phe His
                900                 905                 910

Leu Ser Thr Arg Asn Pro Asp Gly Cys Leu Lys Cys Phe Cys Met Gly
            915                 920                 925

Val Ser Arg His Cys Thr Ser Ser Ser Trp Ser Arg Ala Gln Leu His
            930                 935                 940

Gly Ala Ser Glu Glu Pro Gly His Phe Ser Leu Thr Asn Ala Ala Ser
945                 950                 955                 960

Thr His Thr Thr Asn Glu Gly Ile Phe Ser Pro Thr Pro Gly Glu Leu
                965                 970                 975

Gly Phe Ser Ser Phe His Arg Leu Leu Ser Gly Pro Tyr Phe Trp Ser
```

```
            980                 985                 990
Leu Pro Ser Arg Phe Leu Gly Asp Lys Val Thr Ser Tyr Gly Gly Glu
                995                1000               1005
Leu Arg Phe Thr Val Thr Gln Arg Ser Gln Pro Gly Ser Thr Pro
    1010                1015               1020
Leu His Gly Gln Pro Leu Val Val Leu Gly Asn Asn Ile Ile
    1025                1030               1035
Leu Glu His His Val Ala Gln Glu Pro Ser Pro Gly Gln Pro Ser
    1040                1045               1050
Thr Phe Ile Val Pro Phe Arg Glu Gln Ala Trp Gln Arg Pro Asp
    1055                1060               1065
Gly Gln Pro Ala Thr Arg Glu His Leu Leu Met Ala Leu Ala Gly
    1070                1075               1080
Ile Asp Thr Leu Leu Ile Arg Ala Ser Tyr Ala Gln Gln Pro Ala
    1085                1090               1095
Glu Ser Arg Val Ser Gly Ile Ser Met Asp Val Ala Val Pro Glu
    1100                1105               1110
Glu Thr Gly Gln Asp Pro Ala Leu Glu Val Glu Gln Cys Ser Cys
    1115                1120               1125
Pro Pro Gly Tyr Arg Gly Pro Ser Cys Gln Asp Cys Asp Thr Gly
    1130                1135               1140
Tyr Thr Arg Thr Pro Ser Gly Leu Tyr Leu Gly Thr Cys Glu Arg
    1145                1150               1155
Cys Ser Cys His Gly His Ser Glu Ala Cys Glu Pro Glu Thr Gly
    1160                1165               1170
Ala Cys Gln Gly Cys Gln His His Thr Glu Gly Pro Arg Cys Glu
    1175                1180               1185
Gln Cys Gln Pro Gly Tyr Tyr Gly Asp Ala Gln Arg Gly Thr Pro
    1190                1195               1200
Gln Asp Cys Gln Leu Cys Pro Cys Tyr Gly Asp Pro Ala Ala Gly
    1205                1210               1215
Gln Ala Ala His Thr Cys Phe Leu Asp Thr Asp Gly His Pro Thr
    1220                1225               1230
Cys Asp Ala Cys Ser Pro Gly His Ser Gly Arg His Cys Glu Arg
    1235                1240               1245
Cys Ala Pro Gly Tyr Tyr Gly Asn Pro Ser Gln Gly Gln Pro Cys
    1250                1255               1260
Gln Arg Asp Ser Gln Val Pro Gly Pro Ile Gly Cys Asn Cys Asp
    1265                1270               1275
Pro Gln Gly Ser Val Ser Ser Gln Cys Asp Ala Ala Gly Gln Cys
    1280                1285               1290
Gln Cys Lys Ala Gln Val Glu Gly Leu Thr Cys Ser His Cys Arg
    1295                1300               1305
Pro His His Phe His Leu Ser Ala Ser Asn Pro Asp Gly Cys Leu
    1310                1315               1320
Pro Cys Phe Cys Met Gly Ile Thr Gln Gln Cys Ala Ser Ser Ala
    1325                1330               1335
Tyr Thr Arg His Leu Ile Ser Thr His Phe Ala Pro Gly Asp Phe
    1340                1345               1350
Gln Gly Phe Ala Leu Val Asn Pro Gln Arg Asn Ser Arg Leu Thr
    1355                1360               1365
Gly Glu Phe Thr Val Glu Pro Val Pro Glu Gly Ala Gln Leu Ser
    1370                1375               1380
```

```
Phe Gly Asn Phe Ala Gln Leu Gly His Glu Ser Phe Tyr Trp Gln
    1385            1390                1395

Leu Pro Glu Thr Tyr Gln Gly Asp Lys Val Ala Ala Tyr Gly Gly
    1400            1405                1410

Lys Leu Arg Tyr Thr Leu Ser Tyr Thr Ala Gly Pro Gln Gly Ser
    1415            1420                1425

Pro Leu Ser Asp Pro Asp Val Gln Ile Thr Gly Asn Asn Ile Met
    1430            1435                1440

Leu Val Ala Ser Gln Pro Ala Leu Gln Gly Pro Glu Arg Arg Ser
    1445            1450                1455

Tyr Glu Ile Met Phe Arg Glu Phe Trp Arg Arg Pro Asp Gly
    1460            1465                1470

Gln Pro Ala Thr Arg Glu His Leu Leu Met Ala Leu Ala Asp Leu
    1475            1480                1485

Asp Glu Leu Leu Ile Arg Ala Thr Phe Ser Ser Val Pro Leu Ala
    1490            1495                1500

Ala Ser Ile Ser Ala Val Ser Leu Glu Val Ala Gln Pro Gly Pro
    1505            1510                1515

Ser Asn Arg Pro Arg Ala Leu Glu Val Glu Glu Cys Arg Cys Pro
    1520            1525                1530

Pro Gly Tyr Ile Gly Leu Ser Cys Gln Asp Cys Ala Pro Gly Tyr
    1535            1540                1545

Thr Arg Thr Gly Ser Gly Leu Tyr Leu Gly His Cys Glu Leu Cys
    1550            1555                1560

Glu Cys Asn Gly His Ser Asp Leu Cys His Pro Glu Thr Gly Ala
    1565            1570                1575

Cys Ser Gln Cys Gln His Asn Ala Ala Gly Glu Phe Cys Glu Leu
    1580            1585                1590

Cys Ala Pro Gly Tyr Tyr Gly Asp Ala Thr Ala Gly Thr Pro Glu
    1595            1600                1605

Asp Cys Gln Pro Cys Ala Cys Pro Leu Thr Asn Pro Glu Asn Met
    1610            1615                1620

Phe Ser Arg Thr Cys Glu Ser Leu Gly Ala Gly Gly Tyr Arg Cys
    1625            1630                1635

Thr Ala Cys Glu Pro Gly Tyr Thr Gly Gln Tyr Cys Glu Gln Cys
    1640            1645                1650

Gly Pro Gly Tyr Val Gly Asn Pro Ser Val Gln Gly Gly Gln Cys
    1655            1660                1665

Leu Pro Glu Thr Asn Gln Ala Pro Leu Val Val Glu Val His Pro
    1670            1675                1680

Ala Arg Ser Ile Val Pro Gln Gly Gly Ser His Ser Leu Arg Cys
    1685            1690                1695

Gln Val Ser Gly Ser Pro Pro His Tyr Phe Tyr Trp Ser Arg Glu
    1700            1705                1710

Asp Gly Arg Pro Val Pro Ser Gly Thr Gln Gln Arg His Gln Gly
    1715            1720                1725

Ser Glu Leu His Phe Pro Ser Val Gln Pro Ser Asp Ala Gly Val
    1730            1735                1740

Tyr Ile Cys Thr Cys Arg Asn Leu His Gln Ser Asn Thr Ser Arg
    1745            1750                1755

Ala Glu Leu Leu Val Thr Glu Ala Pro Ser Lys Pro Ile Thr Val
    1760            1765                1770
```

```
Thr Val Glu Glu Gln Arg Ser Gln Ser Val Arg Pro Gly Ala Asp
    1775                1780                1785

Val Thr Phe Ile Cys Thr Ala Lys Ser Lys Ser Pro Ala Tyr Thr
    1790                1795                1800

Leu Val Trp Thr Arg Leu His Asn Gly Lys Leu Pro Thr Arg Ala
    1805                1810                1815

Met Asp Phe Asn Gly Ile Leu Thr Ile Arg Asn Val Gln Leu Ser
    1820                1825                1830

Asp Ala Gly Thr Tyr Val Cys Thr Gly Ser Asn Met Phe Ala Met
    1835                1840                1845

Asp Gln Gly Thr Ala Thr Leu His Val Gln Ala Ser Gly Thr Leu
    1850                1855                1860

Ser Ala Pro Val Val Ser Ile His Pro Pro Gln Leu Thr Val Gln
    1865                1870                1875

Pro Gly Gln Leu Ala Glu Phe Arg Cys Ser Ala Thr Gly Ser Pro
    1880                1885                1890

Thr Pro Thr Leu Glu Trp Thr Gly Gly Pro Gly Gly Gln Leu Pro
    1895                1900                1905

Ala Lys Ala Gln Ile His Gly Gly Ile Leu Arg Leu Pro Ala Val
    1910                1915                1920

Glu Pro Thr Asp Gln Ala Gln Tyr Leu Cys Arg Ala His Ser Ser
    1925                1930                1935

Ala Gly Gln Gln Val Ala Arg Ala Val Leu His Val His Gly Gly
    1940                1945                1950

Gly Gly Pro Arg Val Gln Val Ser Pro Glu Arg Thr Gln Val His
    1955                1960                1965

Ala Gly Arg Thr Val Arg Leu Tyr Cys Arg Ala Ala Gly Val Pro
    1970                1975                1980

Ser Ala Thr Ile Thr Trp Arg Lys Glu Gly Gly Ser Leu Pro Pro
    1985                1990                1995

Gln Ala Arg Ser Glu Arg Thr Asp Ile Ala Thr Leu Leu Ile Pro
    2000                2005                2010

Ala Ile Thr Thr Ala Asp Ala Gly Phe Tyr Leu Cys Val Ala Thr
    2015                2020                2025

Ser Pro Ala Gly Thr Ala Gln Ala Arg Ile Gln Val Val Val Leu
    2030                2035                2040

Ser Ala Ser Asp Ala Ser Pro Pro Val Lys Ile Glu Ser Ser
    2045                2050                2055

Ser Pro Ser Val Thr Glu Gly Gln Thr Leu Asp Leu Asn Cys Val
    2060                2065                2070

Val Ala Gly Ser Ala His Ala Gln Val Thr Trp Tyr Arg Arg Gly
    2075                2080                2085

Gly Ser Leu Pro Pro His Thr Gln Val His Gly Ser Arg Leu Arg
    2090                2095                2100

Leu Pro Gln Val Ser Pro Ala Asp Ser Gly Glu Tyr Val Cys Arg
    2105                2110                2115

Val Glu Asn Gly Ser Gly Pro Lys Glu Ala Ser Ile Thr Val Ser
    2120                2125                2130

Val Leu His Gly Thr His Ser Gly Pro Ser Tyr Thr Pro Val Pro
    2135                2140                2145

Gly Ser Thr Arg Pro Ile Arg Ile Glu Pro Ser Ser His Val
    2150                2155                2160

Ala Glu Gly Gln Thr Leu Asp Leu Asn Cys Val Val Pro Gly Gln
```

```
                        2165                2170                2175

Ala His Ala Gln Val Thr Trp His Lys Arg Gly Gly Ser Leu Pro
    2180                2185                2190

Ala Arg His Gln Thr His Gly Ser Leu Leu Arg Leu His Gln Val
    2195                2200                2205

Thr Pro Ala Asp Ser Gly Glu Tyr Val Cys His Val Val Gly Thr
    2210                2215                2220

Ser Gly Pro Leu Glu Ala Ser Val Leu Val Thr Ile Glu Ala Ser
    2225                2230                2235

Val Ile Pro Gly Pro Ile Pro Pro Val Arg Ile Glu Ser Ser Ser
    2240                2245                2250

Ser Thr Val Ala Glu Gly Gln Thr Leu Asp Leu Ser Cys Val Val
    2255                2260                2265

Ala Gly Gln Ala His Ala Gln Val Thr Trp Tyr Lys Arg Gly Gly
    2270                2275                2280

Ser Leu Pro Ala Arg His Gln Val Arg Gly Ser Arg Leu Tyr Ile
    2285                2290                2295

Phe Gln Ala Ser Pro Ala Asp Ala Gly Gln Tyr Val Cys Arg Ala
    2300                2305                2310

Ser Asn Gly Met Glu Ala Ser Ile Thr Val Thr Val Thr Gly Thr
    2315                2320                2325

Gln Gly Ala Asn Leu Ala Tyr Pro Ala Gly Ser Thr Gln Pro Ile
    2330                2335                2340

Arg Ile Glu Pro Ser Ser Ser Gln Val Ala Glu Gly Gln Thr Leu
    2345                2350                2355

Asp Leu Asn Cys Val Val Pro Gly Gln Ser His Ala Gln Val Thr
    2360                2365                2370

Trp His Lys Arg Gly Gly Ser Leu Pro Val Arg His Gln Thr His
    2375                2380                2385

Gly Ser Leu Leu Arg Leu Tyr Gln Ala Ser Pro Ala Asp Ser Gly
    2390                2395                2400

Glu Tyr Val Cys Arg Val Leu Gly Ser Ser Val Pro Leu Glu Ala
    2405                2410                2415

Ser Val Leu Val Thr Ile Glu Pro Ala Gly Ser Val Pro Ala Leu
    2420                2425                2430

Gly Val Thr Pro Thr Val Arg Ile Glu Ser Ser Ser Ser Gln Val
    2435                2440                2445

Ala Glu Gly Gln Thr Leu Asp Leu Asn Cys Leu Val Ala Gly Gln
    2450                2455                2460

Ala His Ala Gln Val Thr Trp His Lys Arg Gly Gly Ser Leu Pro
    2465                2470                2475

Ala Arg His Gln Val His Gly Ser Arg Leu Arg Leu Leu Gln Val
    2480                2485                2490

Thr Pro Ala Asp Ser Gly Glu Tyr Val Cys Arg Val Val Gly Ser
    2495                2500                2505

Ser Gly Thr Gln Glu Ala Ser Val Leu Val Thr Ile Gln Gln Arg
    2510                2515                2520

Leu Ser Gly Ser His Ser Gln Gly Val Ala Tyr Pro Val Arg Ile
    2525                2530                2535

Glu Ser Ser Ser Ala Ser Leu Ala Asn Gly His Thr Leu Asp Leu
    2540                2545                2550

Asn Cys Leu Val Ala Ser Gln Ala Pro His Thr Ile Thr Trp Tyr
    2555                2560                2565
```

-continued

```
Lys Arg Gly Gly Ser Leu Pro Ser Arg His Gln Ile Val Gly Ser
2570                2575                2580

Arg Leu Arg Ile Pro Gln Val Thr Pro Ala Asp Ser Gly Glu Tyr
2585                2590                2595

Val Cys His Val Ser Asn Gly Ala Gly Ser Arg Glu Thr Ser Leu
2600                2605                2610

Ile Val Thr Ile Gln Gly Ser Gly Ser Ser His Val Pro Ser Val
2615                2620                2625

Ser Pro Pro Ile Arg Ile Glu Ser Ser Ser Pro Thr Val Val Glu
2630                2635                2640

Gly Gln Thr Leu Asp Leu Asn Cys Val Val Ala Arg Gln Pro Gln
2645                2650                2655

Ala Ile Ile Thr Trp Tyr Lys Arg Gly Gly Ser Leu Pro Ser Arg
2660                2665                2670

His Gln Thr His Gly Ser His Leu Arg Leu His Gln Met Ser Val
2675                2680                2685

Ala Asp Ser Gly Glu Tyr Val Cys Arg Ala Asn Asn Asn Ile Asp
2690                2695                2700

Ala Leu Glu Ala Ser Ile Val Ile Ser Val Ser Pro Ser Ala Gly
2705                2710                2715

Ser Pro Ser Ala Pro Gly Ser Ser Met Pro Ile Arg Ile Glu Ser
2720                2725                2730

Ser Ser Ser His Val Ala Glu Gly Glu Thr Leu Asp Leu Asn Cys
2735                2740                2745

Val Val Pro Gly Gln Ala His Ala Gln Val Thr Trp His Lys Arg
2750                2755                2760

Gly Gly Ser Leu Pro Ser His His Gln Thr Arg Gly Ser Arg Leu
2765                2770                2775

Arg Leu His His Val Ser Pro Ala Asp Ser Gly Glu Tyr Val Cys
2780                2785                2790

Arg Val Met Gly Ser Ser Gly Pro Leu Glu Ala Ser Val Leu Val
2795                2800                2805

Thr Ile Glu Ala Ser Gly Ser Ser Ala Val His Val Pro Ala Pro
2810                2815                2820

Gly Gly Ala Pro Pro Ile Arg Ile Glu Pro Ser Ser Ser Arg Val
2825                2830                2835

Ala Glu Gly Gln Thr Leu Asp Leu Lys Cys Val Val Pro Gly Gln
2840                2845                2850

Ala His Ala Gln Val Thr Trp His Lys Arg Gly Gly Asn Leu Pro
2855                2860                2865

Ala Arg His Gln Val His Gly Pro Leu Leu Arg Leu Asn Gln Val
2870                2875                2880

Ser Pro Ala Asp Ser Gly Glu Tyr Ser Cys Gln Val Thr Gly Ser
2885                2890                2895

Ser Gly Thr Leu Glu Ala Ser Val Leu Val Thr Ile Glu Pro Ser
2900                2905                2910

Ser Pro Gly Pro Ile Pro Ala Pro Gly Leu Ala Gln Pro Ile Tyr
2915                2920                2925

Ile Glu Ala Ser Ser Ser His Val Thr Glu Gly Gln Thr Leu Asp
2930                2935                2940

Leu Asn Cys Val Val Pro Gly Gln Ala His Ala Gln Val Thr Trp
2945                2950                2955
```

-continued

```
Tyr Lys Arg Gly Gly Ser Leu Pro Ala Arg His Gln Thr His Gly
    2960                2965                2970

Ser Gln Leu Arg Leu His Leu Val Ser Pro Ala Asp Ser Gly Glu
    2975                2980                2985

Tyr Val Cys Arg Ala Ala Ser Gly Pro Gly Pro Glu Gln Glu Ala
    2990                2995                3000

Ser Phe Thr Val Thr Val Pro Pro Ser Glu Gly Ser Ser Tyr Arg
    3005                3010                3015

Leu Arg Ser Pro Val Ile Ser Ile Asp Pro Pro Ser Ser Thr Val
    3020                3025                3030

Gln Gln Gly Gln Asp Ala Ser Phe Lys Cys Leu Ile His Asp Gly
    3035                3040                3045

Ala Ala Pro Ile Ser Leu Glu Trp Lys Thr Arg Asn Gln Glu Leu
    3050                3055                3060

Glu Asp Asn Val His Ile Ser Pro Asn Gly Ser Ile Ile Thr Ile
    3065                3070                3075

Val Gly Thr Arg Pro Ser Asn His Gly Thr Tyr Arg Cys Val Ala
    3080                3085                3090

Ser Asn Ala Tyr Gly Val Ala Gln Ser Val Val Asn Leu Ser Val
    3095                3100                3105

His Gly Pro Pro Thr Val Ser Val Leu Pro Glu Gly Pro Val Trp
    3110                3115                3120

Val Lys Val Gly Lys Ala Val Thr Leu Glu Cys Val Ser Ala Gly
    3125                3130                3135

Glu Pro Arg Ser Ser Ala Arg Trp Thr Arg Ile Ser Ser Thr Pro
    3140                3145                3150

Ala Lys Leu Glu Gln Arg Thr Tyr Gly Leu Met Asp Ser His Ala
    3155                3160                3165

Val Leu Gln Ile Ser Ser Ala Lys Pro Ser Asp Ala Gly Thr Tyr
    3170                3175                3180

Val Cys Leu Ala Gln Asn Ala Leu Gly Thr Ala Gln Lys Gln Val
    3185                3190                3195

Glu Val Ile Val Asp Thr Gly Ala Met Ala Pro Gly Ala Pro Gln
    3200                3205                3210

Val Gln Ala Glu Glu Ala Glu Leu Thr Val Glu Ala Gly His Thr
    3215                3220                3225

Ala Thr Leu Arg Cys Ser Ala Thr Gly Ser Pro Ala Pro Thr Ile
    3230                3235                3240

His Trp Ser Lys Leu Arg Ser Pro Leu Pro Trp Gln His Arg Leu
    3245                3250                3255

Glu Gly Asp Thr Leu Ile Ile Pro Arg Val Ala Gln Gln Asp Ser
    3260                3265                3270

Gly Gln Tyr Ile Cys Asn Ala Thr Ser Pro Ala Gly His Ala Glu
    3275                3280                3285

Ala Thr Ile Ile Leu His Val Glu Ser Pro Pro Tyr Ala Thr Thr
    3290                3295                3300

Val Pro Glu His Ala Ser Val Gln Ala Gly Glu Thr Val Gln Leu
    3305                3310                3315

Gln Cys Leu Ala His Gly Thr Pro Pro Leu Thr Phe Gln Trp Ser
    3320                3325                3330

Arg Val Gly Ser Ser Leu Pro Gly Arg Ala Thr Ala Arg Asn Glu
    3335                3340                3345

Leu Leu His Phe Glu Arg Ala Ala Pro Glu Asp Ser Gly Arg Tyr
```

|   |   |   |   |   |   |   |   |   |   |
|---|---|---|---|---|---|---|---|---|---|
|   | 3350 |   |   |   | 3355 |   |   |   | 3360 |

Arg Cys Arg Val Thr Asn Lys Val Gly Ser Ala Glu Ala Phe Ala
            3365                    3370                    3375

Gln Leu Leu Val Gln Gly Pro Pro Gly Ser Leu Pro Ala Thr Ser
            3380                    3385                    3390

Ile Pro Ala Gly Ser Thr Pro Thr Val Gln Val Thr Pro Gln Leu
            3395                    3400                    3405

Glu Thr Lys Ser Ile Gly Ala Ser Val Glu Phe His Cys Ala Val
            3410                    3415                    3420

Pro Ser Asp Arg Gly Thr Gln Leu Arg Trp Phe Lys Glu Gly Gly
            3425                    3430                    3435

Gln Leu Pro Pro Gly His Ser Val Gln Asp Gly Val Leu Arg Ile
            3440                    3445                    3450

Gln Asn Leu Asp Gln Ser Cys Gln Gly Thr Tyr Ile Cys Gln Ala
            3455                    3460                    3465

His Gly Pro Trp Gly Lys Ala Gln Ala Ser Ala Gln Leu Val Ile
            3470                    3475                    3480

Gln Ala Leu Pro Ser Val Leu Ile Asn Ile Arg Thr Ser Val Gln
            3485                    3490                    3495

Thr Val Val Val Gly His Ala Val Glu Phe Glu Cys Leu Ala Leu
            3500                    3505                    3510

Gly Asp Pro Lys Pro Gln Val Thr Trp Ser Lys Val Gly Gly His
            3515                    3520                    3525

Leu Arg Pro Gly Ile Val Gln Ser Gly Gly Val Val Arg Ile Ala
            3530                    3535                    3540

His Val Glu Leu Ala Asp Ala Gly Gln Tyr Arg Cys Thr Ala Thr
            3545                    3550                    3555

Asn Ala Ala Gly Thr Thr Gln Ser His Val Leu Leu Leu Val Gln
            3560                    3565                    3570

Ala Leu Pro Gln Ile Ser Met Pro Gln Glu Val Arg Val Pro Ala
            3575                    3580                    3585

Gly Ser Ala Ala Val Phe Pro Cys Ile Ala Ser Gly Tyr Pro Thr
            3590                    3595                    3600

Pro Asp Ile Ser Trp Ser Lys Leu Asp Gly Ser Leu Pro Pro Asp
            3605                    3610                    3615

Ser Arg Leu Glu Asn Asn Met Leu Met Leu Pro Ser Val Arg Pro
            3620                    3625                    3630

Gln Asp Ala Gly Thr Tyr Val Cys Thr Ala Thr Asn Arg Gln Gly
            3635                    3640                    3645

Lys Val Lys Ala Phe Ala His Leu Gln Val Pro Glu Arg Val Val
            3650                    3655                    3660

Pro Tyr Phe Thr Gln Thr Pro Tyr Ser Phe Leu Pro Leu Pro Thr
            3665                    3670                    3675

Ile Lys Asp Ala Tyr Arg Lys Phe Glu Ile Lys Ile Thr Phe Arg
            3680                    3685                    3690

Pro Asp Ser Ala Asp Gly Met Leu Leu Tyr Asn Gly Gln Lys Arg
            3695                    3700                    3705

Val Pro Gly Ser Pro Thr Asn Leu Ala Asn Arg Gln Pro Asp Phe
            3710                    3715                    3720

Ile Ser Phe Gly Leu Val Gly Gly Arg Pro Glu Phe Arg Phe Asp
            3725                    3730                    3735

Ala Gly Ser Gly Met Ala Thr Ile Arg His Pro Thr Pro Leu Ala
            3740                    3745                    3750

```
Leu Gly His Phe His Thr Val Thr Leu Leu Arg Ser Leu Thr Gln
3755                3760                3765

Gly Ser Leu Ile Val Gly Asp Leu Ala Pro Val Asn Gly Thr Ser
3770                3775                3780

Gln Gly Lys Phe Gln Gly Leu Asp Leu Asn Glu Glu Leu Tyr Leu
3785                3790                3795

Gly Gly Tyr Pro Asp Tyr Gly Ala Ile Pro Lys Ala Gly Leu Ser
3800                3805                3810

Ser Gly Phe Ile Gly Cys Val Arg Glu Leu Arg Ile Gln Gly Glu
3815                3820                3825

Glu Ile Val Phe His Asp Leu Asn Leu Thr Ala His Gly Ile Ser
3830                3835                3840

His Cys Pro Thr Cys Arg Asp Arg Pro Cys Gln Asn Gly Gly Gln
3845                3850                3855

Cys His Asp Ser Glu Ser Ser Tyr Val Cys Val Cys Pro Ala
3860                3865                3870

Gly Phe Thr Gly Ser Arg Cys Glu His Ser Gln Ala Leu His Cys
3875                3880                3885

His Pro Glu Ala Cys Gly Pro Asp Ala Thr Cys Val Asn Arg Pro
3890                3895                3900

Asp Gly Arg Gly Tyr Thr Cys Arg Cys His Leu Gly Arg Ser Gly
3905                3910                3915

Leu Arg Cys Glu Glu Gly Val Thr Val Thr Thr Pro Ser Leu Ser
3920                3925                3930

Gly Ala Gly Ser Tyr Leu Ala Leu Pro Ala Leu Thr Asn Thr His
3935                3940                3945

His Glu Leu Arg Leu Asp Val Glu Phe Lys Pro Leu Ala Pro Asp
3950                3955                3960

Gly Val Leu Leu Phe Ser Gly Gly Lys Ser Gly Pro Val Glu Asp
3965                3970                3975

Phe Val Ser Leu Ala Met Val Gly Gly His Leu Glu Phe Arg Tyr
3980                3985                3990

Glu Leu Gly Ser Gly Leu Ala Val Leu Arg Ser Ala Glu Pro Leu
3995                4000                4005

Ala Leu Gly Arg Trp His Arg Val Ser Ala Glu Arg Leu Asn Lys
4010                4015                4020

Asp Gly Ser Leu Arg Val Asn Gly Gly Arg Pro Val Leu Arg Ser
4025                4030                4035

Ser Pro Gly Lys Ser Gln Gly Leu Asn Leu His Thr Leu Leu Tyr
4040                4045                4050

Leu Gly Gly Val Glu Pro Ser Val Pro Leu Ser Pro Ala Thr Asn
4055                4060                4065

Met Ser Ala His Phe Arg Gly Cys Val Gly Glu Val Ser Val Asn
4070                4075                4080

Gly Lys Arg Leu Asp Leu Thr Tyr Ser Phe Leu Gly Ser Gln Gly
4085                4090                4095

Ile Gly Gln Cys Tyr Asp Ser Ser Pro Cys Glu Arg Gln Pro Cys
4100                4105                4110
```

-continued

| | | | | | | | | | | | |
|---|---|---|---|---|---|---|---|---|---|---|---|
| Gln | His 4115 | Gly | Ala | Thr | Cys 4120 | Met | Pro | Ala | Gly | Glu 4125 | Tyr |
| Glu | Phe | Gln | | | | | | | | | |
| Cys | Leu 4130 | Cys | Arg | Asp | Gly 4135 | Phe | Lys | Gly | Asp | Leu 4140 | Cys |
| Glu | His | Glu | | | | | | | | | |
| Glu | Asn 4145 | Pro | Cys | Gln | Leu 4150 | Arg | Glu | Pro | Cys | Leu 4155 | His |
| Gly | Gly | Thr | | | | | | | | | |
| Cys | Gln 4160 | Gly | Thr | Arg | Cys 4165 | Leu | Cys | Leu | Pro | Gly 4170 | Phe |
| Ser | Gly | Pro | | | | | | | | | |
| Arg | Cys 4175 | Gln | Gln | Gly | Ser 4180 | Gly | His | Gly | Ile | Ala 4185 | Glu |
| Ser | Asp | Trp | | | | | | | | | |
| His | Leu 4190 | Glu | Gly | Ser | Gly 4195 | Gly | Asn | Asp | Ala | Pro 4200 | Gly |
| Gln | Tyr | Gly | | | | | | | | | |
| Ala | Tyr 4205 | Phe | His | Asp | Asp 4210 | Gly | Phe | Leu | Ala | Phe 4215 | Pro |
| Gly | His | Val | | | | | | | | | |
| Phe | Ser 4220 | Arg | Ser | Leu | Pro 4225 | Glu | Val | Pro | Glu | Thr 4230 | Ile |
| Glu | Leu | Glu | | | | | | | | | |
| Val | Arg 4235 | Thr | Ser | Thr | Ala 4240 | Ser | Gly | Leu | Leu | Leu 4245 | Trp |
| Gln | Gly | Val | | | | | | | | | |
| Glu | Val 4250 | Gly | Glu | Ala | Gly 4255 | Gln | Gly | Lys | Asp | Phe 4260 | Ile |
| Ser | Leu | Gly | | | | | | | | | |
| Leu | Gln 4265 | Asp | Gly | His | Leu 4270 | Val | Phe | Arg | Tyr | Gln 4275 | Leu |
| Gly | Ser | Gly | | | | | | | | | |
| Glu | Ala 4280 | Arg | Leu | Val | Ser 4285 | Glu | Asp | Pro | Ile | Asn 4290 | Asp |
| Gly | Glu | Trp | | | | | | | | | |
| His | Arg 4295 | Val | Thr | Ala | Leu 4300 | Arg | Glu | Gly | Arg | Arg 4305 | Gly |
| Ser | Ile | Gln | | | | | | | | | |
| Val | Asp 4310 | Gly | Glu | Glu | Leu 4315 | Val | Ser | Gly | Arg | Ser 4320 | Pro |
| Gly | Pro | Asn | | | | | | | | | |
| Val | Ala 4325 | Val | Asn | Ala | Lys 4330 | Gly | Ser | Val | Tyr | Ile 4335 | Gly |
| Gly | Ala | Pro | | | | | | | | | |
| Asp | Val 4340 | Ala | Thr | Leu | Thr 4345 | Gly | Gly | Arg | Phe | Ser 4350 | Ser |
| Gly | Ile | Thr | | | | | | | | | |
| Gly | Cys 4355 | Val | Lys | Asn | Leu 4360 | Val | Leu | His | Ser | Ala 4365 | Arg |
| Pro | Gly | Ala | | | | | | | | | |
| Pro | Pro 4370 | Pro | Gln | Pro | Leu 4375 | Asp | Leu | Gln | His | Arg 4380 | Ala |

METHOD OF INDUCING CARDIOMYOCYTES PROLIFERATION AND TREATING HEART DISEASES

RELATED APPLICATIONS

This application is a National Phase of PCT Patent Application No. PCT/IL2016/051165 having International filing date of Oct. 27, 2016, which claims the benefit priority of Israel Patent Application No. 242380 filed on Oct. 29, 2015. The contents of the above applications are all incorporated by reference as if fully set forth herein in their entirety.

SEQUENCE LISTING STATEMENT

The ASCII file, entitled 73739SequenceListing.txt, created on Apr. 29, 2018, comprising 238,036 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to methods of inducing proliferation of cardiomyocytes and methods of treating heart diseases.

Heart disease and in particular myocardial infarction (MI), is the leading cause of death in the world. The severity of heart disease is due to the post-mitotic nature of mammalian adult cardiac muscle cells—the cardiomyocytes (CMs) {Bergmann, 2009 #9; Senyo, 2013 #86} and their limited capacity to replenish damaged tissue {Poss, 2007 #30; Ausoni, 2009 #17}. In contrast, extensive CM proliferation and subsequently robust cardiac regeneration occurs in lower vertebrates such as newt {Ausoni, 2009 #17} and zebrafish {Poss, 2007 #30; Jopling, 2010 #68; Ausoni, 2009 #17}. Similarly, neonatal murine CM turnover is sufficient to repair damaged myocardium following injury; however this ability is greatly diminished during the first week after birth {Porrello, 2011 #11; Porrello, 2012 #38}. During this time, there is a transition in CM ploidy from mono to bi-nucleation, concurrent with a switch from hyperplasia (increase in cell number) to hypertrophy (increase in cell size) {Li, 1996 #61; Soonpaa, 1998 #89}. Induced cardiac injury in mice at the day of birth results in nearly complete regeneration however this capacity is diminished by day 7. At this time point fibrotic scar dominates the replenishment of muscle tissue through CM proliferation {Porrello, 2011 #11} therefore leading to impaired cardiac function {Weisman, 1988 #90}. Many studies focus on the proliferation of endogenous CMs in order to contribute to heart regeneration. Recently, it was shown that adult CMs can re-enter the cell cycle and proliferate by modulating several pathways such as: FGF1 accompanied with P38 inhibition {Engel, 2006 #127}, extracellular Periostin {Kuhn, 2007 #28}, NRG1 via Erbb2 {D'Uva, 2015 #99; Bersell, 2009 #128} Hippo inhibition {Heallen, 2013 #100} and inhibition of the cell cycle regulator Meis1 {Mahmoud, 2013 #80}.

Heart pathologies, primarily MI, are often accompanied by ECM remodeling, mainly deposition of a rigid scar which reduces heart function {Weisman, 1988 #90; Baum, 2011 #12; Bayomy, 2012 #3}. Alterations in ECM structure following injury are attributed to activity of matrix metalloproteases (MMPs) {Phatharajaree, 2007 #92}, mainly the gelatinase family, MMP2 and MMP9 {DeCoux, 2014 #91}. Deletion of either MMP2 {Hayashidani, 2003 #94} or MMP9 {Ducharme, 2000 #93} following MI attenuated ECM remodeling and improved overall heart function. Despite the adverse effects of ECM remodeling following cardiac injury, ECM plays an integral role in cellular migration {Ridley, 2003 #95; Berk, 2007 #97}, differentiation {Shamis, 2011 #18; Streuli, 1999 #96} and proliferation {Berk, 2007 #97} of any cell type.

Through utilization of ECM decellularization and acid solubilization of fetal, neonatal and adult cardiac ECM, cardiac ECM was shown to significantly contribute to the regulation of CM proliferation {Williams, 2014 #84}. Seeded on neonatal cells, ECM derived from fetal and neonatal ages displayed higher proliferation levels compared to adult derived ECM {Williams, 2014 #84}. Although manipulation of CM intrinsic factors was shown to expand the proliferative capacity of the mammalian heart {D'Uva, 2015 #99; Mahmoud, 2013 #80; Heallen, 2013 #100}, the roles of the extracellular environment or its components in cardiac regeneration remain unclear.

Agrin is an extracellular heparan sulfate proteoglycan (HSPG) with a core protein size of 210 kDa {Williams. 2008 #71}. The neural form of Agrin (n-Agrin) has been extensively researched due to its involvement in the aggregation of acetylcholine receptors (AChRs) via the muscle specific kinase (MuSK)-Lrp4 receptor complex {Burden, 2013 #76}. Elevated expression of non-neuronal Agrin has been correlated with several types of carcinoma {Theocharis, 2010 #102} and more recently has been implicated in the progression of hepatocellular carcinoma (HCC) by controlling motility and proliferation of cells through interaction with Lrp4 {Chakraborty, 2015 #101}. Additionally, a small fragment of Agrin (the c-terminal 22 kDa peptide, CAF22) has been shown to bind and inhibit Na+ K+ channels that modulate CM beating {Hilgenberg, 2009 #103}, similarly to Digoxin, a drug commonly taken after various cardiac episodes {Hilgenberg, 2009 #103; Schwinger, 2003 #104}. A recent study focused on the interaction of Agrin with the dystroglycan complex as a key component in processes of innate immunity, and is required for monocyte and macrophage differentiation through interaction with Grb2 and subsequent ERK activation {Mazzon, 2012 #73}.

Dystroglycan is comprised of two units ($\alpha$ and $\beta$) {Henry, 1996 #105} and acts as a transmembrane bridge connecting ECM components (such as Agrin, Laminin and Perlecan) with the muscle cell inner myoskeleton by interacting with Dystrophin and its associated complex {Henry, 1996 #105; Davies, 2006 #106; Ervasti, 1990 #108}. Interruption of Dystrophin complex is the leading cause for various muscular dystrophies including Duchenne muscular dystrophy {Davies, 2006 #106; Campbell, 1989 #107; Ervasti, 1990 #108}. Mice lacking Dystrophin (Mdx), present elevated CM turnover in non-ischemic cardiomyopathy model {Richardson, 2015 #110}; In contrast, a recent study that employed post-natal day 1 heart resection on Mdx mice revealed impaired regenerative response and elevated fibrosis relative to wildtype mice {Morikawa, 2015 #109}. Nonetheless, the role of Agrin, Dystroglycan and their downstream elements has never been studied in the context of cardiac regeneration.

Additional background art includes:
U.S. Application Number 20070014871
U.S. Application Number 20100095387
U.S. Application Number 20060223753
U.S. Application Number 20140377212
U.S. Application Number 20110104120
U.S. Application Number 20070014733

SUMMARY OF THE INVENTION

According to an aspect of some embodiments of the present invention there is provided use of a therapeutically effective amount of an Agrin peptide which induces proliferation of cardiomyocytes in the manufacture of a medicament for treating a heart disease.

According to an aspect of some embodiments of the present invention there is provided use of an agent which inhibits the Dystroglycan complex on cardiomyocytes in the manufacture of a medicament for treating a heart disease.

According to an aspect of some embodiments of the present invention there is provided a method of inducing proliferation of cardiomyocytes, the method comprising contacting the cardiomyocytes with an effective amount of an Agrin peptide which induces proliferation of the cardiomyocytes.

According to an aspect of some embodiments of the present invention there is provided a method of inducing proliferation of cardiomyocytes, the method comprising contacting the cardiomyocytes with an agent which inhibits the Dystroglycan complex on the cardiomyocytes, thereby inducing proliferation of cardiomyocytes.

According to some embodiments of the invention, the agent is selected from the group consisting of a small molecule and a peptide and a polynucleotide.

According to some embodiments of the invention, the agent comprises an agrin peptide which induces proliferation of the cardiomyocytes.

According to some embodiments of the invention, the agent induces Erk activation.

According to some embodiments of the invention, the agent inhibits sarcomerogenesis.

According to an aspect of some embodiments of the present invention there is provided a method of treating a heart disease in a subject in need thereof, the method comprising administering to the subject a therapeutically effective amount of an Agrin peptide which induces proliferation of cardiomyocytes, thereby treating the heart disease.

According to an aspect of some embodiments of the present invention there is provided an implantable device comprising an Agrin peptide which induces proliferation of cardiomyocytes.

According to some embodiments of the invention, the Agrin peptide is not a part of a fusion polypeptide.

According to some embodiments of the invention, the Agrin peptide is in a soluble form.

According to some embodiments of the invention, the Agrin peptide comprises a Laminin G-like 1 domain (G1) and a Laminin G-like 2 domain (G2).

According to some embodiments of the invention, the Agrin peptide is 90-110 KDa.

According to some embodiments of the invention, the Agrin peptide comprises a fragment of human Agrin.

According to some embodiments of the invention, the cardiomyocytes are selected from the group consisting of adult cardiomyocytes, juvenile cardiomyocytes and neonatal cardiomyocytes.

According to some embodiments of the invention, the method is effected in vivo.

According to some embodiments of the invention, the method is effected ex vivo.

According to some embodiments of the invention, the method is effected in vitro.

According to some embodiments of the invention, the cardiomyocytes are comprised in a tissue.

According to some embodiments of the invention, the heart disease is an ischemic heart disease.

According to an aspect of some embodiments of the present invention there is provided an isolated peptide comprising Laminin G-like 2 (G2) domain the peptide being no more than 200 amino acids in length.

According to some embodiments of the invention, the peptide is as set forth in SEQ ID NO: 8.

According to an aspect of some embodiments of the present invention there is provided a pharmaceutical composition comprising the peptide.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-M show that P1 cardiac ECM increases CM cell cycle reentry in an MMP dependent manner. (FIG. 1A) Experimental design for ECM contribution to CM cell cycle re-entry in P1 and P7 cultures. (FIG. 1B) Heart sections were stained with DAPI in order to assess the removal of cells. (FIG. 1C) Sections were Imaged by SEM, treated samples are free of cellular components. (FIG. 1D) Representative fields of heart cultures stained with DAPI (blue) cTNT (green) and Ki67 (red). White arrows display Ki67$^+$/cTNT$^+$ cells. (FIGS. 1E-F) P1 (FIG. 1E) or P7 (FIG. 1F) percent of proliferating CMs in response to day 1 and day 7 ECM. (FIGS. 1G-H) P1 (FIG. 1G) or P7 (FIG. 1H) percent of proliferating CM (Ki67$^+$/cTNT$^+$) cells in response to day 1 and day 7 ECM with or without broad MMP inhibitor (marimastat). (FIG. 1I) Scheme of MMP derived ECM fragments contribution to CM cell cycle activity. (FIGS. 1J-K) Percent of P1 (FIG. 1J) or P7 (FIG. 1K) proliferating CMs in response to the presence of MMP9/12 cleaved substrates of day 1 and day 7 ECM fragments. (FIG. 1l) Van diagram presenting the LC/MS results. (FIG. 1M) Quantitative PCR (qPCR) analysis of genes obtained from the LC/MS in P1 and P7 whole heart lysates.

Figure 1B:
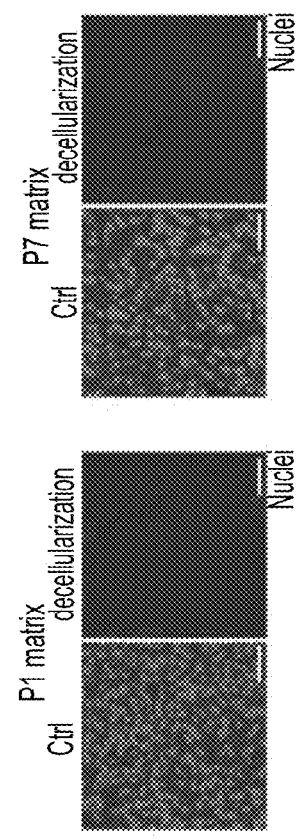
Figure 1C:
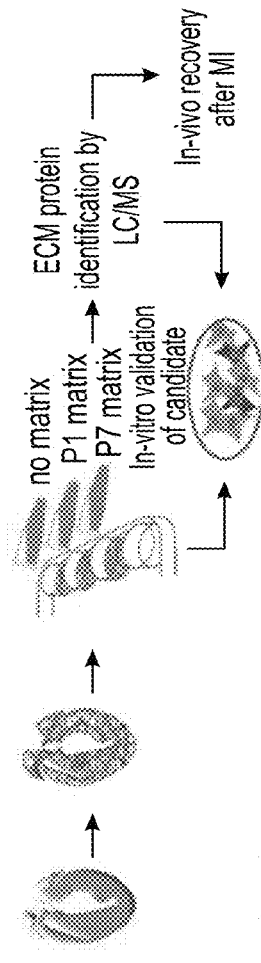
Figure 1E:
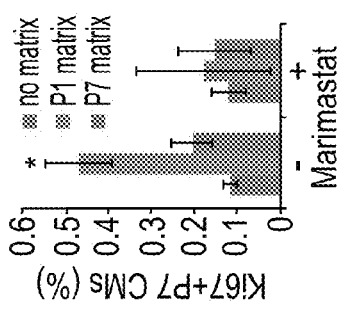
Figure 1F:
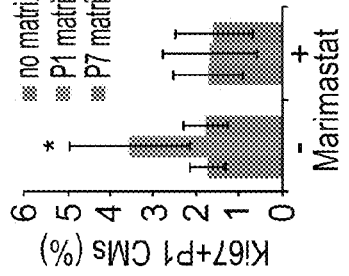
Figure 1G:
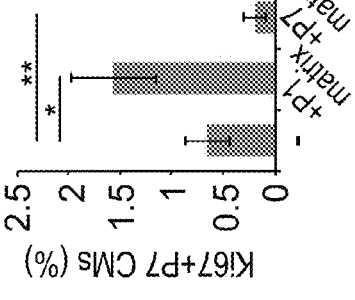
Figure 1H:
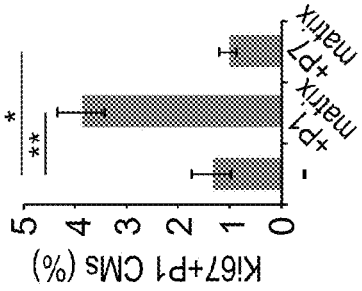
Figure 1D:
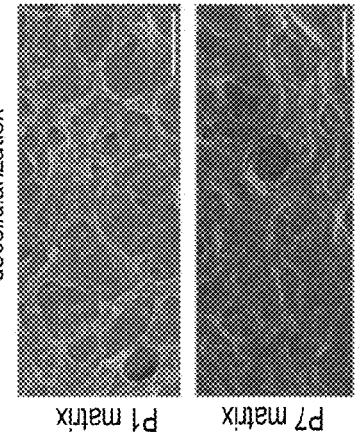
Figure 1N:
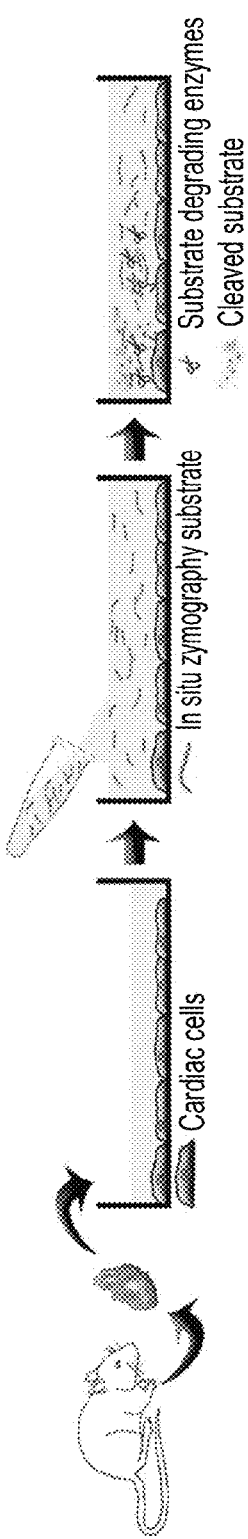
Figure 1O:
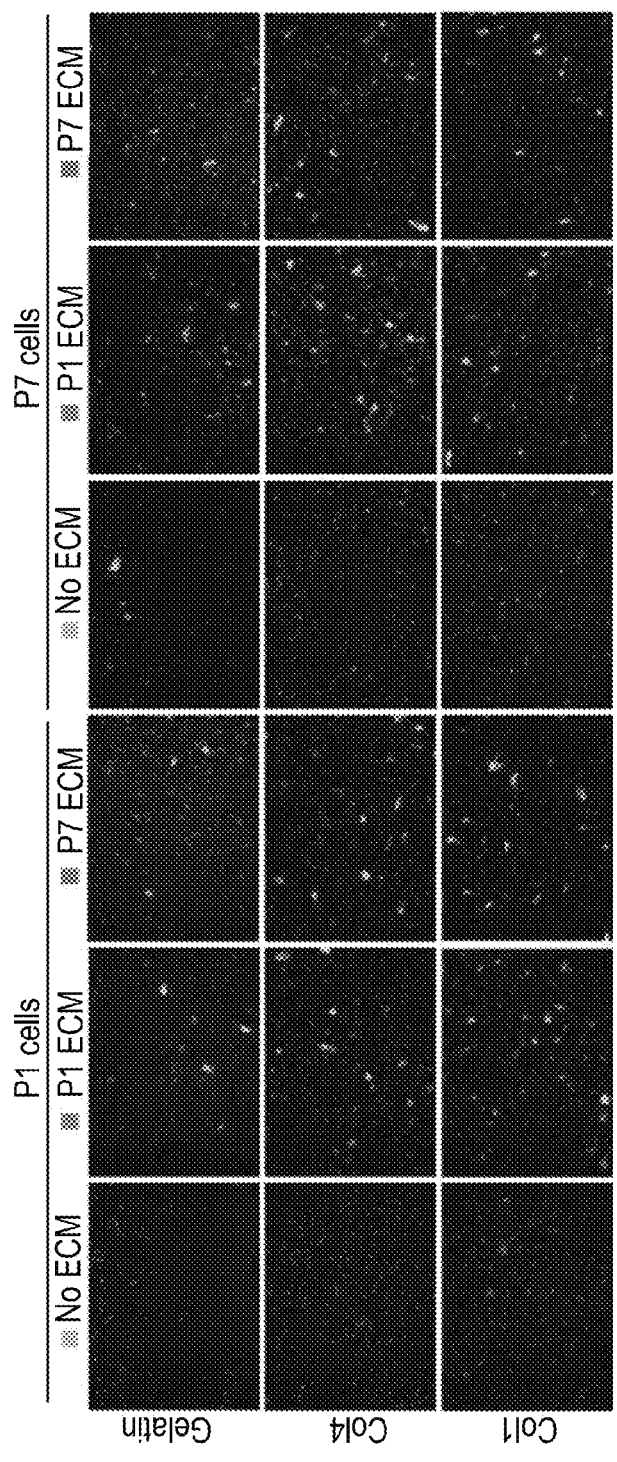
Figure 1P:
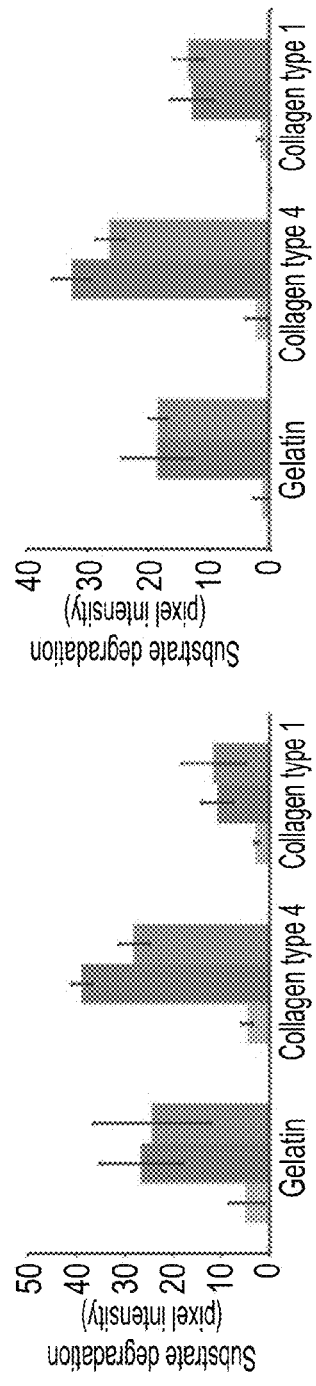

FIGS. 1N-P show that P1 and P7 ECM promote elevated gelatinase activity. (FIG. 1N) A schematic diagram in situ zymography (ISZ) assay. (FIG. 1O) Immunofluorescence evaluation of Col1, Col4 and gelatin degradation in response to P1 and P7 ECM. (FIG. 1P) Quantification of ISZ assay.

Figure 2G:
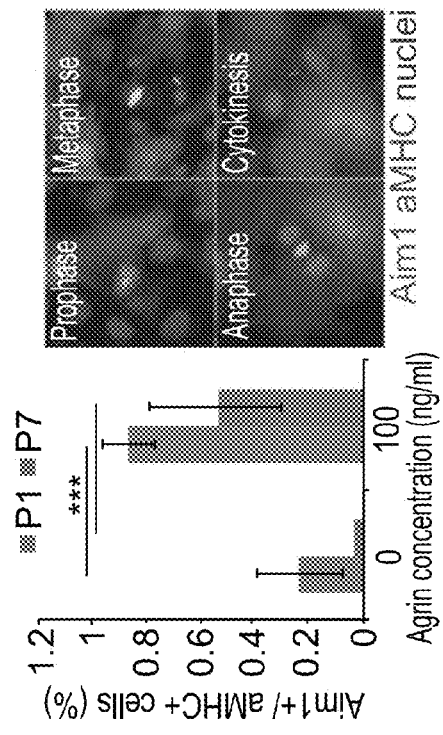
Figure 2H:
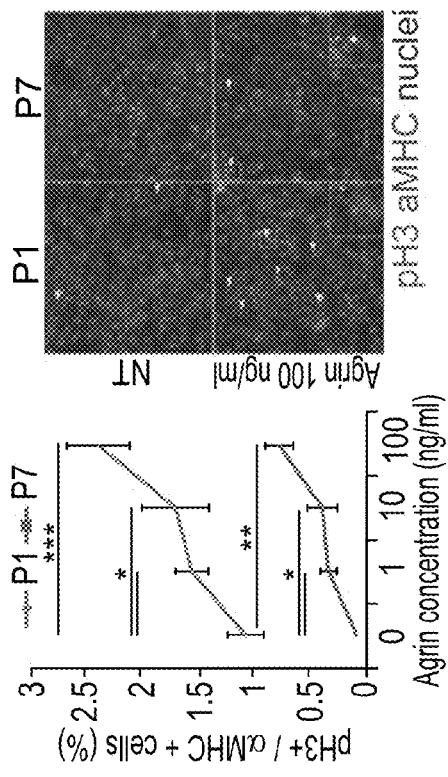
Figure 2I:
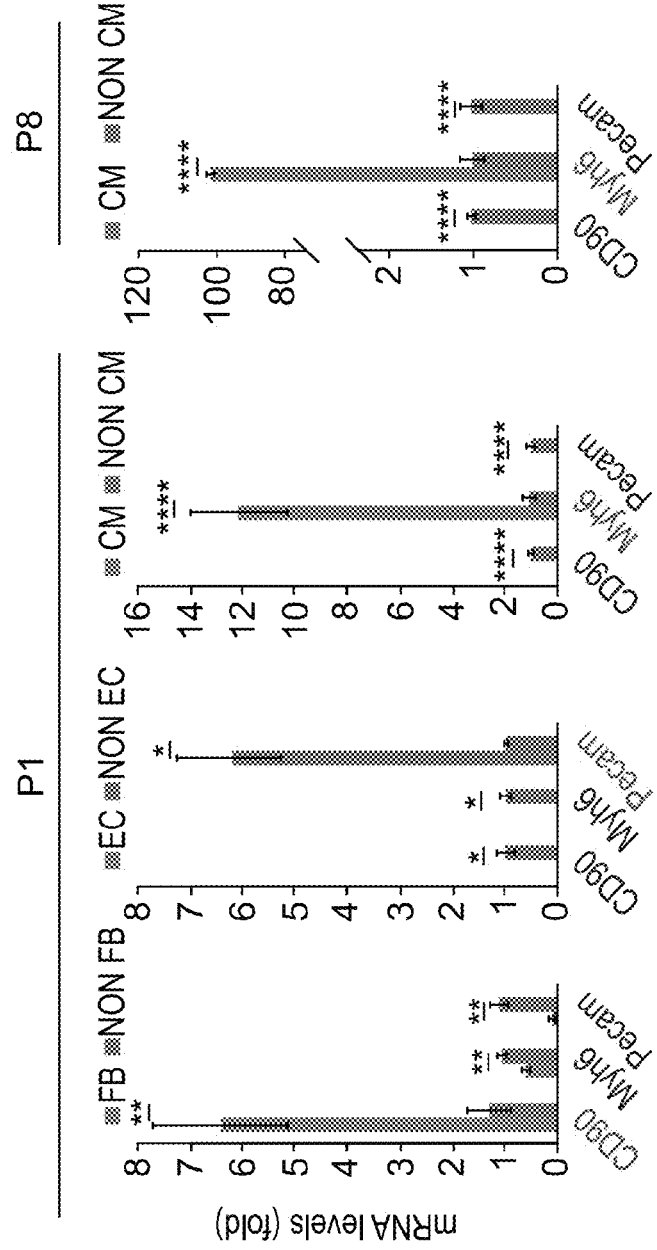

FIGS. 2A-I show that endocardial derived Agrin promotes CM proliferation. (FIG. 2A) qPCR of Agrin gene from P1 and P7 heart lysates. (FIG. 2B) Western blot analysis of Agrin from P1 and P7 heart lysates. (FIG. 2C) Images of P1 and P7 heart sections stained for Agrin (green) cTnT (red) and counterstained with DAPI (blue). (FIG. 2D) qPCR analysis of 6 cell populations (FB, non-FB, CM, non-CM, EC, non-EC) for Agrin. Immunofluorescence evaluation of P1 and P7 CM (cTnT or tomato-αMHC) number (FIG. 2E), cell cycle (Ki67; FIG. 2F) mitosis (pH3; FIG. 2G) or cytokinesis (Aim1; FIG. 2H) in response to Agrin administration in vitro. (FIG. 2I) qPCR of genes from P1 and P8 heart lysate. qPCR analysis of 6 cell populations (FB, non-FB, CM, non-CM, EC, non-EC) for CD90 (FB marker), αMHC (CM marker) and Pecam (EC marker).

Figure 3I:
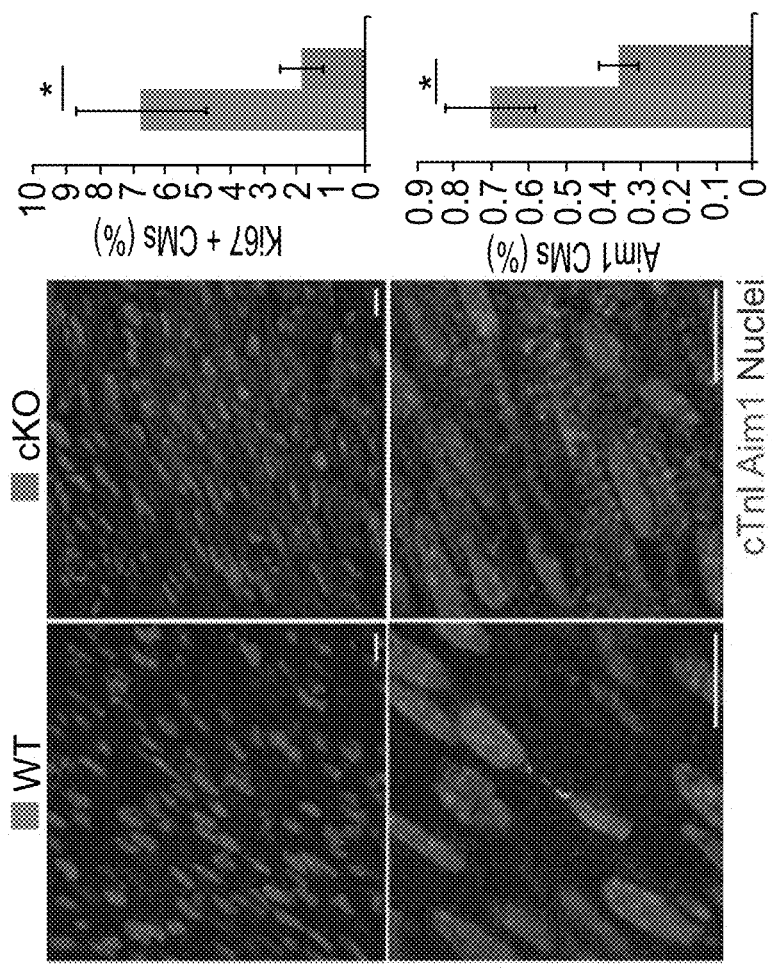
Figure 3H:
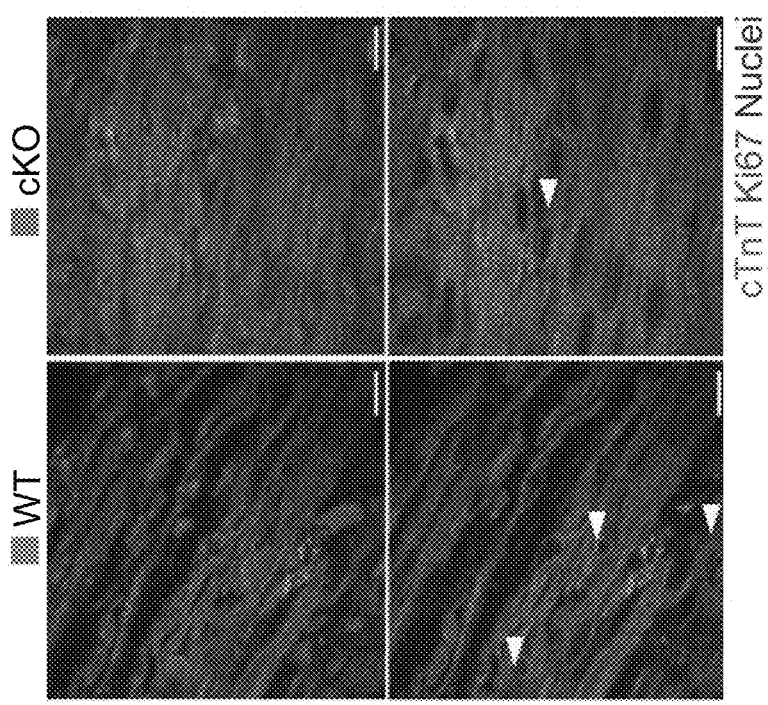

FIGS. 3A-O show that Agrin is required for P1 cardiac regeneration following surgical resection. (FIG. 3A) A schematic diagram depicting the generation of cardiac restricted Agrin knockout (Agrin-cK0) mice. (FIG. 3B) Western Blot analysis of Agrin and sarcomaric protein levels in P1 WT and Agrin-cK0 heart lysates. (FIG. 3C) qPCR of Agrin in P1 WT and Agrin-cKO heart lysates. (FIG. 3D) Immunofluorescence analysis of Agrin in P1 WT and Agrin-cKO. (FIG. 3E) Immunofluorescence analysis of WGA membrane staining in P1 WT and Agrin-cKO depicting changes in cell size (FIG. 3F). (FIG. 3G) qPCR analysis of a pathological hypertrophic marker (i.e., Acta1) in P1 WT and Agrin-cKO heart lysates. In vivo evaluation of P1 CM cell-cycle re-entry (Ki67; FIG. 3H) and cytokinesis (Aim1; FIG. 3I) by immunofluorescence analysis in WT and Agrin-cKO left ventricle heart sections. (FIG. 3J) Scheme of P1 resection experiment. (FIG. 3K) Histological sections of P1 WT and Agrin-cKO stained with Masson's trichrome and Sirius red. (FIGS. 3L-M) Scar quantification based on Masson's trichrome staining of heart sections of 4 weeks post resection WT and Agrin-cKO. (FIGS. 3N,O) In vivo evaluation of CM cell-cycle re-entry by immunofluorescence analysis of Ki67 (FIG. 3N) or Aim1 (FIG. 3O) in sections taken from resected WT and Agrin-cK0 hearts.

FIGS. 4A-I show that Agrin inoculation is sufficient for cardiac regeneration following MI. (FIG. 4A) A schematic diagram depicting the LAD ligation experiment in both juvenile and adult. (FIG. 4B-4E) In vivo evaluation of CM cell-cycle re-entry by immunofluorescence analysis of Ki67 (FIG. 4 B, D) or Aim1 (FIG. 4C, E) in heart sections 7 days post MI in juvenile (FIG. 4B, C) and adult (FIG. 4D, E) mice. (FIG. 4F, G) Serial echocardiographic measurements of ejection fraction (EF), fractional shortening (FS) and wall thickness of uninjured and injured PBS and Agrin treated juvenile (FIG. 4F) and adult (FIG. 4G) mice following MI, according to the schema in FIG. 4A. (FIG. 4H, 4I) Scar quantification based on Masson's trichrome staining of heart sections of PBS and Agrin treated juvenile (FIG. 4H) and adult (FIG. 4I) mice.

Figure 5A:
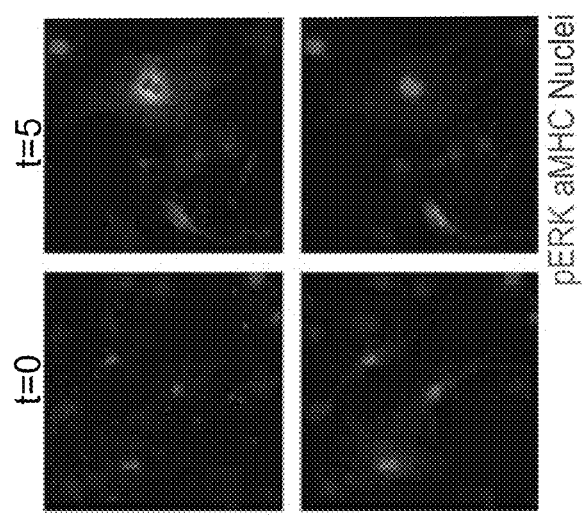

FIGS. 5A-J show that Agrin promotes CM proliferation through Dag1 and ERK activation. (FIG. 5A) qPCR Of Dag1 gene from P1 and P7 heart lysates. (FIG. 5B) Western blot analysis Dag1 from P1 and P7 heart lysates. (FIG. 5C) qPCR analysis of 6 cell populations (FB, non-FB, CM, non-CM, EC, non-EC) for Dag1. (FIG. 5D) Western blot analysis of phospho-ERK (pERK) and general-ERK (gERK) in P7 control and Agrin treated cultures. (FIG. 5E) CM ERK activation analysis by immunofluorescence staining for pERK of P7 control and Agrin treated cultures. (FIG. 5F) Western blot analysis of pERK and gERK in P7 control, Dag1 inhibition, Agrin and Agrin with Dag1 inhibition treated cultures. (FIG. 5G-H) CM cell cycle activity analysis by immunofluorescence staining following Agrin treatment with either MEK inhibition (FIG. 5G) or Dag1 inhibition (FIG. 5H). (FIG. 5I) Immunofluorescence evaluation of P7 CM cell cycle activity (Ki67) in response to Agrin administration in WT and mdx in vitro. (FIG. 5J) Serial Immunofluorescence counting of tomato labeled CMs treated with various compounds shown to inhibit $Na^+/K^+$ pumps.

FIGS. 6A-D show that in vitro Agrin administration promotes human iPSC-derived CMs proliferation. (FIG. 6A) Serial Immunofluorescence evaluation of iPSC-CM cell cycle activity (Ki67) in response to Agrin administration. (FIG. 6B) Day 4 Immunofluorescence analysis of cell cycle activity. (FIGS. 6C-D) Immunofluorescence evaluation of iPSC—CM cell cycle activity either by Ph3 (FIG. 6C) or Aim1 (FIG. 6D) in response to human—Agrin administration in a dose dependent manner.

Figure 7A:
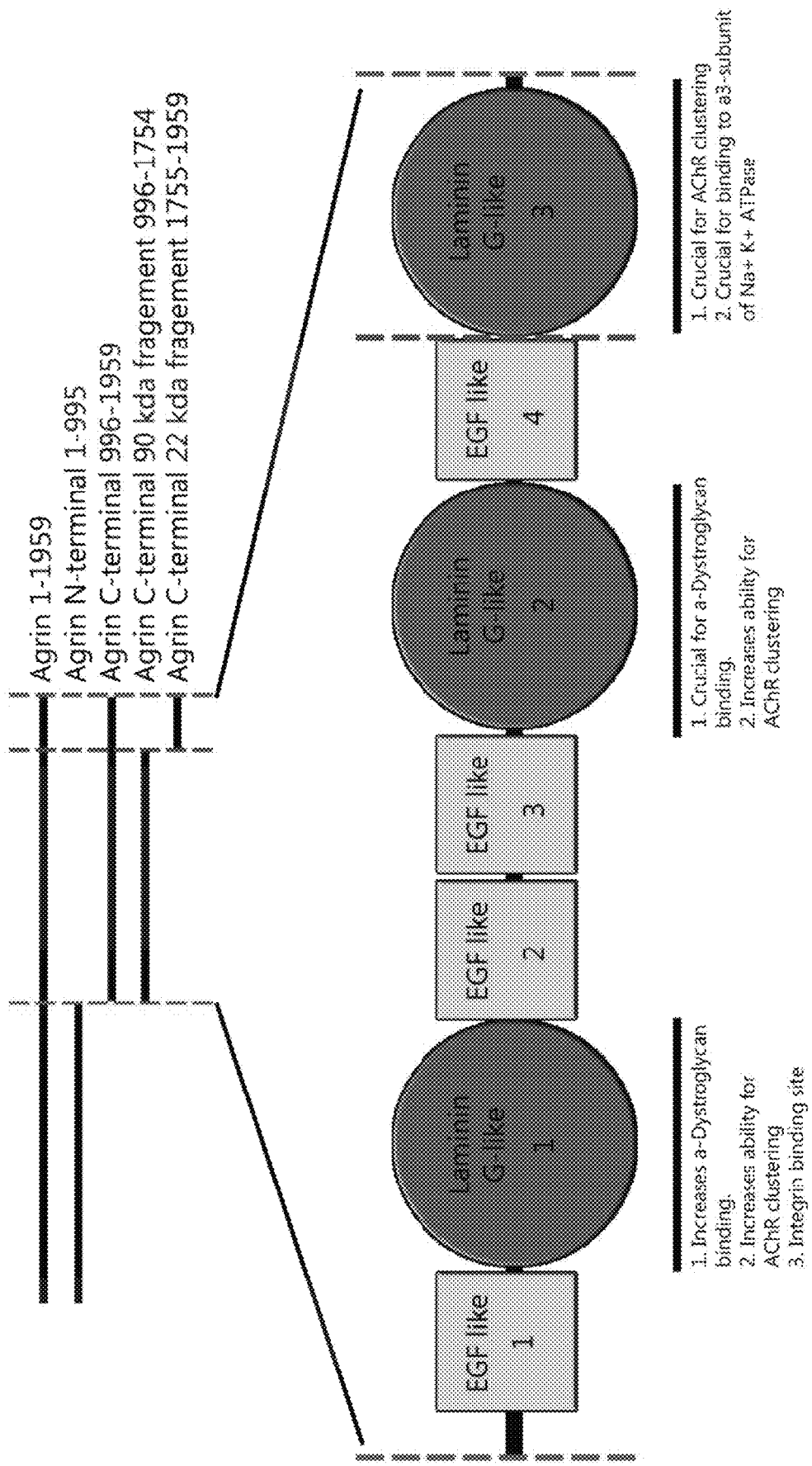

FIGS. 7A-B illustrate the protein structure of Agrin (based on Singhal and Martin 2011 Develop. Neurol. 982-1005) and its alignment in human, mouse and rat (SEQ ID NOs: 38, 9, 6, respectively).

Figure 8F:
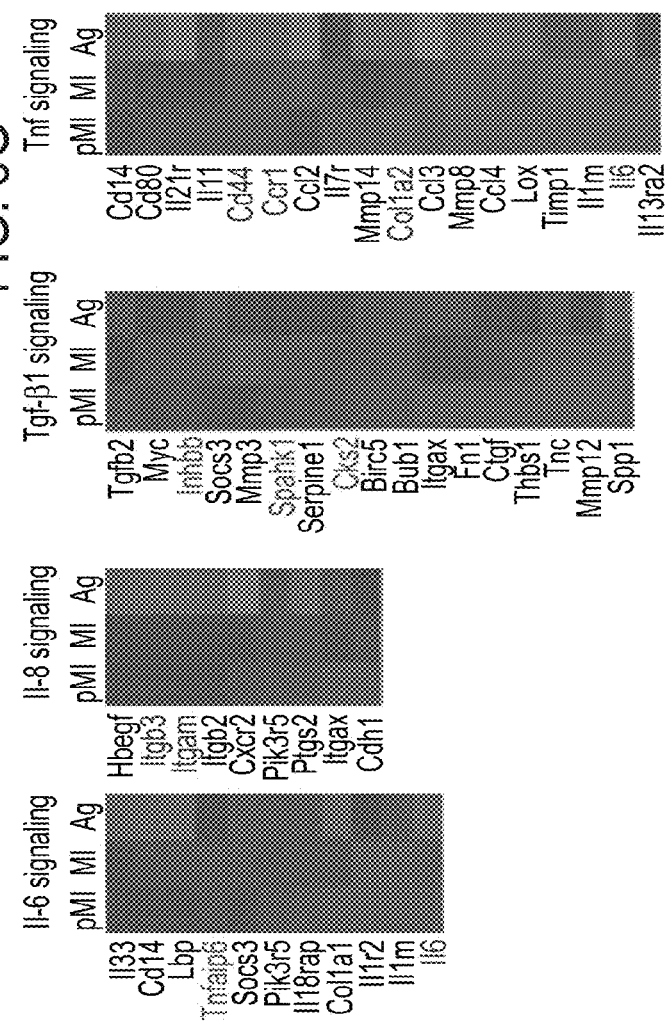
Figure 8G:
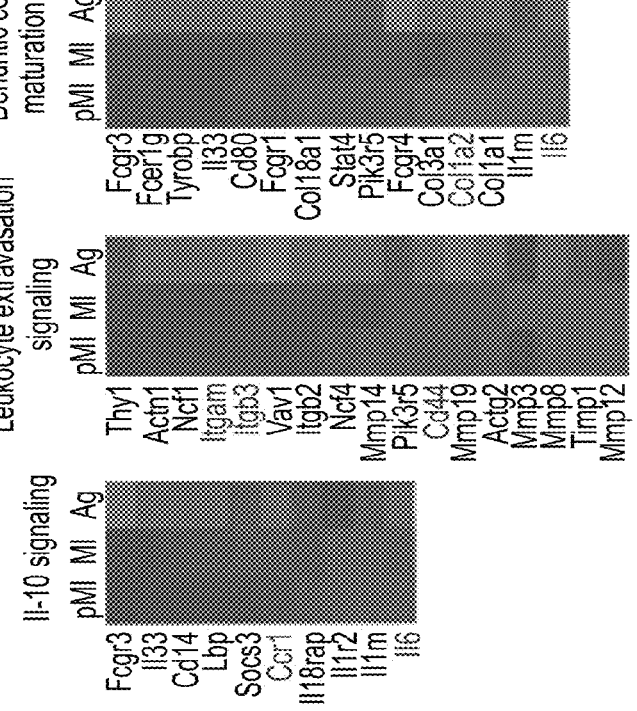
Figure 8H:
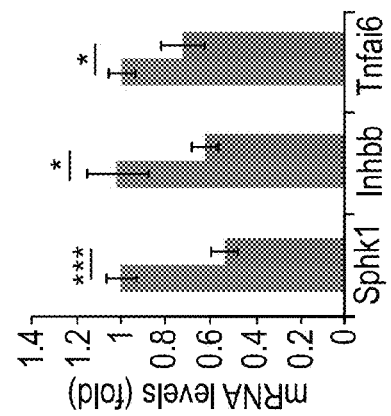

FIGS. 8A-H show agrin transcription effects in myoinfarcted (MI) hearts. RNA sequencing was performed on MI hearts treated with Agrin/PBS, to evaluate Agrin transcriptional effects in the infarcted adult heart. (FIG. 8A) Schematic diagram depicting the experimental design: adult hearts were subjected to LAD ligation, and subjected to either PBS or Agrin injection. 3 days post treatment, hearts were collected from Agrin, PBS and sham operated mice, and RNA was purified and subjected to RNA-seq. (FIG. 8B) Volcano plot of differentially expressed genes in infarcted Agrin vs. PBS (MI) treated hearts. Fold expression change against p value is plotted. Significant increased or decreased genes are indicated in red or blue, respectively. Filled circles indicate relevant genes that are known to participate in important pathways in heart regeneration and immune modulation. (FIG. 8C) Heat map depicting differentially expressed genes affected by Agrin. RNA-seq gene expression data was compared to an MI differentially expressed genes data base1. Differentially expressed genes that showed similar pattern in the present MI setting (PBS vs. sham) and in the preexisting database were compared. These genes are referred to as "MI signature". The relative expression of these genes in the data base MI (Ounzain, Left panel), the present MI (Experimental MI, middle panel) and MI treated with Agrin (Agrin MI vs. PBS MI, Experimental MI+Agrin, right panel). (FIGS. 8D-E) The genes shown in FIG. 8C were analyzed using ingenuity pathway analysis software. Prominent significantly enriched terms are shown for (FIG. 8D) canonical pathways and (8E) upstream regulators. (FIGS. 8F-G) Heat maps depicting the relative expression of relevant genes in prominent (FIG. 8F) canonical pathways and (FIG. 8G) upstream regulators. (FIG. 8H) Real time validation of several genes shown in (FIG. 8F) and (FIG. 8G).

DESCRIPTION OF SPECIFIC EMBODIMENTS OF THE INVENTION

The present invention, in some embodiments thereof, relates to methods of inducing proliferation of cardiomyocytes and methods of treating heart diseases.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Heart disease, including myocardial infarction (MI), is the leading cause of death in the world. The severity of heart disease is due to the post-mitotic nature of human adult cardiac muscle cells—the cardiomyocytes (CMs) {Bergmann, 2009 #9; Senyo, 2013 #86} and their limited capacity to replenish damaged tissue {Poss, 2007 #30; Ausoni, 2009 #17}. In contrast, the neonatal murine CM turnover is sufficient to repair damaged myocardium following injury; however this ability is greatly diminished during the first week after birth.

Whilst searching for novel treatment modalities that can boost the proliferative nature of juvenile/adult CMs, the present inventors have employed a novel method for identifying murine cardiac ECM compositions that promote CM proliferation and identified Agrin, a proteoglycan expressed by cardiac endothelial cells at birth but its levels decline after 7 days. Treatment with recombinant Agrin induces CM cell cycle reentry and division in-vitro. At birth, Agrin conditional knockout (cKO) CMs display mature and more differentiated phenotype accompanied by reduced proliferation and impaired cardiac regeneration. In contrast, Agrin administration following myocardial infarction (MI) induces CM proliferation that leads to reduced scarring and overall improved cardiac function in both neonatal and adult mice. Mechanistically, the present inventors suggest that Agrin functions via modulation of the Dystroglycan complex by blocking sarcomerogenesis and not through its canonical MuSK related signaling. These findings thus render any agent, which inhibits the dystroglycan complex in CMs a potential therapy for heart diseases. Transcriptional analysis suggests that Agrin promotes heart regeneration not only through cardiomyocyte proliferation by also through immune modulation, which might change cardiomyocyte survival thereby reducing infarct and scar size.

Thus, according to an aspect of the invention there is provided a method of inducing proliferation of CMs, the method comprising contacting the cardiomyocytes with an agent, which inhibits the Dystroglycan complex on the CMs, thereby inducing proliferation of CMs.

According to another aspect of the invention there is provided a method of inducing proliferation of cardiomyocytes, the method comprising contacting the cardiomyocytes with an effective amount of an agrin peptide which induces proliferation of the cardiomyocytes.

As used herein "a cardiomyocyte" or "cardiomyocytes" (abbreviated as, CM, CMs), also known as myocardiocytes or cardiac myocytes, are the muscle cells (myocytes) that make up the cardiac muscle. The term refers to cardiomyocytes of any species including mammalian, e.g., human at any stage of development. According to a specific embodiment, the cardiomyocyte is a neonatal CM (e.g., for human up 6 months after birth). According to a specific embodiment, the cardiomyocyte is an adult cardiomyocyte (e.g., for human at least 16-18 years after birth).

Thus, according to a specific embodiment, the cardiomyocytes are of a subject having a heart disease.

According to a specific embodiment, the cardiomyocytes are of a donor healthy subject.

According to a specific embodiment, the cardiomyocytes may be naturally occurring.

According to a specific embodiment, the CMs have been ex-vivo differentiated into cardiomyocytes (e.g., from pluripotent stem cells e.g., embryonic stem cells (hESCs) and induced pluripotent stem cells (iPSCs)). Methods of differentiating stem cells into CMs are well known in the art. For example, an iPSC can be co-cultured with visceral endoderm-like cells (see, e.g., Mummery et al. (2003) Circulation 107:2733). An iPS cell can also be induced to undergo cardiomyogenesis without co-culture with a feeder cell or other cell. For example, as described in U.S. Pat. No. 7,297,539. The CMs may be fully differentiated when contacted with the agent (e.g., Agrin). According to another embodiment, the cells are committed to the cardiac lineage and the agent (e.g., Agrin) is added to the culture during or following the differentiation process.

According to a specific embodiment, the cardiomyocytes are human CMs.

According to a specific embodiment, the CMs are a cell-line.

According to a specific embodiment, the CMs are primary CMs.

As used herein the term "inducing proliferation" refers to an increase in CM proliferation which is statistically significant (as compared to untreated cells of the same origin and developmental stage) and is a result of contacting the cardiomyocytes with the agent e.g., Agrin.

As mentioned, the cells are contacted with an agent, which inhibits the dystroglycan complex on CMs. Our data suggest that Agrin interacts with the dystroglycan complex since an antibody against this molecule inhibits Agrin-induced effects on CM proliferation and ERK activation. Alternatively or additionally, the agent modulates the structural activity of dystroglycan as a bridging molecule between the CM cytoskeleton and the ECM, thus allowing the CM to proliferate.

As mentioned, the agent described herein is capable of inducing immune modulation (see FIGS. 8A-H) by which increasing cardiomyocyte survival, anti inflammatory and/or anti fibrotic effects.

As used herein "immune modulation" refers to induced changes in gene expression (e.g., RNA as determined by RNA-Seq) of canonical pathway genes—and/or upstream regulators (see FIGS. 8A-H which are hereby incorporated).

As used herein, the term "agent" refers to a substance which can be of a biological nature e.g., proteinaceous substance e.g., peptide (e.g., further described hereinbelow) or an antibody, nucleic acid substance e.g., a polynucleotide or an oligonucleotide, or a chemical nature e.g., small molecule.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

The term "isolated" refers to at least partially separated from the natural environment e.g., from a recombinant host cell.

Other agents which can be used to inhibit the dystroglycan complex can be identified by contacting the agent with cardiomyocytes that express the dystroglycan complex and identifying an agent which binds the dystroglycan complex and optionally induces Erk activation and ultimately CM proliferation or inhibit sarcomerogenesis. Protein binding can be assayed using numerous assays known in the art e.g., ELISA assay, co-immunoprecipitation, membrane binding, FRET, surface Plasmon resonance and the like.

Alternatively or additionally, and as mentioned, the cells are contacted with an "Agrin peptide".

As used herein the term "Agrin" refers to the protein product of the AGRN gene. The term is meant to include polynucleotide sequences encoding Agrin or expression products as RNA or a protein.

An "Agrin peptide" refers to an Agrin peptide which is shorter than the full-length agrin (e.g., in the case of human Agrin shorter than the 2068/2045 amino acids which make up the full length human agrins) and is capable of inducing proliferation of cardiomyocytes. According to a specific embodiment the Agrin peptide is provided in a soluble form.

According to a specific embodiment the agrin peptide is from human Agrin NP_001292204 (SEQ ID NO: 4) or NP_940978 (SEQ ID NO: 5) or Uniprot O00468 SEQ ID NO: 38.

According to a specific embodiment, the Agrin peptide is of a human ortholog e.g., NP_786930 (SEQ ID NO: 6).

It will be appreciated that the present teachings contemplate the treatment of one species (e.g., human) with an Agrin peptide of a second species (e.g., rat) as long as they exhibit the desired activity (i.e., induced CM proliferation) on the treated subject/cells.

According to a specific embodiment, the Agrin peptide comprises a Laminin G-like 2 (G2) domain and optionally a Laminin G-like 1 (G1) domain.

Thus according to a specific embodiment, the Agrin peptide comprises the G2 domain as set forth in SEQ ID NO: 8 or G1 and G2 as set forth in SEQ ID NO: 7.

Accordingly there is provided an isolated peptide comprising Laminin G-like 2 (G2) domain the peptide being no more than 200 amino acids in length.

According to a specific embodiment the peptide is as set forth in SEQ ID NO: 8.

Without being bound by theory, it is suggested that such a configuration which comprises at least the Laminin G-like 2 (G2) and possibly G1 and/or G3 domains is required for alpha-dystroglycan/DAG1 binding.

According to a specific embodiment, such an Agrin peptide promotes sarcomere disassembly and cardiomyocyte proliferation leading to heart regeneration.

According to a specific embodiment, the Agrin peptide does not exert its function via binding to the MuSK receptor. Indeed no MuSK receptor is expressed in the heart as evident from RNA-seq profiles [41].

According to a specific embodiment, the Agrin peptide is 50-500 amino acids long. According to a specific embodiment, the Agrin peptide is 100-400 amino acids long. According to a specific embodiment, the Agrin peptide is 100-300 amino acids long. According to a specific embodiment, the Agrin peptide is 150-200 amino acids long. According to a specific embodiment, the Agrin peptide is 100-200 amino acids long.

According to a specific embodiment, the Agrin peptide is 80-150 kDa. According to a specific embodiment, the Agrin peptide is 80-120 kDa. According to a specific embodiment, the Agrin peptide is 80-110 kDa. According to a specific embodiment, the Agrin peptide is 90-110 kDa.

Agrin peptides are commercially available from R&D systems e.g., 6624-AG, 550-AG or 550-AG/CF.

According to a specific embodiment, the Agrin peptide binds the dystroglycan complex via the Laminin G1-G2 domains [42]. The inventors suggest that Agrin inhibits its activity thereby leading to Erk activation and optionally inhibits sarcromerogenesis.

Methods of determining Erk (also known as extracellular-signal-regulated kinases (ERKs) or classical MAP kinases) activation are well known in the art and include, but are not limited to, in vitro kinase assays and the use of anti-phosphorylated MAPK antibodies.

According to a specific embodiment, the Agrin is not a part of a fusion polypeptide where the Agrin is serving as a targeting moiety for the delivery of a therapeutically effective peptide.

According to another specific embodiment, the Agrin is a part of a fusion polypeptide where the Agrin is serving both as a targeting moiety and an effector moiety (i.e., for inducing CM proliferation).

According to a specific embodiment, the Agrin is provided in a soluble form. Accordingly, the Agrin is not part or attached to an extracellular matrix composition.

Methods of determining CM proliferation are well known in the art, and include, but are not limited to, manual cell counting, MTT assay and a thymidine incorporation assay. According to some embodiments both ascertaining the nature of the cells as well as determining their proliferation are done.

For example, in some embodiments, the presence of proliferative cardiomyocytes is validated by confirming expression of at least one cardiomyocyte-specific marker produced by the cell. For example, the cardiomyocytes express cardiac transcription factors, sarcomere proteins, and gap junction proteins. Suitable cardiomyocyte-specific proteins include, but are not limited to, cardiac troponin I, cardiac troponin-C, tropomyosin, caveolin-3, GATA-4, myosin heavy chain, myosin light chain-2a, myosin light chain-2v, ryanodine receptor, and atrial natriuretic factor.

As another example, in some embodiments, cardiomyocytes are ascertained by detecting responsiveness to pharmacological agents such as beta-adrenergic agonists (e.g., isoprenaline), adrenergic beta-antagonists (e.g., esmolol), cholinergic agonists (e.g., carbochol), and the like.

Alternatively or additionally, validating the nature of the CMs is done by detecting electrical activity of the cells. Electrical activity can be measured by various methods, including extracellular recording, intracellular recording (e.g., patch clamping), and use of voltage-sensitive dyes. Such methods are well known to those skilled in the art.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder. According to a specific embodiment, the peptide (or polypeptide) is a recombinant product (i.e., of recombinant DNA technology). According to a specific embodiment, the agrin is above 95% pure (e.g., no other active ingredient proteins are present in the formulation).

Peptide bonds (—CO—NH—) within the peptide may be substituted, for example, by N-methylated amide bonds (—N(CH3)-CO—), ester bonds (—C(=O)—O—), ketomethylene bonds (—CO—CH2-), sulfinylmethylene bonds (—S(=O)—CH2-), α-aza bonds (—NH—N(R)—CO—), wherein R is any alkyl (e.g., methyl), amine bonds (—CH2-NH—), sulfide bonds (—CH2-S—), ethylene bonds (—CH2-CH2-), hydroxyethylene bonds (—CH(OH)—

CH2-), thioamide bonds (—CS—NH—), olefinic double bonds (—CH=CH—), fluorinated olefinic double bonds (—CF=CH—), retro amide bonds (—NH—CO—), peptide derivatives (—N(R)—CH2-CO—), wherein R is the "normal" side chain, naturally present on the carbon atom.

These modifications can occur at any of the bonds along the peptide chain and even at several (2-3) bonds at the same time.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr.

The peptides of some embodiments of the invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids. Tables 1 and 2 below list naturally occurring amino acids (Table 1), and non-conventional or modified amino acids (e.g., synthetic, Table 2) which can be used with some embodiments of the invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| ornithine | Orn | hydroxyproline | Hyp |
| α-aminobutyric acid | Abu | aminonorbornyl-carboxylate | Norb |
| D-alanine | Dala | aminocyclopropane-carboxylate | Cpro |
| D-arginine | Darg | N-(3-guanidinopropyl)glycine | Narg |
| D-asparagine | Dasn | N-(carbamylmethyl)glycine | Nasn |
| D-aspartic acid | Dasp | N-(carboxymethyl)glycine | Nasp |
| D-cysteine | Dcys | N-(thiomethyl)glycine | Ncys |
| D-glutamine | Dgln | N-(2-carbamylethyl)glycine | Ngln |
| D-glutamic acid | Dglu | N-(2-carboxyethyl)glycine | Nglu |
| D-histidine | Dhis | N-(imidazolylethyl)glycine | Nhis |
| D-isoleucine | Dile | N-(1-methylpropyl)glycine | Nile |
| D-leucine | Dleu | N-(2-methylpropyl)glycine | Nleu |
| D-lysine | Dlys | N-(4-aminobutyl)glycine | Nlys |
| D-methionine | Dmet | N-(2-methylthioethyl)glycine | Nmet |
| D-ornithine | Dorn | N-(3-aminopropyl)glycine | Norn |
| D-phenylalanine | Dphe | N-benzylglycine | Nphe |
| D-proline | Dpro | N-(hydroxymethyl)glycine | Nser |
| D-serine | Dser | N-(1-hydroxyethyl)glycine | Nthr |
| D-threonine | Dthr | N-(3-indolylethyl) glycine | Nhtrp |
| D-tryptophan | Dtrp | N-(p-hydroxyphenyl)glycine | Ntyr |
| D-tyrosine | Dtyr | N-(1-methylethyl)glycine | Nval |
| D-valine | Dval | N-methylglycine | Nmgly |
| D-N-methylalanine | Dnmala | L-N-methylalanine | Nmala |
| D-N-methylarginine | Dnmarg | L-N-methylarginine | Nmarg |
| D-N-methylasparagine | Dnmasn | L-N-methylasparagine | Nmasn |
| D-N-methylasparatate | Dnmasp | L-N-methylaspartic acid | Nmasp |
| D-N-methylcysteine | Dnmcys | L-N-methylcysteine | Nmcys |
| D-N-methylglutamine | Dnmgln | L-N-methylglutamine | Nmgln |
| D-N-methylglutamate | Dnmglu | L-N-methylglutamic acid | Nmglu |
| D-N-methylhistidine | Dnmhis | L-N-methylhistidine | Nmhis |
| D-N-methylisoleucine | Dnmile | L-N-methylisolleucine | Nmile |
| D-N-methylleucine | Dnmleu | L-N-methylleucine | Nmleu |
| D-N-methyllysine | Dnmlys | L-N-methyllysine | Nmlys |
| D-N-methylmethionine | Dnmmet | L-N-methylmethionine | Nmmet |
| D-N-methylornithine | Dnmorn | L-N-methylornithine | Nmorn |
| D-N-methylphenylalanine | Dnmphe | L-N-methylphenylalanine | Nmphe |
| D-N-methylproline | Dnmpro | L-N-methylproline | Nmpro |
| D-N-methylserine | Dnmser | L-N-methylserine | Nmser |
| D-N-methylthreonine | Dnmthr | L-N-methylthreonine | Nmthr |
| D-N-methyltryptophan | Dnmtrp | L-N-methyltryptophan | Nmtrp |
| D-N-methyltyrosine | Dnmtyr | L-N-methyltyrosine | Nmtyr |
| D-N-methylvaline | Dnmval | L-N-methylvaline | Nmval |

TABLE 2-continued

| Non-conventional amino acid | Code | Non-conventional amino acid | Code |
| --- | --- | --- | --- |
| L-norleucine | Nle | L-N-methylnorleucine | Nmnle |
| L-norvaline | Nva | L-N-methylnorvaline | Nmnva |
| L-ethylglycine | Etg | L-N-methyl-ethylglycine | Nmetg |
| L-t-butylglycine | Tbug | L-N-methyl-t-butylglycine | Nmtbug |
| L-homophenylalanine | Hphe | L-N-methyl-homophenylalanine | Nmhphe |
| α-naphthylalanine | Anap | N-methyl-α-naphthylalanine | Nmanap |
| penicillamine | Pen | N-methylpenicillamine | Nmpen |
| γ-aminobutyric acid | Gabu | N-methyl-γ-aminobutyrate | Nmgabu |
| cyclohexylalanine | Chexa | N-methyl-cyclohexylalanine | Nmchexa |
| cyclopentylalanine | Cpen | N-methyl-cyclopentylalanine | Nmcpen |
| α-amino-α-methylbutyrate | Aabu | N-methyl-α-amino-α-methylbutyrate | Nmaabu |
| α-aminoisobutyric acid | Aib | N-methyl-α-aminoisobutyrate | Nmaib |
| D-α-methylarginine | Dmarg | L-α-methylarginine | Marg |
| D-α-methylasparagine | Dmasn | L-α-methylasparagine | Masn |
| D-α-methylaspartate | Dmasp | L-α-methylaspartate | Masp |
| D-α-methylcysteine | Dmcys | L-α-methylcysteine | Mcys |
| D-α-methylglutamine | Dmgln | L-α-methylglutamine | Mgln |
| D-α-methyl glutamic acid | Dmglu | L-α-methylglutamate | Mglu |
| D-α-methylhistidine | Dmhis | L-α-methylhistidine | Mhis |
| D-α-methylisoleucine | Dmile | L-α-methylisoleucine | Mile |
| D-α-methylleucine | Dmleu | L-α-methylleucine | Mleu |
| D-α-methyllysine | Dmlys | L-α-methyllysine | Mlys |
| D-α-methylmethionine | Dmmet | L-α-methylmethionine | Mmet |
| D-α-methylornithine | Dmorn | L-α-methylornithine | Morn |
| D-α-methylphenylalanine | Dmphe | L-α-methylphenylalanine | Mphe |
| D-α-methylproline | Dmpro | L-α-methylproline | Mpro |
| D-α-methylserine | Dmser | L-α-methylserine | Mser |
| D-α-methylthreonine | Dmthr | L-α-methylthreonine | Mthr |
| D-α-methyltryptophan | Dmtrp | L-α-methyltryptophan | Mtrp |
| D-α-methyltyrosine | Dmtyr | L-α-methyltyrosine | Mtyr |
| D-α-methylvaline | Dmval | L-α-methylvaline | Mval |
| N-cyclobutylglycine | Ncbut | L-α-methylnorvaline | Mnva |
| N-cycloheptylglycine | Nchep | L-α-methylethylglycine | Metg |
| N-cyclohexylglycine | Nchex | L-α-methyl-t-butylglycine | Mtbug |
| N-cyclodecylglycine | Ncdec | L-α-methyl-homophenylalanine | Mhphe |
| N-cyclododecylglycine | Ncdod | α-methyl-α-naphthylalanine | Manap |
| N-cyclooctylglycine | Ncoct | α-methylpenicillamine | Mpen |
| N-cyclopropylglycine | Ncpro | α-methyl-γ-aminobutyrate | Mgabu |
| N-cycloundecylglycine | Ncund | α-methyl-cyclohexylalanine | Mchexa |
| N-(2-aminoethyl)glycine | Naeg | α-methyl-cyclopentylalanine | Mcpen |
| N-(2,2-diphenylethyl)glycine | Nbhm | N-(N-(2,2-diphenylethyl) carbamylmethyl-glycine | Nnbhm |
| N-(3,3-diphenylpropyl)glycine | Nbhe | N-(N-(3,3-diphenylpropyl) carbamylmethyl-glycine | Nnbhe |
| 1-carboxy-1-(2,2-diphenyl ethylamino)cyclopropane | Nmbc | 1,2,3,4-tetrahydroisoquinoline-3-carboxylic acid | Tic |
| phosphoserine | pSer | phosphothreonine | pThr |
| phosphotyrosine | pTyr | O-methyl-tyrosine | |
| 2-aminoadipic acid | | hydroxylysine | |

The peptides of some embodiments of the invention are preferably utilized in a linear form, although it will be appreciated that in cases where cyclization does not severely interfere with peptide characteristics, cyclic forms of the peptide can also be utilized.

Since the present peptides are preferably utilized in therapeutics or diagnostics which require the peptides to be in soluble form, the peptides of some embodiments of the invention preferably include one or more non-natural or natural polar amino acids, including but not limited to serine and threonine which are capable of increasing peptide solubility due to their hydroxyl-containing side chain.

The peptides of some embodiments of the invention are preferably utilized in a linear form, although it will be appreciated that in cases where cyclization does not severely interfere with peptide characteristics, cyclic forms of the peptide can also be utilized.

It will be appreciated that the proteinaceous agents of some embodiments of the invention, can also utilize functional homologues which exhibit the desired activity (i.e., induced proliferation of CMs). Such homologues can be, for example, at least, 60%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the human sequence e.g., human Agrin e.g., SEQ ID NO: 4, 5, 7 or 8, as determined using the BestFit software of the Wisconsin sequence analysis package, utilizing the Smith and Waterman algorithm, where gap weight equals 50, length weight equals 3, average match equals 10 and average mismatch equals −9.

The peptides of some embodiments of the invention may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound.

Alternatively, the peptides are produced using recombinant DNA technology.

A variety of prokaryotic or eukaryotic cells can be used as host-expression systems to express the polypeptides/peptides of some embodiments of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the polypeptides of some embodiments of the invention.

For the sake of simplicity agrin and the agent are collectively referred to herein as "an agent" or "agents", although it should be appreciated that each possibility of an agent represents a separate embodiment of the present invention.

According to a specific embodiment, the proteinaceous agent can be attached (or conjugated) to non-proteinaceous moieties which increase their bioavailability and half-life in the circulation.

The phrase "non-proteinaceous moiety" as used herein refers to a molecule not including peptide bonded amino acids that is attached to the above-described proteinaceous agents. Exemplary non-proteinaceous and preferably non-toxic moieties which may be used according to the present teachings include, but are not limited to, polyethylene glycol (PEG), Polyvinyl pyrrolidone (PVP), poly(styrene comaleic anhydride) (SMA), and divinyl ether and maleic anhydride copolymer (DIVEMA).

Such a molecule is highly stable (resistant to in-vivo proteolytic activity probably due to steric hindrance conferred by the non-proteinaceous moiety) and may be produced using common solid phase synthesis methods which are inexpensive and highly efficient, as further described hereinbelow. However, it will be appreciated that recombinant techniques may still be used, whereby the recombinant peptide product is subjected to in-vitro modification (e.g., PEGylation).

Thus, such non-proteinaceous non-toxic moieties may also be attached to the above mentioned agents to promote stability and possibly solubility of the molecules.

Bioconjugation of such a non-proteinaceous moiety (such as PEGylation) can confer the proteins amino acid sequence with stability (e.g., against protease activities) and/or solubility (e.g., within a biological fluid such as blood, digestive fluid) while preserving its biological activity and prolonging its half-life.

Bioconjugation is advantageous particularly in cases of therapeutic proteins which exhibit short half-life and rapid clearance from the blood. The increased half-lives of bioconjugated proteins in the plasma results from increased size of protein conjugates (which limits their glomerular filtration) and decreased proteolysis due to polymer steric hindrance. Generally, the more polymer chains attached per peptide, the greater the extension of half-life. However, measures are taken not to reduce the specific activity of the protein of the present invention (e.g., CM proliferation).

Bioconjugation of the proteinaceous agent with PEG (i.e., PEGylation) can be effected using PEG derivatives such as N-hydroxysuccinimide (NHS) esters of PEG carboxylic acids, monomethoxyPEG2-NHS, succinimidyl ester of carboxymethylated PEG (SCM-PEG), benzotriazole carbonate derivatives of PEG, glycidyl ethers of PEG, PEG p-nitrophenyl carbonates (PEG-NPC, such as methoxy PEG-NPC), PEG aldehydes, PEG-orthopyridyl-disulfide, carbonyldimidazol-activated PEGs, PEG-thiol, PEG-maleimide. Such PEG derivatives are commercially available at various molecular weights [See, e.g., Catalog, Polyethylene Glycol and Derivatives, 2000 (Shearwater Polymers, Inc., Huntsvlle, Ala.)]. If desired, many of the above derivatives are available in a monofunctional monomethoxyPEG (mPEG) form. In general, the PEG added to the anti HER3 antibody amino acid sequence of the present invention should range from a molecular weight (MW) of several hundred Daltons to about 100 kDa (e.g., between 3-30 kDa). Larger MW PEG may be used, but may result in some loss of yield of PEGylated peptides. The purity of larger PEG molecules should be also watched, as it may be difficult to obtain larger MW PEG of purity as high as that obtainable for lower MW PEG. It is preferable to use PEG of at least 85% purity, and more preferably of at least 90% purity, 95% purity, or higher. PEGylation of molecules is further discussed in, e.g., Hermanson, Bioconjugate Techniques, Academic Press San Diego, Calif. (1996), at Chapter 15 and in Zalipsky et al., "Succinimidyl Carbonates of Polyethylene Glycol," in Dunn and Ottenbrite, eds., Polymeric Drugs and Drug Delivery Systems, American Chemical Society, Washington, D.C. (1991).

According to a specific embodiment, the methods described herein for inducing CM proliferation are effected in vivo.

According to a specific embodiment, the methods described herein for inducing CM proliferation are effected in vitro.

According to a specific embodiment, the methods described herein for inducing CM proliferation are effected ex vivo.

According to a specific embodiment the cardiomyocytes are comprised in a tissue (a vascularized tissue).

The ability to induce CM proliferation renders the present teachings particularly suitable for the treatment of heart diseases where there is damage to the cardiac tissue or there is a risk for such damage.

Thus, according to an aspect of the invention there is provided a use of a therapeutically effective amount of an Agrin peptide which induces proliferation of cardiomyocytes in the manufacture of a medicament for treating a heart disease.

Alternatively, according to an aspect of the invention there is provided a use of a therapeutically effective amount of an Agrin peptide which induces proliferation of cardiomyocytes in the manufacture of a medicament for treating a heart disease.

Alternatively, according to an aspect of the invention there is provided a use of an agent which inhibits the Dystroglycan complex on cardiomyocytes in the manufacture of a medicament for treating a heart disease.

Alternatively, according to an aspect of the invention there is provided a method of treating a heart disease in a subject in need thereof, the method comprising administering to the subject a therapeutically effective amount of an Agrin peptide which induces proliferation of cardiomyocytes, thereby treating the heart disease.

Alternatively, according to an aspect of the invention there is provided a method of treating a heart disease in a subject in need thereof, the method comprising administering to the subject a therapeutically effective amount of an agent which inhibits the Dystroglycan complex on cardiomyocytes, thereby treating the heart disease.

The term "treating" refers to inhibiting, preventing or arresting the development of a pathology (i.e., heart disease, disorder or condition, e.g., ischemic heart disease) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age that suffer from the pathology. Preferably, this term encompasses individuals who are at risk to develop the pathology.

According to a specific embodiment, the heart disease is an ischemic heart disease.

An ischemic heart disease refers to a lack of oxygen flow to the heart or portion thereof, resulting in myocardial ischemic damage. As used herein, the phrase myocardial ischemic damage includes damage caused by reduced blood flow to the myocardium. Non-limiting examples of causes of an ischemic heart disease and myocardial ischemic damage include: decreased aortic diastolic pressure, increased intraventricular pressure and myocardial contraction, coronary artery stenosis (e.g., coronary ligation, fixed coronary stenosis, acute plaque change (e.g., rupture, hemorrhage), coronary artery thrombosis, vasoconstriction), aortic valve stenosis and regurgitation, and increased right atrial pressure. Non-limiting examples of adverse effects of myocardial ischemia and myocardial ischemic damage include myocyte damage (e.g., myocyte cell loss, myocyte hypertrophy, myocyte cellular hyperplasia), angina (e.g., stable angina, variant angina, unstable angina, sudden cardiac death), myocardial infarction, and congestive heart failure. Damage due to myocardial ischemia may be acute or chronic, and consequences may include scar formation, cardiac remodeling, cardiac hypertrophy, wall thinning, dilatation, and associated functional changes. The existence and etiology of acute or chronic myocardial damage and/or myocardial ischemia may be diagnosed using any of a variety of methods and techniques well known in the art including, e.g., non-invasive imaging (e.g., MRI, echocardiography), angiography, stress testing, assays for cardiac-specific proteins such as cardiac troponin, and evaluation of clinical symptoms. These methods and techniques as well as other appropriate techniques may be used to determine which subjects are suitable candidates for the treatment methods described herein.

According to a specific embodiment, the ischemic heart disease in the present invention includes, for example, coronary arteriosclerosis, acute myocardial infarction (AMI), myocardial infarction (MI), old MI, angina pectoris (AP) including stable angina, unstable angina, and effort angina, ischemic cardiomyopathy, heart failure, and other disease which causes necrosis of heart muscle that results from prolonged ischemia. As necrosis of heart muscle progresses, the damaged myocardiac tissue are replaced with fibrous tissue, thickness of the myocardial wall in the infarct zone gets thinner, and the cardiac inner cavity dilates, therefore cardiac function such as contractility deteriorates and results in heart failure.

Coronary arteriosclerosis is characterized by arteriosclerosis in the coronary artery that supplies nutrients to the heart. Angina pectoris is characterized by attacks of chest pain caused by impaired blood flow in the coronary artery. Myocardial infarction is characterized by myocardial necrosis caused by impaired blood flow in the coronary artery and by fatal complications coming therewith such as arrhythmia, cardiac failure, cardiac rupture, and pump failure. Impaired blood flow to the heart, a vital organ, is an essential characteristic of these ischemic heart diseases.

"Post-infarction myocardial remodeling" refers to a series of changes such as the hypertrophy of myocardial cells at non-infarction sites, increase in interstitial tissue (extracellular matrix), and the dilation of cardiac lumens, which occur in compensation for reduced cardiac function caused by thickening at infarction sites after myocardial infarction. Since long-term prognosis after myocardial infarction is correlated with the degree of left ventricular dysfunction, the suppression of myocardial remodeling is important for maintaining and conserving the function of the left ventricle.

The agents (e.g., Agrin peptide) of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agent (e.g., Agrin peptide) accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, intravenous, intraperitoneal, intranasal, or intraocular injections.

Alternately, one may administer the pharmaceutical composition in a local rather than systemic manner, for example, via injection of the pharmaceutical composition directly into a tissue region of a patient. For example by direct intraventricular, intracardiac, e.g., into the right or left ventricular cavity, into the common coronary artery. Also contemplated is administration of the composition directly to the myocardium e.g., either during open heart surgery or guided by imaging e.g., ultrasound.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (e.g., Agrin peptide) effective to prevent, alleviate or ameliorate symptoms of a disorder (e.g., ischemic heart disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide for example, a cardiac tissue levels of the active ingredient that are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

The agent is delivered by an appropriate means to the site of defect (e.g., as described above). The site and subject are observed and tested for regeneration of the defective myocardium to determine that an effective amount of the composition has been delivered, particularly to observe new tissue growth, and also to determine that the new tissue has the contractility necessary for it to function usefully as myocardium. Tissue growth and contractility can be tested and observed by standard means, for example as described in Badylak et al, The Heart Surgery Forum, Extracellular Matrix for Myocardial Repair 6(2) E20-E26 (2003).

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The agents as described herein can also be immobilized to an implant (e.g., stent) where they can be slowly released therefrom.

The agent as described herein can be combined with other treatment modalities. These other treatments include medication (e.g., blood pressure medication, calcium channel blockers, digitalis, anti-arrhythmics, ACE inhibitors, anti-coagulants, immunosuppressants, pain relievers, vasodilators, etc.), angioplasty, stent placement, coronary artery bypass graft, cardiac assist device (e.g., left ventricular assist device, balloon pump), pacemaker placement, heart transplantation, etc. In certain embodiments, the agent provides a bridge to recover for a subject waiting to undergo heart transplantation.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Methods

Isolation of Cardiac Cells

Primary cardiac cells were isolated from ICR 1-day-old (P1) and 7-day-old (P7) mice using a neonatal dissociation kit (gentleMACS), according to the manufacturer's instructions, and cultured in gelatin-coated (0.02%, G1393, Sigma) wells with DMEM/F12 medium supplemented with L-glutamine, Na-pyruvate, non-essential amino acids, penicillin, streptomycin, 5% horse serum and 10% FBS at 37° C. and 5% $CO_2$. In experiments involving administration of either c-terminal recombinant Agrin (550-AG) (R&D Systems), ECM fragments or broad MMP inhibitors (GM6001, Marimastat), the cells were allowed to adhere for 48 h prior to treatment. Subsequently, the medium was replaced with FBS-free medium containing 5% horse serum and the indicated treatment doses for 72 h. Cells were fixed in 4% paraformaldehyde (PFA) and stained for markers of interest.

Preparation of Heart Derived ECM

Hearts were taken from ICR mice (1 and 7 day old), and were washed with phosphate-buffered saline (PBS). Hearts were embedded in optimal cutting temperature solution (OCT, tissue-tek) and frozen in −20° C. Hearts were cut transversely into 100 µm fragments using a cryostat. Organ fragments were immersed in 2% Triton X-100 and 20 mM EDTA solution in double distilled water (DDW) overnight at room temperature. The matrixes were then washed with PBS and subsequently placed in 10% Penicillin-Streptomycin Amphotericin B Solution (Biological industries) for sterilization until placement with cells. Prior to matrix administration, fragments were washed with a cell culture medium without FBS (as previously described) and homogenized using gentleMACS M tubes (Miltenyi Biotec Inc). The matrix was then added to cell cultures.

Tissue Culture Immunostaining

Adherent cells were grown on a gelatin-coated 96 well plate. The cells were fixed with 4% PFA in PBS for 10 minutes and permeabilized with 0.2% Triton X-100 in PBS for 5 minutes. The cells were blocked by incubation in PBS containing 0.1% Triton and 3% BSA for 1 hour at room temperature. For immunostaining, the cells were incubated for 2 hours with the following monoclonal antibodies diluted in the blocking solution: Anti-cTnT (1:200, ab33589, Abcam) and anti-cTnI (1:200, ab47003, Abcam) antibodies were used to identify CMs. Anti-Ki67 antibody (1:200, 275R, Cell Marque), anti-phosphorylated-histone3 (pH3) (1:200, SC-8656-R, Santa Cruz Biotechnology) and anti-aurora B (Aim1, 1:100, 611082, BD Transduction Laboratories) antibodies were used to analyse cell-cycle re-entry, DNA synthesis, karyokinesis and cytokinesis, respectively. Cells were then washed 3 times with PBS and stained for 45 minutes at room temperature with a suitable secondary antibody. This was followed by 5 minutes of DAPI (4,6-diamidino-2-phenylindole dihydrochloride) staining. The cells were viewed under a Nikon fluorescence microscope.

Quantitative Real Time RT-PCR—

Total RNA was isolated using the nucleospin RNA II kit (Macherey Nagel) according to the manufacturer's protocol. cDNA was synthesized by using the High Capacity cDNA Reverse Transcription Kit (Applied Biosystems) according to the manufacturer's protocol. qRT-PCR was performed using SYBR Green PCR Master Mix (Applied Biosystems) on Steponeplus Real-Time PCR system (Applied Biosystems). Values for the specific genes were normalized to HPRT housekeeping control. Primer sequences are provided in Table 3 below.

TABLE 3

| Gene | Forward primer | Reverse primer |
| --- | --- | --- |
| hprt | TGGCCGGCAGCGTTTCTGAG/37 | GTCGGCTCGCGGCAAAAAGC/10 |
| Acta1 | GACATCAAAGAGAAGCTGTG/11 | ACTCCATACCGATAAAGGAAG/12 |
| Pecam | CCAGAAACATCATCATAACCG/17 | CATCGCCACCTTAATAGTTG/18 |
| CD90 | GTCAGGCTGGTCACCTTCTG/19 | AACTCTTGGCACCATGAACC/20 |
| aMHC | GCTGGGCTCCCTGGACATTGAC/21 | CCTGGGCCTGGATTCTGGTGAT/22 |
| Vcan | CCAGTGTGAACTTGATTTTGATGAA/23 | AACATAACTTGGGAGACAGAGACATCT/24 |
| Tgfbi | CATCGACGCCCAGATGAAGA/25 | TGGTGAACAGGGTCCCAAAC/26 |
| Dag1 | CGGAGGAGCGAACACCTG/27 | GTTGGATCCTCACCCTCTGC/28 |
| Agrn | TTCGATGGTCCTTGTGACCC/29 | AGATAGGTGTGTGTTGGGCG/30 |
| Col18a1 | GTGCCCATCGTCAACCTGAA/31 | AGTTGACCCTGGGAGCCAGA/32 |
| Dcn | CCTTCTGGCACAAGTCTCTTGG/33 | TCGAAGATGACACTGGCATCGG/34 |
| Lum | TCGAGCTTGATCTCTCCTAT/35 | TGGTCCCAGGTCTTACAGAA/36 |

Western Blot Analysis

Western blotting was performed with the SDS-PAGE Electrophoresis System. Total heart tissue extracts were prepared, and transferred to PVDF membranes. The following primary antibodies were used: anti-Agrn (sc-374117, Santa Cruz), anti alpha-dystroglycan (05-298, Millipore), anti-Gapdh (2118, Cell signaling technologies), Anti-cTnT (ab33589, Abcam) and anti-cTnI (ab47003, Abcam), anti-ERK2 (sc-154, Santa Cruz), anti-phospho-ERK (no. 4370, Cell Signaling), anti alpha-tubulin (T5168, Sigma-Aldrich). A horseradish peroxidase anti-mouse, anti-rabbit or anti-goat (Sigma) was used as the secondary antibody.

Immunofluorescence Analysis

Heart sections underwent deparaffinization and microwave antigen retrieval in EDTA or citric acid buffer, followed by gradual chilling. Samples were permeabilized with 0.5% Triton X-100 in PBS for 5 min and blocked with 5% bovine serum albumin (BSA) in PBS containing 0.1% Triton for 1 h at room temperature. Then samples were incubated overnight at 4° C. with the following antibodies diluted in 3% BSA blocking solution and 1% horse serum. Anti-cTnT (1:200, ab33589, Abcam) and anti-cTnI(1:200, ab47003, Abcam) antibodies were used to identify CMs. Anti-Ki67 antibody (1:200, 275R, Cell Marque), anti-phosphorylated-histone3 (pH3) (1:200, SC-8656-R, Santa Cruz Biotechnology) and anti-aurora B (Aim1, 1:100, 611082, BD Transduction Laboratories) antibodies were used to analyse cell-cycle re-entry, DNA synthesis, karyokinesis and cytokinesis, respectively. Other antibodies used in the study: anti-Agrn (1:200, sc-374117, Santa Cruz), anti phospho-ERK2 (1:200, M8159, Sigma Aldrich). After three washes with PBS, 10 min each, samples were stained for 1 h at room temperature with fluorescent secondary antibodies (Abcam) followed by 10 min of DAPI (4',6-diamidino-2-phenylindole dihydrochloride) staining for nuclei visualization. Slides mounted with Immu-mount (9990412, Thermo Scientific) and viewed under a fluorescence microscope (Nikon Intensilight or Nikon eclipse 90i, Nikon) or spinning-disc confocal microscope (Carl Zeiss).

Mouse Experiments

Experiments were approved by the Animal Care and Use Committee of the Weizmann Institute of Science. To track the cardiac muscle cell lineage, αMHC-Cre and ROSA26-tdTomato mice were intercrossed. αMHC-Cre mice carry the Cre coding sequence inserted after the alpha myosin heavy chain promoter (αMHC), which can drive high-efficiency gene recombination in CMs. ROSA26-tdTomato indicator mice harbor a conditional red fluorescent protein variant allele that requires CRE-mediated recombination for expression. This system allowed clear visualization of RFP-labeled CMs in culture. ROSA26-tdTomato and αMHC-Cre mice were maintained on a C57BL/6 background. To test the effect of Agrin in cardiac regeneration Agrn$^{flox/flox}$ (43) were intercrossed to Agrn$^{flox/flox}$; Mesp1-Cre mice (44). Mesp1 is expressed in the nascent mesoderm during early gastrulation and it marks the most cardiac progenitor populations which include the majority of heart cells (CMs, Fibroblasts and endothelial cells). The conditional knockout mouse allowed to understand the contribution of Agrin to cardiac regeneration in neonatal pups (P1).

Myocardial Infarction

Myocardial infarction at P7 or adult stages were induced by ligation of the left anterior descending coronary artery. P7 mice were anaesthetized by cooling on an ice bed for 4 min, whereas adult mice were sedated with isoflurane (Abbott Laboratories) and, following tracheal intubation, were artificially ventilated. Lateral thoracotomy at the third intercostal space was performed by blunt dissection of the intercostal muscles following skin incision. Following ligation of the left anterior descending coronary artery, Intramyocardial injections of Agrin (50 µl at 20 µg/ml) or PBS were administered. Following treatment, thoracic wall incisions were sutured with 6.0 non-absorbable silk sutures, and the skin wound closed using a skin adhesive. Mice were then warmed for several minutes until recovery.

Echocardiography

Heart function was evaluated by transthoracic echocardiography performed on sedated mice (isoflurane, Abbott Laboratories) using a Vevo 770 VisualSonics device.

Histology

Mouse heart tissues were fixed in 4% paraformaldehyde (PFA) and sectioned. For analysis of juvenile and adult cardiac regeneration following myocardial infarction procedure, paraffin sections were cut through the entire ventricle from apex to base into serial sections with intervals of 0.4 mm. For analysis of neonatal cardiac regeneration following resection, paraffin sections were cut frontally to include base to apex in each section. Haematoxylin-eosin (H&E), Masson's trichrome and Sirius red staining were performed according to standard procedures and used to for detection of fibrosis. Scar size was quantified in the section containing the papillary muscle region using ImageJ software based on Masson's trichrome staining. Adult and juvenile scar size was calculated as scar size relative to total section size, whereas neonatal scar size was calculated as scar size relative to LV size.

Example 2

P1 Cardiac ECM Increases CM Proliferation in a MMP Dependent Manner

The effect of the cardiac ECM on CM turnover during the regenerative timeframe in mice was determined {Porrello, 2011 #11}. For that purpose P1 and P7 hearts underwent decellularization (FIG. 1A) to produce cell free ECM fragments as confirmed by DAPI staining and scanning electron microscopy (FIGS. 1B-C). In vitro administration of P1 ECM fragments promoted an increase in both P1 and P7 CM cell-cycle activity, whereas P7 ECM fragments reduced cell cycle re-entry (FIGS. 1D-F).

To gain further insights into the mechanism by which P1 ECM induces CM proliferation, a broad MMP inhibitor (Marimastat) was administered to the culture. Addition of the inhibitor to CM cultures containing ECM fragments derived from P1 hearts abolished the activation of CM proliferation by the P1 ECM explants (FIGS. 1G-H). Addition of the inhibitor to either control cultures or to cultures with ECM fragments derived from P7 hearts, did not influence CM proliferation rate (FIGS. 1G-H).

In order to validate the involvement of MMP2/9 in releasing ECM-related peptides that induce CM proliferation, in situ zymography (ISZ) assay that measures the cleavage of substrates, collagen type 1 (Col1), collagen type 4 (Col4) or gelatin into a fluorescent signal in the presence of ECM fragments was used (FIG. 1N). The highest change observed amongst the three substrates was for Col4 and gelatins, suggesting an involvement of the Gelatinase family of MMPs, MMP2/9 (FIGS. 1O-P).

Next, in order to test if a specific ligand/peptide in the P1 ECM cleaved by MMP2/9 is sufficient to promote CM proliferation, P1 ECM was incubated with MMP2, MMP9, or MMP12 (FIG. 1I). P1 ECM explants digested with MMP2/9 resulted in a striking increase in CM proliferation of either P1 (FIG. 1J) or P7 (FIG. 1K) cells, whereas MMP12 cleaved ligands resulted in increase in CM proliferation, albeit lower.

To identify unique P1 ECM associated proteins that contribute to the enhanced CM proliferation, MMP9 cleaved P1 and P7 ECM related proteins were analyzed by mass spectroscopy (LC/MS) (FIG. 1L). This technique identified a previously reported contribution of Tgfbi, a paralog of Periostin that was shown to promote CM proliferation [12,45]. Other ECM proteins which were enriched in P1 vs. P7 include Col18a1 (Endostatin) and Vcan (FIG. 1M). In addition, Agrin, an ECM HSPG, was identified as enriched in P1 relative to P7 ECM explants (FIG. 1M). Finally, the observed changes in expression levels were validated by qRT-PCR in P1 and P7 whole hearts, which are consistent with the results of the proteomic analysis (FIG. 1M). Taken together a novel methodology to dissect ECM related CM proliferation-promoting molecules was demonstrated and MMP2/9 remodeling of P1 but not P7 cardiac ECM can lead to subsequent release of these ligands that promote CM proliferation in vitro.

Example 3

Endocardial/Endothelial Derived Agrin Promotes CM Proliferation

The expression levels of Agrin in the heart were then tested {Moll, 2001 #111; McKee, 2009 #112}. Immunofluorescence analysis validated previous finding showing the downregulation of Agrin expression (RNA and protein) at P7 hearts, compared to P1 (FIGS. 2A-C). Next, the cell population which produces Agrin was identified. To do so, P1 cardiac cells were separated to 3 different populations: CMs, fibroblasts (FBs) and endothelial cells (ECs). Enrichment of CMs, FBs and ECs cell populations was confirmed using qPCR for known markers of each cell population (αMHC, CD90 and CD31, respectively, FIG. 2I). Agrin mRNA expression was significantly enriched in the EC population relative to all other cell types (FIG. 2D). The reduction of Agrin expression during the first week of life correlates with the loss of cardiac regenerative response in mice, therefore, it may suggest a role for Agrin during the regeneration process (as shown in FIGS. 3A-O).

The ability of Agrin to induce CM proliferation in culture was then determined. Agrin treatment resulted in a dose-dependent increase in CM proliferation, as measured by immunofluorescence staining for markers of cell-cycle activity (Ki67), mitosis (phospho-Histone H3) and cytokinesis (Aurora B kinase), and by counting the number of newly formed CMs at P1 and P7 (FIGS. 2E-H).

Example 4

Agrin is Required for Cardiac Regeneration in Neonatal Mice

In order to understand whether Agrin is required for cardiac regeneration at birth following the surgical resection technique {Porrello, 2011 #11; Porrello, 2012 #38}, Agrin was conditionally deleted in the majority of heart cell populations by crossing Mesp1-Cre$^{+/-}$; Agrin$^{flow/+}$ {Harvey, #113; Kitajima, 2006 #114} with Agrin$^{flox/flox}$ mice (FIG. 3A). Analyses of Agrin protein and mRNA expression in Mesp1-Cre$^{+/-}$; Agrin$^{flox/flox}$ (Agrin-cKO) hearts confirmed that the Agrin flox allele was efficiently deleted in the heart (FIGS. 3B-D). Interestingly, at P1 Agrin-cKO mice expressed elevated sarcomeric proteins (cTnT and cTnI) (FIG. 3C) with a marked increase in sarcomeric organization as seen by cTnT staining (FIG. 3H). WGA membrane staining revealed a small increase in cardiac cell size (FIGS. 3E-F) which was consistent with elevated pathological hypertrophy {Houweling, 2005 #115; Ye, 2003 #116}

{Baum, 2011 #12}Marker, skeletal-actin (Acta1) {Black, 1991 #117} (FIG. 3G). Moreover, CM cell cycle activity was significantly reduced in Agrin-cKO mice after birth (FIGS. 3H-I). These findings suggest that Agrin suppresses CM maturation processes and in the absence of Agrin, CMs display a compensatory mechanism for cardiac hypertrophy and increased differentiation.

Next, the question whether cardiac regeneration is impaired in Agrin-cKO mice was investigated. For that P1 mice underwent cardiac resection and cardiac regeneration was assessed after 1 and 4 weeks (by proliferation or by fibrosis respectfully) (FIG. 3J). Histological examination using Mason's trichrome and Sirius red stain displayed elevated fibrosis in the Agrin-cKO mice relative to wild-type littermate (FIGS. 3K-M). In line with these findings, CM proliferation was significantly reduced in Agrin cKO mice (FIG. 3N). Taken together, the present results suggest Agrin as a crucial component during cardiac regeneration and suggest it may play a role as an inhibitor of CM differentiation during the first postnatal week.

Example 5

Agrin Treatment Promotes Cardiac Regeneration Following MI

Figure 4A:
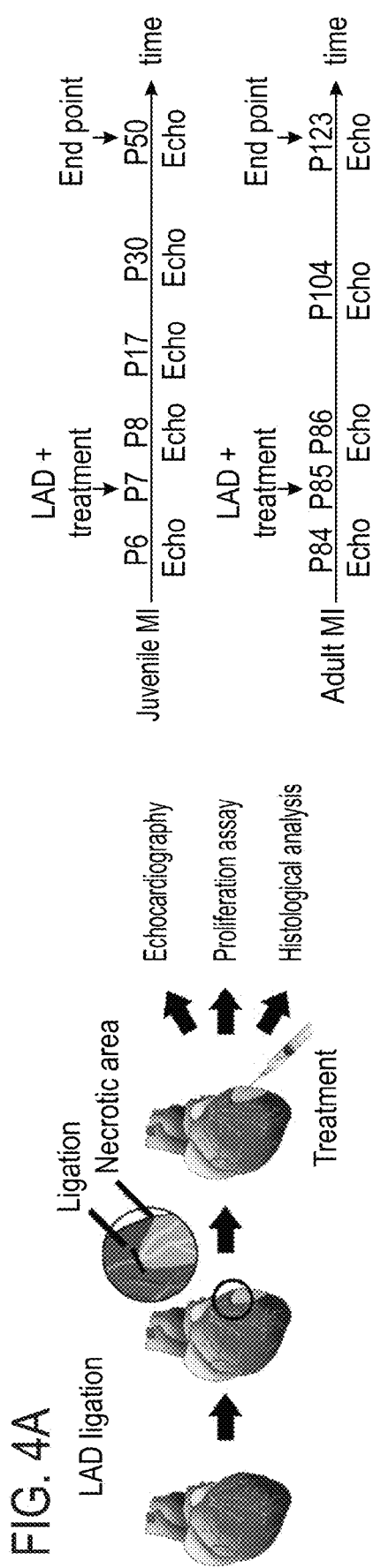
Figure 4C:
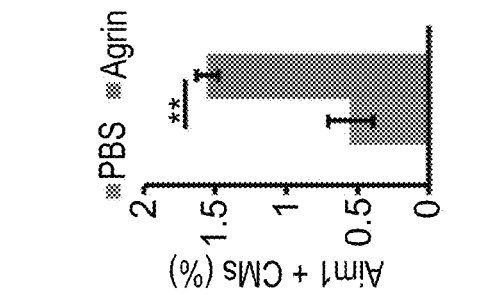
Figure 4C:
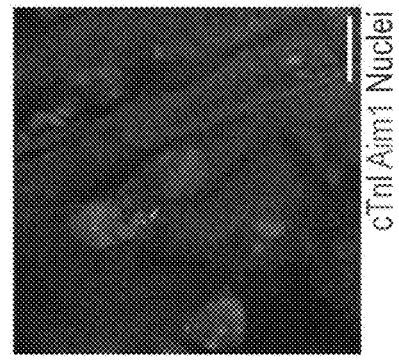
Figure 4C:
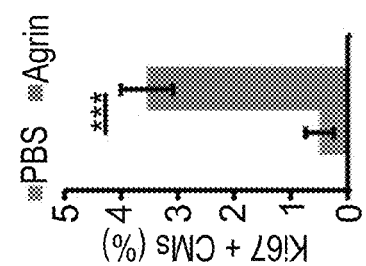
Figure 4C:
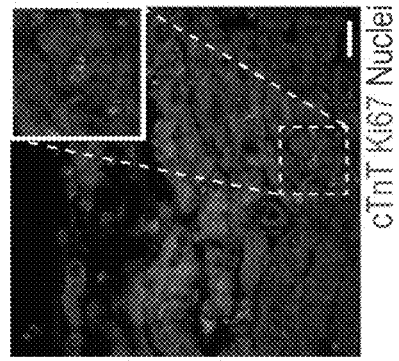
Figure 4G:
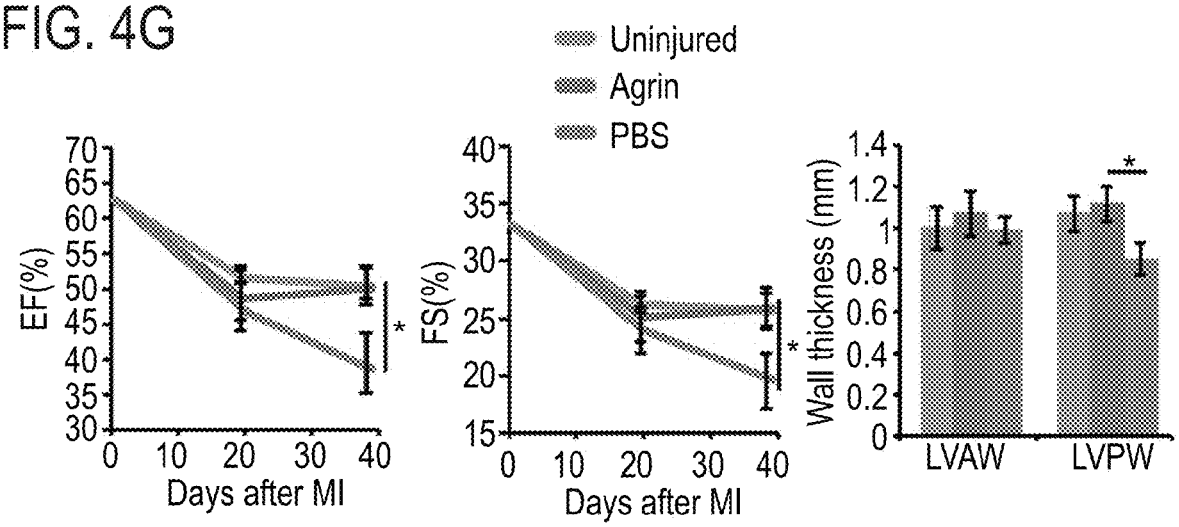
Figure 4H:
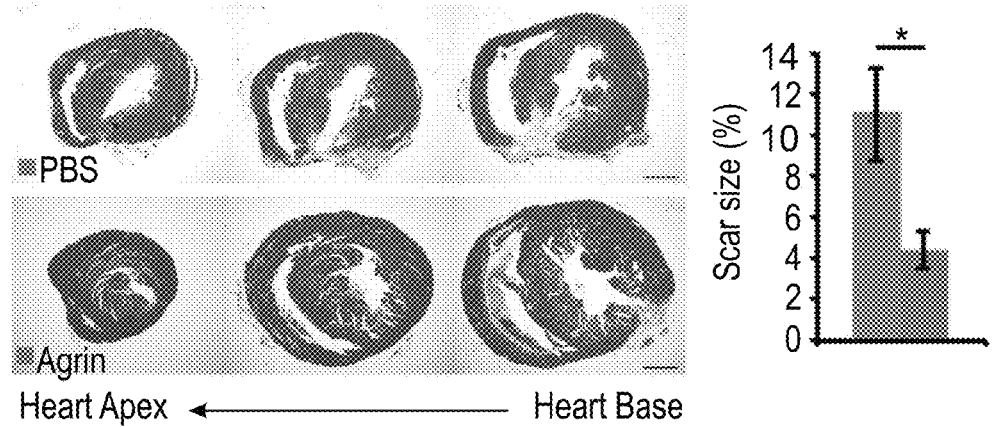
Figure 4I:
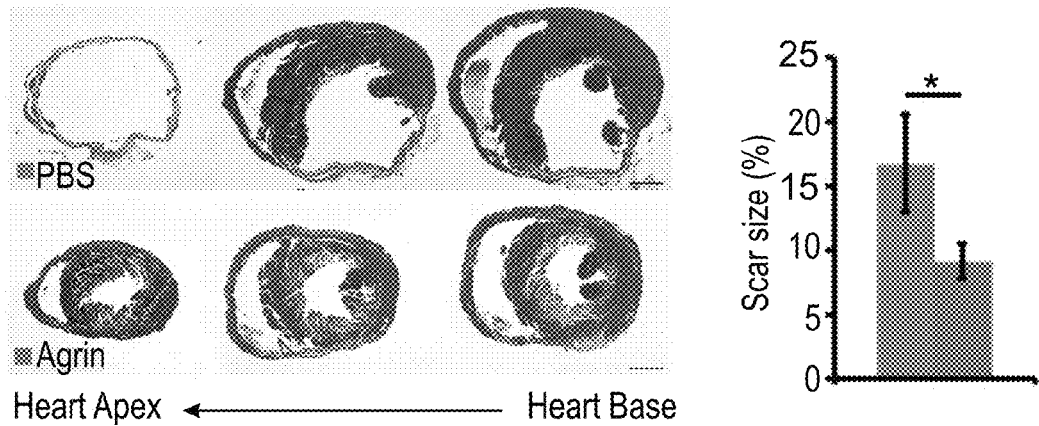

Next, the question whether Agrin could similarly promote CM proliferation and cardiac regeneration in juvenile and adult stages was investigated. Accordingly, P7 and P85 mice were subjected to permanent ligation of the left anterior descending artery (LAD) that were treated with either Agrin or PBS (FIG. 4A). Intramyocardial injection of Agrin (1 µg in 50 µl) induced CM cell cycle re-entry in the healthy myocardium adjacent to the infarcted region of both juvenile and adult hearts (FIGS. 4B-E). A single Agrin injection following MI was sufficient to improve recovery of cardiac function as evident by echocardiography, in both juvenile and adult models (FIGS. 4F-G). Moreover, both juvenile and adult Agrin treated mice showed a significant retention of wall thickness and protection from dilated cardiomyopathy, in contrast to PBS treated mice (FIGS. 4F-G). Histological analyses in both juvenile and adult, revealed significant reduction in fibrosis, albeit fibrotic tissue was present in both treatments (FIGS. 4H-I). Taken together, the present results demonstrate that re-introduction of Agrin to failing hearts facilitates cardiac regeneration as a result of increased CM cell cycle activity and cytokinesis and subsequent reduction of scaring and better cardiac function.

Example 6

Agrin Promotes CM Proliferation Through Dag1 and ERK Activation

Figure 5B:
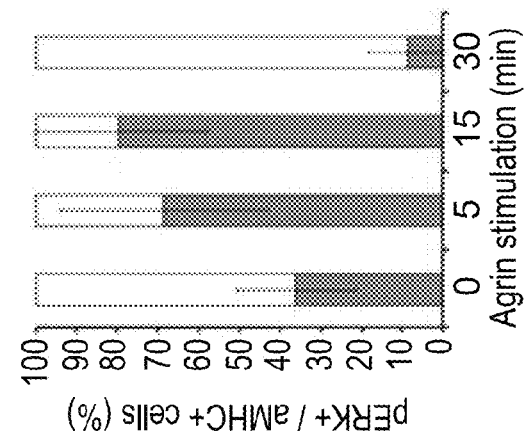
Figure 5C:
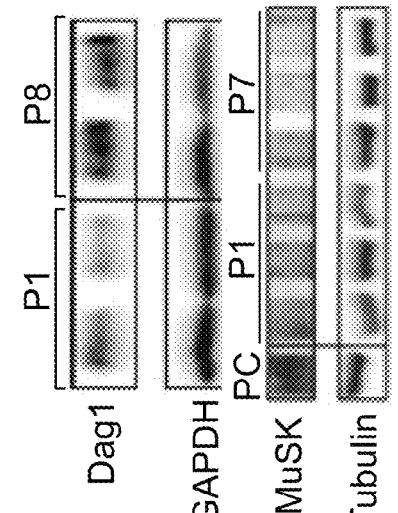
Figure 5D:
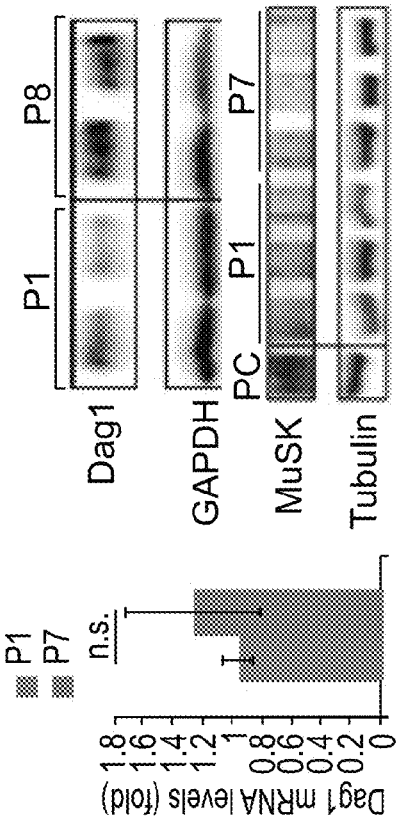
Figure 5E:
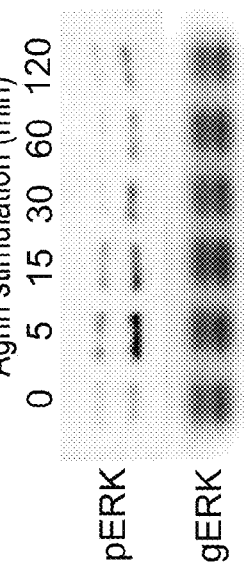
Figure 5F:
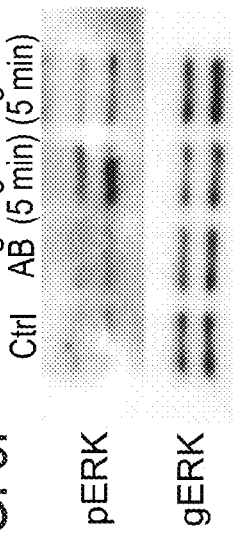

Previous reports on Agrin signaling have implicated inhibition of $Na^+/K^+$ pumps, Lrp4-Musk or α-Dystroglycan as possible receptors modulating its activity. Earlier work focusing on cardiac regeneration in mice following MI has established that cardiac mRNA transcript levels of Lrp4 and MuSK are very low {Haubner, 2012 #130}. Furthermore, it has been shown that Agrin can inhibit $Na^+/K^+$ pumps via direct interaction with CAF22 fragment and therefore affect CM beating {Hilgenberg, 2009 #103}. Improvement in cardiac function can be attributed to several aspects, one of which is synchronization of the beating of the myocardium {Abraham, 2002 #118; Sullivan, 1989 #119}, as well as adult CM proliferation. No increase in CM proliferation by inhibiting the pump was observed (FIG. 5J). Thus it is suggested that Agrin signaling is mediated by Dag1 in CMs. Thus it was hypothesized that Agrin signaling is mediated by Dag1 in CMs. For that, the present inventors aimed to identify the cell population expressing Dag1 which potentially interact with Agrin. Using qPCR for Dag1 revealed expression in all cell types isolated from P1 hearts, however its expression was particularly enriched in CMs, this enrichment became more striking in P8 heart cultures (FIGS. 5A-C). Agrin activity has been associated with ERK activation during monocyte maturation {Aurora, 2014 #125}. Similarly, the present inventors observed transient ERK activation following Agrin treatment in vitro, peaking at 5 minutes with sustained activation up to 15 minutes post treatment in cardiac cell culture as measured by western blot and immunofluorescence (FIGS. 5D-E). Next, the question of the interaction of Agrin with Dag1 and its requirement for ERK activation was examined. Indeed addition of a blocking antibody (IIH6C4) directed against Dag1-Agrin binding site {Aurora, 2014 #125} diminished Agrin-induced ERK activation (FIG. 5F). Furthermore, in order to understand whether the interaction of Agrin with Dag1 and subsequent ERK activation was required for Agrin induced proliferation; IIH6C4 antibody and MEK inhibitor (PD0325901) were added to P7 CM cell cultures and CM proliferation was analyzed (FIGS. 5G-H). As expected, inhibition of either ERK activation or the Dag1-Agrin interaction suppressed Agrin induced CM proliferation.

Following this, the present inventors wanted to examine whether Agrin-Dystroglycan signal was propagated through dystrophin, for that mdx mice [55] in which dystrophin expression is abolished were used.

Cardiac cells from control and Mdx mice were cultured and treated with Agrin. CM proliferation induced by Agrin was not changed between the two types of mice (FIG. 5I). Taken together, Agrin induced CM proliferation via interaction with Dag1 and subsequent ERK activation, in a dystrophin-independent manner.

Example 7

In-Vitro Agrin Administration Promotes Human iPSC-Derived CMs Proliferation

Figure 6A:
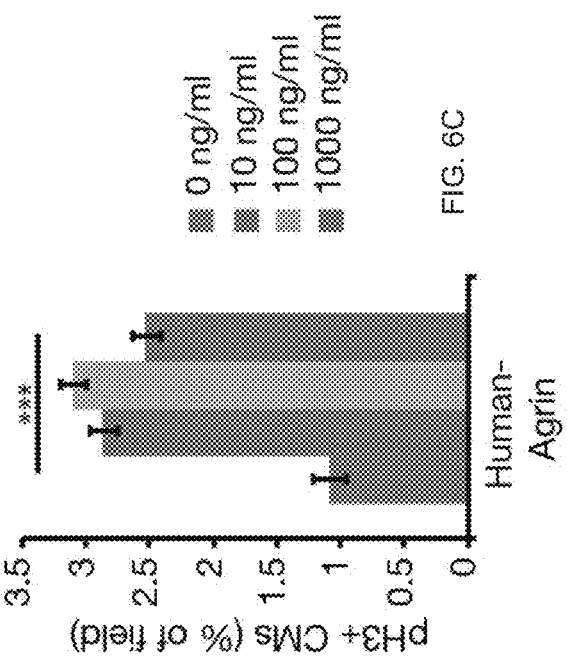
Figure 6B:
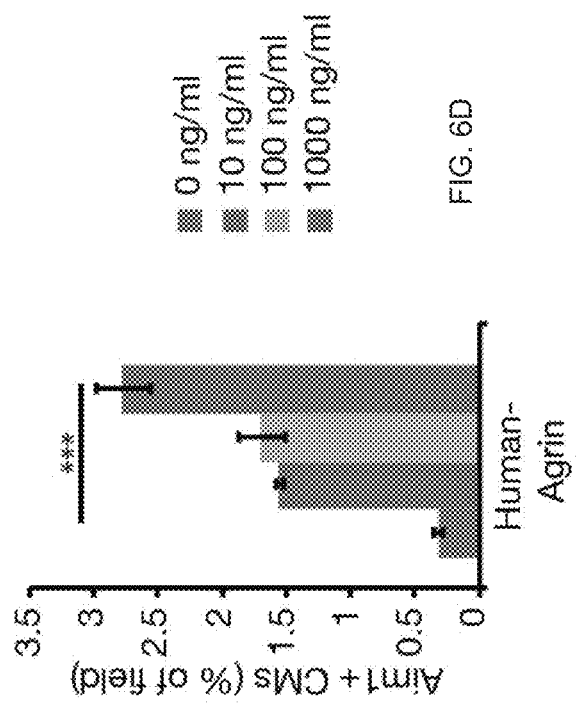
Figure 6C:
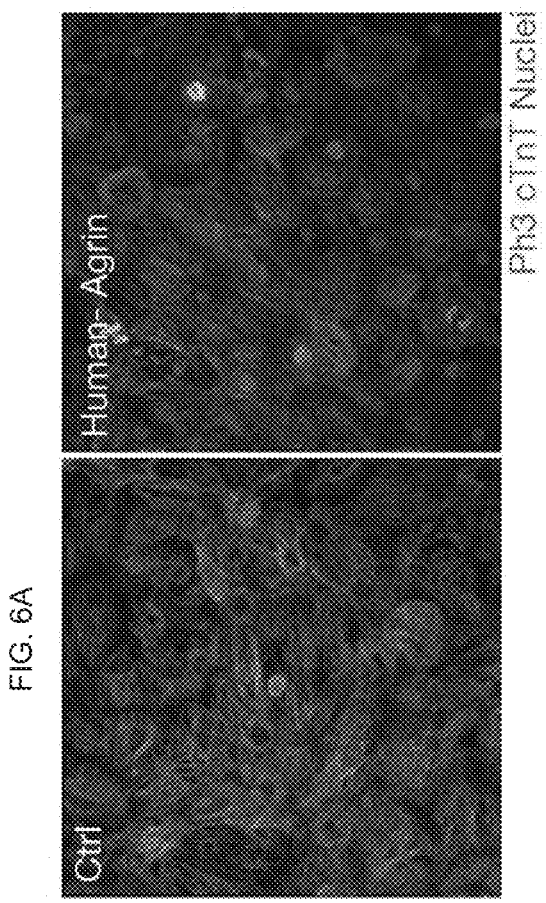
Figure 6D:
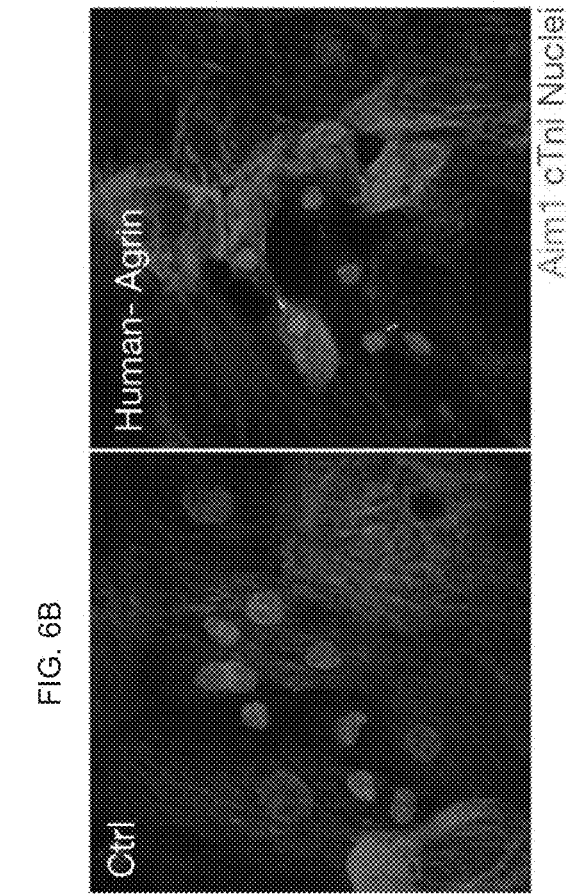

To understand whether Agrin could promote CM proliferation in cells derived from human tissues, Agrin was added to human iPSC derived CMs (hiPSC-CM) and examined by proliferation markers. In vitro administration of Agrin promoted a dose-dependent increase of hiPSC-CM cell-cycle activity (FIGS. 6A-B). Likewise, in vitro administration of human Agrin promoted a dose-dependent increase of hiPSC-CM cell-cycle activity (FIGS. 6C-D).

Example 8

RNA-Sea of Agrin Treated Hearts Revels Implications to Agrin Immune-Related Mechanism To asses Agrin genome wide transcriptional effect in the infarcted hearts, RNA-seq analysis of Agrin treated MI hearts was performed. Adult (3 months) mice were subjected to LAD ligation or sham operation (see FIG. 4A). The LAD ligated animals were injected with either Agrin or PBS (vehicle) epimyocardialy immediately after MI (FIG. 8A). Hearts were collected 3 days post treatment, and RNA samples were purified and subjected to RNA-seq. Genome wide expression of infarcted hearts treated with either PBS or Agrin was compared. 175 genes were differentially expressed (threshold of fold change >1.5, p-value<0.05, see FIG. 8B). To focus on the relevant transcriptional effect, present data was compared to a former established RNA-seq of wild type infarcted hearts, performed by Ounzain et al. Genome-wide profiling of the cardiac transcriptome after myocardial infarction identifies novel heart-specific long non-coding RNAs. Eur Heart J 36, 353-368a, doi:10.1093/eurheartj/ehu180 (2015).

This comparison allowed defining the common genes that are differentially expressed in infracted untreated hearts, serving as an "MI signature". It was found that 558 genes were differentially expressed (mostly up regulated) in infarcted hearts compared to sham operated hearts, both in the present settings and in Ounzain's datasets (FIG. 8C). Looking at these genes in the infarcted hearts treated with Agrin, it was found that most of them showed the opposite trend in Agrin treated hearts compared to PBS treated hearts (FIG. 8C), indicating that these genes comprise the Agrin-affected transcriptional network.

To gain insight into the cellular and molecular processes this gene set portrays, the gene set was analyzed using ingenuity pathway analysis (IPA) software. Interestingly, looking at both canonical pathways (FIG. 8D) and upstream regulators (FIG. 8E), it was found that many relate to modulation of the MI-related immune response; i.e., 116 is known to promote cardiomyocytes apoptosis, Tgf-beta is well established as a fibrosis promoter and several canonical pathways regulating immune cells migration and maturation (Leukocytes extravasation signaling, Dendritic cell maturation) were also implicated. Examples for genes involved in the different enriched terms are given in FIGS. 8F-H. Taken together, this data suggested that Agrin promotes heart regeneration not only through cardiomyocyte proliferation by also by immune modulation, which might change cardiomyocyte survival thereby reducing infarct and scar size.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Other References are Cited Throughout the Application

1 Bergmann, O., et al., *Evidence for Cardiomyocyte Renewal in Humans*. Science, 2009. 324(5923): p. 98-102.
2 Senyo, S. E., et al., *Mammalian heart renewal by pre-existing cardiomyocytes*. Nature, 2013. 493(7432): p. 433-436.
3 Poss, K. D., *Getting to the heart of regeneration in zebrafish*. Seminars in Cell & Developmental Biology, 2007. 18(1): p. 36-45.
4 Ausoni, S. and S. Sartore, *From fish to amphibians to mammals: in search of novel strategies to optimize cardiac regeneration*. The Journal of Cell Biology, 2009. 184(3): p. 357-364.
5 Jopling, C., et al., *Zebrafish heart regeneration occurs by cardiomyocyte dedifferentiation and proliferation*. Nature, 2010. 464(7288): p. 606-609.
6 Porrello, E. R., et al., *Transient Regenerative Potential of the Neonatal Mouse Heart*. Science, 2011. 331(6020): p. 1078-1080.
7 Porrello, E. R., et al., *Regulation of neonatal and adult mammalian heart regeneration by the miR-15 family*. Proceedings of the National Academy of Sciences, 2012.
8 Li, F., et al., *Rapid Transition of Cardiac Myocytes from Hyperplasia to Hypertrophy During Postnatal Development*. Journal of Molecular and Cellular Cardiology, 1996. 28(8): p. 1737-1746.
9 Soonpaa, M. H. and L. J. Field, *Survey of Studies Examining Mammalian Cardiomyocyte DNA Synthesis*. Circulation Research, 1998. 83(1): p. 15-26.
10 Weisman, H. F., et al., *Cellular mechanisms of myocardial infarct expansion*. Circulation, 1988. 78(1): p. 186-201.
11 Engel, F. B., et al., *FGF1/p38 MAP kinase inhibitor therapy induces cardiomyocyte mitosis, reduces scarring, and rescues function after myocardial infarction*. Proceedings of the National Academy of Sciences, 2006. 103(42): p. 15546-15551.
12 Kuhn, B., et al., *Periostin induces proliferation of differentiated cardiomyocytes and promotes cardiac repair*. Nat Med, 2007. 13(8): p. 962-969.
3 D'Uva, G., et al., *ERBB2 triggers mammalian heart regeneration by promoting cardiomyocyte dedifferentiation and proliferation*. Nat Cell Biol, 2015. 17(5): p. 627-638.
14 Bersell, K., et al., *Neuregulin1/ErbB4 Signaling Induces Cardiomyocyte Proliferation and Repair of Heart Injury*. Cell, 2009. 138(2): p. 257-270.
15 Heallen, T., et al., *Hippo signaling impedes adult heart regeneration*. Development, 2013. 140(23): p. 4683-4690.
16 Mahmoud, A. I., et al., *Meis1 regulates postnatal cardiomyocyte cell cycle arrest*. Nature, 2013. 497(7448): p. 249-253.
17 Baum, J. and H. S. Duffy, *Fibroblasts and Myofibroblasts: What Are We Talking About?* Journal of Cardiovascular Pharmacology, 2011. 57(4): p. 376-379 10.10/97FJC.0b013e3182116e39.
18 Bayomy, A. F., et al., *Regeneration in heart disease—Is ECM the key?* Life Sciences, 2012. 91(17-18): p. 823-827.
19 Phatharajaree, W., A. Phrommintikul, and N. Chattipakorn, *Matrix metalloproteinases and myocardial infarction*. The Canadian Journal of Cardiology, 2007. 23(9): p. 727-733.
20 DeCoux, A., et al., *Myocardial matrix metalloproteinase-2: inside out and upside down*. Journal of Molecular and Cellular Cardiology, 2014. 77: p. 64-72.
21 Hayashidani, S., et al., *Targeted deletion of MMP-2 attenuates early LV rupture and late remodeling after experimental myocardial infarction*. American Journal of Physiology—Heart and Circulatory Physiology, 2003. 285(3): p. H1229-H1235.
22 Ducharme, A., et al., *Targeted deletion of matrix metalloproteinase-9 attenuates left ventricular enlargement and collagen accumulation after experimental myocardial infarction*. Journal of Clinical Investigation, 2000. 106(1): p. 55-62.

23 Ridley, A. J., et al., *Cell Migration: Integrating Signals from Front to Back.* Science, 2003. 302(5651): p. 1704-1709.
24 Berk, B. C., K. Fujiwara, and S. Lehoux, *ECM remodeling in hypertensive heart disease.* Journal of Clinical Investigation, 2007. 117(3): p. 568-575.
25 Shamis, Y., et al., *Organ specific scaffolds for in vitro expansion, differentiation and organization of primary lung cells.* Tissue Engineering Part C—Methods, 2011. 17(8): p. 861-870.
26 Streuli, C., *Extracellular matrix remodelling and cellular differentiation.* Current Opinion in Cell Biology, 1999. 11(5): p. 634-640.
27 Williams, C., et al., *Young developmental age cardiac extracellular matrix promotes the expansion of neonatal cardiomyocytes in vitro.* Acta Biomaterialia, 2014. 10(1): p. 194-204.
28 Williams, S., C. Ryan, and C. Jacobson, *Agrin and neuregulin, expanding roles and implications for therapeutics.* Biotechnology Advances, 2008. 26(3): p. 187-201.
29 Burden, S. J., N. Yumoto, and W. Zhang, *The Role of MuSK in Synapse Formation and Neuromuscular Disease.* Cold Spring Harbor Perspectives in Biology, 2013. 5(5.(
30 Theocharis, A. D., et al., *Proteoglycans in health and disease: novel roles for proteoglycans in malignancy and their pharmacological targeting.* FEBS Journal, 2010. 277(19): p. 3904-3923.
31 Chakraborty, S., et al., *An oncogenic role of Agrin in regulating focal adhesion integrity in hepatocellular carcinoma.* Nat Commun, 2015. 6.
32 Hilgenberg, L. G. W., et al., *Agrin Regulation of α3 Sodium-Potassium ATPase Activity Modulates Cardiac Myocyte Contraction.* Journal of Biological Chemistry, 2009. 284(25): p. 16956-16965.
33 Schwinger, R. H. G., et al., *The Na, K-ATPase in the failing human heart.* Cardiovascular Research, 2003. 57(4): p. 913-920.
34 Mazzon, C., et al., *Agrin is required for survival and function of monocytic cells.* Blood, 2012. 119(23): p. 5502-5511.
35 Henry, M. D. and K. P. Campbell, *Dystroglycan: an extracellular matrix receptor linked to the cytoskeleton.* Current Opinion in Cell Biology, 1996. 8(5): p. 625-631.
36 Davies, K. E. and K. J. Nowak, *Molecular mechanisms of muscular dystrophies: old and new players.* Nat Rev Mol Cell Biol, 2006. 7(10): p. 762-773.
37 Ervasti, J. M., et al., *Deficiency of a glycoprotein component of the dystrophin complex in dystrophic muscle.* Nature, 1990. 345(6273): p. 315-319.
38 Campbell, K. P. and S. D. Kahl, *Association of dystrophin and an integral membrane glycoprotein.* Nature, 1989. 338(6212): p. 259-262.
39 Richardson, G. D., S. Laval, and W. A. Owens, *Cardiomyocyte Regeneration in the mdx Mouse Model of Non-ischemic Cardiomyopathy.* Stem Cells and Development, 2015: p. 1672-1679.
40 Morikawa, Y., et al., *Actin cytoskeletal remodeling with protrusion formation is essential for heart regeneration in Hippo-deficient mice.* Science Signaling, 2015. 8(375): p. ra41-ra41.
41 Haubner, B. J., et al., *Complete cardiac regeneration in a mouse model of myocardial infarction.* Aging (Albany N.Y.), 2012. 4(12): p. 966-977.
42 Singhal, N. and P. T. Martin, *Role of extracellular matrix proteins and their receptors in the development of the vertebrate neuromuscular junction.* Developmental Neurobiology, 2011. 71(11): p. 982-1005.
43 Harvey, S. J., et al., *Disruption of Glomerular Basement Membrane Charge through Podocyte-Specific Mutation of Agrin Does Not Alter Glomerular Permselectivity.* The American Journal of Pathology, 2007. 171(1): p. 139-152.
44 Saga, Y., et al., *MesP1 is expressed in the heart precursor cells and required for the formation of a single heart tube.* Development, 1999. 126(15): p. 3437-3447.
45 Hoersch, S. and M. Andrade-Navarro, *Periostin shows increased evolutionary plasticity in its alternatively spliced region.* BMC Evolutionary Biology, 2010. 10(1): p. 30.
46 Moll, J., et al., *An agrin minigene rescues dystrophic symptoms in a mouse model for congenital muscular dystrophy.* Nature, 2001. 413(6853): p. 302-307.
47 McKee, K. K., S. Capizzi, and P. D. Yurchenco, *Scaffold forming and Adhesive Contributions of Synthetic Laminin-binding Proteins to Basement Membrane Assembly.* The Journal of Biological Chemistry, 2009. 284:(13) p. 8984-8994.
48 Kitajima, S., et al., *Mesp1-nonexpressing cells contribute to the ventricular cardiac conduction system.* Developmental Dynamics, 2006. 235(2): p. 395-402.
49 Houweling, A. C., et al., *Expression and regulation of the atrial natriuretic factor encoding gene Nppa during development and disease.* Cardiovascular Research, 2005. 67(4): p. 583-593.
50 Ye, P. and M. J. West, *Cosegregation analysis of natriuretic peptide genes and blood pressure in the spontaneously hypertensive rat.* Clinical and Experimental Pharmacology and Physiology, 2003. 30(12): p. 930-936.
51 Black, F. M., et al., *The vascular smooth muscle alpha-actin gene is reactivated during cardiac hypertrophy provoked by load.* The Journal of Clinical Investigation, 1991. 88(5: (p. 1581-1588.
52 Abraham, W. T., et al., *Cardiac Resynchronization in Chronic Heart Failure.* New England Journal of Medicine, 2002. 346(24): p. 1845-1853.
53 Sullivan, M., et al., *Increased exercise capacity after digoxin administration in patients with heart failure.* Journal of the American College of Cardiology, 1989. 13(5): p. 1138-1143.
54 Aurora, A. B., et al., *Macrophages are required for neonatal heart regeneration.* The Journal of Clinical Investigation, 2014. 124(3): p. 1382-1392.
55 Im, W. B., et al., *Differential Expression of Dystrophin Isoforms in Strains of mdx Mice with Different Mutations.* Human Molecular Genetics, 1996. 5(8): p. 1149-1153.

What is claimed is:

1. A method of inducing proliferation of cardiomyocytes, the method comprising contacting the cardiomyocytes with an effective amount of an Agrin peptide which induces proliferation of the cardiomyocytes, wherein said agrin peptide is not a part of a fusion polypeptide and wherein said agrin peptide comprises a laminin G-like 1 domain (G1) and a laminin G-like 2 domain (G2).

2. The method of claim 1, wherein said peptide induces immune modulation.

3. The method of claim 1, wherein said agrin peptide induces Erk activation.

4. The method of claim 1, wherein said agrin peptide inhibits sarcomerogenesis.

5. The method of claim 1, wherein said agrin peptide is in a soluble form.

6. The method of claim 1, wherein said agrin peptide comprises a fragment of human agrin.

7. The method of claim 1, wherein said cardiomyocytes are selected from the group consisting of adult cardiomyocytes, juvenile cardiomyocytes and neonatal cardiomyocytes.

8. A method of inducing proliferation of cardiomyocytes, the method comprising contacting the cardiomyocytes with an agrin peptide which inhibits the Dystroglycan complex on the cardiomyocytes wherein said agrin peptide induces proliferation of the cardiomyocytes and is not a part of a fusion polypeptide and wherein said agrin peptide comprises a laminin G-like 1 domain (G1) and a laminin G-like 2 domain (G2), thereby inducing proliferation of cardiomyocytes.

9. A method of treating a heart disease in a subject in need thereof, the method comprising administering to the subject a therapeutically effective amount of an agrin peptide which induces proliferation of cardiomyocytes, wherein said agrin peptide induces proliferation of the cardiomyocytes and is not a part of a fusion polypeptide and wherein said agrin peptide comprises a laminin G-like 1 domain (G1) and a laminin G-like 2 domain (G2), thereby treating the heart disease.

10. The method of claim 9, wherein said heart disease is an ischemic heart disease.

11. An implantable device comprising an agrin peptide which induces proliferation of cardiomyocytes, wherein said agrin peptide induces proliferation of the cardiomyocytes and is not a part of a fusion polypeptide and wherein said agrin peptide comprises a laminin G-like 1 domain (G1) and a laminin G-like 2 domain (G2).

12. The device of claim 11, wherein said agrin peptide induces immune modulation.

\* \* \* \* \*